United States Patent
Mantoulidis et al.

(10) Patent No.: US 12,281,099 B2
(45) Date of Patent: Apr. 22, 2025

(54) ISOINDOLINONE SUBSTITUTED INDOLES AND DERIVATIVES AS RAS INHIBITORS

(71) Applicant: Boehringer Ingelheim International GmbH, Ingelheim am Rhein (DE)

(72) Inventors: Andreas Mantoulidis, Vienna (AT); Andreas Gollner, Vienna (AT); Dirk Kessler, Vienna (AT); Laetitia Janine Martin, Saint Louis (FR); Harald Weinstabl, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 737 days.

(21) Appl. No.: 17/430,011

(22) PCT Filed: Feb. 25, 2020

(86) PCT No.: PCT/EP2020/054897
§ 371 (c)(1),
(2) Date: Aug. 11, 2021

(87) PCT Pub. No.: WO2020/173935
PCT Pub. Date: Sep. 3, 2020

(65) Prior Publication Data
US 2022/0144810 A1 May 12, 2022

(30) Foreign Application Priority Data
Feb. 26, 2019 (EP) ..................... 19159299

(51) Int. Cl.
| | | |
|---|---|---|
| *C07D 403/04* | (2006.01) | |
| *A61P 35/00* | (2006.01) | |
| *C07D 401/14* | (2006.01) | |
| *C07D 403/14* | (2006.01) | |
| *C07D 405/04* | (2006.01) | |
| *C07D 405/14* | (2006.01) | |
| *C07D 471/04* | (2006.01) | |
| *C07D 487/04* | (2006.01) | |

(52) U.S. Cl.
CPC ............ *C07D 403/04* (2013.01); *A61P 35/00* (2018.01); *C07D 401/14* (2013.01); *C07D 403/14* (2013.01); *C07D 405/04* (2013.01); *C07D 405/14* (2013.01); *C07D 471/04* (2013.01); *C07D 487/04* (2013.01)

(58) Field of Classification Search
CPC ............... C07D 403/04; C07D 401/14; C07D 403/14; C07D 405/04; C07D 405/14; C07D 471/04; C07D 487/04; C07D 401/12; C07D 403/06; C07D 405/06; C07D 405/12; C07D 209/34; A61P 35/00
See application file for complete search history.

(56) References Cited

FOREIGN PATENT DOCUMENTS

| | | | |
|---|---|---|---|
| WO | WO-2008119741 A2 * | 10/2008 | ........... C07D 403/04 |
| WO | 2014152588 A1 | 9/2014 | |
| WO | 2015054572 A1 | 4/2015 | |
| WO | 2016049524 A1 | 3/2016 | |
| WO | 2016168540 A1 | 10/2016 | |
| WO | 201715562 A1 | 1/2017 | |
| WO | 2018064510 A1 | 4/2018 | |
| WO | 2018068017 A1 | 4/2018 | |
| WO | 2018119183 A2 | 6/2018 | |
| WO | 2018140513 A1 | 8/2018 | |
| WO | 2018140514 A1 | 8/2018 | |

OTHER PUBLICATIONS

Cacchi et al. 2-(Aminomethyl)-3-arylindoles from 3-(o-Trifluoroacetamidoaryl)-1-propargylic Alcohols, Aryl Halides, and Amines: A Domino Palladium-Catalyzed Three-Component Approach. Synthesis, 49(18), 4163-4172. https://doi.org/10.1055/s-0036-1589016 (Year: 2017).*
El-Haj, B., Ahmed, S., Garawi, M., & Ali, H. Linking Aromatic Hydroxy Metabolic Functionalization of Drug Molecules to Structure and Pharmacologic Activity. Molecules, 23(9), 2119. https://doi.org/10.3390/molecules23092119 (Year: 2018).*
Moriyama, K., Hamada, T., Ishida, K., & Togo, H. 1,3-Iodo-amination of 2-methyl indoles via Csp2-Csp3 dual functionalization with iodine reagent. Chemical Communications, 54(34), 4258-4261. https://doi.org/10.1039/c8cc00352a (Year: 2018).*
Tang, H., Zhang, X., Song, A., & Zhang, Z.. TsOH•H2O-Catalyzed Friedel-Crafts of Indoles of 3-Hydroxyisobenzofuran-1(3H)-One with Indoles: Highly Synthesis of 3-Indolyl-Substituted Phthalides. Modern Research in Catalysis, 01(02), 11-14. https://doi.org/10.4236/mrc.2012.12002 (Year: 2012).*

(Continued)

*Primary Examiner* — Yih-Horng Shiao
*Assistant Examiner* — Hoi Yan Lee
(74) *Attorney, Agent, or Firm* — Philip I. Datlow

(57) ABSTRACT

The present invention relates to new isoindolinone or isobenzofuranone substituted indoles and derivatives of formula (I) wherein the groups $R^1$ to $R^7$, $R^{10}$ and n have the meanings given in the claims and specification, their use as inhibitors of RAS-family proteins and their use as medicaments, especially as agents for treatment and/or prevention of oncological diseases.

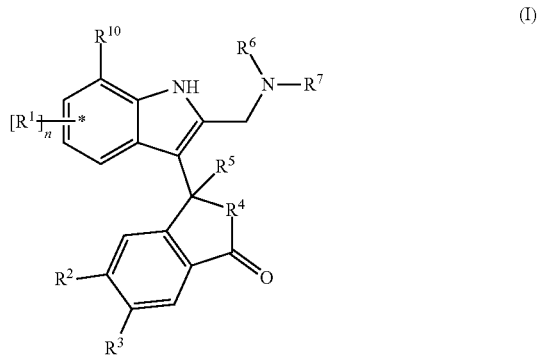

3 Claims, 2 Drawing Sheets

(56) References Cited

OTHER PUBLICATIONS

Shen, S.-C., Sun, X.-W., & Lin, G.-Q. An eco-benign and highly efficient access to 3-heterocyclic-substituted isoindolinones in ammonia water. Green Chemistry, 15(4), 896-896. https://doi.org/10.1039/c3gc40162f (Year: 2013).*
International Search Repot and Written Opinion for corresponding application, PCT/EP2020/054897, date of mailing Apr. 21, 2020.
Kessler et al., "Drugging an undruggable pocket on KRAS", Proc Natl Acad Sci USA, Aug. 6, 2019, 116(32), p. 15823-15829.
Liceras-Boillos et al., "Sos1 disruption mpairs cellular proliferation and viability through an increase in mitochondrial oxidative stress in primary MEFs", Oncogene, 2016, 35(50), pp. 6389-6402.
Maurer et al., "Small-molecule ligands bind to a distinct pocket in Ras and inhibit SOS-mediated nucleotide exchange activity", Proc. Natl. Acad. Sci. USA, 2012, 109(14), pp. 5299-5304.
McCormick et al., "K-Ras protein as a drug target", J. Mol. Med. (Berl)., 2016, 94(3), pp. 253-258.
Milburn et al., "Molecular switch for signal transduction: structural differences between active and inactive forms of protooncogenic ras proteins", Science 2004, 247(4945), pp. 939-945.
Ostrem et al., "Direct small-molecule inhibitors of KRAS: from structural insights to mechanism-based design", Nat. Rev. Drug. Discov., 2016, 15(11), pp. 771-785.
Prior et al., "A comprehensive survey of Ras mutations in cancer", Cancer Res., 2012, 72(10), pp. 2457-2467.
Rodriguez-Viciana et al., "RalGDS comes of age", Cancer Cell., 2005, 7(3), pp. A31205-6.
Sun et al., "Discovery of small molecules that bind to K-Ras and inhibit Sos-mediated activation", Angew. Chem. Int. Ed. Engl., 2012, 51(25), pp. 6140-6143.
Tran et al., "The small molecule BI-2852 induces a nonfunctional dimer of KRAS", Proc Natl Acad Sci USA, Feb. 18, 2020, 117(7), pp. 3363-3364.
Vetter et al., "The guanine nucleotide-binding switch in three dimensions", Science, 2001, 294(5545), pp. 1299-1304.
Young et al., "Ras signaling and therapies", Adv. Cancer Res., 2009, 102, pp. 1-17.

* cited by examiner

ISOINDOLINONE SUBSTITUTED INDOLES AND DERIVATIVES AS RAS INHIBITORS

FIELD OF THE INVENTION

The present invention relates to new isoindolinone or isobenzofuranone substituted indoles and derivatives of Formula (I)

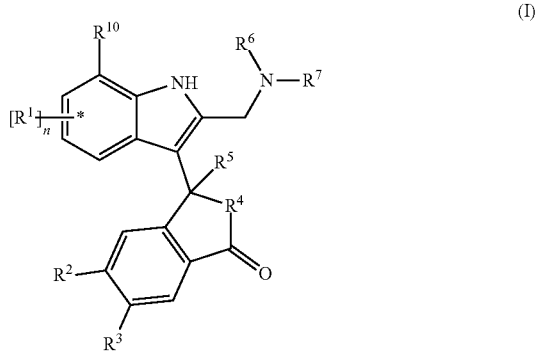

wherein the groups $R^1$ to $R^7$, $R^{10}$ and n have the meanings given in the claims and specification, their use as inhibitors of RAS-family proteins and their use as medicaments, especially as agents for treatment and/or prevention of oncological diseases.

BACKGROUND OF THE INVENTION

The three human RAS genes, KRAS, NRAS and HRAS encode four different RAS proteins (KRAS-4A, KRAS-4B, NRAS and HRAS) which belong to the protein family of small GTPases that function as binary molecular switches involved in cell signaling. Activating mutations in RAS like the glycine 12 mutations are among the most common oncogenic drivers in human cancers. KRAS is the most frequently mutated oncogene, with mutations rates of 86-96% in pancreatic cancers, 40-54% in colorectal cancers and 27-39% in lung adenocarcinomas. NRAS is predominantly mutated in melanoma and hematological malignancies, while HRAS mutations are found in salivary gland and urinary tract cancers.

The RAS family is known to cycle through two different conformational states that are defined by differential binding to nucleotides and corresponding changes in biological activity (FIG. 2). In the off state, RAS proteins are bound to the nucleotide guanosine diphosphate (GDP), while in the on state they are bound to the nucleotide guanosine triphosphate (GTP). The γ-phosphate of GTP holds two regions, switch I and switch II, (Milburn M, et al. Science 2004, 247(4945):939-945) in a compact configuration that allows interaction with downstream effectors, such as CRAF, PI3Kα and RALGDS, as well as with the allosteric site of SOS1 and SOS2. Hydrolysis of the γ-phosphate to produce GDP-RAS causes a conformational change in the switch regions, leading to the formation of an inactive state which is unable to bind effector molecules (Vetter I R & Wittinghofer A. Science, 2001, 294(5545):1299-1304; Ostrem J M & Shokat K M. Nat. Rev. Drug. Discov. 2016, 15(11):771-785). RAS itself has an intrinsic, but weak, GTPase activity that is enhanced by GTPase activating proteins (GAPs) catalyzing RAS inactivation. The exchange of the bound nucleotide GDP into GTP is facilitated by guanine nucleotide exchange factors (GEFs) which, in the case of KRAS, is performed by SOS1 and SOS2 (Liceras-Boillos P, et al. Oncogene, 2016, 35(50):6389-6402). GEFs catalyze the release of GDP from RAS in the cytoplasm and replace it with the more abundant intracellular GTP. Oncogenic mutations in RAS impair GTP hydrolysis, leading to the stabilization of the activated GTP-RAS form and enhanced RAS signaling. The most common mutations occur as single point mutations at codons 12, 13 and 61 (Prior I A et al. Cancer Res., 2012, 72(10):2457-2467).

When in the GTP-bound state, RAS-family proteins are active and engage effector proteins including CRAF and phosphoinositide 3-kinase (PI3K) to promote the RAF/mitogen or extracellular signal-regulated kinases (MEK/ERK) pathway, PI3K/AKT/mammalian target of rapamycin (mTOR) pathway and RalGDS (Ral guanine nucleotide dissociation stimulator) pathway (McCormick et al., J. Mol. Med. (Berl)., 2016, 94(3):253-8; Rodriguez-Viciana et al., Cancer Cell. 2005, 7(3):205-6). These pathways affect diverse cellular processes such as proliferation, survival, metabolism, motility, angiogenesis, immunity and growth (Young et al., Adv. Cancer Res., 2009, 102:1-17; Rodriguez-Viciana et al., Cancer Cell. 2005, 7(3):205-6).

Although KRAS could serve as an excellent drug target for many cancers, direct inhibition of oncogenic RAS has proven to be challenging. Despite decades of research, no therapeutic agent directly targeting RAS has been clinically approved. The main reason for this is the lack of druggable pockets on the surface of RAS. However, in recent years there has been a resurgence of research around RAS, driven by the growing belief that RAS might be able to be drugged with low molecular weight organic molecules. This belief was sparked by the discovery of two pockets on the surface of RAS that could potentially be amenable to small molecule drug discovery. Small molecules that bind to a shallow pocket between the switch I and II regions of KRAS (herein referred as the "Switch I/II pocket (SI/II-P)" have already been disclosed (Sun Q, et al. Angew. Chem. Int. Ed. Engl. 2012, 51(25):6140-6143; Maurer T, et al. Proc. Natl. Acad. Sci. U.S.A. 2012, 109(14):5299-5304).

In addition, covalently linked small molecules which bind to a second pocket on RAS positioned above the switch II loop in GDP-KRAS$^{G12C}$ (herein referred as "switch 11 pocket (SII-P)") have also been disclosed (Ostrem J M & Shokat K M Nat. Rev. Drug. Discov., 2016, 15(11):771-785).

Covalent KRAS$^{G12C}$ inhibitors have been disclosed in prior art documents WO 2014/152588, WO 2015/054572, WO 2016/049524, WO 2016/168540, WO 2017/15562, WO 2018/064510, WO 2018/068017, WO 2018/140513, WO 2018/140514, WO 2018/119183.

The aim of the present invention is to provide new compounds which can be used for the prevention and/or treatment of a disease and/or condition characterised by excessive or abnormal cell proliferation.

It has been found that the compounds of the present invention bind to all wild type RAS-family proteins, furthermore they bind to the active and inactive form (GTP- and GDP-bound forms) of mutant RAS protein, specifically to the Switch I/II pocket (SI/II-P) in particular GDP- and GTP-bound KRAS. Binding to KRAS and blocking the interaction towards its effector proteins, reduces downstream signalling (pERK and pAKT) and inhibits abnormal cell proliferation in KRAS mutant cells.

The compounds of the invention targeting the GTP bound form of KRAS have the following advantages over other compounds in the art that target only GDP-bound KRAS:

Firstly, GTP-KRAS is the major form present in cancer cells carrying KRAS mutations; secondly, it is responsible for activation of downstream effectors; and thirdly, it participates in a feed-forward loop enhancing the GEF activity of SOS1 and SOS2 by binding to an allosteric site.

By binding to both the active and inactive form (GTP- and GDP-bound forms) of mutant KRAS protein, compounds of the invention block the interaction between GDP-KRAS and the catalytic site of SOS1. In contrast to covalent KRAS$^{G12C}$ inhibitors in the art, the compounds of the invention inhibit the interactions between GTP-KRAS and the allosteric site of SOS1 and its downstream effectors (CRAF and PI3Kα).

SUMMARY OF THE INVENTION

The aim of the present invention is to provide new inhibitors of RAS-family proteins, which bind to all three wild type RAS-family proteins, in addition bind to the active and inactive form (GTP- and GDP-bound forms) of mutant KRAS protein. It has been found that compounds of Formula (I) as defined hereinafter act as inhibitors of mutant KRAS by binding to GDP- and GTP-bound KRAS, inhibiting key protein-protein interactions with effectors (eg. SOS1, CRAF and PI3K). Compounds of Formula (I) inhibit the cellular formation of GTP-KRAS and, in contrast to covalent KRAS$^{G12C}$ inhibitors, also inhibit the hydrolysis of GTP-KRAS to GDP-KRAS, effectively inhibiting RAS cycling. Compounds of Formula (I) show reduction of downstream signalling (eg. pERK) and inhibit proliferation in KRAS mutant cells and furthermore inhibit the interaction between GDP-KRAS and the catalytic site of SOS1 and inhibit the interactions between GTP-KRAS and its effectors (CRAF and PI3Kα) and the allosteric site of SOS1.

The compounds of the invention are useful for the prevention and/or treatment of a disease and/or condition characterised by excessive or abnormal cell proliferation, especially in the treatment and/or prevention of cancer.

Figure 1:
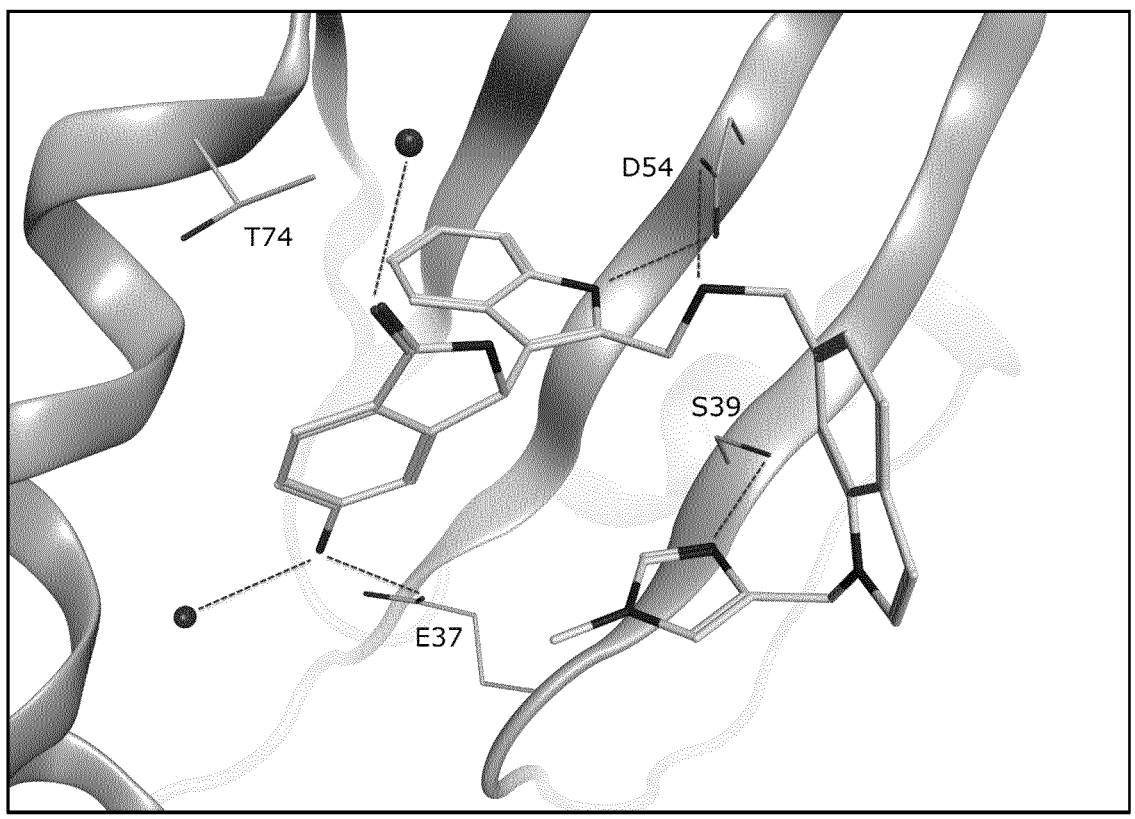
FIG. 1 X-ray structure of 1-093 in GCP-KRAS$^{G12D}$
Figure 2:
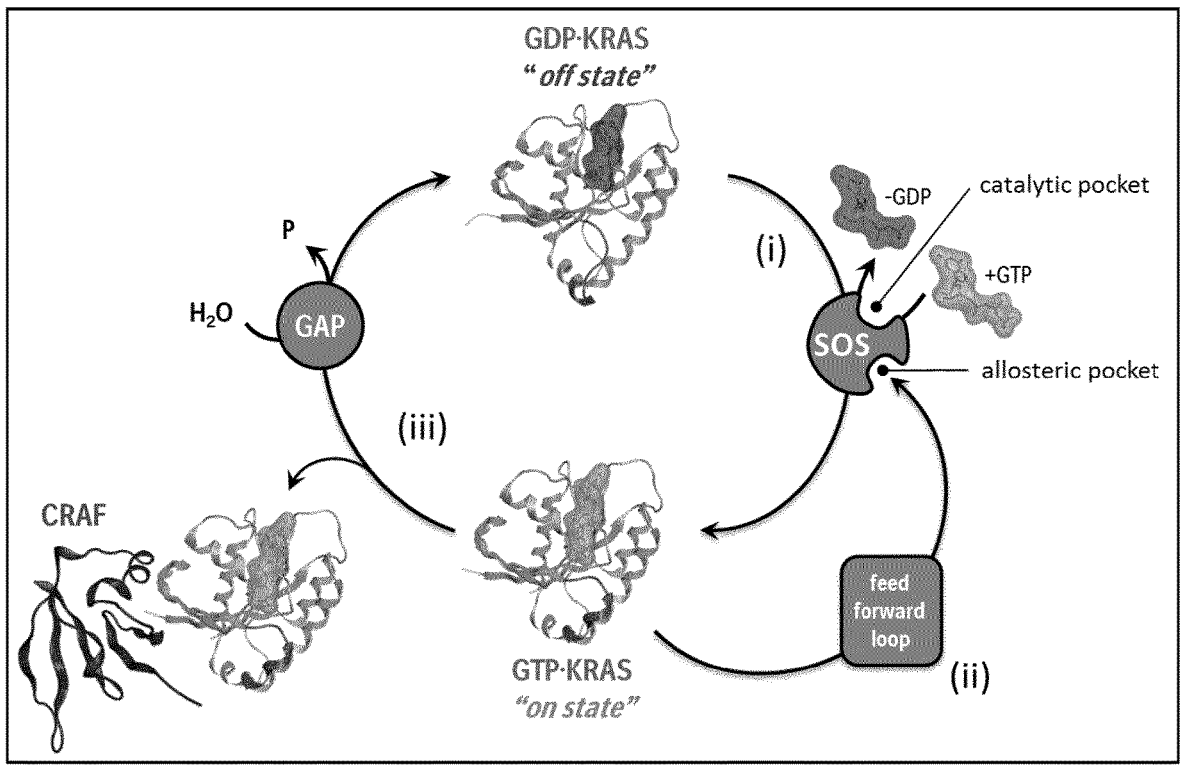
FIG. 2 KRAS Beating Heart Switching Mechanism

KRAS is depicted in Channing Der's "beating heart of cancer" orientation switching between its "off state" with the nucleotide GDP bound and its "on state" with GCP bound. The GDP to GTP exchange is facilitated by guanine nucleotide exchange factors (GEFs), in the case of KRAS this is performed primarily by SOS. The magnesium and γ-phosphate of GTP holds the two switch regions, switch I and switch II, in a compact configuration allowing interaction with downstream effectors, with CRAF shown here for illustration. The three protein-protein inhibition (PPI) intervention points in the KRAS cycle are also shown (i) GDP-KRAS binding to the catalytic site of SOS, (ii) GTP-KRAS binding to the allosteric site of SOS and (iii) GTP-KRAS binding to downstream effectors.

DETAILED DESCRIPTION OF THE INVENTION

The present invention relates to new isoindolinone or isobenzofuranone substituted indoles and derivatives of Formula (I), (I)

wherein
(A0)
each $R^1$ is independently selected from the group consisting of halogen, $C_{1-3}$alkyl and —NH$_2$
n is 0, 1, 2 or 3
(B0)
$R^{10}$ is selected from the group consisting of hydrogen, halogen, $C_{1-3}$alkyl and —NH$_2$
(C0)
$R^2$ and $R^3$ is independently selected from the group consisting of hydrogen, halogen, —OH, —C$_{1-4}$alkylene-R$^q$, —NR$^w$R$^q$, —NHC(O)NR$^w$R$^q$, —C(O)NR$^w$R$^q$, —C(O)OR$^q$, —S(O)$_2$NR$^w$R$^q$ and —NR$^w$S(O)$_2$R$^q$
or $R^2$ and $R^3$ together with the atoms they are attached to form a 5-6 membered heteroaryl optionally substituted by one or more same or different R$^t$
R$^w$ is selected from the group consisting of hydrogen, C$_{1-4}$alkyl, C$_{3-6}$cycloalkyl, —OH, —OC$_{1-4}$alkyl and —NH$_2$
R$^q$ is selected from the group consisting of hydrogen, C$_{1-4}$alkyl, C$_{3-6}$cycloalkyl, —OH, —OC$_{1-4}$alkyl and —NH$_2$
R$^t$ is selected from the group consisting of C$_{1-4}$alkyl, C$_{3-6}$cycloalkyl, —OH, —OC$_{1-4}$alkyl and —NH$_2$
(D0)
$R^4$ is —N(R$^x$)— or —O—
R$^x$ is selected from the group consisting of hydrogen, C$_{1-4}$alkyl, —OH, —OC$_{1-4}$alkyl and —C$_{1-5}$alkylene-O—R$^{y1}$
R$^{y1}$ is selected from the group consisting of hydrogen, C$_{1-4}$alkyl and —NH$_2$
(E0)
$R^5$ is selected from the group consisting of hydrogen, C$_{1-4}$alkyl, —OH, —OC$_{1-4}$alkyl and —C$_{1-5}$alkylene-O—R$^{y2}$
R$^{y2}$ is selected from the group consisting of hydrogen, C$_{1-4}$alkyl and —NH$_2$
(F0)
$R^6$ is hydrogen or C$_{1-3}$alkyl
$R^7$ is selected from the group consisting of —R$^a$—Cy and —R$^a$—R$^b$
or $R^6$ and $R^7$ together with the nitrogen that they are attached to form a 5-13 membered heterocyclyl or a 5-13 membered heteroaryl, wherein said heterocyclyl or heteroaryl is substituted by one or more same or different R$^b$
(G0)
R$^a$ is selected from the group consisting of a covalent bond, —C$_{1-5}$alkylene- and —C$_{1-3}$alkylene-R$^c$—C$_{1-3}$alkylene(NH)CH$_2$—

R$^c$ is selected from the group consisting of a covalent bond, arylene, C$_{5-14}$-carbocyclene, 5-13 membered heteroarylene and 5-13 membered heterocyclene (H0)

Cy is selected from the group consisting of aryl, C$_{5-14}$-carbocyclyl, 5-13 membered heteroaryl and 5-13 membered heterocyclyl; wherein Cy is substituted by —R$^{a1}$—R$^b$ or —R$^{a1}$—Cy' and Cy is optionally further substituted by one or more same or different R$^b$ Cy' is selected from the group consisting of aryl, 5-9 membered heteroaryl and 5-9 membered heterocyclyl; wherein Cy' is substituted by one or more same or different R$^b$ R$^{a1}$ is a covalent bond or —C$_{1-5}$alkylene- (I0)

R$^b$ is selected from the group consisting of hydrogen, C$_{2-3}$alkynyl, C$_{1-4}$alkyl, —OH, —OC$_{1-4}$alkyl, —NH$_2$, —C(O)NH$_2$ and —C$_{1-5}$alkylene-O—C$_{1-5}$alkyl or a salt thereof.

In another embodiment the invention relates to compounds of Formula (I') or a salt thereof

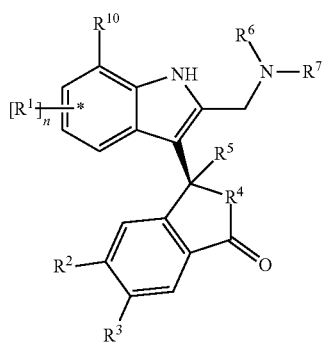

(I')

wherein R$_1$, R$_2$, R$_3$, R$_4$, R$_5$, R$_6$, R$_7$, R$_{10}$ and n are as defined as above.

In one embodiment the invention relates to compounds of Formula (I") or a salt thereof

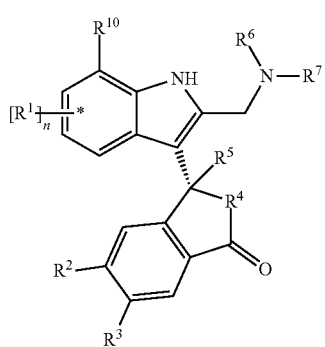

(I")

wherein R$_1$, R$_2$, R$_3$, R$_4$, R$_5$, R$_6$, R$_7$, R$_{10}$ and n are as defined as above.

It is to be understood that compounds of Formulae (I') and (I") each are a subset of compounds of Formula (I) and that whenever the term "compound(s) of Formula (I)" is used this also includes compound(s) of Formulae (I') and (I") unless stated otherwise.

In another embodiment (A1) the invention relates to compounds of Formula (I), wherein
each R$^1$ is independently selected from the group consisting of halogen and C$_{1-3}$alkyl
n is 0, 1, 2 or 3
or a salt thereof.

In another embodiment (A2) the invention relates to compounds of Formula (I), wherein
each R$^1$ is independently selected from the group consisting of —Cl, —F, —NH$_2$ and —CH$_3$
n is 0 or 2
or a salt thereof.

In another embodiment (A3) the invention relates to compounds of Formula (I), wherein
each R$^1$ is —Cl or —F
n is 0, 1 or 2
or a salt thereof.

In another embodiment (A4) the invention relates to compounds of Formula (I), wherein
n is 0
or a salt thereof.

In another embodiment (B1) the invention relates to compounds of Formula (I), wherein
R$^{10}$ is selected from the group consisting of hydrogen, —CH$_3$ and —NH$_2$
or a salt thereof.

In another embodiment (B2) the invention relates to compounds of Formula (I), wherein
R$^{10}$ is selected from the group consisting of hydrogen and —NH$_2$
or a salt thereof.

In another embodiment (B3) the invention relates to compounds of Formula (I), wherein
R$^{10}$ is hydrogen
or a salt thereof.

In another embodiment (C1) the invention relates to compounds of Formula (I), wherein
R$^2$ and R$^3$ is independently selected from the group consisting of halogen, —OH, —NR$^w$R$^q$, —NHC(O)NR$^w$R$^q$, —NR$^w$S(O)$_2$R$^q$
R$^w$ is selected from the group consisting of hydrogen, C$_{1-4}$alkyl, C$_{3-6}$cycloalkyl, —OH, —OC$_{1-4}$alkyl and —NH$_2$
R$^q$ is selected from the group consisting of hydrogen, C$_{1-4}$alkyl, C$_{3-6}$cycloalkyl, —OH, —OC$_{1-4}$alkyl and —NH$_2$
or a salt thereof.

In another embodiment (C2) the invention relates to compounds of Formula (I), wherein
R$^2$ and R$^3$ is independently selected from the group consisting of hydrogen, —OH, and —C$_{1-4}$alkyl
or
R$^2$ and R$^3$ together with the atoms they are attached to form a 5-6 membered heteroaryl with at least one nitrogen as heteroatom, optionally substituted by one or more same or different R$^t$
R$^t$ is selected from the group consisting of C$_{1-4}$alkyl and —OH
or a salt thereof.

In another embodiment (C3) the invention relates to compounds of Formula (I), wherein
R$^2$ and R$^3$ together with the atoms they are attached to form a 5-6 membered heteroaryl with at least one nitrogen as heteroatom, optionally substituted by one or more same or different R$^t$
R$^t$ is selected from the group consisting of C$_{1-4}$alkyl, C$_{3-6}$cycloalkyl, —OH, —OC$_{1-4}$alkyl and —NH$_2$
or a salt thereof.

In another embodiment (C4) the invention relates to compounds of Formula (I), wherein
$R^2$ is —OH
$R^3$ is hydrogen
or a salt thereof.

In another embodiment (D1) the invention relates to compounds of Formula (I), wherein
$R^4$ is —N($R^x$)— or —O—
$R^x$ is selected from the group consisting of hydrogen, —CH$_3$ and —OH, —OCH$_3$ and —C$_{1-3}$alkylene-O—$R^{y1}$
$R^{y1}$ is selected from the group consisting of hydrogen, —CH$_3$ and —NH$_2$
or a salt thereof.

In another embodiment (D2) the invention relates to compounds of Formula (I), wherein
$R^4$ is —N($R^x$)— or —O—
$R^x$ is hydrogen or C$_{1-4}$alkyl
or a salt thereof.

In another embodiment (D3) the invention relates to compounds of Formula (I), wherein
$R^4$ is —N($R^x$)— or —O—
$R^x$ is selected from the group consisting of hydrogen, C$_{1-2}$alkyl and —OCH$_3$
or a salt thereof.

In another embodiment (D4) the invention relates to compounds of Formula (I), wherein
$R^4$ is —N($R^x$)—
$R^x$ is —C$_{1-5}$alkylene-O—$R^{y1}$
$R^{y1}$ is selected from the group consisting of hydrogen, —CH$_3$ and —NH$_2$
or a salt thereof.

In another embodiment (E1) the invention relates to compounds of Formula (I), wherein
$R^5$ is selected from the group consisting of hydrogen, C$_{1-4}$alkyl, —OH and —OC$_{1-4}$alkyl
or a salt thereof.

In another embodiment (E2) the invention relates to compounds of Formula (I), wherein
$R^5$ is —C$_{1-5}$alkylene-O—$R^{y2}$
$R^{y2}$ is selected from the group consisting of hydrogen, C$_{1-4}$alkyl and —NH$_2$
or a salt thereof.

In another embodiment (E3) the invention relates to compounds of Formula (I), wherein
$R^5$ is hydrogen or —CH$_3$
or a salt thereof.

In another embodiment (E4) the invention relates to compounds of Formula (I), wherein
$R^5$ is hydrogen
or a salt thereof.

In another embodiment (F1) the invention relates to compounds of Formula (I), wherein
$R^6$ is hydrogen or —CH$_3$
$R^7$ is —$R^a$-Cy or —$R^a$—$R^b$
or a salt thereof.

In another embodiment (F2) the invention relates to compounds of Formula (I), wherein
$R^6$ is hydrogen or C$_{1-3}$alkyl
$R^7$ is —$R^a$-Cy
or a salt thereof.

In another embodiment (F3) the invention relates to compounds of Formula (I), wherein
$R^6$ and $R^7$ together with the nitrogen that they are attached to form a 5-13 membered heterocyclyl containing one or more additional nitrogen heteroatom(s) or a 5-13 membered heteroaryl containing one or more additional nitrogen heteroatom(s), wherein said heterocyclyl or heteroaryl is substituted by one or more same or different $R^b$
or a salt thereof.

In another embodiment (F4) the invention relates to compounds of Formula (I), wherein
$R^6$ and $R^7$ together with the nitrogen that they are attached to form 5-13 membered heterocyclyl containing one or more additional nitrogen heteroatom(s) substituted by one or more same or different $R^b$
or a salt thereof.

In another embodiment (G1) the invention relates to compounds of Formula (I), wherein
$R^a$ is a covalent bond or —C$_{1-4}$alkylene-
or a salt thereof.

In another embodiment (G2) the invention relates to compounds of Formula (I), wherein
$R^a$ is selected from the group consisting of —CH$_2$—, —CH$_2$—CH$_2$— and —CH(CH$_3$)—
or a salt thereof.

In another embodiment (G3) the invention relates to compounds of Formula (I), wherein
$R^a$ is a covalent bond
or a salt thereof.

In another embodiment (G4) the invention relates to compounds of Formula (I), wherein
$R^a$ is —C$_{1-3}$alkylene-$R^c$—C$_{1-3}$alkylene(NH)CH$_2$—
$R^c$ is selected from the group consisting of a covalent bond, arylene, C$_{5-14}$-carbocyclene, 5-13 membered heteroarylene and 5-13 membered heterocyclene
or a salt thereof.

In another embodiment (G5) the invention relates to compounds of Formula (I), wherein
$R^a$ is —C$_{1-3}$alkylene-$R^c$—C$_{1-3}$alkylene(NH)CH$_2$—
$R^c$ is selected from the group consisting of a covalent bond, arylene, monocyclic C$_{5-7}$-carbocyclene, monocyclic 5-7 membered heteroarylene and monocyclic 5-7 membered heterocyclene
or a salt thereof.

In another embodiment (G6) the invention relates to compounds of Formula (I), wherein
$R^a$ is —C$_{1-2}$alkylene-$R^c$—C$_{1-2}$alkylene(NH)CH$_2$—
$R^c$ is selected from the group consisting of a covalent bond, arylene, monocyclic C$_{5-7}$-carbocyclene, monocyclic 5-7 membered heteroarylene with at least one nitrogen as heteroatom and monocyclic 5-7 membered heterocyclene with at least one nitrogen as heteroatom
or a salt thereof.

In another embodiment (H1) the invention relates to compounds of Formula (I), wherein
Cy is selected from the group consisting of aryl and 5-13 membered heteroaryl wherein said aryl and heteroaryl is substituted by —$R^{a1}$—$R^b$ or —$R^{a1}$—Cy' and one or more same or different $R^b$
Cy' is selected from the group consisting of aryl, 5-9 membered heteroaryl and 5-9 membered heterocyclyl; wherein said aryl, heteroaryl and heterocyclyl is substituted by one or more same or different $R^b$
$R^{a1}$ is a covalent bond or —C$_{1-4}$alkylene-
or a salt thereof.

In another embodiment (H2) the invention relates to compounds of Formula (I), wherein
Cy is selected from the group consisting of aryl and 5-13 membered heteroaryl containing at least one nitrogen as heteroatom wherein said aryl, and heteroaryl is substituted by —R$^{a1}$—R$^b$, —R$^{a1}$-Cy' or one or more same or different R$^b$ Cy' is selected from the group consisting of aryl, 5-9 membered heteroaryl and 5-9 membered heterocyclyl; wherein said aryl, heteroaryl and heterocyclyl is substituted by one or more same or different R$^b$ R$^{a1}$ is a covalent bond or —C$_{1-4}$alkyleneor a salt thereof.

In another embodiment (H3) the invention relates to compounds of Formula (I), wherein Cy is 5-9 membered heteroaryl containing at least one nitrogen as heteroatom optionally substituted by one of —R$^{a1}$—R$^b$, —R$^{a1}$-Cy' or R$^b$ Cy' is selected from the group consisting of aryl and 5-9 membered heteroaryl containing at least one nitrogen as heteroatom; wherein said aryl and heteroaryl is optionally substituted by one or more same or different R$^b$ R$^{a1}$ is a covalent bond or —C$_{1-3}$alkyleneor a salt thereof.

In another embodiment (H4) the invention relates to compounds of Formula (I), wherein Cy is selected from the group consisting of indolyl, indazolyl, benzimidazolyl and benzotriazolyl; optionally substituted by one of —R$^{a1}$—R$^b$, —R$^{a1}$-Cy' or R$^b$ R$^{a1}$ is a covalent bond or —C$_{1-3}$alkyleneor a salt thereof.

In another embodiment (I1) the invention relates to compounds of Formula (I), wherein R$^b$ is selected from the group consisting of hydrogen, C$_{2-3}$alkynyl, C$_{1-4}$alkyl, —OH, —OC$_{1-4}$alkyl, —NH$_2$ and —C(O)NH$_2$ or a salt thereof.

In another embodiment (I2) the invention relates to compounds of Formula (I), wherein R$^b$ is selected from the group consisting of hydrogen, C$_{2-3}$alkynyl, C$_{1-4}$alkyl, —OH and —OC$_{1-4}$alkyl or a salt thereof.

In another embodiment (I3) the invention relates to compounds of Formula (I), wherein R$^b$ is selected from the group consisting of hydrogen, C$_{1-3}$alkyl, —OH and —OC$_{1-3}$alkyl or a salt thereof.

Above mentioned individual embodiments represent structural subgroups (A0) to (A4), (B0) to (B3), (C0) to (C4), (D0) to (D4), (E0) to (E4), (F0) to (F4), (G0) to (G6), (H0) to (H4), (I0) to (I3) of compounds of Formula (I). These structural subgroups may be combined with each other as (A)(B)(C)(D)(E)(F)(G)(H)(I) to specifically define further embodiments of the invention of compounds of Formula (I), (I') or (I"). Accordingly, further embodiments of the invention are herein defined as compounds of Formula (I), as a combination of specific structural subgroups (A)(B)(C)(D)(E)(F)(G)(H)(I) wherein (A) is selected from (A0) to (A4); (B) is selected from (B0) to (B3); (C) is selected from (C0) to (C4); (D) is selected from (D0) to (D4); (E) is selected from (E0) to (E4); (F) is selected from (F0) to (F4); (G) is selected from (G0) to (G6); (H) is selected from (H0) to (H4); (I) is selected from (I0) to (I3).

The present invention further relates to hydrates, solvates, polymorphs, metabolites, prodrugs of compounds of Formula (I), (I') or (I") thereof.

In another embodiment the invention relates to a pharmaceutically acceptable salt of a compound of Formula (I), (I') or (I").

In another aspect, the invention relates to a method of inhibiting RAS-family protein in a cell, comprising contacting the cell with a compound of Formula (I), (I') or (I").

In another aspect, the invention relates to a method of inhibiting GTP- and GDP-bound form of KRAS protein in a cell, comprising contacting the cell with a compound of Formula (I), (I') or (I").

In another aspect, the invention relates to a method of inhibiting KRAS::SOS1 interaction in a KRAS mutant cell, comprising contacting the cell with a compound of Formula (I), (I') or (I").

In another aspect, the invention relates to a method of inhibiting KRAS::CRAF interaction in a KRAS mutant cell, comprising contacting the cell with a compound of Formula (I), (I') or (I").

In another aspect, the invention relates to a method of inhibiting KRAS::PI3Kα interaction in a KRAS mutant cell, comprising contacting the cell with a compound of Formula (I), (I') or (I").

In another aspect, the invention relates to a method of inhibiting proliferation in KRAS mutant cells, comprising contacting the cell with a compound of Formula (I), (I') or (I").

In another aspect, the invention relates to the use of a compound of Formula (I), (I') or (I")—or a pharmaceutically acceptable salt thereof—for the treatment and/or prevention of a disease and/or condition wherein the inhibition of a RAS-family protein, i.e. KRAS, NRAS or HRAS protein, is of therapeutic benefit, including but not limited to inhibition of mutant KRAS protein.

In another aspect, the invention relates to the use of a compound of Formula (I), (I') or (I")—or a pharmaceutically acceptable salt thereof—for the treatment and/or prevention of a disease and/or condition wherein the inhibition of KRAS and SOS1 protein interaction is of therapeutic benefit.

In another aspect, the invention relates to the use of a compound of Formula (I), (I') or (I")—or a pharmaceutically acceptable salt thereof—for the treatment and/or prevention of a disease and/or condition wherein the inhibition of KRAS and CRAF protein interaction is of therapeutic benefit.

In another aspect, the invention relates to the use of a compound of Formula (I), (I') or (I")—or a pharmaceutically acceptable salt thereof—for the treatment and/or prevention of a disease and/or condition wherein the inhibition of KRAS and PI3Kα protein interaction is of therapeutic benefit.

In another aspect, the invention relates a compound of Formula (I), (I') or (I")—or a pharmaceutically acceptable salt thereof—for use as a medicament.

Furthermore, the invention relates to a compound of Formula (I), (I') or (I")—or a pharmaceutically acceptable salt thereof—for the treatment and/or prevention of cancer.

Furthermore, the invention relates to a method of treating and/or preventing cancer comprising administering a therapeutically effective amount of a compound of Formula (I), (I') or (I")—or a pharmaceutically acceptable salt thereof—to a human.

For example, the following cancers, tumors and other proliferative diseases may be treated with compounds of the invention, without being restricted thereto:

Cancers/tumors/carcinomas of the head and neck: e.g. tumors/carcinomas/cancers of the nasal cavity, paranasal sinuses, nasopharynx, oral cavity (including lip, gum, alveolar ridge, retromolar trigone, floor of mouth, tongue, hard palate, buccal mucosa), oropharynx (including base of tongue, tonsil, tonsillar pilar, soft palate, tonsillar fossa, pharyngeal wall), middle ear, larynx (including supraglottis, glottis, subglottis, vocal cords), hypopharynx, salivary glands (including minor salivary glands);

cancers/tumors/carcinomas of the lung: e.g. non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer);

neoplasms of the mediastinum: e.g. neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma);

cancers/tumors/carcinomas of the gastrointestinal (GI) tract: e.g. tumors/carcinomas/cancers of the esophagus, stomach (gastric cancer), pancreas, liver and biliary tree (including hepatocellular carcinoma (HCC), e.g. childhood HCC, fibrolamellar HCC, combined HCC, spindle cell HCC, clear cell HCC, giant cell HCC, carcinosarcoma HCC, sclerosing HCC; hepatoblastoma; cholangiocarcinoma; cholangiocellular carcinoma; hepatic cystadenocarcinoma; angiosarcoma, hemangioendothelioma, leiomyosarcoma, malignant schwannoma, fibrosarcoma, Klatskin tumor), gall bladder, extrahepatic bile ducts, small intestine (including duodenum, jejunum, ileum), large intestine (including cecum, colon, rectum, anus; colorectal cancer, gastrointestinal stroma tumor (GIST)), genitourinary system (including kidney, e.g. renal pelvis, renal cell carcinoma (RCC), nephroblastoma (Wilms' tumor), hypernephroma, Grawitz tumor; ureter; urinary bladder, e.g. urachal cancer, urothelial cancer; urethra, e.g. distal, bulbomembranous, prostatic; prostate (androgen dependent, androgen independent, castration resistant, hormone independent, hormone refractory), penis);

cancers/tumors/carcinomas of the testis: e.g. seminomas, non-seminomas, Gynecologic cancers/tumors/carcinomas: e.g. tumors/carcinomas/cancers of the ovary, fallopian tube, peritoneum, cervix, vulva, vagina, uterine body (including endometrium, fundus);

cancers/tumors/carcinomas of the breast: e.g. mammary carcinoma (infiltrating ductal, colloid, lobular invasive, tubular, adenocystic, papillary, medullary, mucinous), hormone receptor positive breast cancer (estrogen receptor positive breast cancer, progesterone receptor positive breast cancer), Her2 positive breast cancer, triple negative breast cancer, Paget's disease of the breast;

cancers/tumors/carcinomas of the endocrine system: e.g. tumors/carcinomas/cancers of the endocrine glands, thyroid gland (thyroid carcinomas/tumors; papillary, follicular, anaplastic, medullary), parathyroid gland (parathyroid carcinoma/tumor), adrenal cortex (adrenal cortical carcinoma/tumors), pituitary gland (including prolactinoma, craniopharyngioma), thymus, adrenal glands, pineal gland, carotid body, islet cell tumors, paraganglion, pancreatic endocrine tumors (PET; non-functional PET, PPoma, gastrinoma, insulinoma, VIPoma, glucagonoma, somatostatinoma, GRFoma, ACTHoma), carcinoid tumors;

sarcomas of the soft tissues: e.g. fibrosarcoma, fibrous histiocytoma, liposarcoma, leiomyosarcoma, rhabdomyosarcoma, angiosarcoma, lymphangiosarcoma, Kaposi's sarcoma, glomus tumor, hemangiopericytoma, synovial sarcoma, giant cell tumor of tendon sheath, solitary fibrous tumor of pleura and peritoneum, diffuse mesothelioma, malignant peripheral nerve sheath tumor (MPNST), granular cell tumor, clear cell sarcoma, melanocytic schwannoma, plexosarcoma, neuroblastoma, ganglioneuroblastoma, neuroepithelioma, extraskeletal Ewing's sarcoma, paraganglioma, extraskeletal chondrosarcoma, extraskeletal osteosarcoma, mesenchymoma, alveolar soft part sarcoma, epithelioid sarcoma, extrarenal rhabdoid tumor, desmoplastic small cell tumor; sarcomas of the bone: e.g. myeloma, reticulum cell sarcoma, chondrosarcoma (including central, peripheral, clear cell, mesenchymal chondrosarcoma), osteosarcoma (including parosteal, periosteal, high-grade surface, small cell, radiation-induced osteosarcoma, Paget's sarcoma), Ewing's tumor, malignant giant cell tumor, adamantinoma, (fibrous) histiocytoma, fibrosarcoma, chordoma, small round cell sarcoma, hemangioendothelioma, hemangiopericytoma, osteochondroma, osteoid osteoma, osteoblastoma, eosinophilic granuloma, chondroblastoma;

mesothelioma: e.g. pleural mesothelioma, peritoneal mesothelioma;

cancers of the skin: e.g. basal cell carcinoma, squamous cell carcinoma, Merkel's cell carcinoma, melanoma (including cutaneous, superficial spreading, lentigo maligna, acral lentiginous, nodular, intraocular melanoma), actinic keratosis, eyelid cancer;

neoplasms of the central nervous system and brain: e.g. astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g. acoustic), spinal axis tumors;

lymphomas and leukemias: e.g. B-cell non-Hodgkin lymphomas (NHL) (including small lymphocytic lymphoma (SLL), lymphoplasmacytoid lymphoma (LPL), mantle cell lymphoma (MCL), follicular lymphoma (FL), diffuse large cell lymphoma (DLCL), Burkitt's lymphoma (BL)), T-cell non-Hodgkin lymphomas (including anaplastic large cell lymphoma (ALCL), adult T-cell leukemia/lymphoma (ATLL), cutaneous T-cell lymphoma (CTCL), peripheral T-cell lymphoma (PTCL)), lymphoblastic T-cell lymphoma (T-LBL), adult T-cell lymphoma, lymphoblastic B-cell lymphoma (B-LBL), immunocytoma, chronic B-cell lymphocytic leukemia (B-CLL), chronic T-cell lymphocytic leukemia (T-CLL) B-cell small lymphocytic lymphoma (B-SLL), cutaneous T-cell lymphoma (CTLC), primary central nervous system lymphoma (PCNSL), immunoblastoma, Hodgkin's disease (HD) (including nodular lymphocyte predominance HD (NL-PHD), nodular sclerosis HD (NSHD), mixed-cellularity HD (MCHD), lymphocyte-rich classic HD, lymphocyte-depleted HD (LDHD)), large granular lymphocyte leukemia (LGL), chronic myelogenous leukemia (CML), acute myelogenous/myeloid leukemia (AML), acute lymphatic/lymphoblastic leukemia (ALL), acute promyelocytic leukemia (APL), chronic lymphocytic/lymphatic leukemia (CLL), prolymphocytic leukemia (PLL), hairy cell leukemia, chronic myelogenous/myeloid leukemia (CML), myeloma, plasmacytoma, multiple myeloma (MM), plasmacytoma, myelodysplastic syndromes (MDS), chronic myelomonocytic leukemia (CMML);

cancers of unknown primary site (CUP);

All cancers/tumors/carcinomas mentioned above which are characterized by their specific location/origin in the body are meant to include both the primary tumors and the metastatic tumors derived therefrom.

All cancers/tumors/carcinomas mentioned above may be further differentiated by their histopathological classification:

Epithelial cancers, e.g. squamous cell carcinoma (SCC) (carcinoma in situ, superficially invasive, verrucous carcinoma, pseudosarcoma, anaplastic, transitional cell, lymphoepithelial), adenocarcinoma (AC) (well-differentiated, mucinous, papillary, pleomorphic giant cell, ductal, small cell, signet-ring cell, spindle cell, clear cell, oat cell, colloid, adenosquamous, mucoepidermoid, adenoid cystic), mucinous cystadenocarcinoma, acinar cell carcinoma, large cell carcinoma, small cell carcinoma, neuroendocrine tumors (small cell carcinoma, paraganglioma, carcinoid); oncocytic carcinoma;

Nonepithilial cancers, e.g. sarcomas (fibrosarcoma, chondrosarcoma, rhabdomyosarcoma, leiomyosarcoma, hemangiosarcoma, giant cell sarcoma, lymphosarcoma, fibrous histiocytoma, liposarcoma, angiosarcoma, lymphangiosarcoma, neurofibrosarcoma), lymphoma, melanoma, germ cell tumors, hematological neoplasms, mixed and undifferentiated carcinomas;

In another aspect the disease/condition/cancer to be treated/prevented as herein (above and below) defined is selected from the group consisting of pancreatic cancer, colorectal cancer, lung cancer, multiple myeloma, melanoma, uterine cancer, endometrial cancer, thyroid cancer, acute myeloid leukaemia, bladder cancer, urothelial cancer, gastric cancer, cervical cancer, head and neck squamous cell carcinoma, diffuse large B cell lymphoma, oesophageal cancer, chronic lymphocytic leukaemia, hepatocellular cancer, breast cancer, ovarian cancer, prostate cancer, glioblastoma, renal cancer and sarcomas, salivary gland cancers and urinary tract cancers.

The compounds of the invention may be used on their own or in combination with one or several other pharmacologically active substances such as state-of-the-art or standard-of-care compounds, such as e.g. cell proliferation inhibitors, anti-angiogenic substances, steroids or immune modulators/checkpoint inhibitors, and the like.

Pharmacologically active substances which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF) and/or their corresponding receptors), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab and trastuzumab); antimetabolites (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); antitumour antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP activator, Mcl-1, MDM2/MDMX), MEK inhibitors, ERK inhibitors, FLT3 inhibitors, BRD4 inhibitors, IGF-1R inhibitors, TRAILR2 agonists, Bcl-xL inhibitors, Bcl-2 inhibitors, Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, proteasome inhibitors, immunotherapeutic agents such as immune checkpoint inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3×BCMA, CD3×CD33, CD3×CD19), PSMA×CD3), tumor vaccines and various chemotherapeutic agents such as amifostin, anagrelid, clodronat, filgrastin, interferon, interferon alpha, leucovorin, procarbazine, levamisole, mesna, mitotane, pamidronate and porfimer.

In a further aspect, the present invention relates to a compound of Formula (I), (I') or (I")—or a pharmaceutically acceptable salt thereof—for use in the treatment and/or prevention of above mentioned diseases and conditions.

In a further aspect the present invention relates to the use of a compound of Formula (I), (I') or (I")—or a pharmaceutically acceptable salt thereof—for the preparation of a medicament for the treatment and/or prevention of above mentioned diseases and conditions.

In a further aspect of the present invention the present invention relates to methods for the treatment or prevention of above mentioned diseases and conditions, which method comprises the administration of a therapeutically effective amount of a compound of Formula (I), (I') or (I")—or a pharmaceutically acceptable salt thereof—to a human being.

In another aspect the invention relates to a pharmaceutical preparation comprising a compound of Formula (I), (I') or (I")—or a pharmaceutically acceptable salt thereof—and at least one other cytostatic and/or cytotoxic active substance.

In another aspect the invention relates to a pharmaceutical composition comprising at least one compound of Formula (I), (I') or (I")—or a pharmaceutically acceptable salt thereof—and optionally at least one pharmaceutically acceptable carrier.

Suitable preparations for administering the compounds of the invention will be apparent to those with ordinary skill in the art and include for example tablets, pills, capsules, suppositories, lozenges, troches, solutions—particularly solutions for injection (s.c., i.v., i.m.) and infusion (injectables)—elixirs, syrups, sachets, emulsions, inhalatives or dispersible powders.

The dosage range of the compounds of Formula (I) applicable per day is usually from 1 mg to 2000 mg, preferably from 150 to 1000 mg.

The dosage for intravenous use is from 1 mg to 1000 mg with different infusion rates, preferably between 5 mg and 500 mg with different infusion rates.

However, it may sometimes be necessary to depart from the amounts specified, depending on the body weight, age, the route of administration, severity of the disease, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts it may be advisable to divide them up into a number of smaller doses spread over the day.

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$alkyl means an alkyl group or radical having 1 to 6 carbon atoms.

In groups like OH, $NH_2$, S(O), $S(O)_2$, CN (cyano), COOH, $CF_3$ or the like, the skilled artisan can see the radical attachment point(s) to the molecule from the free valences of the group itself.

For combined groups comprising two or more subgroups, the first named subgroup is the radical attachment point, for example, the substituent "—$C_{1-3}$-alkyl-aryl" means an aryl group which is bound to a $C_{1-3}$-alkyl group, the former of which is bound to the core or to the group to which the substituent is attached.

In case a compound of the present invention is depicted in form of a chemical name and as a formula in case of any discrepancy the formula shall prevail. An asterisk is may be used in sub-formulas to indicate the bond which is connected to the core molecule as defined.

The term "$C_{1-n}$alkyl", wherein n is an integer selected from 2, 3, 4, 5 or 6, either alone or in combination with another radical denotes an acyclic, saturated, branched or linear, monovalent hydrocarbon radical with 1 to n C atoms. For example, the term "$C_{1-5}$alkyl" embraces the radicals —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$C(CH_3)_2CH_2CH_3$, —$CH_2C(CH_3)_3$, —$CH(CH_3)CH(CH_3)_2$ and —$CH(CH_2CH_3)_2$.

Further examples of $C_{1-6}$alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl (neo-pentyl; —$CH_2C(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The term "$C_{1-n}$alkylene" wherein n is an integer selected from 2, 3, 4, 5 or 6, preferably 3 or 5, either alone or in combination with another radical, denotes an acyclic, straight or branched chain divalent alkyl radical containing from 1 to n carbon atoms. For example the term $C_{1-4}$-alkylene includes —$CH_2$—, —$CHCH_2$—, —$CH(CH_3)$—, —$CH_2CH_2CH_2$—, —$C(CH_3)_2$—, —$CH(CH_2CH_3)$—, —$CH(CH_3)CH_2$, —$CH_2CH(CH_3)$—, —$CH_2CH_2CH_2CH_2$—, —$CH_2CH_2CH(CH_3)$—, —$CH(CH_3)CH_2CH_2$—, —$CH_2CH(CH_3)CH_2$—, —$CH_2C(CH_3)_2$—, —$C(CH_3)_2CH_2$—, —$CH(CH_3)CH(CH_3)$—, —$CH_2CH$ (CH₂CH₃)—, —CH(CH₂CH₃)CH₂—, —CH(CH₂CH₂CH₃)—, —CH(CH(CH₃))₂— and —C(CH₃)(CH₂CH₃)—.

Other examples of C₁₋₆alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The term "$C_{2-n}$alkenyl", is used for a group as defined in the definition for "$C_{1-n}$alkyl" with at least two carbon atoms, if at least two of those carbon atoms of said group are bonded to each other by a double bond.

The term "$C_{2-n}$alkenylene" is used for a group as defined in the definition for "$C_{1-n}$alkylene" with at least two carbon atoms, if at least two of those carbon atoms of said group are bonded to each other by a double bond.

The term "$C_{2-n}$alkynyl", is used for a group as defined in the definition for "$C_{1-n}$alkyl" with at least two carbon atoms, if at least two of those carbon atoms of said group are bonded to each other by a triple bond.

The term "$C_{2-n}$alkynylene" is used for a group as defined in the definition for "$C_{1-n}$alkylene" with at least two carbon atoms, if at least two of those carbon atoms of said group are bonded to each other by a triple bond.

The term "$C_{3-n}$cycloalkyl", wherein n is an integer from 3 to n, either alone or in combination with another radical denotes a cyclic, saturated, unbranched hydrocarbon radical with 3 to n C atoms. For example, the term $C_{3-7}$cycloalkyl includes cyclopropyl, cyclobutyl, cyclopentyl, cyclohexyl and cycloheptyl.

The term "$C_{3-n}$cycloalkenyl", wherein n is an integer 3 to n, either alone or in combination with another radical, denotes a cyclic, unsaturated, but non-aromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl cycloheptadienyl and cycloheptatrienyl.

The term "halogen" denotes fluorine, chlorine, bromine and/or iodine atoms.

By the term "halo" added to an "alkyl", "alkylene" or "cycloalkyl" group (saturated or unsaturated) is such an alkyl or a cycloalkyl group wherein one or more hydrogen atoms are replaced by a halogen atom selected from among fluorine, chlorine or bromine, preferably fluorine and chlorine, particularly preferred is fluorine. Examples of haloalkyl (haloalkenyl, haloalkynyl) are —CF₃, —CHF₂, —CH₂F, —CF₂CF₃, —CHFCF₃, —CH₂CF₃, —CF₂CH₃, —CHFCH₃, —CF₂CF₂CF₃, —CF₂CH₂CH₃, —CF═CF₂, —CCl═CH₂, —CBr═CH₂, —C≡C—CF₃, —CHFCH₂CH₃, —CHFCH₂CF₃ etc.

If a haloalkyl (haloalkenyl, haloalkynyl) is to be further substituted, the substitutions may take place independently of one another, in the form of mono- or polysubstitutions in each case, on all the hydrogen-carrying carbon atoms.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl). Corresponding groups are for example —CH₂F and —CHF—, —CHFCH₂F and —CHFCHF— or —CFCH₂F etc.

The above definitions also apply if the corresponding halogen-containing groups are part of another (combined) group.

The term "carbocyclyl" as used either alone or in combination with another radical, means a mono- bi- or tricyclic ring structure consisting of 3 to 14 carbon atoms. The term "carbocyclyl" refers to fully saturated and aromatic ring systems and partially saturated ring systems. The term "carbocyclyl" encompasses fused, bridged and spirocyclic systems.

The term "aryl" as used herein, either alone or in combination with another radical, denotes a carbocyclic aromatic monocyclic group containing 6 carbon atoms which is optionally further fused to a second five- or six-membered, carbocyclic group which is optionally aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocyclyl" is intended to include all the possible isomeric forms.

Thus, the term "heterocyclyl" includes the following exemplary structures which are not depicted as radicals as each form are optionally attached through a covalent bond to any atom so long as appropriate valences are maintained:

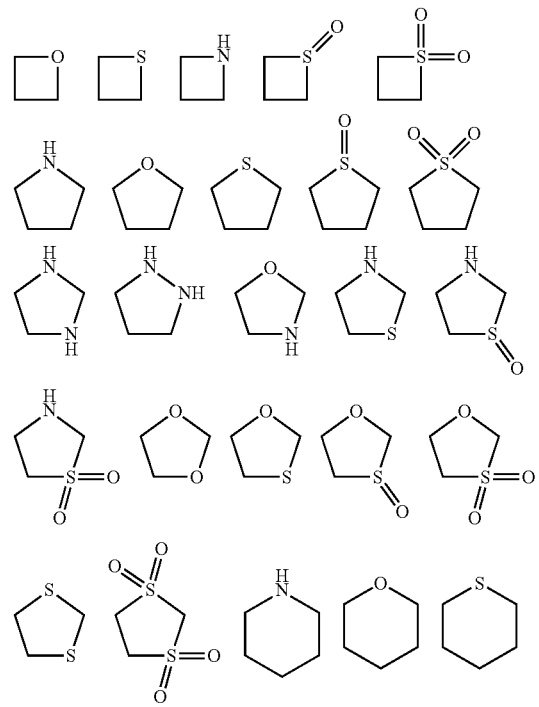

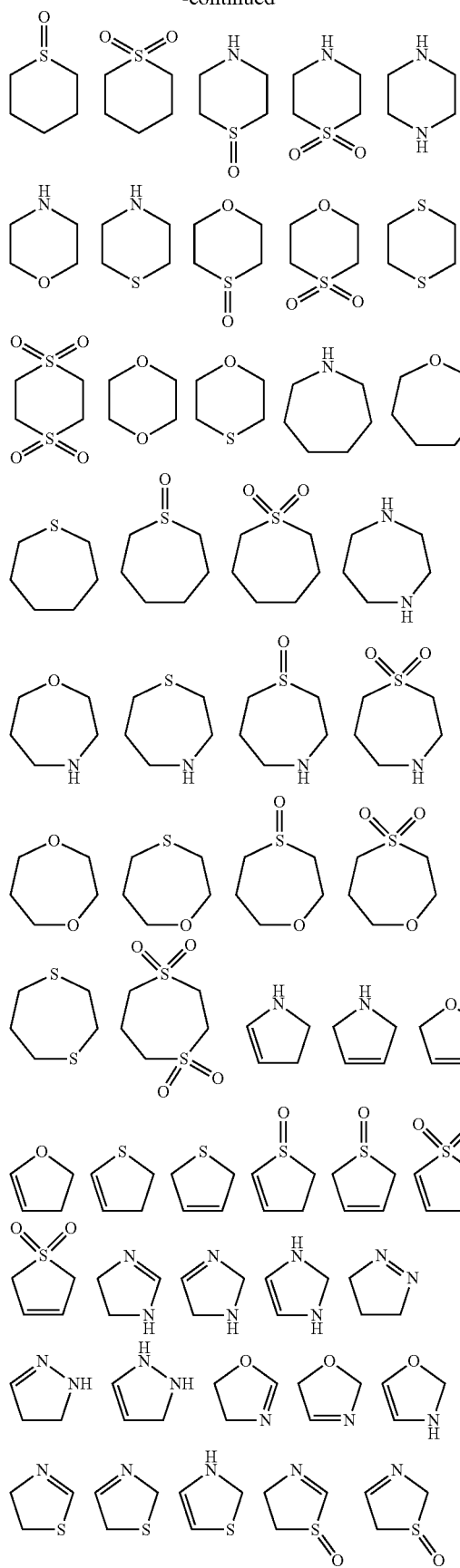
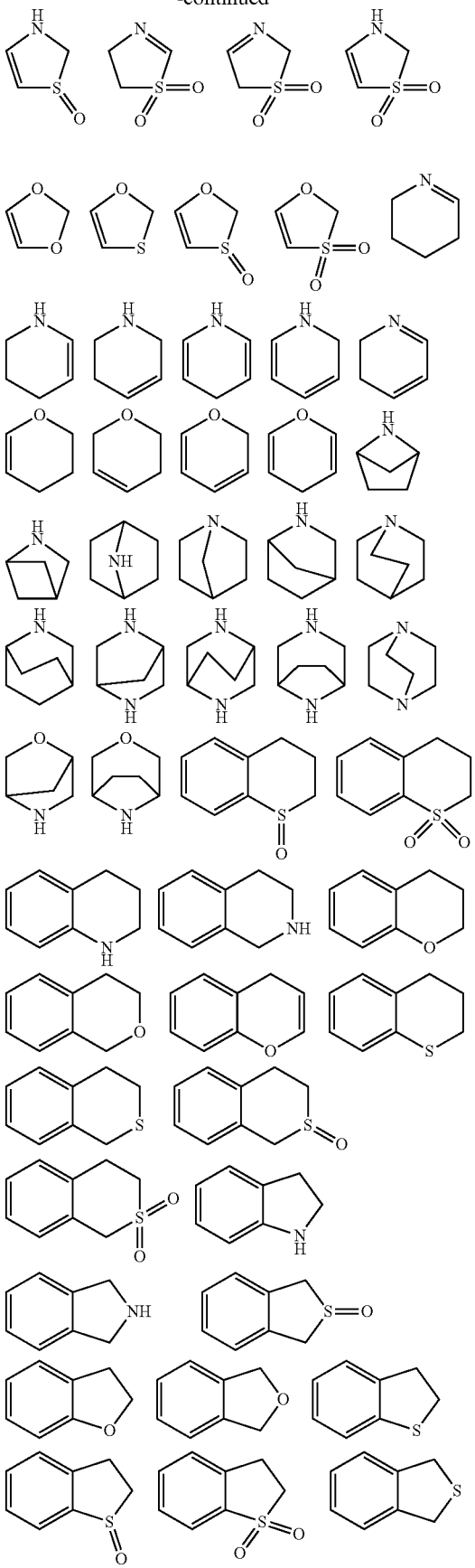

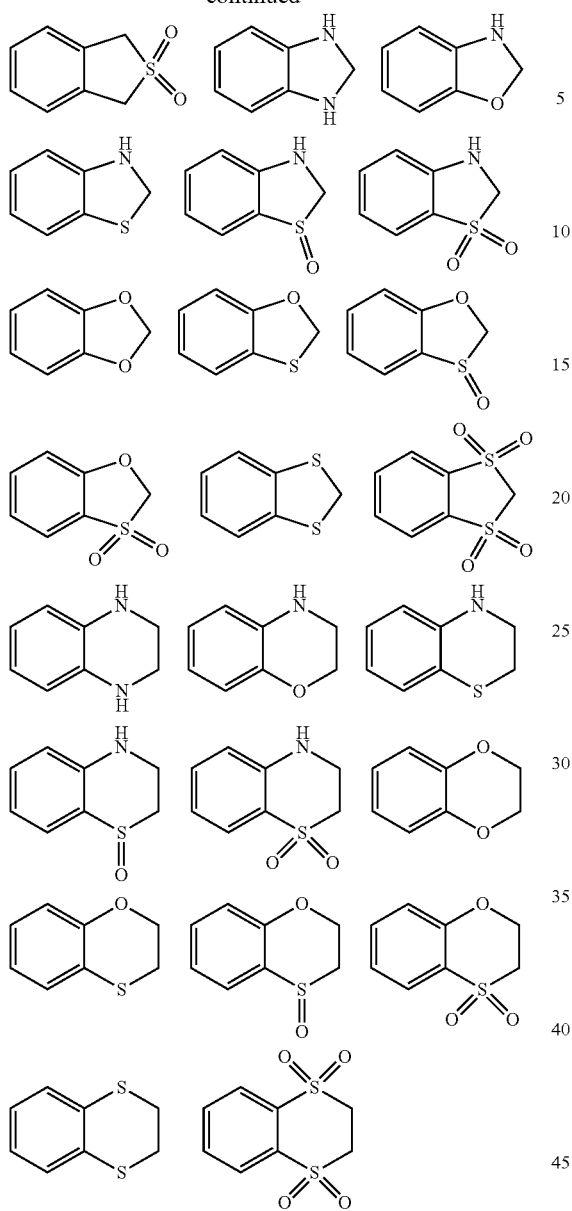

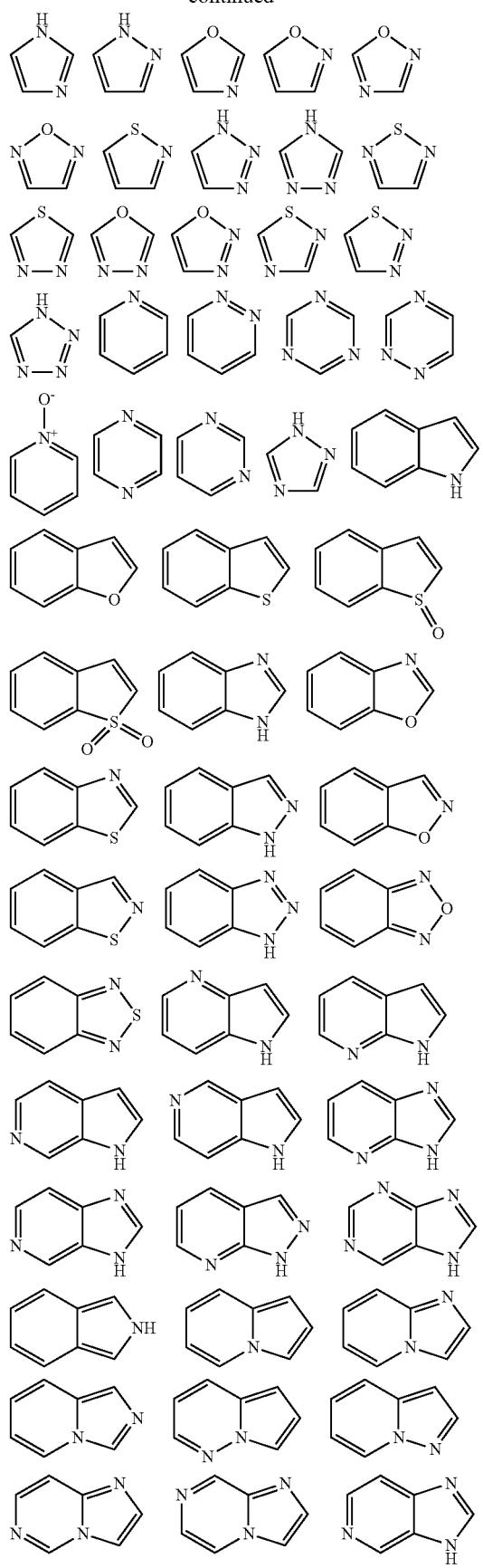

The term "heteroaryl" means a mono- or polycyclic-ring systems containing one or more heteroatoms selected from N, O or S(O)$_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form are optionally attached through a covalent bond to any atom so long as appropriate valences are maintained:

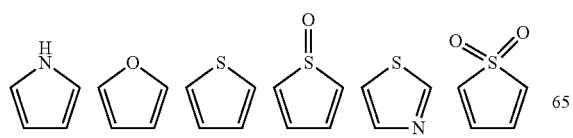

-continued

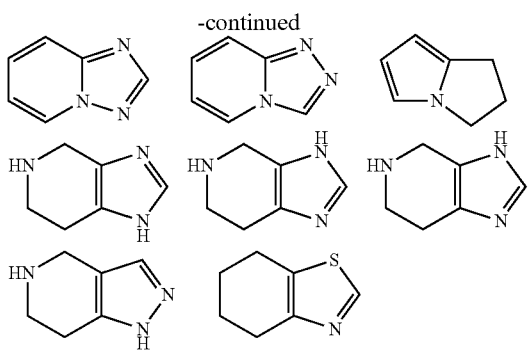

Preferably, heteroaryls are 5-6 membered monocyclic or 9-10 membered bicyclic, each with 1 to 4 heteroatoms independently selected from oxygen, nitrogen and sulfur.

The term "substituted" as used herein, means that any one or more hydrogens on the designated atom is replaced with a selection from the indicated group, provided that the designated atom's normal valence is not exceeded, and that the substitution results in a stable compound.

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates and hydrates of the free compound or solvates and hydrates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases, or by resolution of a racemic mixture using an appropriate resolving agent, e.g. by means of diastereomeric salt formation of the racemic compound with optically active acids or bases, subsequent resolution of the salts and release of the desired compound from the salt, or by derivatization of the corresponding racemic compounds with optically active chiral auxiliary reagents, subsequent diastereomer separation and removal of the chiral auxiliary group, or by kinetic resolution of a racemate (e.g. by enzymatic resolution); by enantioselective crystallization from a conglomerate of enantiomorphous crystals under suitable conditions, or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound, which contains a basic or acidic moiety, by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

In a representation such as for example

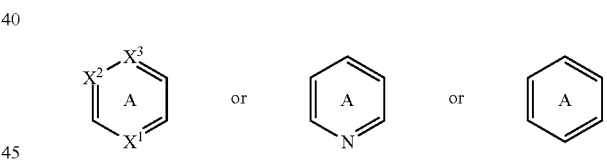

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

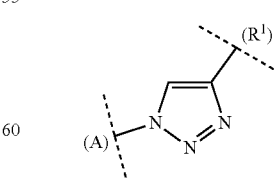

or (R²)—C(O)NH— or (R²)—NHC(O)—;

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

As used herein the term "prodrug" refers to (i) an inactive form of a drug that exerts its effects after metabolic processes within the body converting it to a usable or active form, or (ii) a substance that gives rise to a pharmacologically active metabolite, although not itself active (i.e. an inactive precursor).

The terms "prodrug" or "prodrug derivative" mean a covalently-bonded derivative, carrier or precursor of the parent compound or active drug substance which undergoes at least some biotransformation prior to exhibiting its pharmacological effect(s). Such prodrugs either have metabolically cleavable or otherwise convertible groups and are rapidly transformed in vivo to yield the parent compound, for example, by hydrolysis in blood or by activation via oxidation as in case of thioether groups. Most common prodrugs include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; Bioreversible Carriers in Drug Design, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

Examples

Abbreviations

| | |
|---|---|
| Ac | acetyl |
| ACN | acetonitrile |
| AIBN | azobisisobutyronitrile |
| aq. | aquatic, aqueous |
| BN | benzyl |
| Boc | tert-butyloxycarbonyl |
| Bu | butyl |
| c | concentration |
| CAN | ceric ammonium nitrate |
| CAS | Chemical abstracts service |
| CDI | 1,1'-carbonyldiimidazole |
| d | day(s) |
| DCM | dichloro methane |
| DIPEA | N-ethyl-N,N-diisopropylamine (Hunig's base) |
| DMF | N,N-dimethylformamide |
| DMPU | 1,3-Dimethyl-3,4,5,6-tetrahydro-2(1H)-pyrimidinone |
| DMSO | dimethylsulphoxide |
| EDTA | ethylenediaminetetraacetic acid |
| ESI | electron spray ionization |
| Et | ethyl |
| EtOAc | ethyl acetate |
| EtOH | ethanol |
| h | hour |
| HPLC | high performance liquid chromatography |
| i | iso |
| conc. | concentrated |
| LC | liquid chromatography |
| Me | methyl |
| MeOH | methanol |
| min | minutes |
| MS | mass spectrometry |
| NBS | N-bromo-succinimide |
| NP | normal phase |
| PBS | phosphate-buffered saline |
| rac | racemic |
| Rf ($R_f$) | retention factor |
| RP | reversed phase |
| rt | ambient temperature |
| SFC | supercritical fluid chromatography |
| TBAI | tetrabutylammonium iodide |
| TBS | tert.-butyldimethylsilyl |
| TBSCI | tert.-butyldimethylsilyl chloride |
| TEA | triethyl amine |
| tert | tertiary |
| TFA | trifluoroacetic acid |
| THF | tetrahydrofuran |
| TLC | thin layer chromatography |
| $t_{ret}$ | retention time (HPLC) |
| TRIS | tris(hydroxymethyl)-aminomethane |
| UV | ultraviolet |

Features and advantages of the present invention will become apparent from the following detailed examples, which illustrate the principles of the invention by way of example without restricting its scope:

Preparation of the Compounds According to the Invention

General

The compounds according to the present invention and their intermediates may be obtained using methods of synthesis which are known to the one skilled in the art and described in the literature of organic synthesis.

Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Starting materials may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software AutoNom (Beilstein) or MarvinSketch (ChemAxon, product version 17.24.3). If a compound is to be represented both by a structural formula and by its nomenclature, in the event of a conflict the structural formula is decisive.

The compounds according to the invention are prepared by the methods of synthesis described hereinafter in which the substituents of the general formula have the meanings given herein before. These methods are intended as an illustration of the invention without restricting its subject matter and the scope of the compounds claimed to these examples.

Where the preparation of starting compounds is not described, they are commercially obtainable or their synthesis is described in the prior art or they may be prepared analogously to known prior art compounds or methods described herein. Substances described in the literature can be prepared according to the published methods of synthesis.

Microwave reactions are carried out in an microwave reactor made by Biotage or in an Explorer made by CEM or in Synthos 3000 or Monowave 3000 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out on Agilent or Gilson systems with columns made by Waters (names: SunFire™ Prep C18, OBD™ 10 µm, 50×150 mm or SunFire™ Prep C18 OBD™ 5 µm, 30×50 mm or XBridge™ Prep C18, OBD™ 10 µm, 50×150 mm or XBridge™ Prep C18, OBD™ 5 µm, 30×150 mm or XBridge™ Prep C18, OBD™ 5 µm, 30×50 mm) and YMC (names: Actus-Triart Prep C18, 5 µm, 30×50 mm).

Different gradients of $H_2O$/acetonitrile are used to elute the compounds, while for Agilent systems 5% acidic modifier (20 mL HCOOH to 1 L $H_2O$/acetonitrile (1/1)) is added to the water (acidic conditions). For Gilson systems the water is added 0.1% HCOOH.

For the chromatography under basic conditions for Agilent systems $H_2O$/acetonitrile gradients are used as well, while the water is made alkaline by addition of 5% basic modifier (50 g $NH_4HCO_3$+50 mL $NH_3$ (25% in $H_2O$) to 1 L with $H_2O$). For Gilson systems the water is made alkaline as follows: 5 mL $NH_4HCO_3$ solution (158 g in 1 L $H_2O$) and 2 mL $NH_3$ (28% in $H_2O$) are replenished to 1 L with $H_2O$.

The supercritical fluid chromatography (SFC) of the intermediates and example compounds according to the invention is carried out on a JASCO SFC-system with the following columns: Chiralcel OJ (250×20 mm, 5 µm), Chiralpak AD (250×20 mm, 5 µm), Chiralpak AS (250×20 mm, 5 µm), Chiralpak IC (250×20 mm, 5 µm), Chiralpak IA (250×20 mm, 5 µm), Chiralcel OJ (250×20 mm, 5 µm), Chiralcel OD (250×20 mm, 5 µm), Phenomenex Lux C2 (250×20 mm, 5 µm).

The analytical HPLC (reaction control) of intermediate and final compounds is carried out using columns made by Waters (names: XBridge™ C18, 2.5 µm, 2.1×20 mm or XBridge™ C18, 2.5 µm, 2.1×30 mm or Aquity UPLC BEH C18, 1.7 µm, 2.1×50 mm) and YMC (names: Triart C18, 3.0 µm, 2.0×30 mm) and Phenomenex (names: Luna C18, 5.0 µm, 2.0×30 mm). The analytical equipment is also equipped with a mass detector in each case.

HPLC-Mass Spectroscopy/UV-Spectrometry

The retention times/MS-ESI$^+$ for characterizing the example compounds according to the invention are produced using an HPLC-MS apparatus (high performance liquid chromatography with mass detector). Compounds that elute at the injection peak are given the retention time $t_{ret}$=0.00.

HPLC-Methods (Preparative)

Prep. HPLC1
   HPLC: 333 and 334 Pumps
   Column: Waters X-Bridge C18 OBD, 10 µm, 30×100 mm, Part. No. 186003930
   Solvent: A: 10 mM $NH_4HCO_3$ in $H_2O$; B: Acetonitrile (HPLC grade)
   Detection: UV/Vis-155
   Flow: 50 mL/min
   Gradient: 0.00-1.50 min: 1.5% B
      1.50-7.50 min: varying
      7.50-9.00 min: 100% B Prep. HPLC2
   HPLC: 333 and 334 Pumps
   Column: Waters Sunfire C18 OBD, 10 µm, 30×100 mm, Part. No. 186003971
   Solvent: A: $H_2O$+0.2% HCOOH; B: Acetonitrile (HPLC grade)+0.2% HCOOH
   Detection: UV/Vis-155
   Flow: 50 mL/min
   Gradient: 0.00-1.50 min: 1.5% B
      1.50-7.50 min: varying
      7.50-9.00 min: 100% B HPLC-Methods (Analytic)

LCMSBAS1
   HPLC: Agilent 1100 Series
   MS: Agilent LC/MSD SL
   Column: Phenomenex Mercury Gemini C18, 3 µm, 2×20 mm, Part. No. 00M-4439-B0-CE
   Solvent: A: 5 mM $NH_4HCO_3$/20 mM $NH_3$ in $H_2O$; B: acetonitrile (HPLC grade)
   Detection: MS: positive and negative mode
   Mass range: 120-900 m/z
   Flow: 1.00 mL/min
   Column temperature: 40° C.
   Gradient: 0.00-2.50 min: 5% B→95% B
      2.50-2.80 min: 95% B
      2.81-3.10 min: 95% B→5% B LCMS3BAS1
   HPLC: Agilent 1100 Series
   MS: Agilent LC/MSD (API-ES+/−3000 V, Quadrupol, G6140)
   Column: Waters, Xbridge C18, 2.5 µm, 2.1×20 mm column
   Solvent: A: 20 mM $NH_4HCO_3$/$NH_3$ in $H_2O$ pH 9; B: acetonitrile (HPLC grade)
   Detection: MS: positive and negative mode
   Mass range: 120-900 m/z
   Flow: 1.00 mL/min
   Column temperature: 60° C.
   Gradient: 0.00-1.50 min: 10%→95% B
      1.50-2.00 min: 95% B
      2.00-2.10 min: 95%→10% B General Reaction Scheme and Summary of the Synthesis Route Towards Compounds of Formula (I) According to the Invention

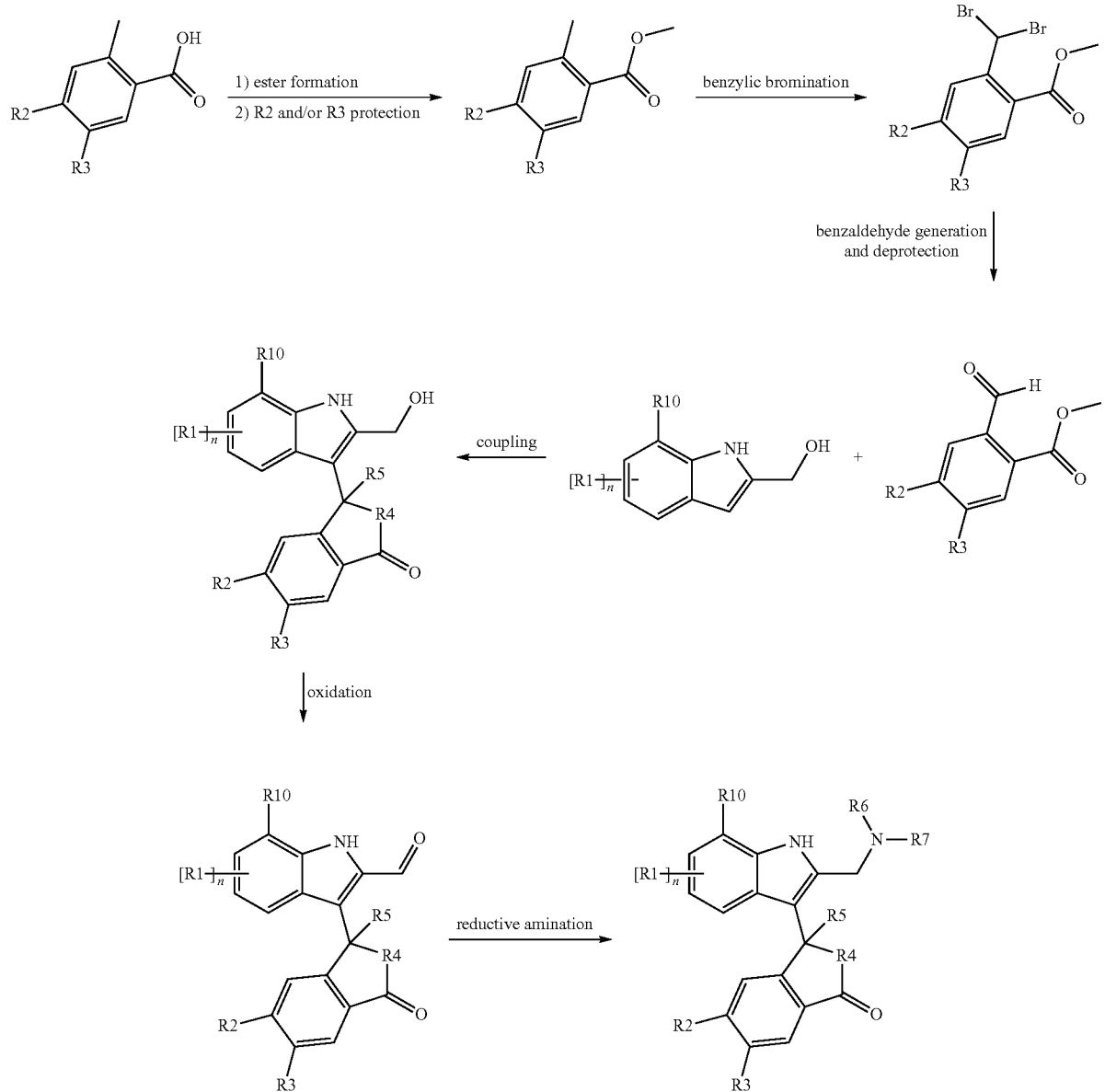

Scheme 1

Compounds of Formula (I) according to the invention can be prepared stepwise starting with a synthesis depicted in Scheme 1.

Scheme 1 outlines the general synthesis towards isoindolinone indoles.

Due to the observed eutomer/distomer behavior of the chiral isoindolinones a chirally defined synthesis route or the option for a chiral separation of used building blocks or a late stage chiral separation is preferred. The chiral separation is possible in larger quantities for the benzylic alcohol building block or on the final compounds via SFC.

The aldehyde as a key intermediate can be prepared via oxidation of the benzylic alcohol and the alcohol is synthesized from indole intermediates via condensation reaction with aldehydes. Aldehyde can be synthesized starting from the commercial available carboxylic acid. After esterification and protection of the phenolic hydroxyl group, the aldehyde is generated via oxidation of the methyl group by NBS, followed by silver catalyzed hydrolysis.

For $R^1 \neq H$ the indole intermediates are commercial available or can be prepared from commercial available building blocks like the corresponding acid or ester by reduction.

Alternative to the aldehyde-ester other cyclic derivatives like anhydrides, lactames, hydroxyl-isoindolinones etc. can be used in the coupling reaction.

$R^2$ and $R^3$ can also form heterocycles like indoles, indazoles etc. with could be part of the coupling partner or built up after the coupling step.

Enantiomeric pure compounds are prepared from the corresponding chiral alcohols or after the reductive amination via SFC. The enantiomers of the final compounds showed clear eutomer/distomer behavior in the in-vitro assay, with the isoindolinone (3S)-stereoisomer as the eutomer.

Synthesis of Intermediates

Experimental Procedure for the Synthesis of methyl 4-hydroxy-2-methylbenzoate

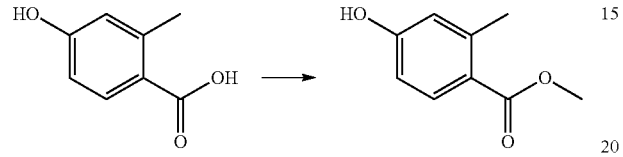

To a stirred solution of 4-hydroxy-2-methylbenzoic acid (50.0 g; 329 mmol; commercial available from Combi-Blocks) in MeOH (500 mL) thionyl chloride (48.9 ml; 657.3 mmol) is added under ice cooled condition and the reaction mixture is heated at 80° C. for 4 h. The solvent is evaporated and the residue is dissolved in dichloromethane (500 mL) and NaHCO$_3$ (300 mL). The organic phase is separated and the aqueous portion is extracted with dichloromethane twice (2*200 mL). The organic phases are combined, washed with brine, dried over Na$_2$SO$_4$, filtered and concentrated in vacuo to yield methyl 4-hydroxy-2-methylbenzoate as an off white solid. HPLC method: LCMSBAS1: $t_{ret}$ [min]=0.67; [M–H]$^+$= 165.

Experimental Procedure for the Synthesis of methyl 4-[(tert-butyldimethylsilyl)oxy]-2-methylbenzoate

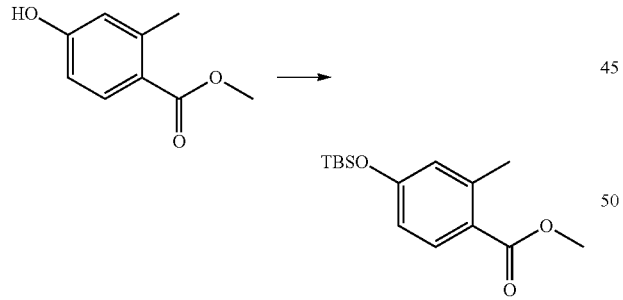

TBSCl (10.83 g; 72 mmol) is added to a stirred solution of 4-hydroxy-2-methylbonzoic acid methyl ester (10.0 g; 60 mmol) in DMF (100 mL) at 0° C. After 15 min DIPEA (22.2 mL; 120 mmol) is added to the reaction mixture and stirring is continued for overnight at room temperature. The reaction mixture is treated with water and extracted with hexane, washed with water, the combined organic phases are dried over Na$_2$SO$_4$ and concentrated under reduced pressure to obtain the crude TBS protected compound methyl 4-[(tert-butyldimethylsilyl)oxy]-2-methylbenzoate which is used without further purification. HPLC method: LCMSBAS1: $t_{ret}$ [min]=1.71; [M–H]$^+$=281.

Experimental Procedure for the Synthesis of methyl 4-[(tert-butyldimethylsilyl)oxy]-2-(dibromomethyl)benzoate

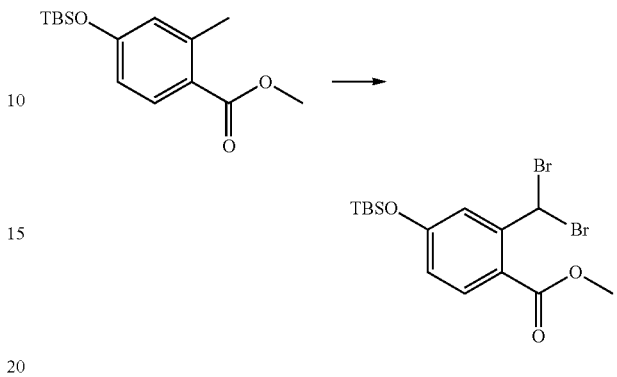

To N-Bromosuccinimide (361.5 g; 2031 mmol) and AIBN (74.11 g; 451.3 mmol) were added to a stirred solution of methyl 4-[(tert-butyldimethylsilyl)oxy]-2-methylbenzoate (126.56 g; 451.3 mmol) in benzene (3.1 L) at room temperature. The reaction mixture was heated to reflux overnight. The reaction mass was dissolved in DCM and filtered to remove excess NBS and then dissolved in hexane and filtered again. The filtrate was concentrated to get the liquid crude material methyl 4-[(tert-butyldimethylsilyl)oxy]-2-(dibromomethyl)benzoate, which was used directly for the next step. HPLC method: LCMSBAS1: $t_{ret}$ [min]=1.82; [M+H]$^+$=437/439/441 bromine isotopes.

Experimental Procedure for the Synthesis of methyl 2-formyl-4-hydroxybenzoate

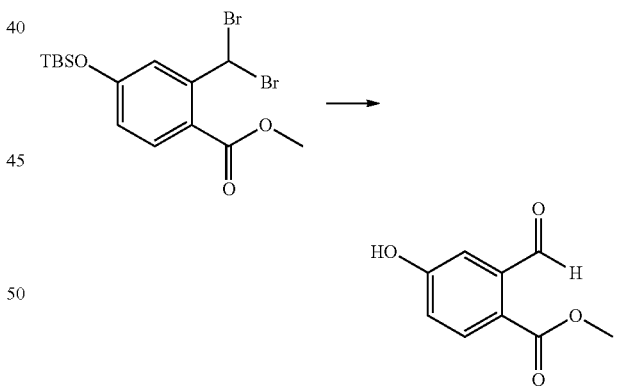

Silver nitrate (52.912 g; 311 mmol) was added to a stirred solution of methyl 4-[(tert-butyldimethylsilyl)oxy]-2-(dibromomethyl)benzoate (65.0 g; 148.33 mmol) in acetone/water (5:1) (900 mL) and the reaction mixture was stirred at room temperature for 16 h. The reaction mixture was filtered and concentrated in vacuo, taken up in EtOAc (50 mL) and was washed with water (3×20 mL). The organic phases are dried over Na$_2$SO$_4$, filtered and concentrated under reduced pressure. The crude brown oil was purified by column chromatography over silica gel using EtOAc/Hex (1:9, v/v) as eluent to obtain an off white solid. The solid material was then washed by 5% EtOAc/Hex to yield methyl 2-formyl- 4-hydroxybenzoate (11.0 g; 61.0 mmol; 41.2%). HPLC method: LCMSBAS1: $t_{ret}$ [min]=0.20; [M–H]$^+$=181.

Experimental Procedure for the Synthesis of 5-hydroxy-3-(2-hydroxymethyl-1H-indol-3-yl)-2,3-dihydro-isoindol-1-one

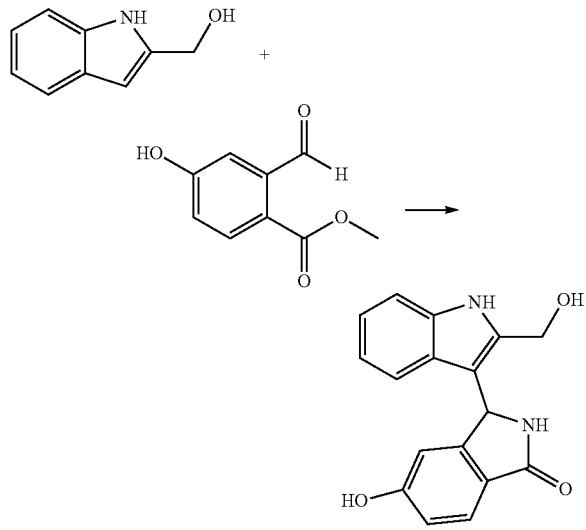

A suspension of (1H-indol-2-yl)methanol (1.078 g; 6.594 mmol; commercial from Aldrich), methyl 2-formyl-4-hydroxy-benzoate (1.0 g; 5.495 mmol) and ammonia solution (28% in water, 7.816 mL; 54.952 mmol) in water (10 mL) is stirred in a capped 20 mL microwave vial and heated overnight at 85° C. The reaction mixture is diluted and dissolved with ACN, filtered and purified by preparative RP-HPLC using a ACN/water gradient as eluent to give 5-hydroxy-3-(2-hydroxymethyl-1H-indol-3-yl)-2,3-dihydro-isoindol-1-one (1.048 g; 3.561 mmol; 64.8%). HPLC method: LCMSBAS1: $t_{ret}$ [min]=0.46; [M+H]$^+$=295.

The alcohol (1 g; 340 µmol) was separated via preparative chiral SFC to give (3S)-5-hydroxy-3-[2-(hydroxymethyl)-1H-indol-3-yl]-2,3-dihydro-1H-isoindol-1-one (493 mg; 168 µmol) and (3R)-5-hydroxy-3-[2-(hydroxymethyl)-1H-indol-3-yl]-2,3-dihydro-1H-isoindol-1-one (484 mg; 164.5 µmol).

Experimental Procedure for the Synthesis of 3-(6-hydroxy-3-oxo-2,3-dihydro-1H-isoindol-1-yl)-1H-indole-2-carbaldehyde

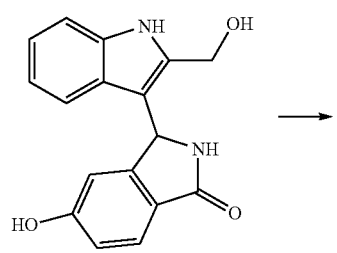

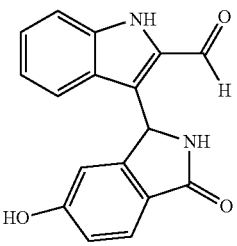

5-Hydroxy-3-[2-(hydroxymethyl)-1H-indol-3-yl]-2,3-dihydro-1H-isoindol-1-one (2.0 g; 6.59 mmol) and MnO$_2$ (6.367 g; 65.92 mmol) are suspended in MeOH and heated to reflux for 30 min. The hot suspension is filtered and washed with hot MeOH (100 mL). After cooling, MeOH is removed under reduced pressure and the crude product is purified by flash chromatography on SiO$_2$ using a DCM/MeOH gradient (0-10% MeOH). The product containing fractions are combined, concentrated under reduced pressure, dissolved in ACN/water (1:1) and freeze dried to give 3-(6-hydroxy-3-oxo-2,3-dihydro-1H-isoindol-1-yl)-1H-indole-2-carbaldehyde (1.3 g; 4.45 mmol; 67.5%). HPLC method: LCMSBAS1: $t_{ret}$ [min]=0.53; [M+H]$^+$=293.

In a similar procedure from the chiral separated alcohols e.g. (3S)-5-hydroxy-3-[2-(hydroxymethyl)-1H-indol-3-yl]-2,3-dihydro-1H-isoindol-1-one (156 mg; 530 µmol) the chiral aldehyde 3-[(1S)-6-hydroxy-3-oxo-2,3-dihydro-1H-isoindol-1-yl]-1H-indole-2-carbaldehyde (149 mg; 510 µmol) can be synthesized.

Experimental Procedure for the Synthesis of 5-hydroxy-3-[2-(hydroxymethyl)-1H-indol-3-yl]-1,3-dihydro-2-benzofuran-1-one

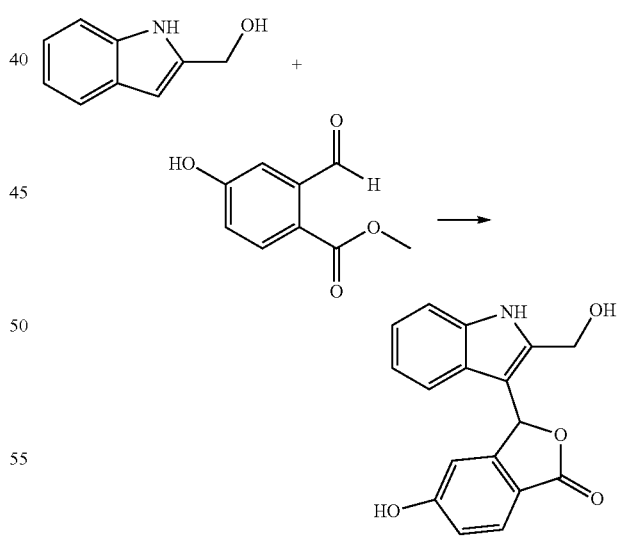

A suspension of (1H-indol-2-yl)methanol (454 mg; 2.775 mmol; commercial from Aldrich), methyl 2-formyl-4-hydroxy-benzoate (0.5 g; 2.775 mmol) and DIPEA (473 µL; 2.775 mmol) in water (7 mL) is stirred for 5 h at 85° C. The reaction mixture is diluted and dissolved with ACN, filtered and purified by preparative RP-HPLC using a ACN/water gradient (1-50% ACN in water) as eluent to give 5-hydroxy-3-[2-(hydroxymethyl)-1H-indol-3-yl]-1,3-dihydro-2-benzofuran-1-one (436 mg; 1.477 mmol; 53.2%). HPLC method: LCMSBAS1: $t_{ret}$ [min]=0.47; [M+H]$^+$=296.

Experimental Procedure for the Synthesis of 3-(6-hydroxy-3-oxo-1,3-dihydro-2-benzofuran-1-yl)-1H-indole-2-carbaldehyde

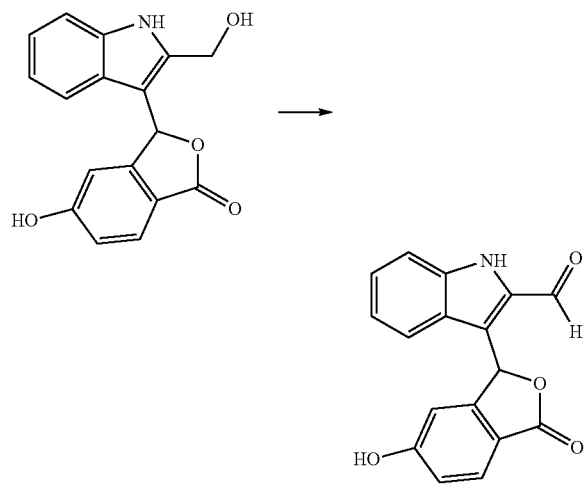

5-hydroxy-3-[2-(hydroxymethyl)-1H-indol-3-yl]-1,3-dihydro-2-benzofuran-1-one (2.0 g; 6.705 mmol) and $MnO_2$ (6.477 g; 67.05 mmol) are suspended in MeOH and heated to reflux for 30 min. The hot suspension is filtered and washed with hot MeOH (100 mL). After cooling, MeOH is removed under reduced pressure and the crude product is purified by flash chromatography on $SiO_2$ using a DCM/MeOH gradient (0-10% MeOH). The product containing fractions are combined, concentrated under reduced pressure, dissolved in ACN/water (1:1) and freeze dried to give 3-(6-hydroxy-3-oxo-1,3-dihydro-2-benzofuran-1-yl)-1H-indole-2-carbaldehyde (1.8 g; 6.138 mmol; 91.5%). HPLC method: LCMSBAS1: $t_{ret}$ [min]=0.55; [M+H]+=294.

Experimental Procedure for the Synthesis of 1-(1-methyl-1H-imidazol-4-ylmethyl)-1H-indole-6-carbonitrile

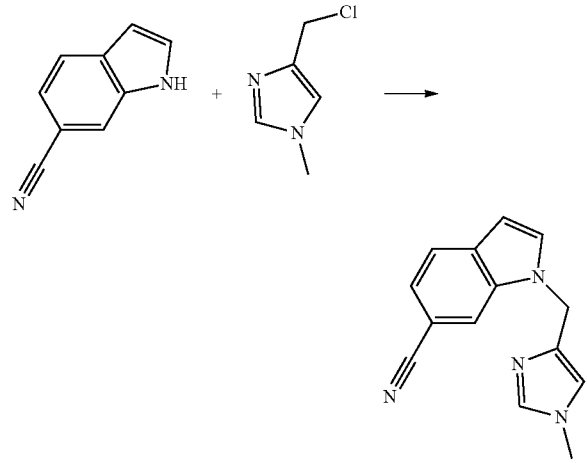

In a 50 mL round-bottom flask 6-cyanoindole (200 mg; 1.337 mmol; commercial available from AstaTech) is dissolved in 1,3-dimethyl-3,4,5,6-tetrahydro-2(1H)-pyrimidinone (DMPU; 2.0 mL; 16.54 mmol), cooled in an ice-bath and treated with sodium hydride (55%; 128.3 mg; 2.94 mmol) and stirred at room temperature for additional 2 h. Tetrabutylammonium iodide (TBAI, 49.37 mg; 0.134 mmol) and 4-(chloromethyl)-1-methyl-1H-imidazole (261.78 mg; 2.005 mmol; commercial available from Allweys) are added to the reaction mixture and stirred overnight at room temperature. Reaction control showed incomplete 6-cyanoindole consumption and therefore an additional equivalent sodium hydride and 4-(chloromethyl)-1-methyl-1H-imidazole are added again in two portions and stirred for additional 32 h. The reaction mixture is quenched by adding MeOH (2 mL), diluted with water and extracted with EtOAc. The combined organic layers are dried over $MgSO_4$, filtered and concentrated under reduced pressure. The crude product is purified by preparative RP-HPLC using an ACN/water gradient (5-50% CAN, acidic condition) as eluent to yield 1-(1-methyl-1H-imidazol-4-ylmethyl)-1H-indole-6-carbonitrile (209 mg; 885 µmol; 66.2%). HPLC method: LCMSBAS1: [M+H]$^+$=237; $t_{ret}$ [min]=0.99.

Experimental Procedure for the Synthesis of C-[1-(1-Methyl-1H-imidazol-4-ylmethyl)-1H-indol-6-yl]-methylamine

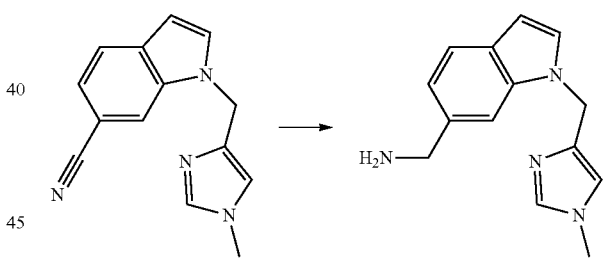

1-(1-methyl-1H-imidazol-4-ylmethyl)-1H-indole-6-carbonitrile (95 mg; 402 µmol) is dissolved in ammonia in MeOH (7N solution; 3 mL; 21 mmol) and hydrogenated over Raney-Ni (4 mg; 40 µmol) under pressure overnight. After complete consumption of the starting material the reaction mixture is filtrated, concentrated under reduced pressure and purified by preparative RP-HPLC using an ACN/water (5-50% ACN, basic condition) gradient. The product containing fractions are freeze dried to yield unstable 1-{1-[((1-methyl-1H-imidazol-4-yl)methyl]-1H-indol-6-yl}methanamine (56 mg; 233 µmol; 58%), which was immediately used for the next reaction step. HPLC method: LCMS3BAS1: [M+H]$^+$=240; $t_{ret}$ [min]=0.99.

Experimental Procedure for the Synthesis of 1-{[4-(benzyloxy)phenyl]methyl}-1H-indole-6-carbonitrile

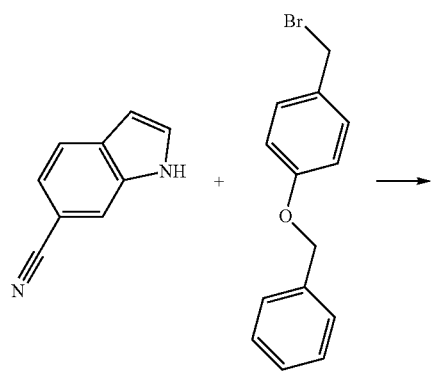

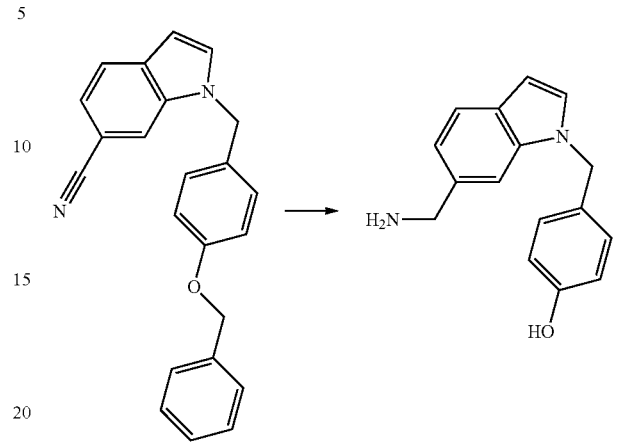

The crude product 1-{[4-(benzyloxy)phenyl]methyl}-1H-indole-6-carbonitrile (385 mg; 1.138 mmol) is dissolved in 8M ammonia in MeOH and hydrogenated over 20% Palladium hydroxide on carbon (159.8 mg; 228 µmol) under a pressure of 8 bar $H_2$ for 4 h at room temperature. After complete consumption of the starting material the reaction mixture is filtrated, concentrated under vacuo and purified by preparative RP-HPLC using an ACN/water gradient under basic conditions. The product containing fractions are combined and freeze dried to yield 4-{[6-(aminomethyl)-1H-indol-1-yl]methyl}phenol (261 mg; 1.034 mmol; 90.9%), which was immediately used for the next reaction step. HPLC method: LCMS3BAS1: $[M-H]^+=251$; $t_{ret}$ [min]=0.97.

Experimental Procedure for the Synthesis of 1-(1H-imidazol-4-ylmethyl)-1H-indole-6-carbonitrile

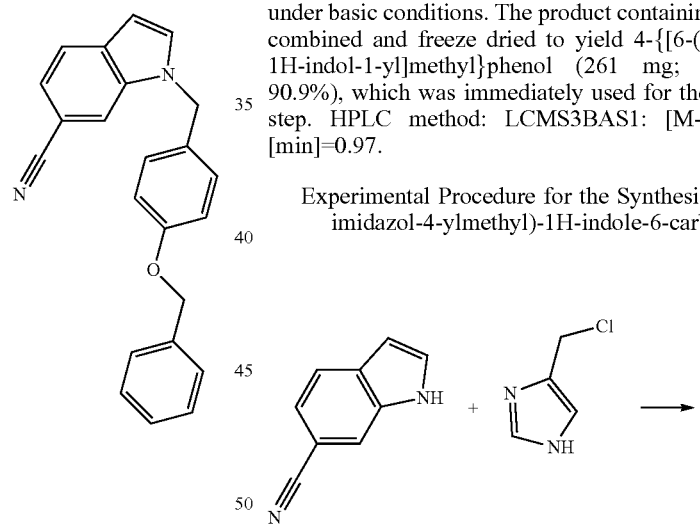

To a solution of 6-cyanoindole (200 mg; 1.337 mmol; commercial available from AstaTech) in DMF (20 mL) is added KOH (132.1 mg; 1.138 mmol) at 0° C. and stirred for 20 min before 1-(benzyloxy)-4-(bromomethyl)benzene (444.52 mg; 1.604 mmol; commercial available from Enamine) are added. The reaction mixture is stirred at 0° C. for 30 min and then warmed to room temperature over 30 min. The reaction mixture is diluted with water and extracted with EtOAc. The combined organic layer is dried over $MgSO_4$, filtered and concentrated under reduced pressure. The crude product 1-{[4-(benzyloxy)phenyl]methyl}-1H-indole-6-carbonitrile (385 mg; 1.138 mmol; 85.1% yield) is used for the next reaction step without further purification.

Experimental Procedure for the Synthesis of 4-{[6-(aminomethyl)-1H-indol-1-yl]methyl}phenol In a 50 mL round-bottom flask 6-cyanoindole (200 mg; 1.337 mmol; commercial available from AstaTech) is dissolved in 1,3-dimethyl-3,4,5,6-tetrahydro-2(1H)-pyrimidinone (DMPU; 3 mL; 24.810 mmol), cooled in an ice-bath and treated with sodium hydride (175 mg; 4.010 mmol). The reaction mixture is stirred at room temperature for before 4-(chloromethyl)-1H-imidazole hydrochloride (306.8 mg;

2.005 mmol; commercial available from ChemBridge-BB) and tetrabutylammonium iodide (49.37 mg; 0.134 mmol) are added and the mixture is stirred at room temperature overnight. Another equivalent sodium hydride and 4-(chloromethyl)-1H-imidazole hydrochloride are added and stirring is continued for 3 h. The reaction mixture is quenched with MeOH and diluted with ACN/water, filtered through a syringe filter and purified by preparative HPLC (Gilson; column: SunFire Prep C18, 10 μm (50*150), gradient: ACN/water (acidic condition; 5-50% ACN in 10 min. flowrate: 150 mL/min wavelength: 238 nm). The product containing fractions are pooled and freeze dried to yield 1-(1H-Imidazol-4-ylmethyl)-1H-indole-6-carbonitrile (45 mg; 202 μmol; 15.1%). HPLC method: LCMSBAS1: [M+H]$^+$=223; $t_{ret}$ [min]=0.92.

Experimental Procedure for the Synthesis of 1-{1-[(1H-imidazol-4-yl)methyl]-1H-indol-6-yl}methanamine

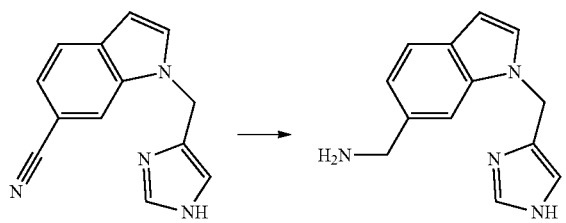 [SMILES: N#Cc1ccc2ccn(Cc3c[nH]cn3)c2c1 ; NCc1ccc2ccn(Cc3c[nH]cn3)c2c1]

In a Parr-reactor 1-(1H-Imidazol-4-ylmethyl)-1H-indole-6-carbonitrile (45 mg; 202 μmol) is dissolved in 7N ammonia in MeOH (2 mL; 14.0 mmol) and THF (1 mL) and a tip of a spatula of Raney-Ni (2.05 mg; 20 μmol) is added. The reactor is closed, flushed with nitrogen and filled with 4 bar of H$_2$. The reaction mixture is stirred at room temperature overnight. A spoon of celite is added to the reaction mixture, the catalyst is filtered off through a celite pad and washed with MeOH and THF. The solvent is removed under reduced pressure and the crude product 1-{1-[(1H-imidazol-4-yl)methyl]-1H-indol-6-yl}methanamine (35 mg; 155 μmol; 76.4%) is used immediately for the next reaction step.

Experimental Procedure for the Synthesis of tert-butyl N-[3-(6-cyano-1H-indol-1-yl)propyl]carbamate

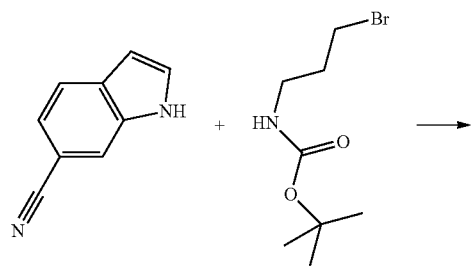

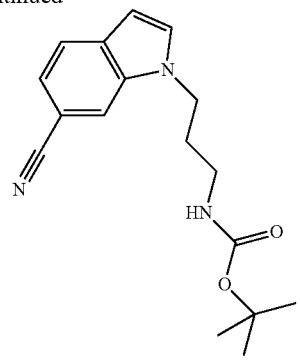

In a 50 mL round-bottom flask 6-cyanoindole (200 mg; 1.337 mmol) and potassium hydroxide (132.08 mg; 2.005 mmol) are taken up in DMF (2.5 mL) and stirred at room temperature for 20 min before 3-(Boc-amino)propyl bromide (334.18 mg; 1.403 mmol) and tetrabutylammonium iodide (49.37 mg; 0.134 mmol) are added and the mixture is stirred at room temperature overnight. The reaction mixture is diluted with ACN/water and the formed precipitate is filtered off, washed with water and dried at 50° C. under vacuum to yield tert-butyl N-[3-(6-cyano-1H-indol-1-yl)propyl]carbamate (348 mg; 1.162 mmol; 87.0%). HPLC method: LCMSBAS1: [M–H]$^+$=298; $t_{ret}$ [min]=0.45.

Experimental Procedure for the Synthesis of tert-butyl N-{3-[6-(aminomethyl)-1H-indol-1-yl]propyl}carbamate

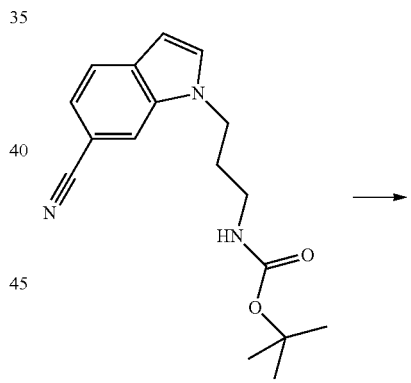

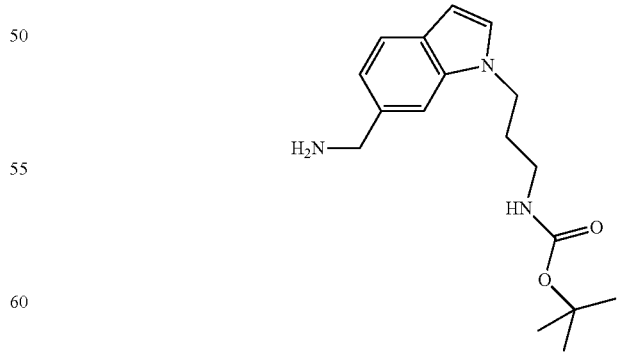

In a Parr-reactor tert-butyl N-[3-(6-cyano-1H-indol-1-yl)propyl]carbamate (150 mg; 501 μmol) is dissolved in ammonia in MeOH solution (7N; 2 mL; 14.000 mmol) and THF (1 mL) and a tip of a spatula of Raney-Ni (5.07 mg; 50 μmol)

is added. The reactor is closed, flushed with nitrogen and filled with 4 bar of $H_2$. The reaction mixture is stirred at room temperature overnight. A spoon of celite is added to the reaction mixture, the catalyst is filtered off through a celite pad and washed with MeOH and THF. The solvent is removed under reduced pressure and the crude product tert-butyl N-{3-[6-(aminomethyl)-1H-indol-1-yl]propyl}carbamate (127 mg; 419 µmol; 83.5%) is used immediately for the next reaction step.

Experimental Procedure for the Synthesis of N-[(1H-indol-6-yl)methyl]carbamate

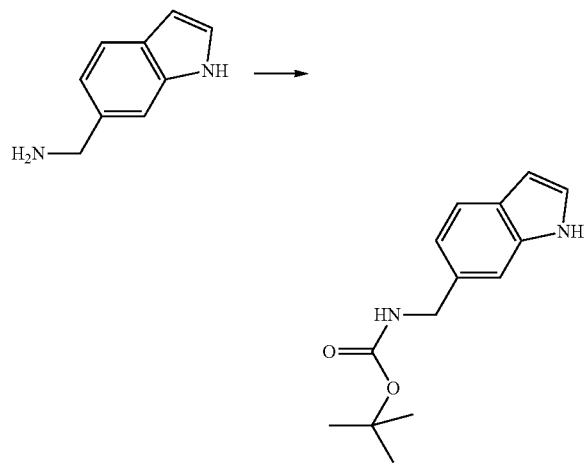

In a 50 mL round-bottom flask (1H-indol-6-yl)methanamine (300 mg; 2.052 mmol; commercial available from Aldrich) is dissolved in DCM (5 mL) and cooled to 0° C. before BOC-anhydride (424 mg; 1.943 mmol) is added and the mixture is stirred at room temperature for 1 h. The solvent is removed under reduced pressure, the residue is dissolved in ACN/H₂O/MeOH, filtered through a syringe filter and purified via prep. RP-HPLC (Gilson; column: XBridge Prep C18, 10 µm (50*150), gradient: ACN/H₂O (basic conditions 20-98% ACN in 9 min. flowrate: 150 mL/min wavelength: 222 nm). The product containing fractions are combined and freeze dried to yield tert-butyl N-[(1H-indol-6-yl)methyl]carbamate (468 mg; 1.9 mmol; 92.6%). HPLC method: LCMSBAS1: [M−H]⁺=245; $t_{ret}$ [min]=1.19.

Experimental Procedure for the Synthesis of tert-butyl N-{[1-(carbamoylmethyl)-1H-indol-6-yl]methyl}carbamate

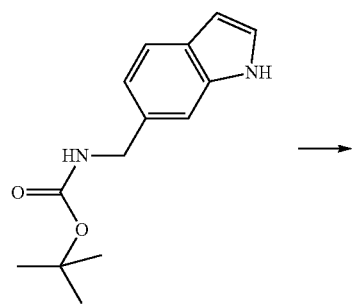

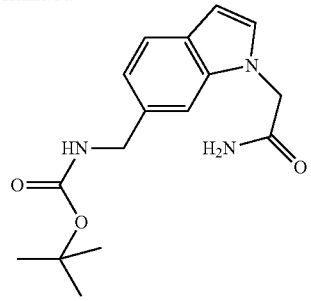

In a glass vial tert-butyl N-[(1H-indol-6-yl)methyl]carbamate (50 mg; 203 µmol) and potassium hydroxide (20.061 mg; 305 µmol) are taken up in DMF (1.0 mL) and stirred vigorously in an ice-bath for 20 min before 2-bromoacetamide (42.010 mg; 305 µmol) is added and the mixture is stirred at 0° C. for 30 min. The ice-bath is removed and the mixture is allowed to warm to room temperature. The reaction mixture is diluted with ACN/H₂O, filtered through a syringe filter and purified by prep. RP-HPLC-MS (8B_0550_DAD). The product containing fractions are combined and freeze dried to yield tert-butyl N-{[1-(carbamoylmethyl)-1H-indol-6-yl]methyl}carbamate (39 mg; 129 µmol; 63.3%). HPLC method: LCMSBAS1: [M+H]⁺= 304; $t_{ret}$ [min]=1.04.

Experimental Procedure for the Synthesis of 2-[6-(aminomethyl)-1H-indol-1-yl]acetamide

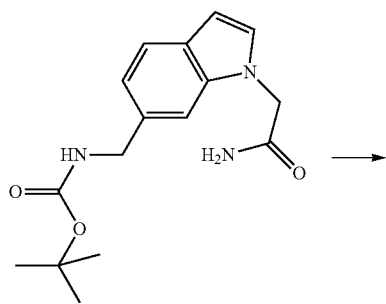

In a 100 mL round-bottom flask tert-butyl N-{[1-(carbamoylmethyl)-1H-indol-6-yl]methyl}carbamate (39 mg; 129 µmol) is dissolved in DCM (1.5 mL). TFA (0.25 mL; 3.245 mmol) is added and it is stirred at room temperature for 1 h. The reaction mixture is basified with aq. ammonia. The solvent is evaporated and the crude product 2-[6-(aminomethyl)-1H-indol-1-yl]acetamide is taken to the next step without further purification.

Experimental Procedure for the Synthesis of 3-(1-Methyl-1H-imidazol-4-ylmethyl)-1H-indole-6-carbonitrile

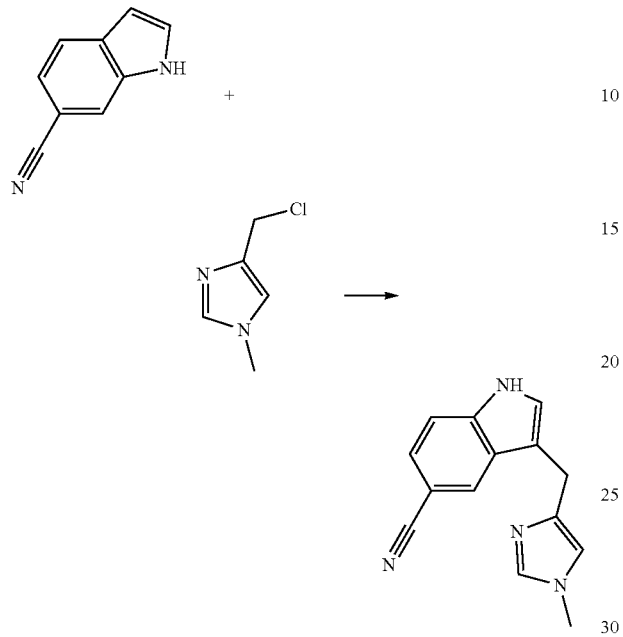

In a 50 mL round-bottom flask 6-cyanoindole (400 mg; 2.673 mmol; commercial available from AstaTech) is dissolved in DMF (4.0 mL) and treated with potassium carbonate (812.8 mg; 5.881 mmol) and stirred at 50° C. for 30 min. 4-(chloromethyl)-1-methyl-1H-imidazole (523.56 mg; 4.010 mmol; commercial available from Allweys) and tetrabutylammonium iodide (98.74 mg; 267 µmol) are added and the mixture is stirred at 60° C. for 3 days. The reaction mixture is diluted with ACN/H$_2$O, filtered through a syringe filter and purified by prep. RP-HPLC (Gilson; column: XBridge Prep C18, 10 µm (50*150), gradient: ACN/water (basic conditions; 5-60% ACN in 9 min. flowrate: 150 mL/min wavelength: 242 nm). The product containing fractions are combined and freeze-dried to yield 3-(1-Methyl-1H-imidazol-4-ylmethyl)-1H-indole-6-carbonitrile (87 mg; 368 µmol; 13.8%). HPLC method: LCMSBAS1: [M+H]$^+$= 237; $t_{ret}$ [min]=0.92.

Experimental Procedure for the Synthesis of 1-{3-[(1-methyl-1H-imidazol-4-yl)methyl]-1H-indol-5-yl}methanamine

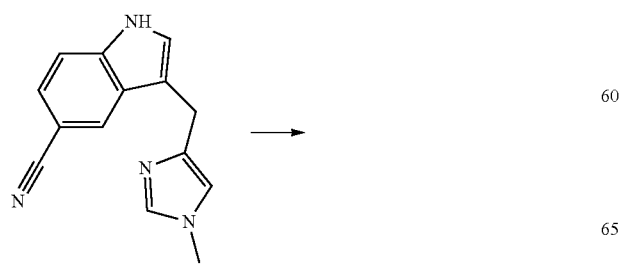

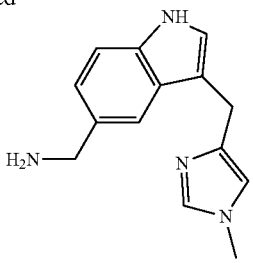

In a Parr-reactor 3-(1-methyl-1H-imidazol-4-ylmethyl)-1H-indole-6-carbonitrile (85 mg; 360 µmol) is dissolved in 7N ammonia in MeOH (3.0 mL; 21 mmol) and a tip of a spatula of Raney-Ni (3.64 mg; 36 µmol) is added. The reactor is closed, flushed with N$_2$, filled with 4 bar of H$_2$ and stirred at room temperature overnight. A spoon of celite is added to the reaction mixture, the catalyst is filtered off through a celite pad and washed with MeOH. The solvent is removed under reduced pressure and the residue 1-{3-[(1-methyl-1H-imidazol-4-yl)methyl]-1H-indol-5-yl}methanamine is taken to the next step without further purification (85 mg; 354 µmol; 98.3%).

Experimental Procedure for the Synthesis of 5-hydroxy-3-[2-(hydroxymethyl)-1H-indol-3-yl]-2-methyl-2,3-dihydro-1H-isoindol-1-one and 5-hydroxy-3-[2-(hydroxymethyl)-1H-indol-3-yl]-1,3-dihydro-2-benzofuran-1-one

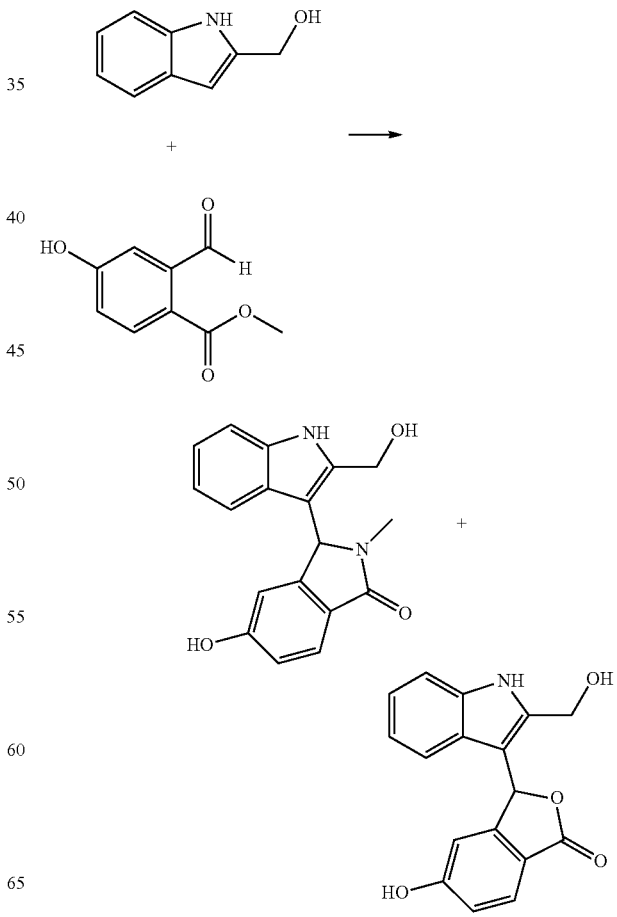

A suspension of (1H-indol-2-yl)methanol (1.815 g; 11.101 mmol; commercial from Aldrich), methyl 2-formyl-4-hydroxy-benzoate (1.0 g; 5.551 mmol) and methylamine (2M solution in THF; 2.775 mL; 5.551 mmol) in water (10 mL) is stirred and heated at 85° C. overnight. The reaction mixture is concentrated under reduced pressure and is purified by flash chromatography on SiO$_2$ using a DCM/MeOH gradient (0-5% MeOH) to give 5-hydroxy-3-[2-(hydroxymethyl)-1H-indol-3-yl]-2-methyl-2,3-dihydro-1H-isoindol-1-one (740 mg; 2.4 mmol; 43.2%) (HPLC method: LCMSBAS1: [M+H]$^+$=309; $t_{ret}$ [min]=0.62 min) and the lactone 5-hydroxy-3-[2-(hydroxymethyl)-1H-indol-3-yl]-1,3-dihydro-2-benzofuran-1-one (453 mg; 1.534 mmol; 27.6%) (HPLC method: LCMSBAS1: [M+H]$^+$=296; $t_{ret}$ [min]=0.47 min) as a side product.

Chiral separation of 5-hydroxy-3-[2-(hydroxymethyl)-1H-indol-3-yl]-2-methyl-2,3-dihydro-1H-isoindol-1-one (700 mg; 2.27 mmol) was done via chiral SFC to give (3S)-5-hydroxy-3-[2-(hydroxymethyl)-1H-indol-3-yl]-2-methyl-isoindolin-1-one (190 mg; 616 μmol; 27.1%) and (3R)-5-hydroxy-3-[2-(hydroxymethyl)-1H-indol-3-yl]-2-methyl-isoindolin-1-one (230 mg; 746 μmol; 32.9%). HPLC method: LCMSBAS1: [M+H]$^+$=309; $t_{ret}$ [min]=0.67.

Experimental Procedure for the Synthesis of (1H-Indol-2-ylmethyl)-dimethyl-amine

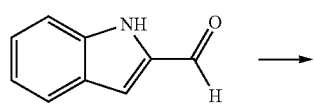

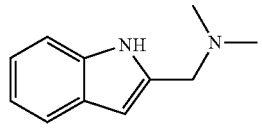

The aldehyde 1H-indole-2-carbaldehyde (300 mg; 2.067 mmol; commercial available from ABCR) and dimethylamine hydrochloride (515.905 mg; 6.2 mmol) are dissolved in DMF (3.0 mL). After 15 min stirred at room temperature, sodium triacetoxyborohydride (2.19 g; 10.334 mmol) is added and the reaction mixture is stirred at room temperature overnight. ACN/water (1:1; 0.6 mL) is added to the reaction mixture, filtered through a syringe filter and the filtrate is purified by preparative RP-H PLC using an ACN/water (10-70% ACN, basic conditions) gradient. The product containing fractions are combined and freeze dried to yield (1H-Indol-2-ylmethyl)-dimethyl-amine (291 mg; 1.67 mmol; 80.8%). HPLC method: LCMSBAS1: [M−H]$^+$=173; $t_{ret}$ [min]=1.06 min.

Experimental Procedure for the Synthesis of 5-hydroxy-2-methoxy-isoindole-1,3-dione

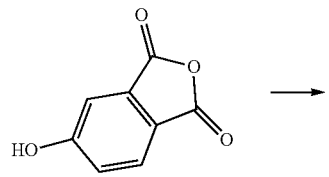

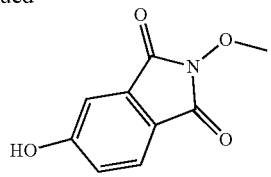

In a glass vial 4-hydroxyphthalic anhydride (300 mg; 1.828 mmol; commercial available from ArkPharm) and methoxyamine hydrochloride (167.935 mg; 2.011 mmol) are dissolved/suspended in AcOH (2.0 mL) and stirred at 90° C. overnight. The reaction mixture is concentrated under reduced pressure. The residue is dissolved in ACN/H$_2$O, filtered through a syringe filter and purified via prep. RP-HPLC (Gilson; column: SunFire Prep C18, 10 μm (50*150), gradient: ACN/H$_2$O from 5-60% ACN, acidic conditions in 9 min. flowrate: 180 mL/min wavelength: 235 nm). The product containing fractions are pooled and freeze dried to yield 5-hydroxy-2-methoxy-isoindole-1,3-dione (177 mg; 916 μmol; 50.1%).

Experimental Procedure for the Synthesis of 3-(6-hydroxy-2-methyl-3-oxo-2,3-dihydro-1H-isoindol-1-yl)-1H-indole-2-carbaldehyde

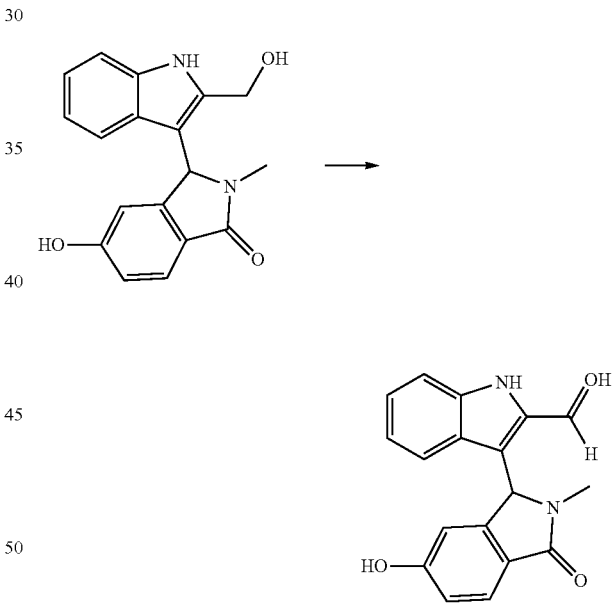

5-hydroxy-3-[2-(hydroxymethyl)-1H-indol-3-yl]-2-methyl-2,3-dihydro-1H-isoindol-1-one (0.74 g; 2.4 mmol) and MnO$_2$ (88%; 2.371 g; 24 mmol) are suspended in DMF (8 mL) and stirred at room temperature overnight. The reaction mixture is filtered over a celite pad and washed with EtOAc. The solvent is removed under reduced pressure and the crude product 3-(6-hydroxy-2-methyl-3-oxo-2,3-dihydro-1H-isoindol-1-yl)-1H-indole-2-carbaldehyde (735 mg; 2.16 mmol; 90%) is used directly without further purification. HPLC method: LCMSBAS1: $t_{ret}$ [min]=0.74; [M+H]$^+$=307).

Experimental Procedure for the Synthesis of ethyl 5-chloro-1H-indole-2-carboxylate

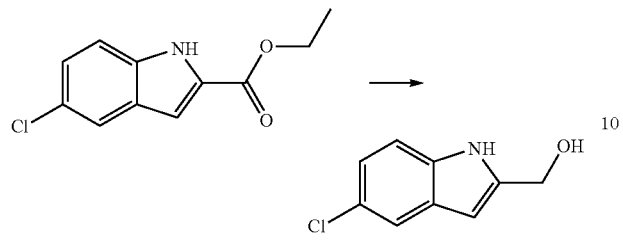

Ethyl 5-chloro-1H-indole-2-carboxylate (2.0 g; 8.763 mmol; commercial from CombiBlocks) is dissolved in dry THF (20 mL), treated at 0° C. with a 2M lithium aluminium hydride solution in THF (5.258 mL; 10.516 mmol) and stirred for 2 h. The reaction mixture is quenched at 0° C. by addition of water, diluted with EtOAc, stirred for 30 min and filtered. The phases are separated and the water phase is extracted with EtOAc (3*20 mL). The combined organic phases are concentrated under reduced pressure, diluted with ACN/water and purified by preparative RP-HPLC using an ACN/water (25-98% ACN, acidic conditions) gradient. The product containing fractions are combined and freeze dried to yield (5-chloro-1H-indol-2-yl)methanol (1.352 g; 7.444 mmol; 84.9%). HPLC method: LCMSBAS1: [M−H]$^+$=180; $t_{ret}$ [min]=0.94 min.

Experimental Procedure for the Synthesis of 3-[5-chloro-2-(hydroxymethyl)-1H-indol-3-yl]-5-hydroxy-2,3-dihydro-1H-isoindol-1-one

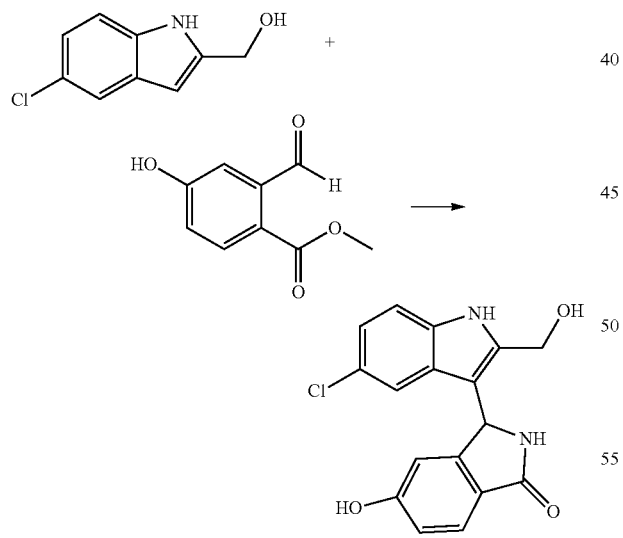

A suspension of (5-chloro-1H-indol-2-yl)methanol (150 mg; 826 μmol), methyl 2-formyl-4-hydroxy-benzoate (148.79 mg; 826 μmol) and ammonia solution (28% in water; 1.175 mL; 8.26 mmol) in water (1.5 mL) is stirred and heated at 85° C. overnight. The reaction mixture is diluted with DMF, filtrated and purified by preparative RP-HPLC using a ACN/water gradient (20-90%) as eluent to give 3-[5-chloro-2-(hydroxymethyl)-1H-indol-3-yl]-5-hydroxy-2,3-dihydro-1H-isoindol-1-one (163 mg; 496 μmol; 60.0%). HPLC method: LCMSBAS1: [M+H]$^+$=329; $t_{ret}$ [min]=0.67 min.

Experimental Procedure for the Synthesis of 5-chloro-3-(6-hydroxy-3-oxo-2,3-dihydro-1H-isoindol-1-yl)-1H-indole-2-carbaldehyde

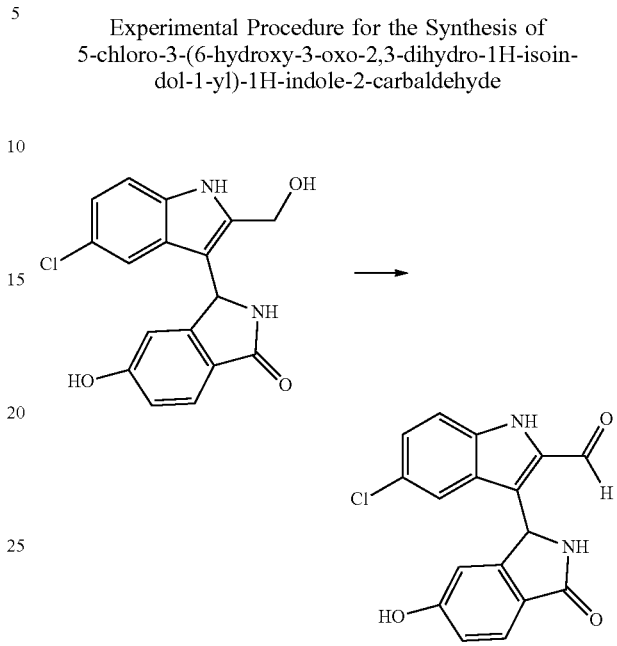

3-[5-chloro-2-(hydroxymethyl)-1H-indol-3-yl]-5-hydroxy-2,3-dihydro-1H-isoindol-1-one (160 mg; 487 μmol) and MnO$_2$ (480.8 mg; 4.867 mmol) are suspended in DMF (2 mL) and stirred for 2 h. The reaction mixture is treated again with MnO$_2$ (480.8 mg; 4.867 mmol) and stirred for additional 2 h, filtered and washed with DMF and ACN. The crude mixture is concentrated under reduced pressure and purified by preparative RP-HPLC using a ACN/water gradient (15-90%, acidic conditions) as eluent to give 5-chloro-3-(6-hydroxy-3-oxo-2,3-dihydro-1H-isoindol-1-yl)-1H-indole-2-carbaldehyde (126 mg; 386 μmol; 79.2%). HPLC method: LCMSBAS1: [M+H]$^+$=327; $t_{ret}$ [min]=0.69 min.

Experimental Procedure for the Synthesis of (5-fluoro-1H-indol-2-yl)-methanol

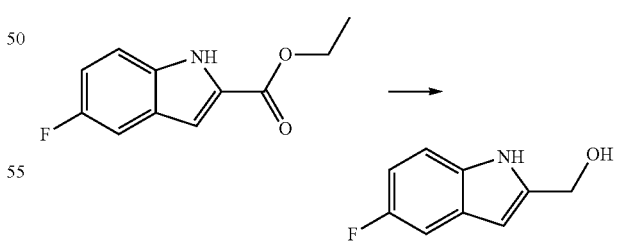

To a stirred solution of LAH (440 mg; 11,583 mmol) in THF (20 mL) at 0° C. was added ethyl 5-fluoro-1H-indole-2-carboxylate (2.0 g; 9,652 mmol; commercial available from Fischer Scientific) in THF. The reaction mixture is stirred at room temperature for 4 h. The reaction is quenched by addition of a saturated sodium sulphate solution and extracted with EtOAc. The organic phase is dried over Na$_2$SO$_4$, filtered and concentrated under reduced pressure to yield (5-fluoro-1H-indol-2-yl)-methanol (1.55 g; 9.385 mmol; 97.2%) which is used in the next reaction without any further purification.

Experimental Procedure for the Synthesis of 3-[5-fluoro-2-(hydroxymethyl)-1H-indol-3-yl]-5-hydroxy-2,3-dihydro-1H-isoindol-1-one

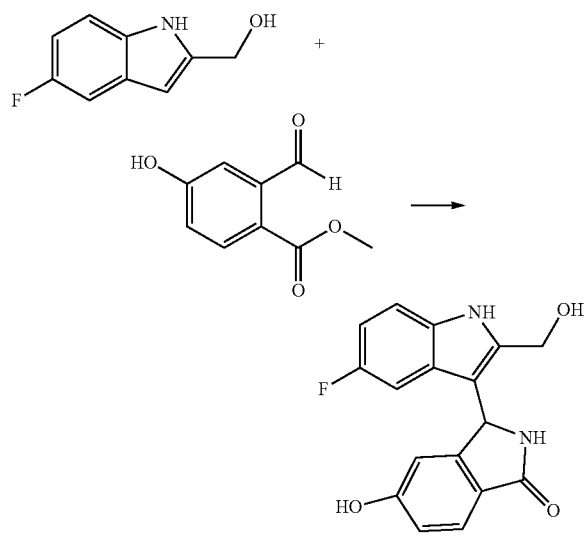

A suspension of (5-fluoro-1H-indol-2-yl)-methanol (550 mg; 3.33 mmol) and methyl 2-formyl-4-hydroxybenzoate (500 mg; 2.775 mmol) in THF (0.5 mL) are treated with an excess ammonia solution and heated at 90° C. for 16 h. The reaction mixture is concentrated under reduced pressure and the residue is purified by flash chromatography on SiO₂ using EtOAc/MeOH (90:10) as eluent to give 3-[5-fluoro-2-(hydroxymethyl)-1H-indol-3-yl]-5-hydroxy-2,3-dihydro-1H-isoindol-1-one.

Experimental Procedure for the Synthesis of 5-fluoro-3-(6-hydroxy-3-oxo-2,3-dihydro-1H-isoindol-1-yl)-1H-indole-2-carbaldehyde

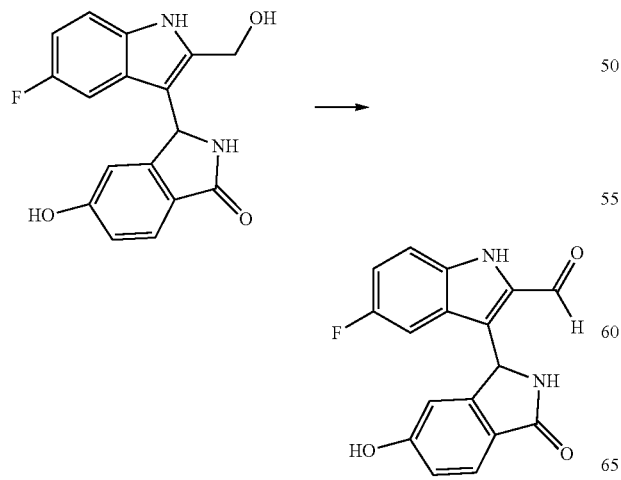

3-(5-Fluoro-2-hydroxymethyl-1H-indol-3-yl)-5-hydroxy-2,3-dihydro-isoindol-1-one (1.0 g; 3.202 mmol) and MnO₂ (1.949 g; 22.415 mmol) are suspended in acetone (10 mL) and stirred at 50° C. for 16 h. The reaction mixture is filtered and concentrated under reduced pressure. The crude mixture is purified by flash chromatography on SiO₂ using hexane/EtOAc (80:20) as eluent to give 5-fluoro-3-(6-hydroxy-3-oxo-2,3-dihydro-1H-isoindol-1-yl)-1H-indole-2-carbaldehyde (900 mg; 2.901 mmol; 90.6%).

Experimental Procedure for the Synthesis of (6-fluoro-1H-indol-2-yl)-methanol

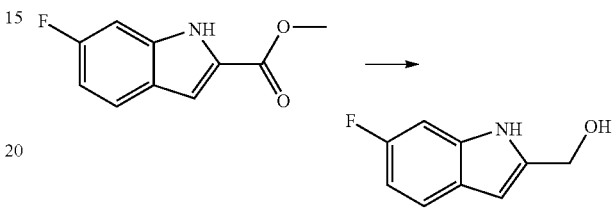

In a 100 mL round-bottom flask methyl 6-fluoro-1H-indole-2-carboxylate (250 mg; 1.229 mmol) is taken up in dry THF (20 mL) and cooled to 0° C. in an ice-bath. Then LAH (737.68 µl; 1.475 mmol) is added dropwise and the mixture is stirred at 0° C. for 2 h. The reaction mixture is cautiously quenched with water, acidified with some drops of 4N HCl and extracted with DCM twice. The combined organic layers are concentrated under reduced pressure. The residue is dissolved in ACN/H₂O, filtered through a syringe filter and purified via prep. RP-HPLC (Gilson; column: SunFire Prep C18, 10 µm (50*150), gradient: ACN/water, basic conditions, 10-70% ACN in 9 min. flowrate: 150 mL/min wavelength: 218 nm). The product containing fractions are pooled and freeze dried to yield (6-fluoro-1H-indol-2-yl)-methanol (175 mg; 1.06 mmol; 86.2%). HPLC method: LCMSBAS1: [M+H]⁺=166; $t_{ret}$ [min]=0.87 min.

Experimental Procedure for the Synthesis of 3-(6-fluoro-2-hydroxymethyl-1H-indol-3-yl)-5-hydroxy-2,3-dihydro-isoindol-1-one

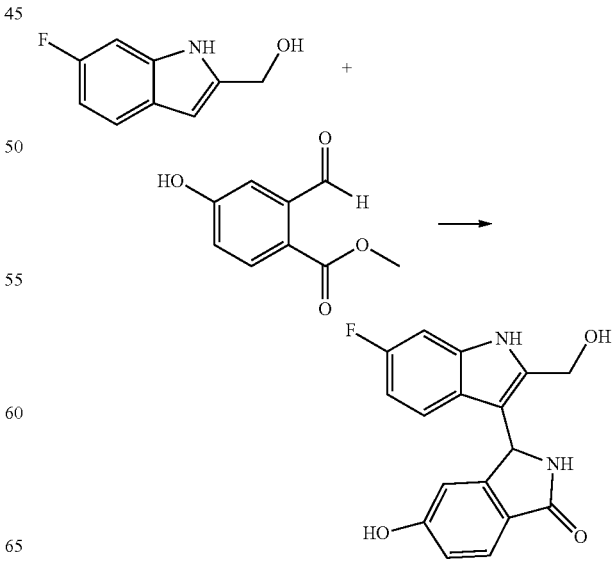

In a 5 mL microwave-tube (6-fluoro-1H-indol-2-yl)-methanol (170 mg; 926 µmol), methyl 2-formyl-4-hydroxybenzoate (202.3 mg; 1.112 mmol) and ammonia solution 28% (1.32 ml; 9.263 mmol) are suspended in water (1.7 mL), the vial is capped and the mixture is stirred at 85° C. overnight. The reaction mixture is diluted with ACN and some DMF to completely dissolve the precipitated solid. The mixture is filtered through a syringe filter and purified via prep. RP-HPLC (Gilson; column: SunFire Prep C18, 10 µm (50*150), gradient: ACN/water (acidic condition, 5-60% ACN in 9 min. flowrate: 150 mL/min wavelength: 215 nm). The product containing fractions are pooled and freeze dried and the remaining staring material is re-isolated. The reaction yielded 3-(6-fluoro-2-hydroxymethyl-1H-indol-3-yl)-5-hydroxy-2,3-dihydro-isoindol-1-one (165 mg; 528 µmol; 57%). HPLC method: LCMSBAS1: [M+H]+=313; $t_{ret}$ [min]=0.67 min.

Experimental Procedure for the Synthesis of 6-fluoro-3-(6-hydroxy-3-oxo-2,3-dihydro-1H-isoindol-1-yl)-1H-indole-2-carbaldehyde

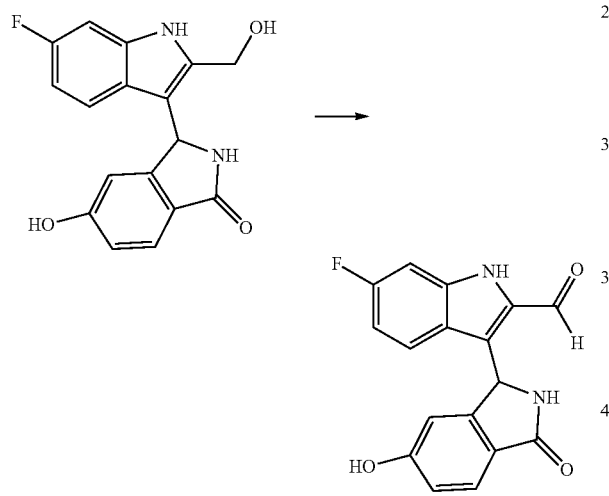

In a 100 mL round-bottom flask 3-(6-fluoro-2-hydroxymethyl-1H-indol-3-yl)-5-hydroxy-2,3-dihydro-isoindol-1-one (165 mg; 528 µmol) is dissolved in MeOH (5.0 mL) and manganese dioxide (510.4 mg; 5.283 mmol) is added. The reaction mixture is stirred at reflux for 2 h. The hot reaction mixture is filtered to remove the MnO₂ and washed with hot MeOH (3*15 mL). The filtrate is concentrated under reduced pressure. The yellow resin is dissolved in ACN/H₂O and freeze dried to yield 6-fluoro-3-(6-hydroxy-3-oxo-2,3-dihydro-1H-isoindol-1-yl)-1H-indole-2-carbaldehyde (148 mg; 477 µmol; 90.3%). HPLC method: LCMSBAS1: [M+H]+=311; $t_{ret}$ [min]=0.74 min.

Experimental Procedure for the Synthesis of (5,6-difluoro-1H-indol-2-yl)methanol

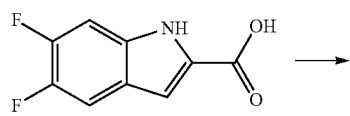

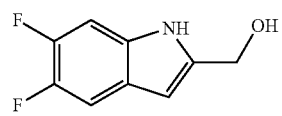

In a 100 mL round-bottom flask 5,6-difluoro-1H-indole-2-carboxylic acid (250 mg; 1.229 mmol; commercial available from CombiBlocks) is taken up in THF (5 mL) and CDI (452 mg; 1.911 mmol) is added. The reaction mixture is heated to 50° C. for 1 h and then cooled down to room temperature. An aqueous solution of NaBH₄ (288 mg in 2 mL water; 7.609 mmol) is added slowly and the reaction mixture is stirred at room temperature for 16 h. The reaction mixture is diluted with water and extracted with EtOAc. The organic phase was washed with brine, dried over MgSO₄, filtered and concentrated under reduced pressure. The residue is purified over silica gel. The product containing fractions are pooled and concentrated under reduced pressure to yield (5,6-difluoro-1H-indol-2-yl)methanol (350 mg; 1.911 mmol; 75.3%).

Experimental Procedure for the Synthesis of 3-[5,6-difluoro-2-(hydroxymethyl)-1H-indol-3-yl]-5-hydroxy-2,3-dihydro-1H-isoindol-1-one

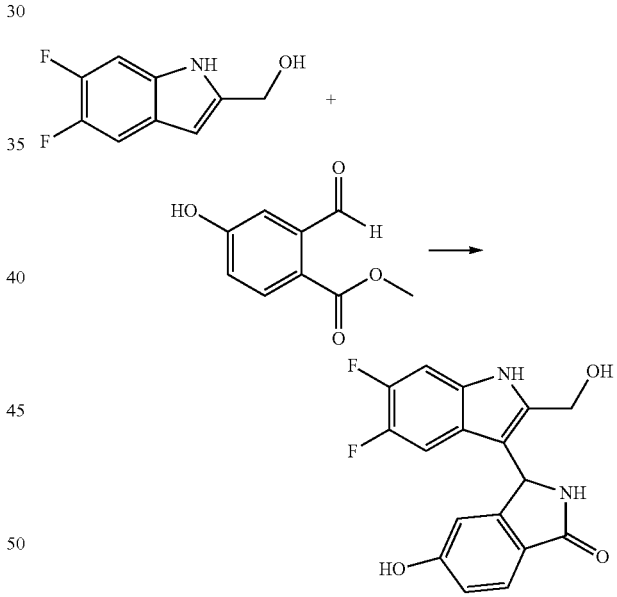

To a suspension of methyl 2-formyl-4-hydroxybenzoate (450 mg; 2.498 mmol) and (5,6-difluoro-1H-indol-2-yl)methanol (503 mg; 2.748 mmol) in water (5 mL) and THF (0.5 mL) was added a 7N ammonium hydroxide solution (3.891 mL; 24.978 mmol) in a sealed tube. The reaction mixture was heated to 85° C. for 16 h. The reaction mixture was extracted with 20% THF/EtOAc and the mixture is concentrated under reduced pressure. The crude product is purified by flash chromatography on SiO₂ using DCM/MeOH (90:10) as eluent. The product containing fractions are concentrated and freeze dried to yield 3-[5,6-difluoro-2-(hydroxymethyl)-1H-indol-3-yl]-5-hydroxy-2,3-dihydro-1H-isoindol-1-one (450 mg; 1.362 mmol; 54.5%).

Experimental Procedure for the Synthesis of 5,6-difluoro-3-(6-hydroxy-3-oxo-2,3-dihydro-1H-isoindol-1-yl)-1H-indole-2-carbaldehyde

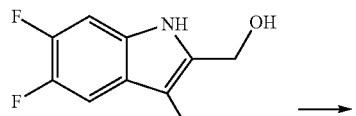

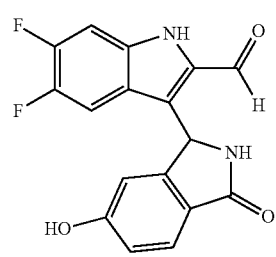

3-[5,6-difluoro-2-(hydroxymethyl)-1H-indol-3-yl]-5-hydroxy-2,3-dihydro-1H-isoindol-1-one (450 mg; 1.362 mmol) is dissolved in MeOH (10 mL) and manganese dioxide (947.6 mg; 10.9 mmol) is added. The reaction mixture is stirred at 50° C. for 16 h. The hot reaction mixture is filtered through a pad of celite to remove the MnO$_2$ and washed with hot MeOH. The filtrate is concentrated under reduced pressure to yield 5,6-difluoro-3-(6-hydroxy-3-oxo-2,3-dihydro-1H-isoindol-1-yl)-1H-indole-2-carbaldehyde (400 mg; 1.219 mmol; 89.4%), which is directly used without further purification in the next step.

Experimental Procedure for the Synthesis of 5- and 6-bromo-3-hydroxy-3-methyl-2,3-dihydro-1H-isoindol-1-one

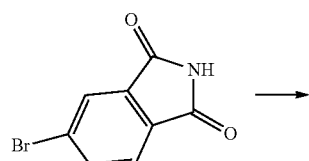

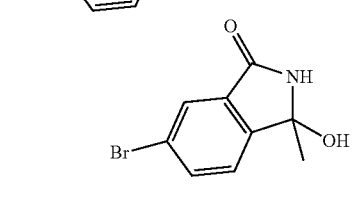

To a suspension of 4-bromophthalimide (1.0 g; 4.424 mmol; commercial available from Enamine) in DCM (70 mL) at 0° C. is added methylmagnesium bromide (3M solution in diethyl ether; 4.424 mL; 13.273 mmol) dropwise, stirred 3 h at 0° C. and at room temperature overnight. Reaction is carefully quenched with saturated NH$_4$Cl-solution and extracted with DCM (3×50 mL). The combined organic layers are dried over Na$_2$SO$_4$, filtered and concentrated under reduced pressure to yield 5- and 6-bromo-3-hydroxy-3-methyl-2,3-dihydro-1H-isoindol-1-one (1.05 g; 4.338 mmol; 98.0%). HPLC method: LCMSBAS1: [M+H]$^+$=224/242; t$_{ret}$ [min]=0.76 min.

Experimental Procedure for the Synthesis of 5- and 6-bromo-3-[2-(hydroxymethyl)-1H-indol-3-yl]-3-methyl-2,3-dihydro-1H-isoindol-1-one

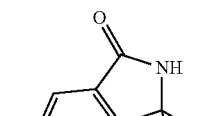

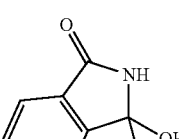

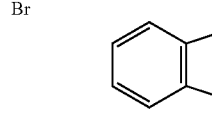

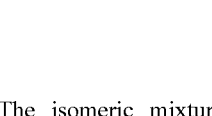

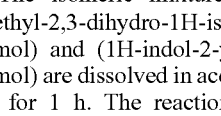

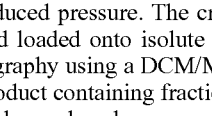

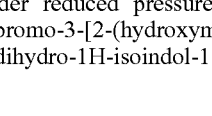

The isomeric mixture 5- and 6-Bromo-3-hydroxy-3-methyl-2,3-dihydro-1H-isoindol-1-one (555 mg; 2.293 mmol) and (1H-indol-2-yl)methanol (374.923 mg; 2.293 mmol) are dissolved in acetic acid (10 mL) and stirred at 70° C. for 1 h. The reaction mixture is concentrated under reduced pressure. The crude material is dissolved in DCM and loaded onto isolute and purified by silica gel chromatography using a DCM/MeOH gradient (0-5% MeOH). The product containing fractions are combined and concentrated under reduced pressure to yield both isomeres 5- and 6-bromo-3-[2-(hydroxymethyl)-1H-indol-3-yl]-3-methyl-2,3-dihydro-1H-isoindol-1-one (295 mg; 795 μmol; 34.7%).

Experimental Procedure for the Synthesis of 5-hydroxy-3-[2-(hydroxymethyl)-1H-indol-3-yl]-3-methyl-2,3-dihydro-1H-isoindol-1-one and 6-hydroxy-3-[2-(hydroxymethyl)-1H-indol-3-yl]-3-methyl-2,3-dihydro-1H-isoindol-1-one

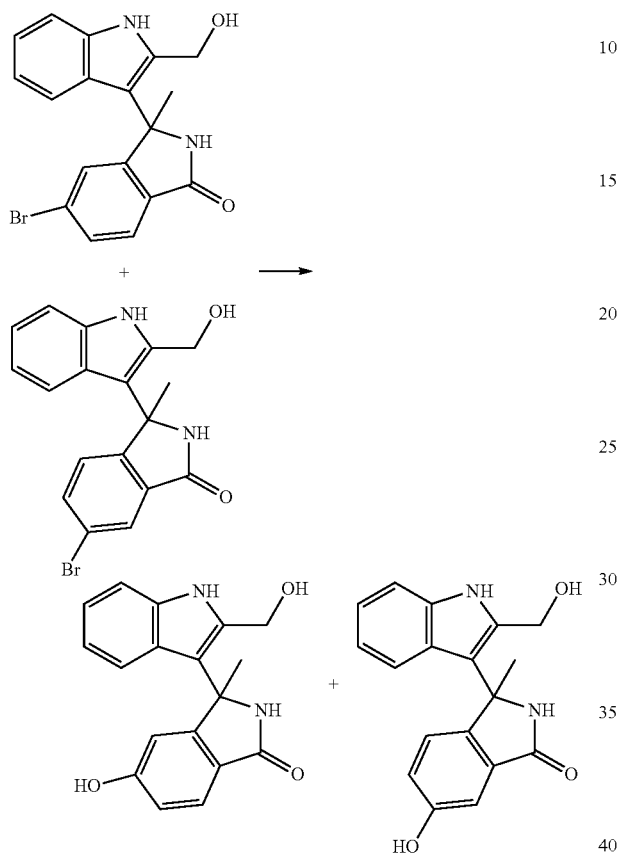

The isomeric mixture 5- and 6-bromo-3-[2-(hydroxymethyl)-1H-indol-3-yl]-3-methyl-2,3-dihydro-1H-isoindol-1-one (295 mg; 795 µmol), bis(pinacolato)diboron (242 mg; 954 µmol), potassium acetate (234 mg; 2.384 mmol) and 1,1'-bis(diphenylphosphino)ferrocenepalladium(II) dichloride DCM complex (66.9 mg; 79 µmol) are dissolved/suspended in dry dioxane (10 mL) and purged with argon. The reaction mixture is stirred at 80° C. for 2 h, then cooled to room temperature and hydrogen peroxide 30% water solution (0.5 mL; 4.410 mmol) is added and the reaction mixture is stirred for 20 min. Additional addition of hydrogen peroxide 30% water solution (0.5 mL; 4.410 mmol) and the reaction mixture is stirred for 20 min. To the reaction mixture saturated aqueous solution of $Na_2S_2O_3$ (1 mL) is added and stirred for 10 minutes. The reaction mixture is loaded onto isolute and purified by normal phase chromatography using a DCM/MeOH gradient (0-10% MeOH). The product containing fractions are concentrated under reduced pressure. No separation of isomeres. The isomeres are separated by prep. RP-HPLC (acidic condition). The product containing fractions are concentrated under reduced pressure to yield 5-hydroxy-3-[2-(hydroxymethyl)-1H-indol-3-yl]-3-methyl-2,3-dihydro-1H-isoindol-1-one (74 mg; 240 µmol; 30.2%; HPLC method: LCMSBAS1: $[M+H]^+=$309; $t_{ret}$ [min]=0.52 min) and 6-hydroxy-3-[2-(hydroxymethyl)-1H-indol-3-yl]-3-methyl-2,3-dihydro-1H-isoindol-1-one (67 mg; 217 µmol; 27.3%; HPLC method: LCMSBAS1: $[M+H]^+=$309; $t_{ret}$ [min]=0.82 min).

Experimental Procedure for the Synthesis of 3-(6-hydroxy-1-methyl-3-oxo-2,3-dihydro-1H-isoindol-1-yl)-1H-indole-2-carbaldehyde

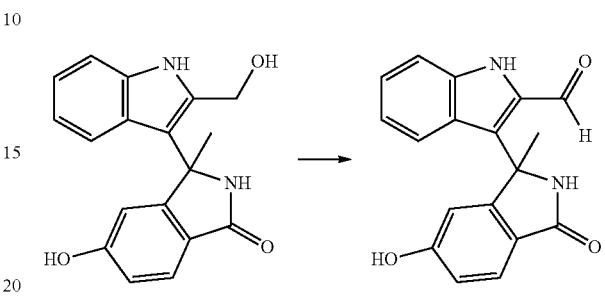

5-Hydroxy-3-[2-(hydroxymethyl)-1H-indol-3-yl]-3-methyl-2,3-dihydro-1H-isoindol-1-one (74 mg; 216 µmol) dissolved in DCM/MeOH (1:1, 10 mL). Then manganese dioxide (213.4 mg; 2.160 mmol) is added and the reaction mixture is stirred at room temperature overnight. The reaction mixture is filtered over a small celite pad and washed with some DCM, MeOH and DMF. The filtrate is concentrated under reduced pressure to yield 3-(6-hydroxy-1-methyl-3-oxo-2,3-dihydro-1H-isoindol-1-yl)-1H-indole-2-carbaldehyde (66 mg; 215 µmol; 99.8%) and used in the next reaction without further purification.

Experimental Procedure for the Synthesis of 5-methyl-6-nitro-2,3-dihydro-1H-isoindole-1,3-dione

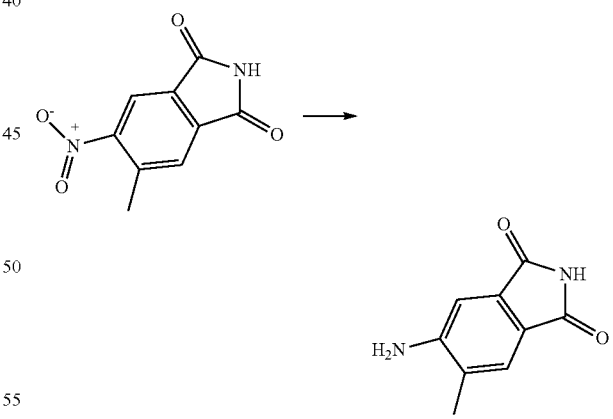

To a stirred solution of 5-methyl-6-nitro-isoindole-1,3-dione (100 mg; 0.485 mmol) in conc. HCl (2.5 mL), Tin(II) chloride dihydrate (350 mg; 1.551 mmol) was added and the reaction mixture was heated at 65° C. for 30 min. TLC analysis showed full conversion of starting material with formation of a new polar spot. The reaction mixture was cooled and the precipitated solid was filtered. It was slurried in water and filtered to yield a yellow solid which was dried in vacuum to yield 5-methyl-6-nitro-2,3-dihydro-1H-isoindole-1,3-dione (70 mg; 397 µmol; 81.9%).

Experimental Procedure for the Synthesis of 5-methyl-6-(4,4,5,5-tetramethyl-1,3,2-dioxaborolan-2-yl)-2,3-dihydro-1H-isoindole-1,3-dione

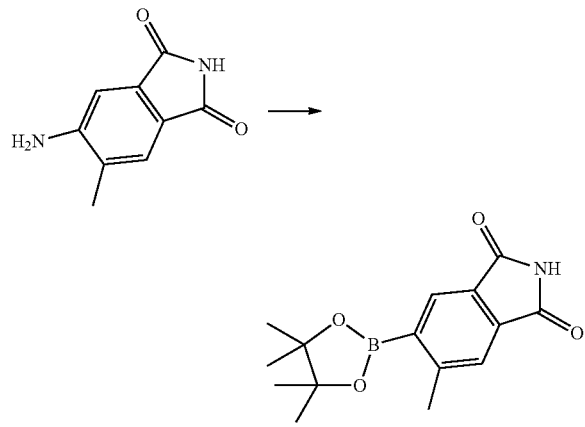

To a stirred solution of 5-Amino-6-methyl-isoindole-1,3-dione (200 mg; 1.135 mmol) and Bis(pinacolato)diboron (865 mg; 3.406 mmol) in ACN (5 mL), tert-Butyl nitrite (405 µL; 3.406 mmol) was added and the reaction mixture was heated at 80° C. for 6 h. TLC analysis showed full conversion of starting material with formation of a new polar spot. The volatiles were removed under reduced pressure to give 5-methyl-6-(4,4,5,5-tetramethyl-1,3,2-dioxaborolan-2-yl)-2,3-dihydro-1H-isoindole-1,3-dione as a brown oil (250 mg; 871 µmol; 76.7%).

Experimental Procedure for the Synthesis of 5-hydroxy-6-methyl-2,3-dihydro-1H-isoindole-1,3-dione

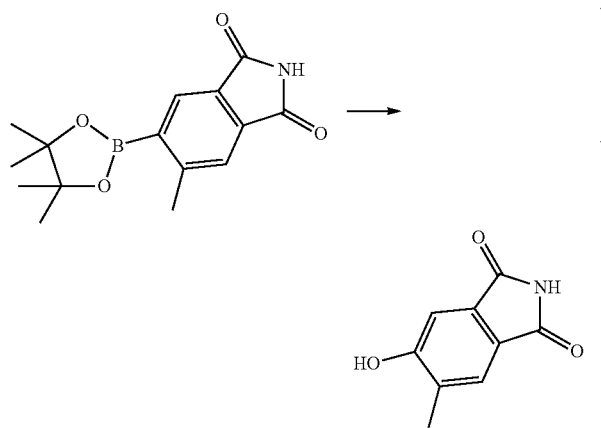

To a stirred solution of 5-Methyl-6-(4,4,5,5-tetramethyl-[1,3,2]dioxaborolan-2-yl)-isoindole-1,3-dione (250 mg; 871 µmol) in MeOH (1 mL):DCM (3 mL) mixture, 30% $H_2O_2$ in water (449 µL; 4.354 mmol) was added and the reaction mixture was stirred at rt for 16 h. TLC analysis showed full conversion of starting material with formation of a new non polar spot. The reaction mixture was diluted with DCM and washed with brine, dried over $Na_2SO_4$ and evaporated. The brown oil is purification by column chromatography over silica gel using EtOAc in hexane (15:85, v/v) as eluent yielding an off white solid of 5-hydroxy-6-methyl-2,3-dihydro-1H-isoindole-1,3-dione (100 mg; 564 µmol; 64.6%).

Experimental Procedure for the Synthesis of 5-amino-6-iodo-2,3-dihydro-1H-isoindole-1,3-dione

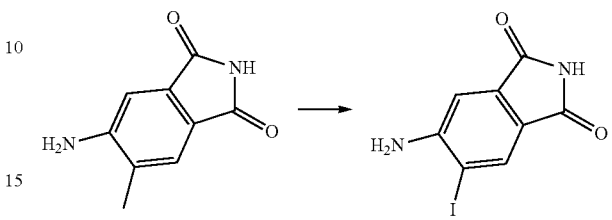

In a 20 mL microwave-tube 4-aminophthalimide (1.4 g; 8.634 mmol; commercial available from Acros) and N-iodosuccinimide (3.885 g; 17.286 mmol) are dissolved in DMF (15 mL) and stirred at 50° C. overnight. The reaction mixture is diluted with EtOAc, filtered and concentrated under reduced pressure. The residue is treated with ACN and the precipitate is filtered and dried to yield 5-amino-6-iodo-2,3-dihydro-1H-isoindole-1,3-dione (1.4 g; 3.645 mmol; 42.2%), which is used without further purification.

Experimental Procedure for the Synthesis of 5-amino-6-[2-(trimethylsilyl)ethynyl]-2,3-dihydro-1H-isoindole-1,3-dione

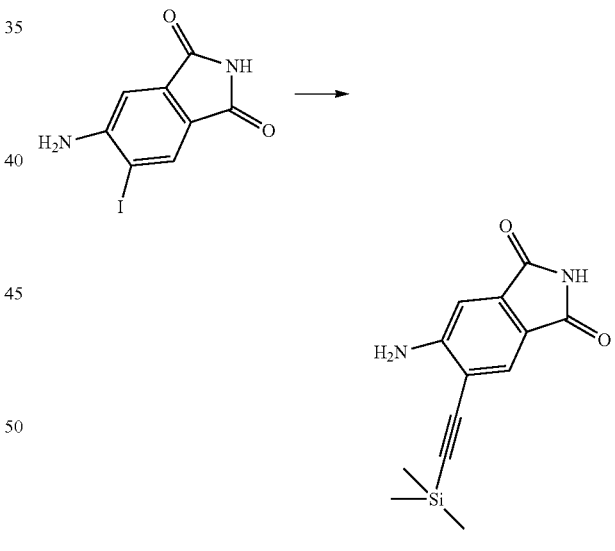

In a 20 mL microwave-tube 5-amino-6-iodo-2,3-dihydro-1H-isoindole-1,3-dione (400 mg; 1.042 mmol), bis(triphenylphosphine)palladium(II) chloride (39.536 mg; 55 µmol), copper(I) iodide (17.521 mg; 92 µmol), trimethylsilylacetylene (922 mg; 9.2 mmol) and TEA (382.6 µL; 2.76 mmol) are dissolved in THF (5 mL) and stirred at 90° C. for 4 h. For full conversion the same amount of reactants are added in three parts and the mixture is stirred in sum for 3 days at 90° C. The reaction mixture is diluted with EtOAc/water and a slight basic pH is adjusted by addition of $NaHCO_3$. The mixture is filtered and the separated organic phase is concentrated under reduced pressure. The residue is treated with DCM and the precipitate is filtered and dried to yield 5-amino-6-[2-(trimethylsilyl)ethynyl]-2,3-dihydro-1H-isoindole-1,3-dione (508 mg; 1.77 mmol; 96.2%), which is used without further purification.

Experimental Procedure for the Synthesis of 5-amino-3-{2-[(dimethylamino)methyl]-1H-indol-3-yl}-6-[2-(trimethylsilyl)ethynyl]-2,3-dihydro-1H-isoindol-1-one and 6-amino-3-{2-[(dimethylamino)methyl]-1H-indol-3-yl}-5-[2-(trimethylsilyl)ethynyl]-2,3-dihydro-1H-isoindol-1-one

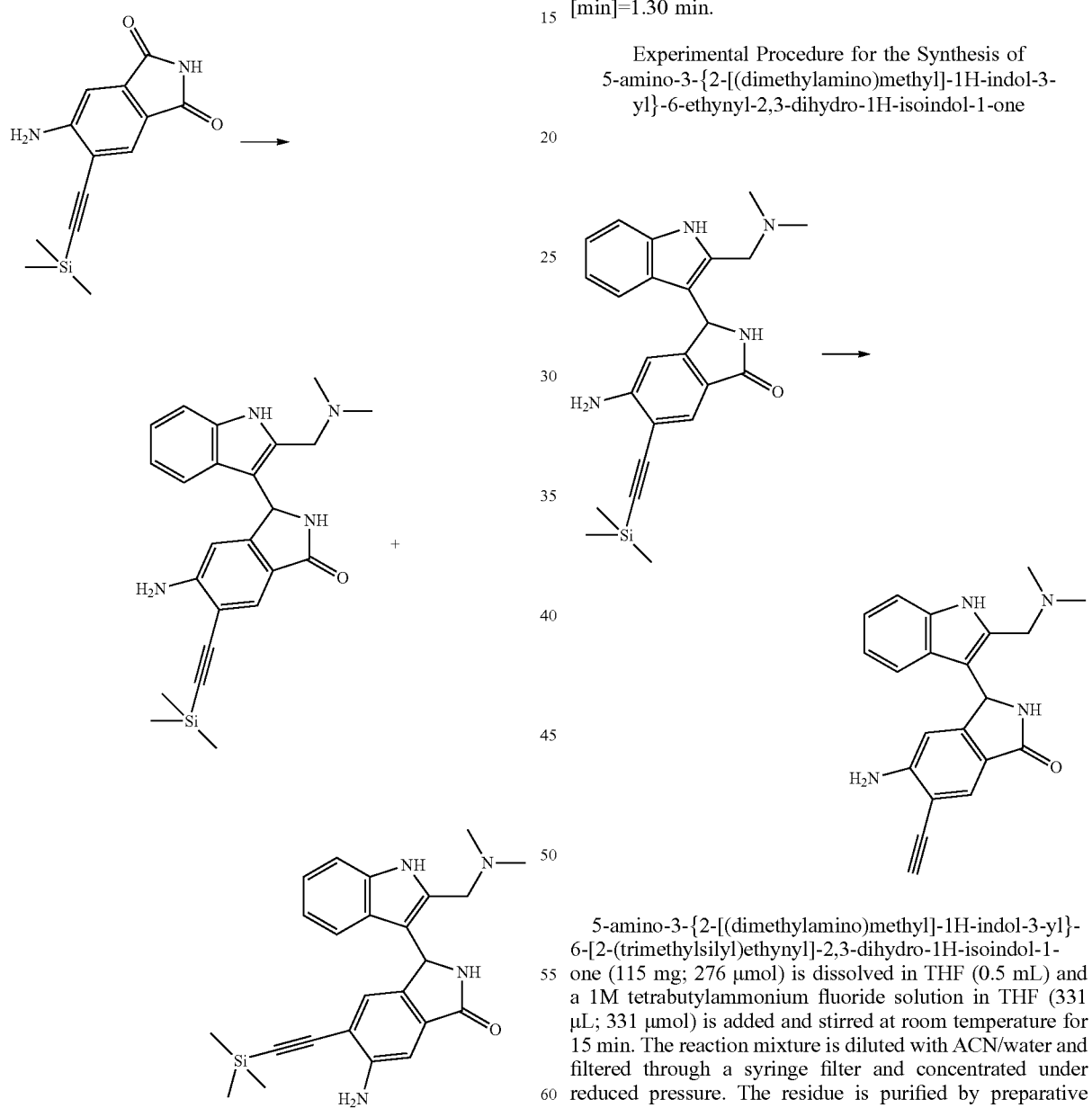

In a 5 mL microwave-tube 5-amino-6-[2-(trimethylsilyl)ethynyl]-2,3-dihydro-1H-isoindole-1,3-dione (508 mg; 1.77 mmol), [(1H-indol-2-yl)methyl]dimethylamine (308.36 mg; 1.77 mmol) and zinc (462.9 mg; 7.08 mmol) are dissolved in AcOH (2 mL) and stirred at 100° C. for 70 min. The reaction mixture is diluted with ACN/water and filtered through a syringe filter and concentrated under reduced pressure. The residue is purified by preparative RP-HPLC (10-60% ACN in water, basic conditions). The product containing fractions are combined, concentrated under reduced pressure and freeze dried to yield 5-amino-3-{2-[(dimethylamino)methyl]-1H-indol-3-yl}-6-[2-(trimethylsilyl)ethynyl]-2,3-dihydro-1H-isoindol-1-one (117 mg; 281 μmol; 15.9%) HPLC method: LCMSBAS1: $[M+H]^+$=417; $t_{ret}$ [min]=1.12 min and the regioisomer 6-amino-3-{2-[(dimethylamino)methyl]-1H-indol-3-yl}-5-[2-(trimethylsilyl)ethynyl]-2,3-dihydro-1H-isoindol-1-one (46 mg; 110 μmol; 6.2%). HPLC method: LCMSBAS1: $[M+H]^+$=417; $t_{ret}$ [min]=1.30 min.

Experimental Procedure for the Synthesis of 5-amino-3-{2-[(dimethylamino)methyl]-1H-indol-3-yl}-6-ethynyl-2,3-dihydro-1H-isoindol-1-one

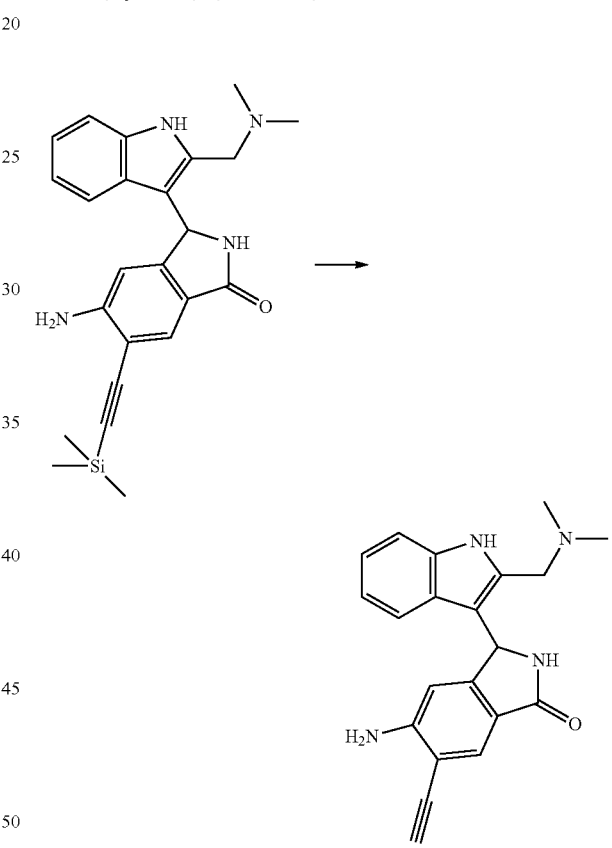

5-amino-3-{2-[(dimethylamino)methyl]-1H-indol-3-yl}-6-[2-(trimethylsilyl)ethynyl]-2,3-dihydro-1H-isoindol-1-one (115 mg; 276 μmol) is dissolved in THF (0.5 mL) and a 1M tetrabutylammonium fluoride solution in THF (331 μL; 331 μmol) is added and stirred at room temperature for 15 min. The reaction mixture is diluted with ACN/water and filtered through a syringe filter and concentrated under reduced pressure. The residue is purified by preparative RP-HPLC (5-60% ACN in water, basic conditions). The product containing fractions are combined, concentrated under reduced pressure and freeze dried to yield 5-amino-3-{2-[(dimethylamino)methyl]-1H-indol-3-yl}-6-ethynyl-2,3-dihydro-1H-isoindol-1-one (86 mg; 175 μmol; 63.3%). HPLC method: LCMSBAS1: $[M+H]^+$=345; $t_{ret}$ [min]=0.88 min.

Experimental Procedure for the Synthesis of 1H,5H,6H,7H-imidazo[4,5-f]isoindole-5,7-dione

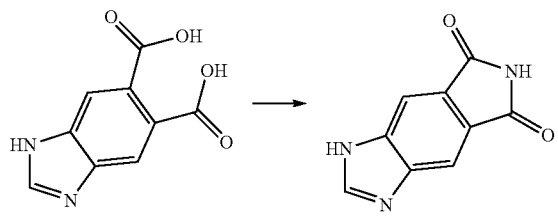 [SMILES: O=C(O)c1cc2nc[nH]c2cc1C(=O)O ; O=C1NC(=O)c2cc3[nH]cnc3cc21]

In a 20 mL microwave-tube benzimidazole-5,6-dicarboxylic acid (500 mg; 2.425 mmol; commercial available from Alfa), urea (145.66 mg; 2.425 mmol) and imidazole (166.78 mg; 2.425 mmol) are dissolved in DMF (10 mL) and heated in a microwave at 150° C. for 45 min. The reaction mixture is filtered and concentrated under reduced pressure to yield 1H,5H,6H,7H-imidazo[4,5-f]isoindole-5,7-dione (250 mg; 1.336 mmol; 55.1%), which is used without further purification. HPLC method: LCMSBAS1: $[M+H]^+$=188; $t_{ret}$ [min]=0.16 min.

Experimental Procedure for the Synthesis of 5,6-diamino-3-{2-[(dimethylamino)methyl]-1H-indol-3-yl}-2,3-dihydro-1H-isoindol-1-one

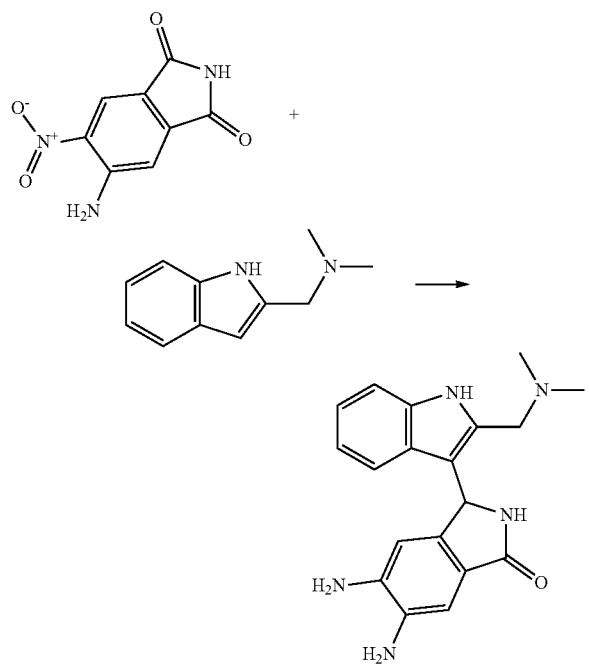

5-Amino-6-nitroisoindoline-1,3-dione (5.0 g; 24.138 mmol; commercial available from BroadPharm), [(1H-indol-2-yl)methyl]dimethylamine (4.206 g; 24.138 mmol) are dissolved in THF (100 mL). Zinc (6.313 g; 96.552 mmol) and conc. HCl (15 mL) are added and the reaction mixture is stirred at room temperature for 90 min. The reaction mixture is neutralized with 8N NaOH, filtered. The solid, which also contained product was suspended in water and re-acidified with 8N HCl, diluted with MeOH and filtered. The combined filtrates are concentrated under reduced pressure and purified twice by preparative RP-HPLC (ACN/water gradient, basic and acidic conditions). The product containing fractions are combined, concentrated under reduced pressure and freeze dried to yield 5,6-diamino-3-{2-[(dimethylamino)methyl]-1H-indol-3-yl}-2,3-dihydro-1H-isoindol-1-one (4.95 g; 14.758 mmol; 61.1%). HPLC method: LCMSBAS1: $[M+H]^+$=336; $t_{ret}$ [min]=0.66 min.

Experimental Procedure for the Synthesis of 5,6-diamino-2,3-dihydro-1H-isoindole-1,3-dione

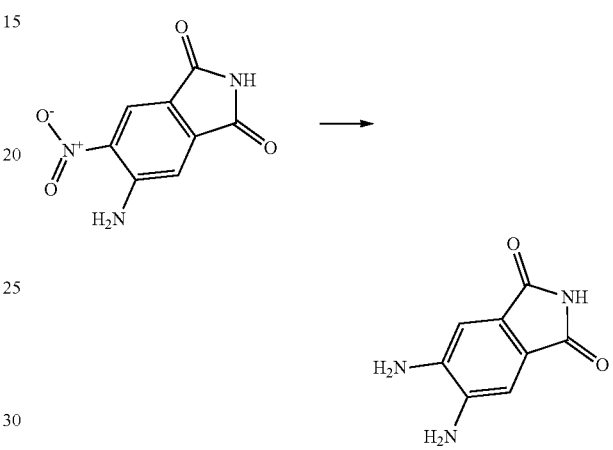

5-Amino-6-nitroisoindoline-1,3-dione (100 mg; 483 μmol; commercial available from BroadPharm) is dissolved in MeOH/DMF. Raney Ni is added and the reactor is pressurized at 6.5 bar with $H_2$. The reaction mixture is filtered and concentrated under reduced pressure to yield 5,6-diamino-2,3-dihydro-1H-isoindole-1,3-dione (25 mg; 141 μmol; 29.2%).

Experimental Procedure for the Synthesis of 1-acetyl-1H,5H,6H,7H-pyrrolo[3,4-f]indazole-5,7-dione

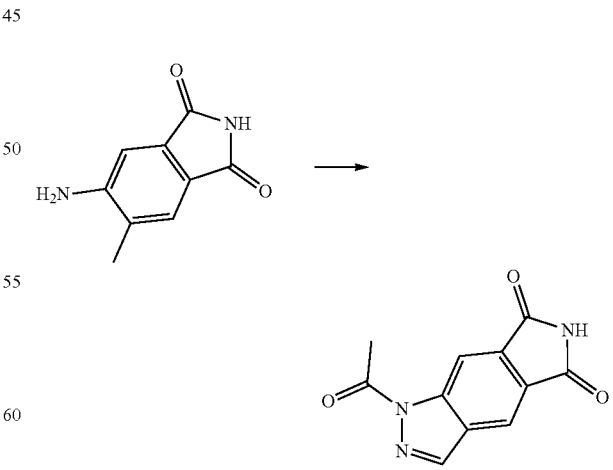

To a solution of 5-amino-6-methyl-isoindole-1,3-dione (1.0 g; 5.676 mmol; commercial available from ABCR), dissolved in $CHCl_3$ (15 mL) is added iso amyl nitrite (1.721 g; 12.488 mmol), acetic anhydride (1.738 g; 17.029 mmol), potassium acetate (1.114 g; 11.353 mmol) and 18-crown-6 ether (0.75 g; 2.838 mmol). The reaction mixture is stirred at 65° C. for 2 h, filtered, washed with DCM and concentrated under reduced pressure. The crude product 1-acetyl-1H,5H,6H,7H-pyrrolo[3,4-f]indazole-5,7-dione is directly used in the next deprotection step.

Experimental Procedure for the Synthesis of 1H,5H,6H,7H-pyrrolo[3,4-f]indazole-5,7-dione

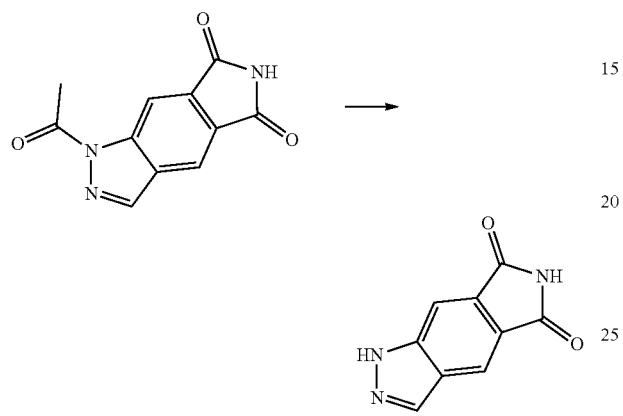

To a solution of the crude 1-acetyl-1H,5H,6H,7H-pyrrolo[3,4-f]indazole-5,7-dione (1.3 g; 5.672 mmol), dissolved in MeOH (15 mL) is added potassium carbonate (1.176 g; 8.508 mmol) and the reaction mixture is stirred at 60° C. for 30 min. Water (25 mL) is added to the reaction mixture and stirred for 1 h at room temperature. The precipitate is filtrated, washed with water and dried at 50° C. to yield 1H,5H,6H,7H-pyrrolo[3,4-f]indazole-5,7-dione (825 mg; 4.408 mmol; 77.7%).

Experimental Procedure for the Synthesis of (7-nitro-1H-indol-2-yl)methanol

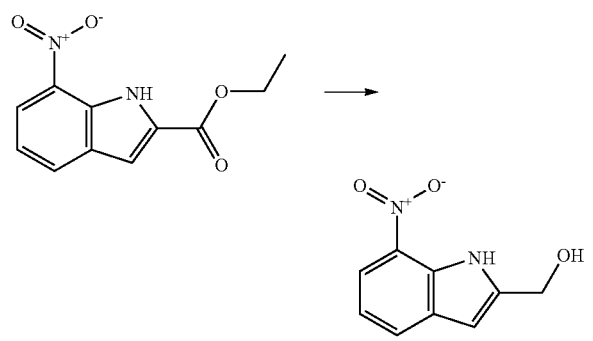

To a solution of ethyl 7-nitroindole-2-carboxylate (100 mg; 427 µmol; commercial available from ABCR), dissolved in dry THF (1 mL) is added dropwise at 0° C. a 1M DIBAH in THF solution (521.4 µL, 512.4 µmol) and the reaction mixture is stirred for 2 h. Reaction control showed only 50% conversion. Therefore another equivalent DIBAH (521.4 µL, 512.4 µmol) is added and the reaction mixture was stirred for 15 min. The reaction mixture is then quenched by careful addition of water and extracted with DCM, dried and concentrated under reduced pressure. The crude product (7-nitro-1H-indol-2-yl)methanol (68 mg; 354 µmol; 82.9%) is directly used in the next step. HPLC method: LCMSBAS1: [M+H]$^+$=193; $t_{ret}$ [min]=0.79 min.

Experimental Procedure for the Synthesis of 5-hydroxy-3-[2-(hydroxymethyl)-7-nitro-1H-indol-3-yl]-2,3-dihydro-1H-isoindol-1-one

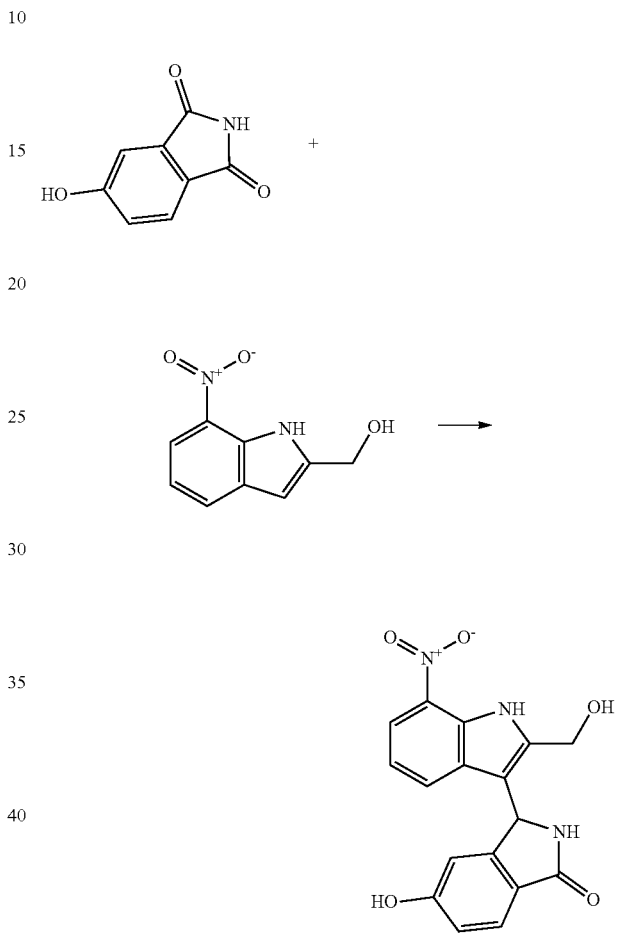

A suspension of 5-hydroxyisoindolinone-1,3-dione (300 mg; 1.839 mmol; commercial available from ArkPharm) and zinc (722 mg; 11.034 mmol) in AcOH (10 mL) is heated to 110° C. for 25 min. The hot reaction mixture is filtered and added to a solution of (7-nitro-1H-indol-2-yl)methanol (283 mg; 1.471 mmol) in AcOH (5 mL). The resolution reaction mixture is heated to 110° C. for 1 h. The reaction mixture is concentrated under reduced pressure and purified by flash chromatography over $SiO_2$ with 10% MeOH in DCM as eluent to yield 5-hydroxy-3-[2-(hydroxymethyl)-7-nitro-1H-indol-3-yl]-2,3-dihydro-1H-isoindol-1-one (as a mixture of regioisomers) (204 mg; 601 µmol; 32.7%).

The pure enantiomers were obtained through chiral separation via chiral SFC. Starting from 5-hydroxy-3-[2-(hydroxymethyl)-7-nitro-1H-indol-3-yl]-2,3-dihydro-1H-isoindol-1-one (300 mg; 884 µmol) the chiral separation resulted in (3S)-5-hydroxy-3-[2-(hydroxymethyl)-7-nitro-1H-indol-3-yl]-2,3-dihydro-1H-isoindol-1-one (61 mg; 180 µmol; 20.3%) and (3R)-5-hydroxy-3-[2-(hydroxymethyl)-7-nitro-1H-indol-3-yl]-2,3-dihydro-1H-isoindol-1-one (70 mg; 206 µmol; 23.3%).

Experimental Procedure for the Synthesis of 3-(6-hydroxy-3-oxo-2,3-dihydro-1H-isoindol-1-yl)-7-nitro-1H-indole-2-carbaldehyde

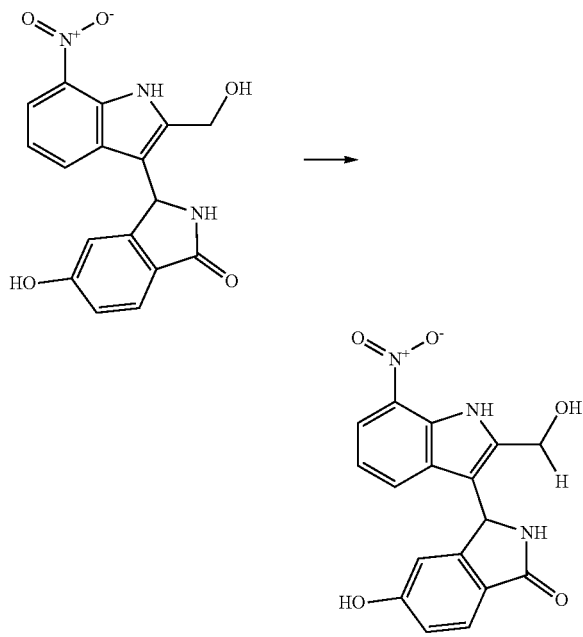

To a solution of 5-hydroxy-3-[2-(hydroxymethyl)-7-nitro-1H-indol-3-yl]-2,3-dihydro-1H-isoindol-1-one (mixture of regioisomers) (70 mg; 206 μmol) in MeOH (20 mL) is added MnO₂ (203.8 mg; 2.063 mmol) and the mixture is stirred at room temperature for 3 h. The reaction mixture is filtered and the filter is washed with MeOH. The filtrate is concentrated under reduced pressure. The crude material is purified by flash chromatography over SiO₂ with 0-10% MeOH in DCM gradient as eluent to yield 3-(6-hydroxy-3-oxo-2,3-dihydro-1H-isoindol-1-yl)-7-nitro-1H-indole-2-carbaldehyde (still a mixture of regioisomers) (65 mg; 193 μmol; 93.4%).

Experimental Procedure for the Synthesis of 3-{2-[(dimethylamino)methyl]-7-nitro-1H-indol-3-yl}-5-hydroxy-2,3-dihydro-1H-isoindol-1-one and 3-{2-[(dimethylamino)methyl]-7-nitro-1H-indol-3-yl}-6-hydroxy-2,3-dihydro-1H-isoindol-1-one

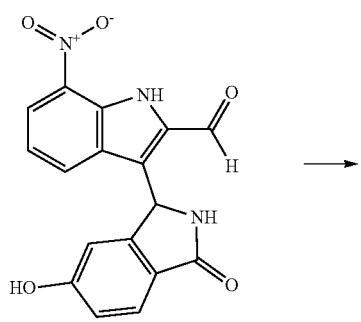

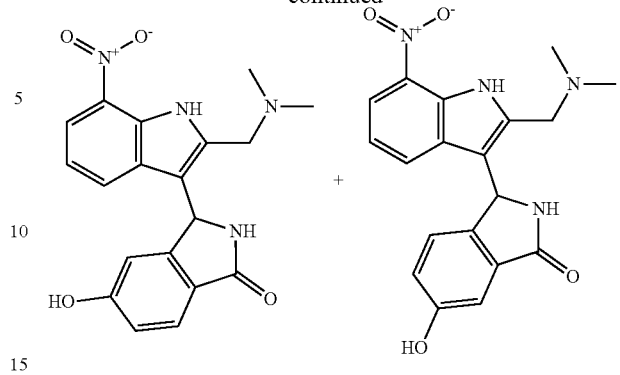

To a solution of 3-(6-hydroxy-3-oxo-2,3-dihydro-1H-isoindol-1-yl)-7-nitro-1H-indole-2-carbaldehyde (mixture of regioisomers) (65 mg; 193 μmol) in THF (5 mL) is added 2M dimethylamine solution in THF (300 μL; 600 μmol) and the mixture is stirred at room temperature for 15 min before sodium triacetoxyborohydride (100 mg; 458 μmol) is added and the reaction mixture is stirred at room temperature overnight. The reaction mixture is concentrated under reduced pressure and the residue is purified twice by flash chromatography over SiO₂ with MeOH/DCM as eluent to yield the two regioisomers 3-{2-[(dimethylamino)methyl]-7-nitro-1H-indol-3-yl}-5-hydroxy-2,3-dihydro-1H-isoindol-1-one (30 mg; 82 μmol; 42.2%) and 3-{2-[(dimethylamino)methyl]-7-nitro-1H-indol-3-yl}-6-hydroxy-2,3-dihydro-1H-isoindol-1-one (13 mg; 35 μmol; 18.3%).

Experimental Procedure for the Synthesis of 7-nitro-1H-indole-2-carbaldehyde

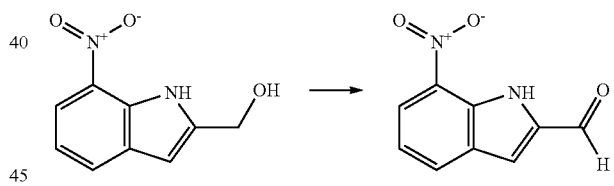

To a solution of (7-nitro-1H-indol-2-yl)methanol (68 mg; 354 μmol) in MeOH is added MnO₂ (362.1 mg; 3.54 mmol) and the mixture is stirred at reflux for 1 h. The reaction mixture is filtered as hot solution and the filter is washed with MeOH. The filtrate is concentrated under reduced pressure to yield 7-nitro-1H-indole-2-carbaldehyde (67.3 mg; 354 μmol; 100%).

Experimental Procedure for the Synthesis of dimethyl[(7-nitro-1H-indol-2-yl)methyl]amine

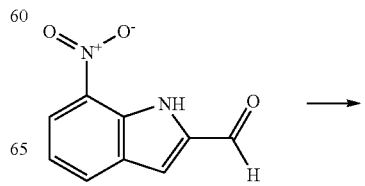

-continued

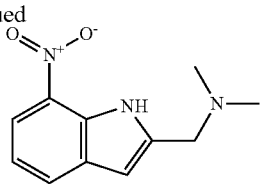

To a solution of 7-nitro-1H-indole-2-carbaldehyde (100 mg; 526 µmol) in THF (10 mL) is added dimethylamine (789 µL; 2M solution in THF; 1.578 mmol) and the mixture is stirred at room temperature for 15 min before sodium triacetoxyborohydride (287.26 mg; 1.315 mmol) is added and the mixture is stirred at room temperature overnight. The reaction mixture concentrated under reduced pressure, dissolved in DCM/MeOH and purified over SiO$_2$. The product containing fractions are pooled and concentrated under reduced pressure to yield dimethyl[(7-nitro-1H-indol-2-yl)methyl]amine (104 mg; 474 µmol; 90.2%).

Experimental Procedure for the Synthesis of 3-{2-[(dimethylamino)methyl]-7-nitro-1H-indol-3-yl}-5-hydroxy-1,3-dihydro-2-benzofuran-1-one

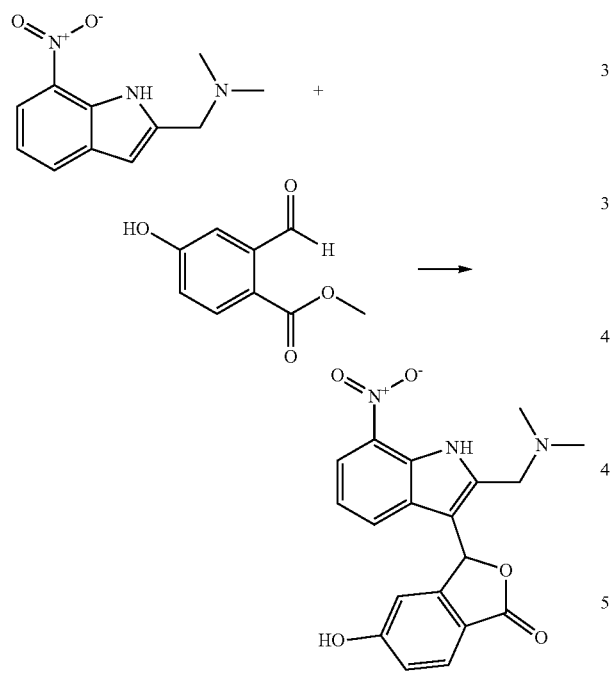

A suspension of dimethyl[(7-nitro-1H-indol-2-yl)methyl]amine (100 mg; 411 µmol) and methyl 2-formyl-4-hydroxybenzoate (74.7 mg; 411 µmol) in water (4 mL) and conc. HCl (2 mL) is stirred at 80° C. overnight resulting in 50% conversion. The reaction mixture is concentrated under reduced pressure and the residue is taken up in water (4 mL) and conc. HCl (2 mL) and stirred at 80° C. for additional 7 h. The reaction mixture after cooled down to room temperature is filtered and washed with a small amount of water. The product is dissolved in MeOH and concentrated under reduced pressure to yield 3-{2-[(dimethylamino)methyl]-7-nitro-1H-indol-3-yl}-5-hydroxy-1,3-dihydro-2-benzofuran-1-one (100 mg; 272 µmol; 66.3%).

Experimental procedure for the synthesis of 5-amino-3-hydroxy-2,3-dihydro-1H-isoindol-1-one

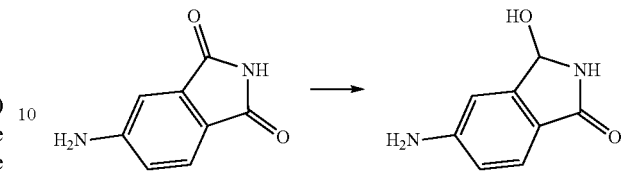

4-Amino-phthalimide (2.0 g; 12.335 mmol; commercial available from Acros) is suspended in MeOH (55 mL). Sodium borohydride (826 mg; 21.4 mmol) is added in three portions and the reaction mixture is stirred at room temperature overnight. The reaction mixture is quenched by addition of water and washed with EtOAc. The product containing water phase is freeze dried and the residue is dissolved in water/ACN (15:1; 16 mL). The precipitate is filtered off and the filtrate is purified by RP-HPLC-MS (0-30% ACN/water gradient; acidic condition). The product containing fractions are pooled and freeze dried to yield 5-amino-3-hydroxy-2,3-dihydro-1H-isoindol-1-one (230 mg; 1.4 mmol; 11.4%).

Experimental Procedure for the Synthesis of 5-amino-3-[2-(hydroxymethyl)-1H-indol-3-yl]-2,3-dihydro-1H-isoindol-1-one

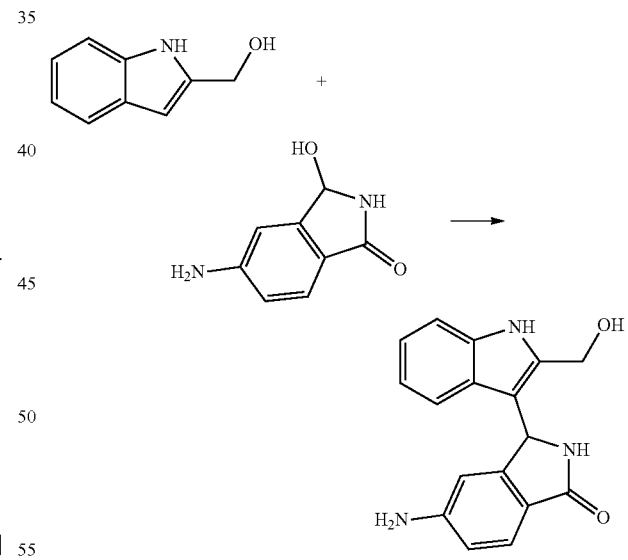

A solution of (1H-indol-2-yl)methanol (151.4 mg; 629 µmol; commercial from Aldrich) and 5-amino-3-hydroxy-2,3-dihydro-1H-isoindol-1-one (76 mg; 463 µmol) in AcOH (2 mL) and heated at 70° C. for 1 h. The reaction mixture is concentrated under reduced pressure and purified by preparative RP-HPLC (ACN/water gradient, acidic condition). The product containing fractions are pooled and freeze dried to give 5-amino-3-[2-(hydroxymethyl)-1H-indol-3-yl]-2,3-dihydro-1H-isoindol-1-one (55.6 mg; 190 µmol; 40.9%). HPLC method: LCMSBAS1: $t_{ret}$ [min]=0.46; [M+H]$^+$=294.

Experimental Procedure for the Synthesis of 3-(6-amino-3-oxo-2,3-dihydro-1H-isoindol-1-yl)-1H-indole-2-carbaldehyde

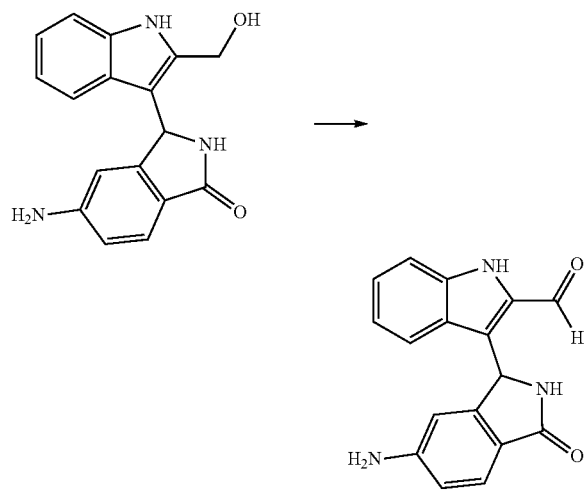

To a solution of 5-amino-3-[2-(hydroxymethyl)-1H-indol-3-yl]-2,3-dihydro-1H-isoindol-1-one (50 mg; 90%; 153 µmol) in dry DCM (3 mL) is added MnO$_2$ (151.6 mg; 88%; 1.534 mmol) and stirred at room temperature for 20 h. The reaction mixture is filtered and concentrated under reduced pressure. The crude product is purified by chromatography over silica gel (MeOH/DCM gradient, 0-5% MeOH). The product containing fractions are pooled and concentrated under reduced pressure to yield 3-(6-amino-3-oxo-2,3-dihydro-1H-isoindol-1-yl)-1H-indole-2-carbaldehyde (25 mg; 86 µmol; 55.9%).

Experimental Procedure for the Synthesis of 2-[(pyrrolidin-1-yl)methyl]-1H-indole

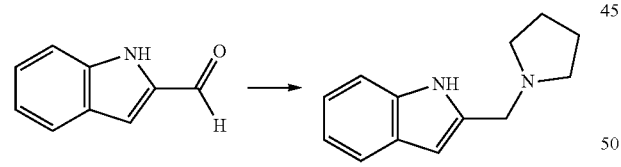

1H-indole-2-carbaldehyde (200 mg; 1.378 mmol; commercial available from ABCR) and pyrrolidine (117.6 mg; 1.653 mmol) are dissolved in AcOH (1.5 mL). After 10 min stirring at room temperature sodium triacetoxyborohydride (876 mg; 4.13 mmol) is added and the reaction mixture is stirred at room temperature for 1 h. The reaction mixture is diluted with EtOAc and washed with a saturated NaHCO$_3$ solution and brine. The organic phase concentrated under reduced pressure purified by RP-HPLC (ACN/water gradient; acidic condition). The product containing fractions are pooled and freeze dried to yield 2-[(pyrrolidin-1-yl)methyl]-1H-indole (200 mg; 999 µmol; 72.5%). HPLC method: LCMSBAS1: [M–H]$^+$=201; $t_{ret}$ [min]=1.14 min.

Experimental Procedure for the Synthesis of 5-amino-3-{2-[(pyrrolidin-1-yl)methyl]-1H-indol-3-yl}-2,3-dihydro-1H-isoindol-1-one and 6-amino-3-{2-[(pyrrolidin-1-yl)methyl]-1H-indol-3-yl}-2,3-dihydro-1H-isoindol-1-one

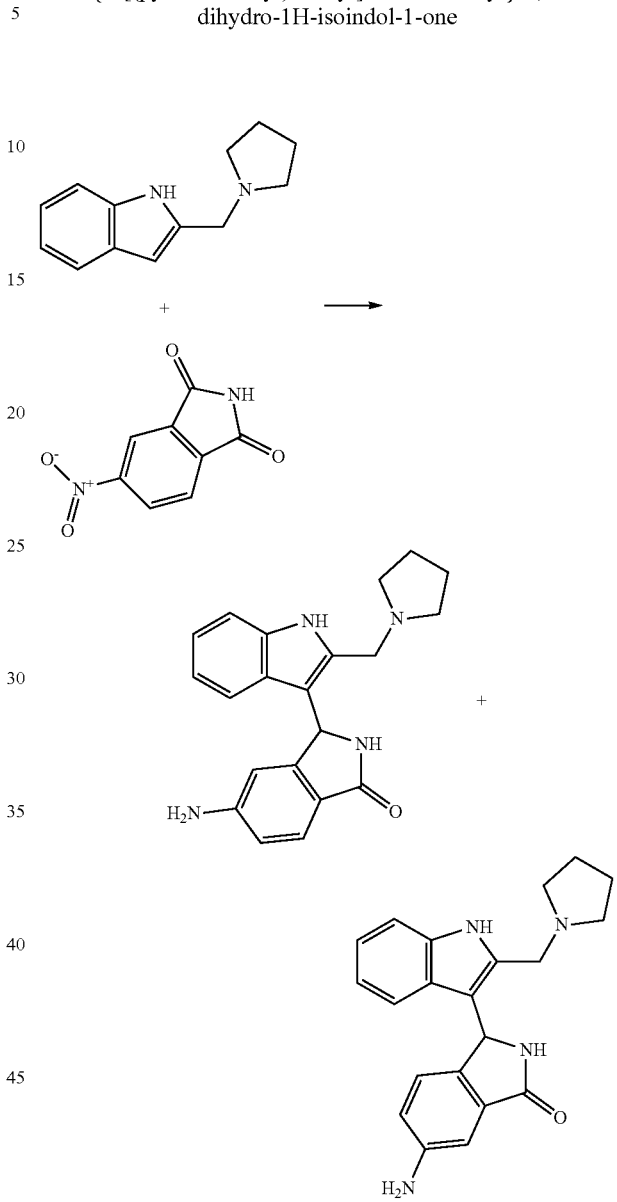

A suspension of 2-[(pyrrolidin-1-yl)methyl]-1H-indole (860 mg; 4.294 mmol), 4-nitrophthalimide (1.3925 g; 8.588 mmol; commercial available from Alfa) and zinc (1.403 g; 21.47 mmol) in THF (10 mL). Conc. HCl (3 mL) is added and the reaction mixture stirred at room temperature. The resolution reaction mixture is filtered, concentrated under reduced pressure and purified by prep. HPLC. The product containing fractions are pooled and freeze dried to yield 5-amino-3-{2-[(pyrrolidin-1-yl)methyl]-1H-indol-3-yl}-2,3-dihydro-1H-isoindol-1-one (380 mg; 1.097 mmol; 25.5%) and the regioisomer 6-amino-3-{2-[(pyrrolidin-1-yl)methyl]-1H-indol-3-yl}-2,3-dihydro-1H-isoindol-1-one (380 mg; 1.097 mmol; 25.5%), which were used directly in the next step without further purification.

Experimental Procedure for the Synthesis of 1-(1,3-dioxo-2,3-dihydro-1H-isoindol-5-yl)-3-ethylurea

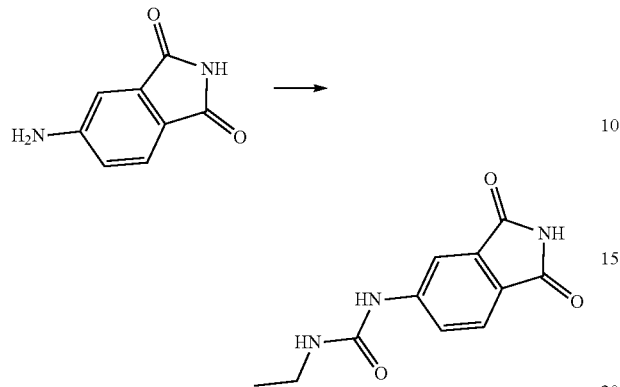

The 4-aminophthalimide (150 mg; 925 μmol), ethyl isocyanate (131.51 mg; 1.85 mmol) and TEA (281 mg; 2.775 mmol) are dissolved in THF (1 mL) and heated to reflux overnight. The reaction mixture is concentrated under reduced pressure, separation of regioisomers and purification done by prep. HPLC (acidic condition). The product containing fractions are pooled and freeze dried to yield 1-(1,3-dioxo-2,3-dihydro-1H-isoindol-5-yl)-3-ethylurea (30 mg; 129 μmol; 13.9%). HPLC method: LCMSBAS1: $[M-H]^+=234$; $t_{ret}$ [min]=0.61 min.

Preparation of Compounds of Formula (I) According to the Invention

Experimental procedure for the synthesis of 3-[2-(aminomethyl)-1H-indol-3-yl]-5-hydroxy-2,3-dihydro-1H-isoindol-1-one

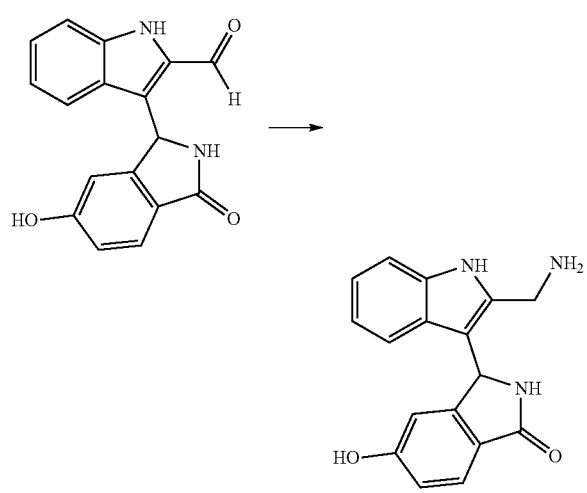

The aldehyde 3-(6-hydroxy-3-oxo-2,3-dihydro-1H-isoindol-1-yl)-1H-indole-2-carbaldehyde (15 mg; 51 μmol) and hydroxylamine hydrochloride (4.28 mg; 62 μmol) are dissolved in ethanol (1.0 mL) and DMF (0.2 mL) and stirred for 1 h. Zinc (10.07 mg; 154 μmol) and conc. HCl (17 μL; 205 μmol) are added and the reaction mixture stirred for 6 h at room temperature. Due to incomplete reaction an additional amount of zinc (13.42 mg; 205 μmol) and conc. HCl (21 μL; 257 μmol) are added and the reaction mixture stirred at room temperature over night. For workup the reaction mixture diluted with water, filtered and purified by preparative RP-HPLC using an ACN/water (2-50% ACN, acidic conditions) gradient. The product containing fractions are combined and freeze dried to yield 3-[2-(aminomethyl)-1H-indol-3-yl]-5-hydroxy-2,3-dihydro-1H-isoindol-1-one (I-001) (14 mg; 48 μmol; 93%). HPLC method: LCMS-BAS1: $[M+H]^+=277$; $t_{ret}$ [min]=0.31 min.

Experimental Procedure for the Synthesis of 3-{2-[(dimethylamino)methyl]-1H-indol-3-yl}-5-hydroxy-2,3-dihydro-1H-isoindol-1-one

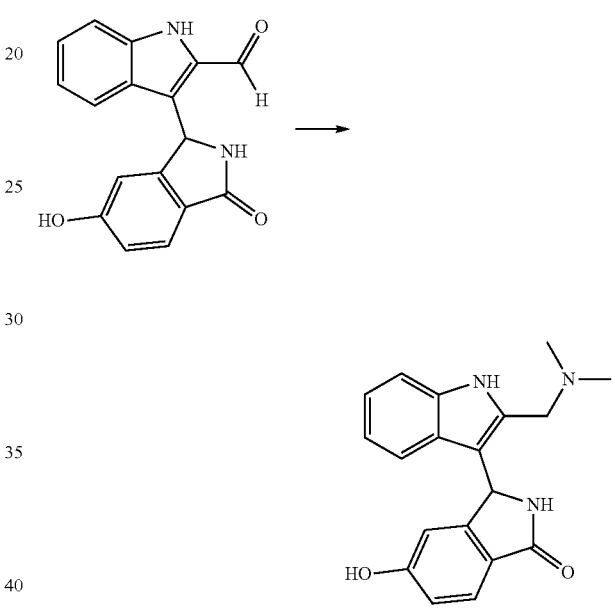

The aldehyde 3-(6-hydroxy-3-oxo-2,3-dihydro-1H-isoindol-1-yl)-1H-indole-2-carbaldehyde (1.0 g; 3.42 mmol) is dissolved in DMF (10 mL) and dimethylamine (8.55 mL; 2 M solution in THF; 17.1 mmol) is added and the reaction flask is pressurized to 4 bar (58 psi) via nitrogen gas and stirred at room temperature for 15 min before sodium triacetoxyborohydride (3.63 g; 17.1 mmol) is added. The reaction mixture is stirred at room temperature overnight. The reaction mixture is filtered, the filtrate is concentrated under reduced pressure and purified by preparative RP-HPLC using a ACN/water (5-50% ACN, basic conditions) gradient. The product containing fractions are combined and freeze dried to yield 3-{2-[(dimethylamino)methyl]-1H-indol-3-yl}-5-hydroxy-2,3-dihydro-1H-isoindol-1-one (I-002) (800 mg; 249 μmol; 72.8%). HPLC method: LCMSBAS1: [M+H]+=322; $t_{ret}$=0.62 min.

3-{2-[(dimethylamino)methyl]-1H-indol-3-yl}-5-hydroxy-2,3-dihydro-1H-isoindol-1-one (I-002) (90 mg; 280 μmol) was separated via chiral SFC to give (I-003) (3S)-3-{2-[(dimethylamino)methyl]-1H-indol-3-yl}-5-hydroxy-2,3-dihydro-1H-isoindol-1-one (35 mg; 109 μmol) and (3R)-3-{2-[(dimethylamino)methyl]-1H-indol-3-yl}-5-hydroxy-2,3-dihydro-1H-isoindol-1-one (35 mg; 109 μmol). HPLC method: LCMSBAS1: [M+H]+=322; $t_{ret}$=0.63 min.

Experimental Procedure for the Synthesis of 5-hydroxy-3-{2-[(pyrrolidin-1-yl)methyl]-1H-indol-3-yl}-1,3-dihydro-2-benzofuran-1-one

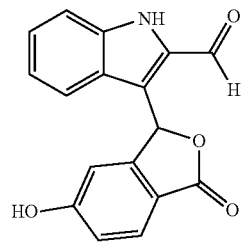

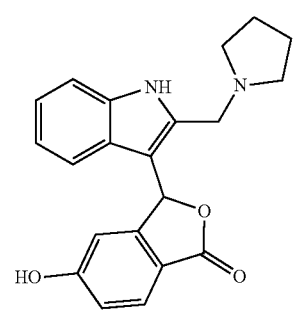

To a solution of 3-(6-hydroxy-3-oxo-2,3-dihydro-1H-isoindol-1-yl)-1H-indole-2-carbaldehyde (50 mg; 170 µmol) and pyrrolidine (13.3 mg; 71.1 µmol) dissolved in DMF (3.5 mL) is stirred at room temperature for 15 min before and sodium triacetoxyborohydride (180.2 mg; 0.85 mmol) is added. The reaction mixture is stirred overnight at room temperature to complete the reductive amination reaction. The solvent is removed and the crude material is dissolved in DMSO, filtered and purified via prep. HPLC. The product containing fractions are pooled, concentrated under reduced pressure and freeze dried to yield 5-hydroxy-3-{2-[(pyrrolidin-1-yl)methyl]-1H-indol-3-yl}-1,3-dihydro-2-benzofuran-1-one (I-004) (36 mg; 103 µmol; 60.8%). HPLC method: LCMSBAS1: [M+H]+=349; t$_{ret}$ [min]=0.81 min.

Experimental Procedure for the Synthesis of 5-hydroxy-3-{2-[(pyrrolidin-1-yl)methyl]-1H-indol-3-yl}-2,3-dihydro-1H-isoindol-1-one

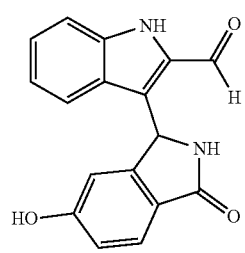

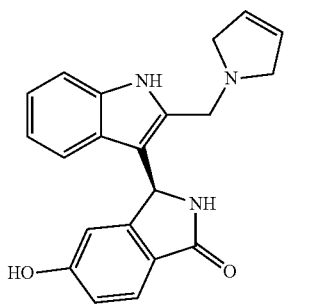

The aldehyde 3-(6-hydroxy-3-oxo-2,3-dihydro-1H-isoindol-1-yl)-1H-indole-2-carbaldehyde (100 mg; 0.325 mmol) is dissolved in acetic acid (1.5 mL) and pyrrolidine (32.255 µL; 0.39 mmol) is added. After 10 min sodium triacetoxyborohydride (207.66 mg; 0.975 mmol) is added and the reaction mixture is stirred at room temperature for 1 h. The reaction mixture is diluted with EtOAc and washed with saturated sodium hydrogencarbonate solution. The organic phase is separated, concentrated in vacuo and purified by preparative RP-HPLC using an ACN/water (acidic conditions) gradient. The product containing fractions are freeze dried to yield 5-hydroxy-3-{2-[(pyrrolidin-1-yl)methyl]-1H-indol-3-yl}-2,3-dihydro-1H-isoindol-1-one (I-023) (70 mg; 201 µmol; 62.0%). HPLC method: LCMSBAS1: [M+H]+=348; t$_{ret}$ [min]=0.88 min.

Experimental Procedure for the Synthesis of 5-hydroxy-3-{2-[(pyrrolidin-1-yl)methyl]-1H-indol-3-yl}-2,3-dihydro-1H-isoindol-1-one, (3S)-3-{2-[(2,5-dihydro-1H-pyrrol-1-yl)methyl]-1H-indol-3-yl}-5-hydroxy-2,3-dihydro-1H-isoindol-1-one and (3R)-3-{2-[(2,5-dihydro-1H-pyrrol-1-yl)methyl]-1H-indol-3-yl}-5-hydroxy-2,3-dihydro-1H-isoindol-1-one

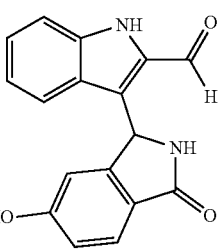

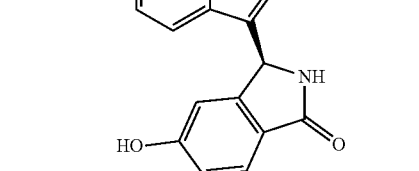

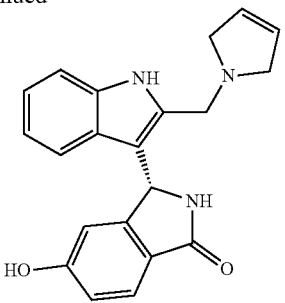

The aldehyde 3-(6-hydroxy-3-oxo-2,3-dihydro-1H-isoindol-1-yl)-1H-indole-2-carbaldehyde (70 mg; 239 µmol) is dissolved in DMF (1 mL) and pyrroline (27.95 mg; 263 µmol) is added.

After 15 min sodium triacetoxyborohydride (253.27 mg; 1.195 mmol) is added and the reaction mixture is stirred at room temperature for 16 h. The reaction mixture is diluted with EtOAc and washed with saturated sodium hydrogencarbonate solution. The organic phase is separated, concentrated in vacuo and purified by preparative RP-HPLC using an ACN/water (acidic conditions) gradient. The product containing fractions are freeze dried to yield 5-hydroxy-3-{2-[(pyrrolidin-1-yl)methyl]-1H-indol-3-yl}-2,3-dihydro-1H-isoindol-1-one (51 mg; 148 µmol; 61.8%). HPLC method: LCMS3_BAS1: [M+H]⁺=346; $t_{ret}$ [min]=0.83 min.

Chiral separation of 5-hydroxy-3-{2-[(pyrrolidin-1-yl)methyl]-1H-indol-3-yl}-2,3-dihydro-1H-isoindol-1-one (47 mg; 136 µmol) via a SFC yielded (3S)-3-{2-[(2,5-dihydro-1H-pyrrol-1-yl)methyl]-1H-indol-3-yl}-5-hydroxy-2,3-dihydro-1H-isoindol-1-one (I-028) (5.8 mg; 17 µmol; 24.7%) and (3R)-3-{2-[(2,5-dihydro-1H-pyrrol-1-yl)methyl]-1H-indol-3-yl}-5-hydroxy-2,3-dihydro-1H-isoindol-1-one (6.7 mg; 19 µmol; 28.5%). HPLC method: LCMS3BAS1: [M+H]+=346; $t_{ret}$ [min]=0.89 min.

Experimental Procedure for the Synthesis of 3-{2-[(benzylamino)methyl]-1H-indol-3-yl}-5-hydroxy-2,3-dihydro-1H-isoindol-1-one

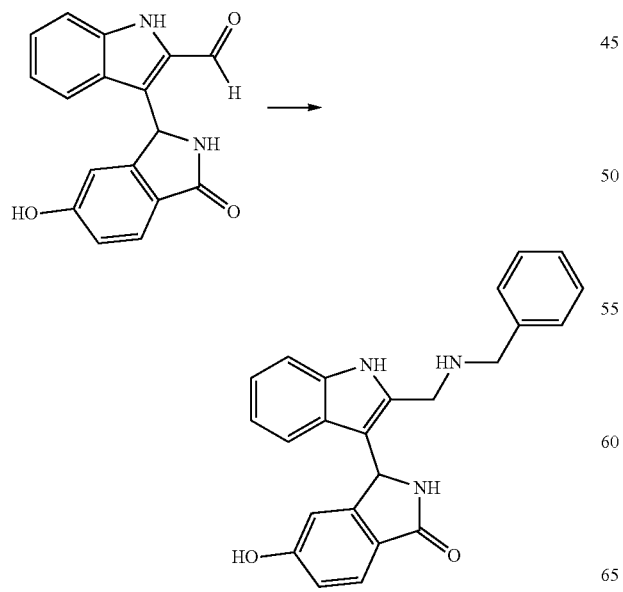

The aldehyde 3-(6-hydroxy-3-oxo-2,3-dihydro-1H-isoindol-1-yl)-1H-indole-2-carbaldehyde (50.0 mg; 171 µmol) and benzylamine (20.16 mg; 188 µmol) are dissolved in DMF (0.5 mL) and stirred for 15 min at room temperature. The reaction mixture is treated with sodium triacetoxyborohydride (181.2 mg; 855 µmol) and stirring is continued for 16 h. The reaction mixture is filtered, the filtrate is concentrated under reduced pressure and purified by preparative RP-HPLC using a ACN/water (5-50% ACN) gradient. The product containing fractions are combined and freeze dried to yield 3-{2-[(benzylamino)methyl]-1H-indol-3-yl}-5-hydroxy-2,3-dihydro-1H-isoindol-1-one (I-041) (51.4 mg; 134 µmol; 78.4%). HPLC method: LCMSBAS1: [M+H]⁺=384; $t_{ret}$ [min]=0.93.

3-{2-[(Benzylamino)methyl]-1H-indol-3-yl}-5-hydroxy-2,3-dihydro-1H-isoindol-1-one (15 mg; 39 µmol) was separated via chiral SFC to give (I-042) (3S)-3-{2-[(benzylamino)methyl]-1H-indol-3-yl}-5-hydroxy-2,3-dihydro-1H-isoindol-1-one (3 mg; 8 µmol) and (3R)-3-{2-[(benzylamino)methyl]-1H-indol-3-yl}-5-hydroxy-2,3-dihydro-1H-isoindol-1-one (3 mg; 8 µmol). HPLC method: LCMS3BAS1: [M+H]⁺=384; $t_{ret}$ [min]=1.0.

Experimental Procedure for the Synthesis of 5-hydroxy-3-[2-({[(1H-indol-6-yl)methyl]amino}methyl)-1H-indol-3-yl]-2,3-dihydro-1H-isoindol-1-one, (3S)-5-hydroxy-3-[2-({[(1H-indol-6-yl)methyl]amino}methyl)-1H-indol-3-yl]-2,3-dihydro-1H-isoindol-1-one and (3R)-5-hydroxy-3-[2-({[(1H-indol-6-yl)methyl]amino}methyl)-1H-indol-3-yl]-2,3-dihydro-1H-isoindol-1-one

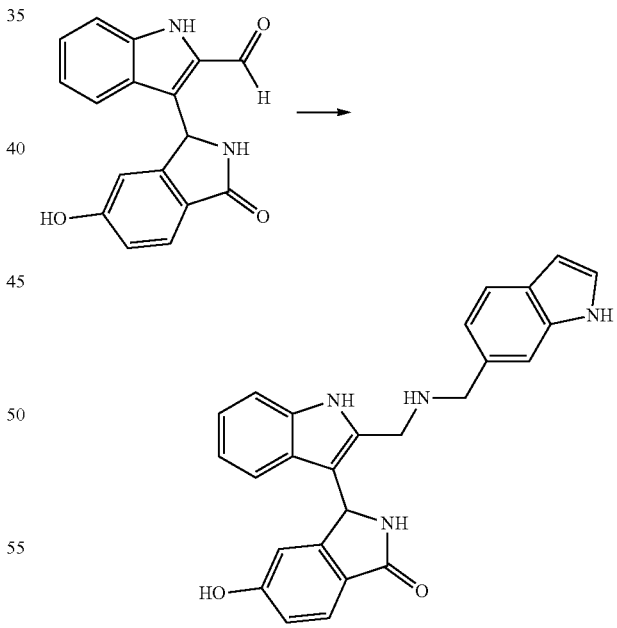

The aldehyde 3-(6-hydroxy-3-oxo-2,3-dihydro-1H-isoindol-1-yl)-1H-indole-2-carbaldehyde (70.0 mg; 239 µmol) and the amine 1H-indole-6-methanamine (40.5 mg; 263 µmol) are dissolved in DMF (1 mL) and stirred for 15 min at room temperature. The reaction mixture is treated with sodium triacetoxyborohydride (253.3 mg; 1.2 mmol) and stirring is continued for 16 h. The reaction mixture is filtered, the filtrate is concentrated under reduced pressure and purified by preparative RP-HPLC using a ACN/water (5-50% CAN, acidic condition) gradient. The product containing fractions are combined and freeze dried to yield 5-hydroxy-3-[2-({[(1H-indol-6-yl)methyl]amino}methyl)-1H-indol-3-yl]-2,3-dihydro-1H-isoindol-1-one (I-061) (68 mg; 134 µmol; 67.3%). HPLC method: LCMSBAS1: [M+H]⁺=423; $t_{ret}$ [min]=0.93.

5-Hydroxy-3-[2-({[(1H-indol-6-yl)methyl]amino}methyl)-1H-indol-3-yl]-2,3-dihydro-1H-isoindol-1-one (60.0 mg; 142 µmol) was separated via chiral SFC to give (I-062) (3S)-5-hydroxy-3-[2-({[(1H-indol-6-yl)methyl]amino}methyl)-1H-indol-3-yl]-2,3-dihydro-1H-isoindol-1-one (16 mg; 38 µmol; 53.3%) and (3R)-5-hydroxy-3-[2-({[(1H-indol-6-yl)methyl]amino}methyl)-1H-indol-3-yl]-2,3-dihydro-1H-isoindol-1-one (17 mg; 40 µmol; 56.7%). LCMS3BAS1: [M+H]⁺=423; $t_{ret}$ [min]=0.99.

Experimental Procedure for the Synthesis of 5-hydroxy-3-[2-({[(1-methyl-1H-indol-6-yl)methyl]amino}methyl)-1H-indol-3-yl]-2,3-dihydro-1H-isoindol-1-one, (S)-5-hydroxy-3-(2-{[(1-methyl-1H-indol-6-ylmethyl)-amino]-methyl}-1H-indol-3-yl)-2,3-dihydro-isoindol-1-one and (R)-5-hydroxy-3-(2-{[(1-methyl-1H-indol-6-ylmethyl)-amino]-methyl}-1H-indol-3-yl)-2,3-dihydro-isoindol-1-one

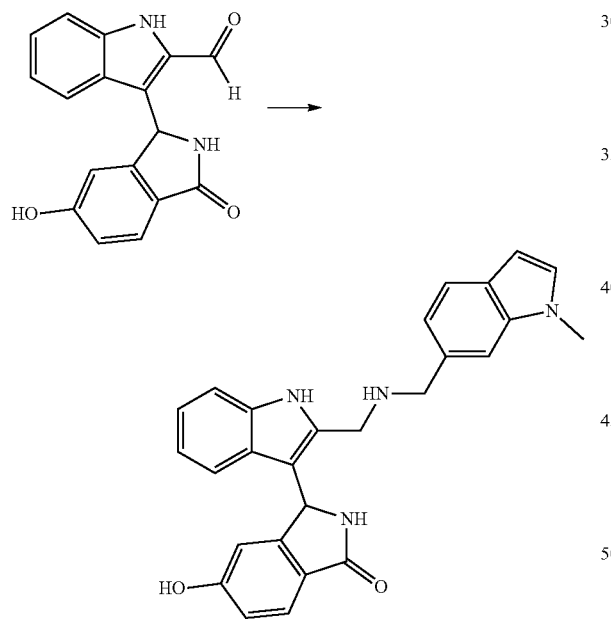

The aldehyde 3-(6-hydroxy-3-oxo-2,3-dihydro-1H-isoindol-1-yl)-1H-indole-2-carbaldehyde (50.0 mg; 96.9%; 166 µmol) and (1-methyl-1H-indole-6-yl)-methylamine (33.6 mg; 199 µmol; commercial available from ABCR) are dissolved in DMF (1 mL) and stirred for 15 min at room temperature. The reaction mixture is treated with sodium triacetoxyborohydride (175.9 mg; 830 µmol) and stirring is continued for 16 h. The reaction mixture is filtered, the filtrate is concentrated under reduced pressure and purified by preparative RP-HPLC using a ACN/water (5-50% ACN) gradient. The product containing fractions are freeze dried to yield 5-hydroxy-3-[2-({[(1-methyl-1H-indol-6-yl)methyl]amino}methyl)-1H-indol-3-yl]-2,3-dihydro-1H-isoindol-1-one (I-070) (51 mg; 117 µmol; 68.3%). HPLC method: LCMSBAS1: [M+H]⁺=437; $t_{ret}$ [min]=1.00.

The pure enantiomers were synthesized analogously starting from the chiral aldehydes 3-[(1S)-6-hydroxy-3-oxo-2,3-dihydro-1H-isoindol-1-yl]-1H-indole-2-carbaldehyde (25 mg; 86 µmol) and 3-[(1R)-6-hydroxy-3-oxo-2,3-dihydro-1H-isoindol-1-yl]-1H-indole-2-carbaldehyde (25 mg; 86 µmol) to yield (S)-5-hydroxy-3-(2-{[(1-methyl-1H-indol-6-ylmethyl)-amino]-methyl}-1H-indol-3-yl)-2,3-dihydro-isoindol-1-one (I-071) (11 mg; 25 µmol; 29.3%) and (R)-5-hydroxy-3-(2-{[(1-methyl-1H-indol-6-ylmethyl)-amino]-methyl}-1H-indol-3-yl)-2,3-dihydro-isoindol-1-one (12 mg; 27 µmol; 32.0%). HPLC method: LCMSBAS1: [M+H]⁺=437; $t_{ret}$ [min]=1.07.

Experimental Procedure for the Synthesis of 3-[2-({[(1-benzyl-1H-indol-6-yl)methyl]amino}methyl)-1H-indol-3-yl]-5-hydroxy-2,3-dihydro-1H-isoindol-1-one, (3S)-3-[2-({[(1-benzyl-1H-indol-6-ylmethyl)-amino]-methyl}-1H-indol-3-yl)-5-hydroxy-2,3-dihydro-1H-isoindol-1-one and 3R)-3-[2-({[(1-benzyl-1H-indol-6-ylmethyl)-amino]-methyl}-1H-indol-3-yl)-5-hydroxy-2,3-dihydro-1H-isoindol-1-one

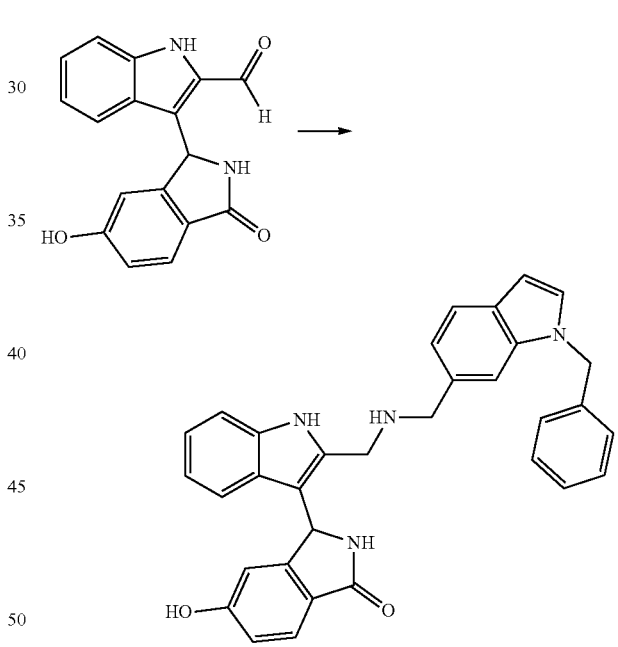

In a glass vial aldehyde 3-(6-hydroxy-3-oxo-2,3-dihydro-1H-isoindol-1-yl)-1H-indole-2-carbaldehyde (12 mg; 96.9%; 40 µmol) is dissolved in DMF (0.5 mL) and (1-benzyl-1H-indol-6-yl)methanamine (10 mg; 42 µmol; commercial available from AbamaChem) is added and stirred at room temperature for 15 min. Sodium triacetoxyborohydride (42.2 mg; 200 µmol) is added and the mixture is stirred at room temperature for 2 h. Sodium triacetoxyborohydride (42.2 mg; 200 µmol) is added again, and the reaction mixture is stirred at room temperature overnight. The reaction mixture is diluted by addition of ACN/H₂O (1:1; 200 µL), filtered through a syringe filter and purified by prep. HPLC (Gilson; column: SunFire Prep C18, 5 µm (30*50), gradient, acidic conditions ACN/water (5:95 to 60:40 in 8 min. flowrate: 50 mL/min wavelength: 222 nm). The product containing fraction is freeze-dried to yield 3-[2-({[(1-benzyl-1H-indol-6-yl)methyl]amino}methyl)-1H-indol-3-yl]-5-hydroxy-2,3-dihydro-1H-isoindol-1-one (I-079) (6 mg; 12 µmol; 29.4%). HPLC method: LCMSBAS1: [M+H]⁺=513; $t_{ret}$ [min]=1.24.

The pure enantiomers were synthesized analogously starting from the chiral aldehydes 3-[(1 S)-6-hydroxy-3-oxo-2,3-dihydro-1H-isoindol-1-yl]-1H-indole-2-carbaldehyde (31 mg; 106 µmol) and 3-[(1R)-6-hydroxy-3-oxo-2,3-dihydro-1H-isoindol-1-yl]-1H-indole-2-carbaldehyde (31 mg; 106 µmol) to yield to yield (3S)-3-[2-({[(1-benzyl-1H-indol-6-ylmethyl)-amino]-methyl}-1H-indol-3-yl)-5-hydroxy-2,3-dihydro-1H-isoindol-1-one (I-080) (12 mg; 23 µmol; 22.1%) and (3R)-3-[2-({[(1-benzyl-1H-indol-6-ylmethyl)-amino]-methyl}-1H-indol-3-yl)-5-hydroxy-2,3-dihydro-1H-isoindol-1-one (I-081) (8 mg; 16 µmol; 14.7%). HPLC method: LCMS3BAS1: [M+H]⁺=513; $t_{ret}$ [min]=1.25.

Experimental Procedure for the Synthesis of 5-hydroxy-3-[2-({[1-(1-methyl-1H-imidazol-4-ylmethyl)-1H-indol-6-ylmethyl]-amino}-methyl)-1H-indol-3-yl]-2,3-dihydro-isoindol-1-one, (S)-5-Hydroxy-3-[2-({[1-(1-methyl-1H-imidazol-4-ylmethyl)-1H-indol-6-ylmethyl]-amino}-methyl)-1H-indol-3-yl]-2,3-dihydro-isoindol-1-one and (R)-5-Hydroxy-3-[2-({[1-(1-methyl-1H-imidazol-4-ylmethyl)-1H-indol-6-ylmethyl]-amino}-methyl)-1H-indol-3-yl]-2,3-dihydro-isoindol-1-one

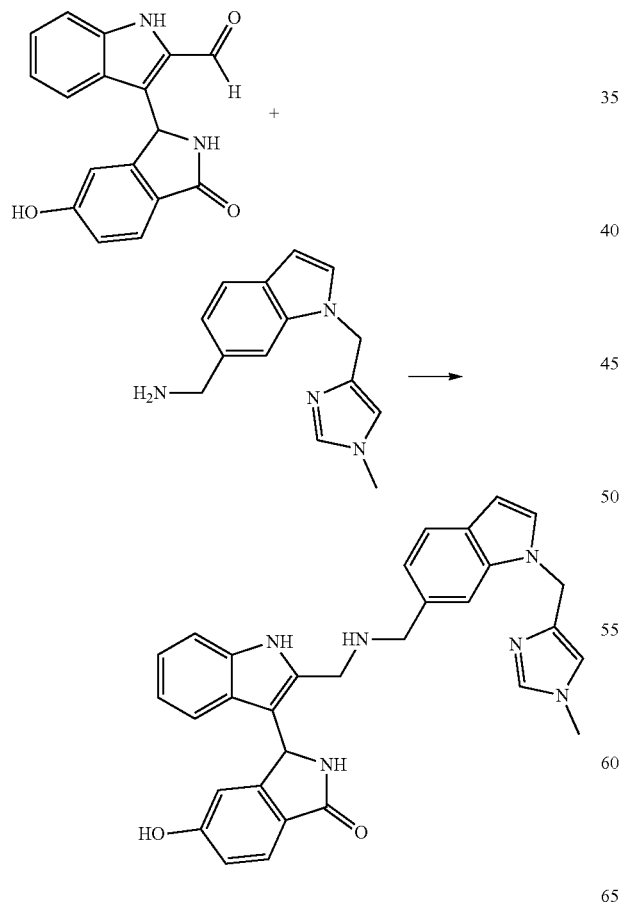

In a glass vial 3-(6-hydroxy-3-oxo-isoindolin-1-yl)-1H-indole-2-carbaldehyde (55 mg; 179 µmol) is dissolved in DMF (1 ml) and C-[1-(1-methyl-1H-imidazol-4-ylmethyl)-1H-indol-6-yl]-methylamine (49.4 mg; 206 µmol) is added. The reaction mixture is stirred at room temperature for 15 min before sodium triacetoxyborohydride (190 mg; 895 µmol) is added and the mixture is stirred at room temperature overnight. The reaction mixture is diluted with ACN/water (1:1; 0.2 mL), filtered through a syringe filter and purified by preparative RP-HPLC using an ACN/water gradient under acidic conditions. The product containing fractions are freeze dried to give 5-hydroxy-3-[2-({[1-(1-methyl-1H-imidazol-4-ylmethyl)-1H-indol-6-ylmethyl]-amino}-methyl)-1H-indol-3-yl]-2,3-dihydro-isoindol-1-one (I-092) (58 mg; 112 µmol; 62.8%). HPLC method: LCMSBAS1: [M+H]⁺=517; $t_{ret}$ [min]=1.03.

5-Hydroxy-3-[2-({[1-(1-methyl-1H-imidazol-4-ylmethyl)-1H-indol-6-ylmethyl]-amino}-methyl)-1H-indol-3-yl]-2,3-dihydro-isoindol-1-one (I-092) (45 mg; 87 µmol) was separated via chiral SFC to give (I-093) (S)-5-Hydroxy-3-[2-({[1-(1-methyl-1H-imidazol-4-ylmethyl)-1H-indol-6-ylmethyl]-amino}-methyl)-1H-indol-3-yl]-2,3-dihydro-isoindol-1-one (13 mg; 25 µmol; 28.9%; >98% ee) and (I-094) (R)-5-Hydroxy-3-[2-({[i-(1-methyl-1H-imidazol-4-ylmethyl)-1H-indol-6-ylmethyl]-amino}-methyl)-1H-indol-3-yl]-2,3-dihydro-isoindol-1-one (15 mg; 29 µmol; 33.3%; only 73% ee due to peak tailing).

Enantiomeric pure (R)-5-Hydroxy-3-[2-({[1-(1-methyl-1H-imidazol-4-ylmethyl)-1H-indol-6-ylmethyl]-amino}-methyl)-1H-indol-3-yl]-2,3-dihydro-isoindol-1-one was also produced starting from the enantiomeric pure aldehyde 3-((R)-6-Hydroxy-3-oxo-2,3-dihydro-1H-isoindol-1-yl)-1H-indole-2-carbaldehyde (30.4 mg; 104 µmol) via reductive amination with C-[1-(1-Methyl-1H-imidazol-4-ylmethyl)-1H-indol-6-yl]-methylamine (25 mg; 104 µmol) which yielded (R)-5-Hydroxy-3-[2-({[1-(1-methyl-1H-imidazol-4-ylmethyl)-1H-indol-6-ylmethyl]-amino}-methyl)-1H-indol-3-yl]-2,3-dihydro-isoindol-1-one (14 mg; 27 µmol; 26.1%). HPLC method: LCMS3BAS1: [M+H]+=517; $t_{ret}$ [min]=1.04.

Experimental Procedure for the Synthesis of 5-hydroxy-3-(2-{[({1-[(4-hydroxyphenyl)methyl]-1H-indol-6-yl}methyl)amino]-methyl}-1H-indol-3-yl)-2,3-dihydro-1H-isoindol-1-one, (3S)-5-hydroxy-3-(2-{[({1-[(4-hydroxyphenyl)methyl]-1H-indol-6-yl}methyl)amino]methyl}-1H-indol-3-yl)-2,3-dihydro-1H-isoindol-1-one and 3R)-5-hydroxy-3-(2-{[({1-[(4-hydroxyphenyl)methyl]-1H-indol-6-yl}methyl)amino]methyl}-1H-indol-3-yl)-2,3-dihydro-1H-isoindol-1-one

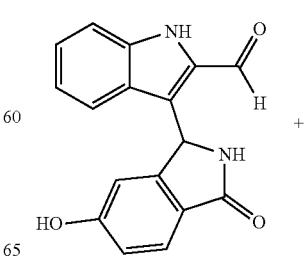

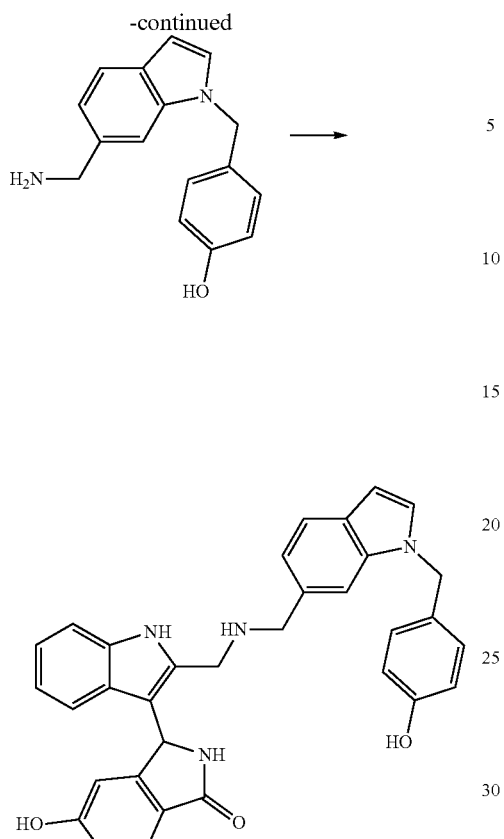

Experimental Procedure for the Synthesis of 5-hydroxy-3-[2-({[1-(1H-imidazol-4-ylmethyl)-1H-indol-6-ylmethyl]-amino}-methyl)-1H-indol-3-yl]-2,3-dihydro-isoindol-1-one

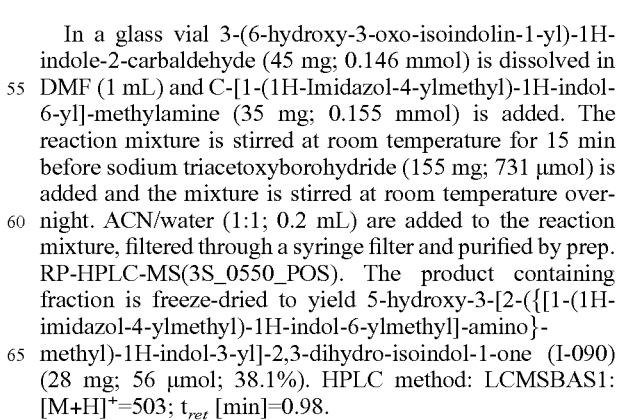

In a glass vial 3-(6-hydroxy-3-oxo-isoindolin-1-yl)-1H-indole-2-carbaldehyde (70 mg; 239 μmol) is dissolved in DMF (1 ml) and 4-{[6-(aminomethyl)-1H-indol-1-yl]methyl}phenol (66.3 mg; 263 μmol) is added. The reaction mixture is stirred at room temperature for 15 min before sodium triacetoxyborohydride (253.27 mg; 1.195 mmol) is added and the mixture is stirred at room temperature overnight. The reaction mixture is filtered through a syringe filter and purified by preparative RP-HPLC using an ACN/water gradient under acidic conditions. The product containing fractions are freeze dried to give 5-hydroxy-3-(2-{[({1-[(4-hydroxyphenyl)methyl]-1H-indol-6-yl}methyl)amino]-methyl}-1H-indol-3-yl)-2,3-dihydro-1H-isoindol-1-one (I-082) (66 mg; 125 μmol; 52.2%). HPLC method: LCMS-BAS1: [M+H]$^+$=529; $t_{ret}$ [min]=1.15.

Chiral separation of 5-hydroxy-3-(2-{[({1-[(4-hydroxyphenyl)methyl]-1H-indol-6-yl}methyl)amino]methyl}-1H-indol-3-yl)-2,3-dihydro-1H-isoindol-1-one (50 mg; 95 μmol) was done via chiral SFC to give (I-083) (3S)-5-hydroxy-3-(2-{[({1-[(4-hydroxyphenyl)methyl]-1H-indol-6-yl}methyl)amino]methyl}-1H-indol-3-yl)-2,3-dihydro-1H-isoindol-1-one (17 mg; 32 μmol; 68.0%) and (3R)-5-hydroxy-3-(2-{[({1-[(4-hydroxyphenyl)methyl]-1H-indol-6-yl}methyl)amino]methyl}-1H-indol-3-yl)-2,3-dihydro-1H-isoindol-1-one (17 mg; 32 μmol; 68.0%). HPLC method: LCMS3BAS1: [M+H]$^+$=529; $t_{ret}$ [min]=1.17.

In a glass vial 3-(6-hydroxy-3-oxo-isoindolin-1-yl)-1H-indole-2-carbaldehyde (45 mg; 0.146 mmol) is dissolved in DMF (1 mL) and C-[1-(1H-Imidazol-4-ylmethyl)-1H-indol-6-yl]-methylamine (35 mg; 0.155 mmol) is added. The reaction mixture is stirred at room temperature for 15 min before sodium triacetoxyborohydride (155 mg; 731 μmol) is added and the mixture is stirred at room temperature overnight. ACN/water (1:1; 0.2 mL) are added to the reaction mixture, filtered through a syringe filter and purified by prep. RP-HPLC-MS(3S_0550_POS). The product containing fraction is freeze-dried to yield 5-hydroxy-3-[2-({[1-(1H-imidazol-4-ylmethyl)-1H-indol-6-ylmethyl]-amino}-methyl)-1H-indol-3-yl]-2,3-dihydro-isoindol-1-one (I-090) (28 mg; 56 μmol; 38.1%). HPLC method: LCMSBAS1: [M+H]$^+$=503; $t_{ret}$ [min]=0.98.

Experimental Procedure for the Synthesis of tert-butyl N-(3-{6-[({[3-(6-hydroxy-3-oxo-2,3-dihydro-1H-isoindol-1-yl)-1H-indol-2-yl]methyl}amino)methyl]-1H-indol-1-yl}propyl)carbamate

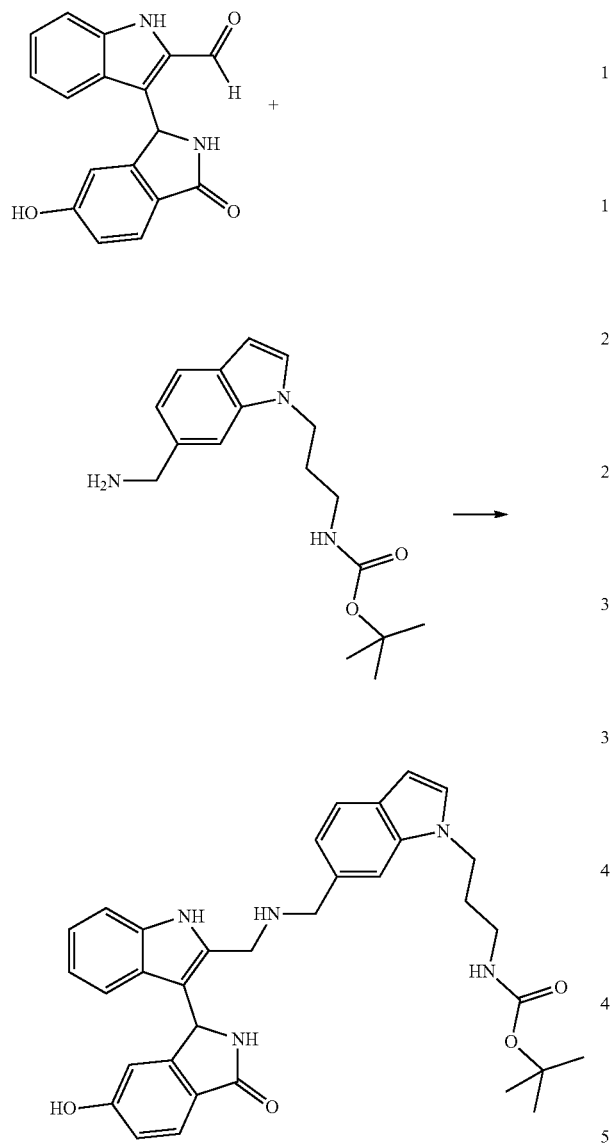

In a glass vial 3-(6-hydroxy-3-oxo-isoindolin-1-yl)-1H-indole-2-carbaldehyde (100 mg; 342 μmol) is dissolved in DMF (1 mL) and tert-butyl N-{3-[6-(aminomethyl)-1H-indol-1-yl]propyl}carbamate (125 mg; 412 μmol) is added. The reaction mixture is stirred at room temperature for 15 min before sodium triacetoxyborohydride (217.53 mg; 1.026 mmol) is added and the mixture is stirred at room temperature overnight. ACN/H$_2$O (1:1; 0.4 mL) are added to the reaction mixture, filtered through a syringe filter and purified by prep. RP-HPLC-MS. The product containing fraction is freeze-dried to yield tert-butyl N-(3-{6-[({[3-(6-hydroxy-3-oxo-2,3-dihydro-1H-isoindol-1-yl)-1H-indol-2-yl]methyl}amino)methyl]-1H-indol-1-yl}propyl)carbamate (150 mg; 259 μmol; 75.6%). HPLC method: LCMSBAS1: [M+H]+=580; t$_{ret}$ [min]=1.17.

Experimental Procedure for the Synthesis of 3-{2-[({[1-(3-aminopropyl)-1H-indol-6-yl]methyl}amino)methyl]-1H-indol-3-yl}-5-hydroxy-2,3-dihydro-1H-isoindol-1-one

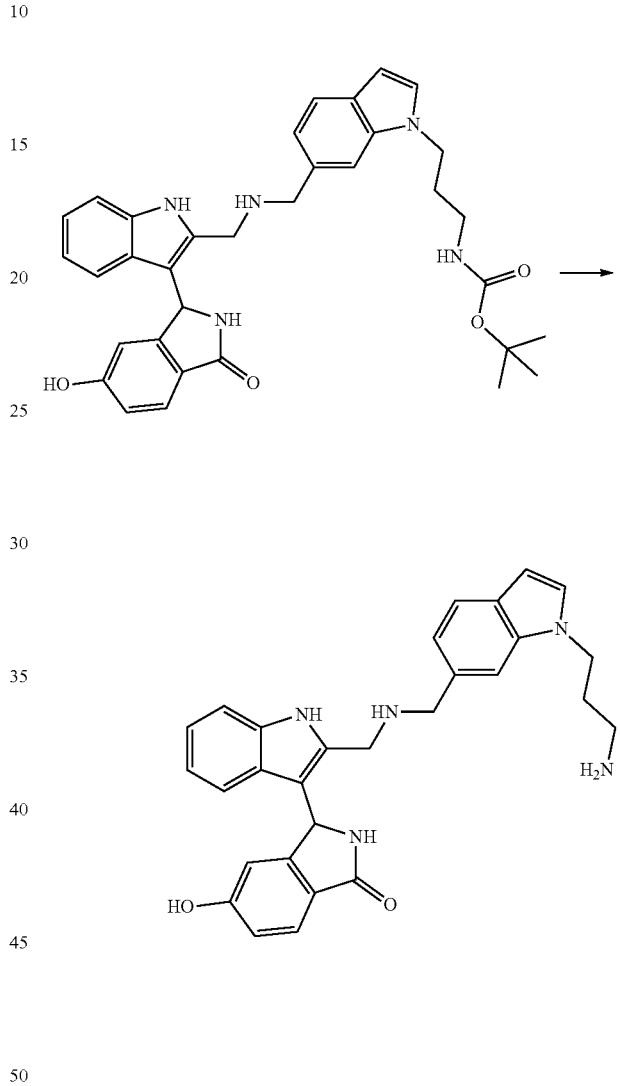

In a 50 mL round-bottom flask tert-butyl N-(3-{6-[({[3-(6-hydroxy-3-oxo-2,3-dihydro-1H-isoindol-1-yl)-1H-indol-2-yl]methyl}amino)methyl]-1H-indol-1-yl}propyl)carbamate (75 mg; 129 μmol) is dissolved in DCM (1.5 mL). TFA (0.5 mL; 6.490 mmol) is added and the reaction mixture is stirred at room temperature for 30 min. The reaction mixture is concentrated under reduced pressure, dissolved in ACN/water and neutralized with aq. ammonia. The suspension is filtered through a syringe filter and purified by prep. RP-HPLC (Gilson; column: XBridge Prep C18, 5 μm (30*50), gradient: ACN/water (basic conditions; 5-60 ACN in 9 min. flowrate: 50 mL/min wavelength: 220 nm). The product containing fraction is freeze-dried to yield 3-{2-[({[1-(3-aminopropyl)-1H-indol-6-yl]methyl}amino)methyl]-1H-indol-3-yl}-5-hydroxy-2,3-dihydro-1H-isoindol-1-one (I-084) (20 mg; 42 μmol; 32.2%) HPLC method: LCMSBAS1: [M+H]+=480; t$_{ret}$ [min]=0.98.

85

Experimental Procedure for the Synthesis of 2-{6-[({[3-(6-hydroxy-3-oxo-2,3-dihydro-1H-isoindol-1-yl)-1H-indol-2-yl]methyl}amino)methyl]-1H-indol-1-yl}acetamide

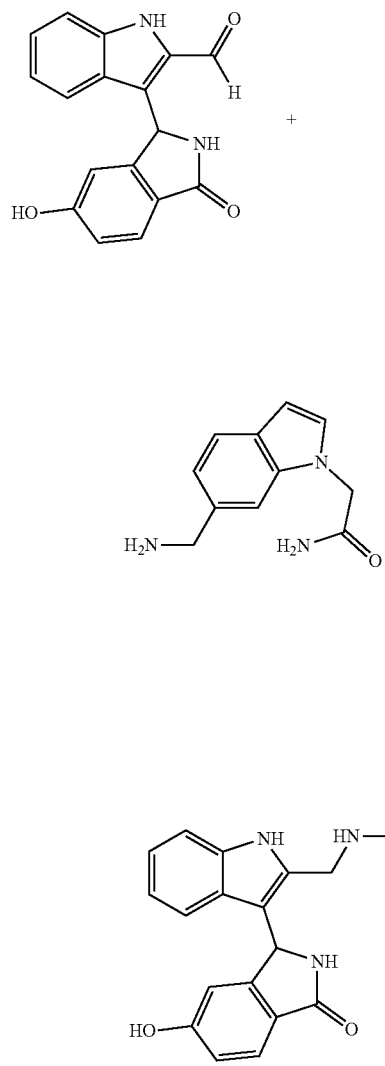

In a glass vial 3-(6-hydroxy-3-oxo-isoindolin-1-yl)-1H-indole-2-carbaldehyde (30 mg; 98 μmol) is dissolved in DMF (1.0 mL) and 2-[6-(aminomethyl)-1H-indol-1-yl]acetamide (20.808 mg; 0.102 mmol) is added. The reaction mixture is stirred at room temperature for 15 min before sodium triacetoxyborohydride (103.327 mg; 488 mol) is added and the mixture is stirred for 2 h. The reaction mixture is diluted with ACN/water (1:1; 0.2 mL), filtered through a syringe filter and purified by prep. RP-HPLC-MS (7S_0550_DAD). The product containing fraction is freeze dried to yield 2-{6-[({[3-(6-hydroxy-3-oxo-2,3-dihydro-1H-isoindol-1-yl)-1H-indol-2-yl]methyl}amino)methyl]-1H-indol-1-yl}acetamide (I-085) (18 mg; 38 μmol; 38.5%). HPLC method: LCMSBAS1: [M+H]$^+$=480; $t_{ret}$ [min]=0.93.

86

Experimental Procedure for the Synthesis of 5-hydroxy-3-[2-({[3-(1-methyl-1H-imidazol-4-ylmethyl)-1H-indol-6-ylmethyl]-amino}-methyl)-1H-indol-3-yl]-2,3-dihydro-isoindol-1-one

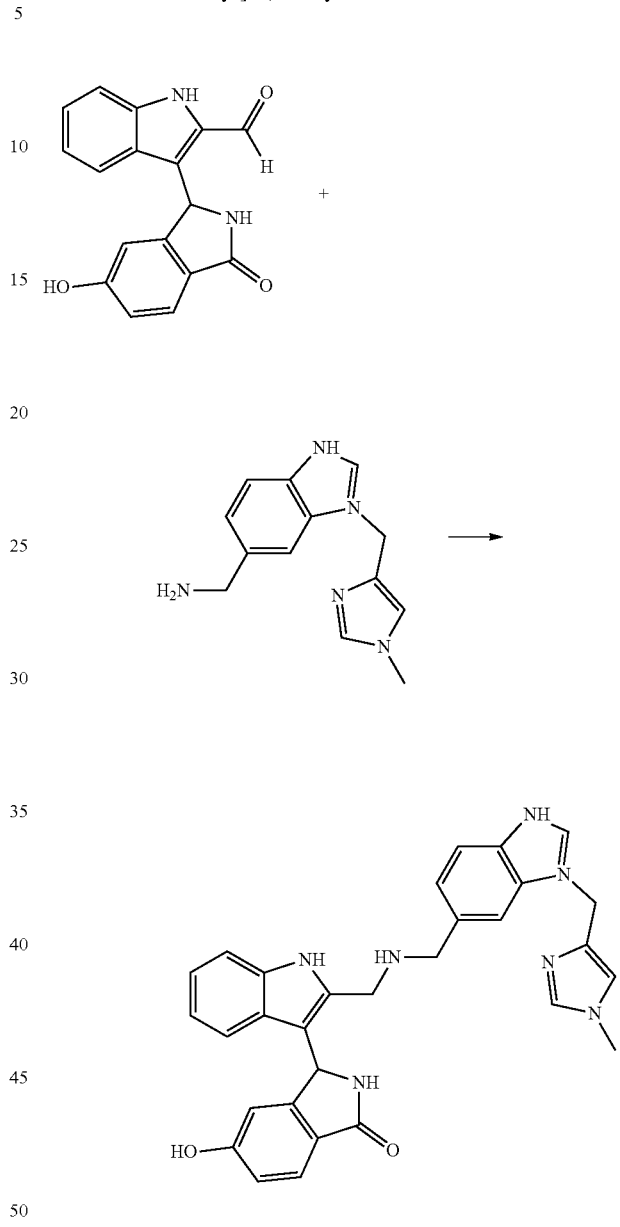

In a glass vial 3-(6-hydroxy-3-oxo-isoindolin-1-yl)-1H-indole-2-carbaldehyde (60 mg; 195 μmol) is dissolved in DMF (1 ml) and C-[3-(1-Methyl-1H-imidazol-4-ylmethyl)-1H-indol-6-yl]-methylamine (75 mg; 250 μmol) is added. The reaction mixture is stirred at room temperature for 15 min before sodium triacetoxyborohydride (206.66 mg; 975 μmol) is added and the mixture is stirred overnight. The reaction mixture is diluted with ACN/water (1:1; 0.2 mL), filtered through a syringe filter and purified twice by preparative RP-HPLC using an ACN/water gradient under acidic conditions. The product containing fraction is freeze dried to give 5-hydroxy-3-[2-({[3-(1-methyl-1H-imidazol-4-ylmethyl)-1H-indol-6-ylmethyl]-amino}-methyl)-1H-indol-3-yl]-2,3-dihydro-isoindol-1-one (I-097) (8 mg; 15 μmol; 7.9%). HPLC method: LCMSBAS1: [M+H]$^+$=517; $t_{ret}$ [min]=0.96.

Experimental Procedure for the Synthesis of 3-{2-[(dimethylamino)methyl]-1H-indol-3-yl}-5-hydroxy-2-methyl-2,3-dihydro-1H-isoindol-1-one, (3S)-3-{2-[(dimethylamino)methyl]-1H-indol-3-yl}-5-hydroxy-2-methyl-2,3-dihydro-1H-isoindol-1-one and (3R)-3-{2-[(dimethylamino)methyl]-1H-indol-3-yl}-5-hydroxy-2-methyl-2,3-dihydro-1H-isoindol-1-one Experimental Procedure for the Synthesis of 3-(2-dimethylaminomethyl-1H-indol-3-yl)-5-hydroxy-2-methoxy-2,3-dihydro-isoindol-1-one

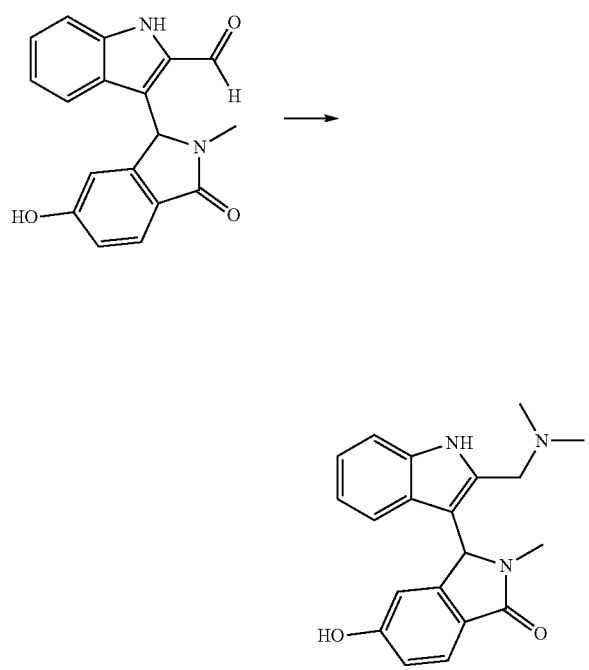

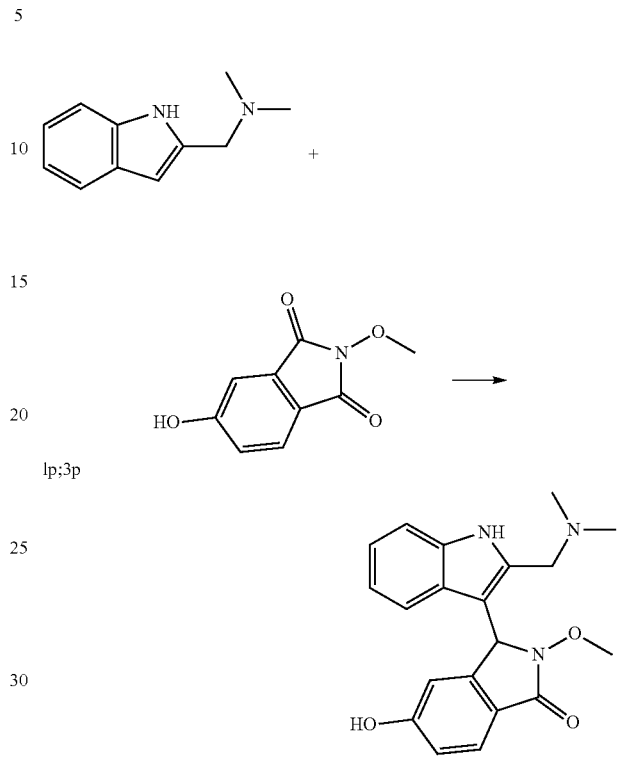

The aldehyde 3-(6-hydroxy-2-methyl-3-oxo-2,3-dihydro-1H-isoindol-1-yl)-1H-indole-2-carbaldehyde (70 mg; 206 µmol) is dissolved in DMF (1 mL) and dimethylamine (131.12 mg as 2 M solution in THF; 309 µmol) is added. The reaction mixture is stirred at room temperature for 15 min before sodium triacetoxyborohydride (89.876 mg; 411 µmol) is added and the reaction mixture is stirred overnight. The reaction mixture is quenched by addition of a drop of water, filtered and the filtrate is purified by preparative RP-HPLC using an ACN/water (acidic conditions) gradient. The product containing fractions are combined and freeze dried to yield 3-{2-[(dimethylamino)methyl]-1H-indol-3-yl}-5-hydroxy-2-methyl-2,3-dihydro-1H-isoindol-1-one (I-016) (29.9 mg; 89 µmol; 43.3%). HPLC method: LCMS-BAS1: [M+H]$^+$=336; t$_{ret}$ [min]=0.82 min.

Enantiomeric pure (3S)-3-{2-[(dimethylamino)methyl]-1H-indol-3-yl}-5-hydroxy-2-methyl-2,3-dihydro-1H-isoindol-1-one (I-017) (65.28 mg; 195 µmol; 29.8%) was also produced starting from the enantiomeric pure aldehyde 3-[(1S)-6-hydroxy-2-methyl-3-oxo-2,3-dihydro-1H-isoindol-1-yl]-1H-indole-2-carbaldehyde (200 mg; 653 µmol) and the distomer (3R)-3-{2-[(dimethylamino)methyl]-1H-indol-3-yl}-5-hydroxy-2-methyl-2,3-dihydro-1H-isoindol-1-one (78.9 mg; 235 µmol; 36.0%) was also produced starting from the enantiomeric pure aldehyde 3-[(1R)-6-hydroxy-2-methyl-3-oxo-2,3-dihydro-1H-isoindol-1-yl]-1H-indole-2-carbaldehyde (200 mg; 653 µmol). HPLC method: LCMSBAS1: [M+H]+=336; t$_{ret}$ [min]=0.91 min.

In a glass vial 5-hydroxy-2-methoxy-isoindole-1,3-dione (50.0 mg; 259 µmol) and (1H-indol-2-ylmethyl)-dimethyl-amine (54.125 mg; 311 µmol) are dissolved in acetic acid (0.5 mL). Zinc (135.414 mg; 2.071 mmol) and conc. HCl (200 µl; 2.330 mmol) are added and the mixture is stirred at room temperature for 10 min. The zinc is filtered off, the filtrate is concentrated under reduced pressure, dissolved in ACN/water and purified by prep. RP-HPLC-MS. The product containing fractions are pooled and freeze dried to yield 3-(2-dimethylaminomethyl-1H-indol-3-yl)-5-hydroxy-2-methoxy-2,3-dihydro-isoindol-1-one (I-018) (36 mg; 102 µmol; 39.6%). HPLC method: LCMSBAS1: [M+H]$^+$=352; t$_{ret}$ [min]=0.88 min.

Experimental Procedure for the Synthesis of 3-{5-chloro-2-[(dimethylamino)methyl]-1H-indol-3-yl}-5-hydroxy-2,3-dihydro-1H-isoindol-1-one

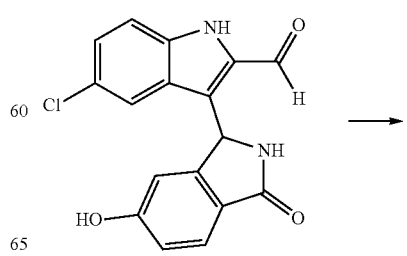

-continued

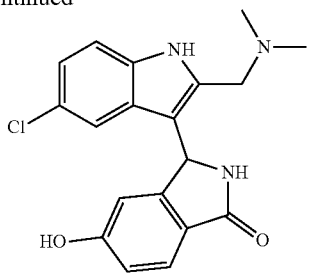

The aldehyde 5-chloro-3-(6-hydroxy-3-oxo-2,3-dihydro-1H-isoindol-1-yl)-1H-indole-2-carbaldehyde (15 mg; 46 µmol) is dissolved in DMF (200 µL), dimethylamine (45.91 µL; 2 M solution in THF; 92 µmol) and acetic acid (65.64 µL; 1.148 mmol) is added. After 20 min stirred at room temperature, sodium triacetoxyborohydride (48.65 mg; 230 µmol) is added and the reaction mixture is stirred at room temperature for 1 h. Water is added and filtered, the filtrate is purified by preparative RP-HPLC using a ACN/water (5-70% MeCN, acidic conditions) gradient. The product containing fractions are combined and freeze dried to yield 3-{5-chloro-2-[(dimethylamino)methyl]-1H-indol-3-yl}-5-hydroxy-2,3-dihydro-1H-isoindol-1-one (I-005) (13 mg; 37 µmol; 79.6%). HPLC method: LCMSBAS1: [M+H]$^+$=356; $t_{ret}$ [min]=0.80 min.

Experimental Procedure for the Synthesis of 3-{2-[(dimethylamino)methyl]-5-fluoro-1H-indol-3-yl}-5-hydroxy-2,3-dihydro-1H-isoindol-1-one

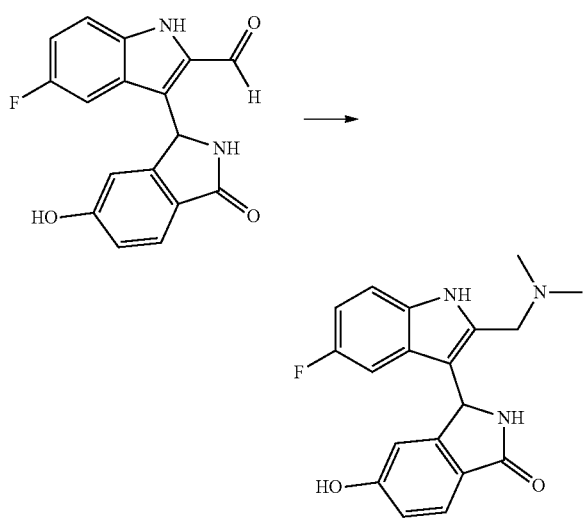

The aldehyde 5-fluoro-3-(6-hydroxy-3-oxo-2,3-dihydro-1H-isoindol-1-yl)-1H-indole-2-carbaldehyde (145 mg; 467 µmol) is dissolved in THF (5 mL) and dimethylamine (580 µL; 2 M solution in THF; 1.16 mmol) is added at 0° C. After 2 h sodium triacetoxyborohydride (297 mg; 1.402 mmol) is added and the reaction mixture is stirred at room temperature for 16 h. The reaction mixture is quenched, extracted with EtOAc. The organic phase is dried over Na$_2$SO$_4$, filtered and concentrated in vacuo. The crude product is purified by flash chromatography on SiO$_2$ using EtOAc/MeOH (90:10) as eluent followed by preparative RP-HPLC. The product containing fractions are combined and freeze dried to yield 3-{2-[(dimethylamino)methyl]-5-fluoro-1H-indol-3-yl}-5-hydroxy-2,3-dihydro-1H-isoindol-1-one (I-007) (25 mg; 74 µmol; 15.8%). HPLC method: LCMS-BAS1: [M+H]$^+$=340; $t_{ret}$ [min]=0.81 min.

Experimental Procedure for the Synthesis of 3-{2-[(dimethylamino)methyl]-5-fluoro-1H-indol-3-yl}-5-hydroxy-2,3-dihydro-1H-isoindol-1-one

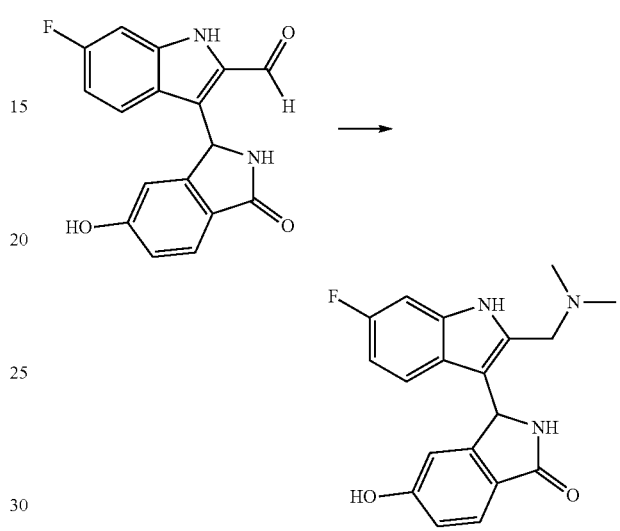

The aldehyde 6-fluoro-3-(6-hydroxy-3-oxo-2,3-dihydro-1H-isoindol-1-yl)-1H-indole-2-carbaldehyde (200 mg; 645 µmol) is dissolved in THF (5 mL) and dimethylamine (580 µL; 2 M solution in THF; 1.16 mmol) is added at 0° C. After 4 h sodium triacetoxyborohydride (410 mg; 1.934 mmol) is added and the reaction mixture is stirred at room temperature for 16 h. The reaction mixture is quenched, extracted with EtOAc. The organic phase is dried over Na$_2$SO$_4$, filtered and concentrated under reduced pressure. The crude product is purified by flash chromatography on SiO$_2$ using EtOAc/MeOH (90:10) as eluent followed by preparative RP-HPLC. The product containing fractions are freeze dried to yield 3-{2-[(dimethylamino)methyl]-5-fluoro-1H-indol-3-yl}-5-hydroxy-2,3-dihydro-1H-isoindol-1-one (I-008) (25 mg; 74 µmol; 11.4%). HPLC method: LCMSBAS1: [M+H]$^+$=340; $t_{ret}$ [min]=0.81 min.

Experimental Procedure for the Synthesis of 3-(6-Fluoro-2-{[(1-methyl-1H-indol-6-ylmethyl)-amino]-methyl}-1H-indol-3-yl)-5-hydroxy-2,3-dihydro-isoindol-1-one

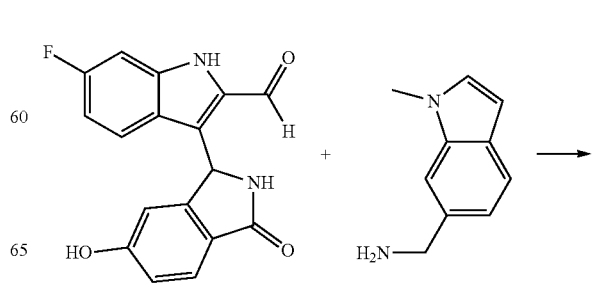

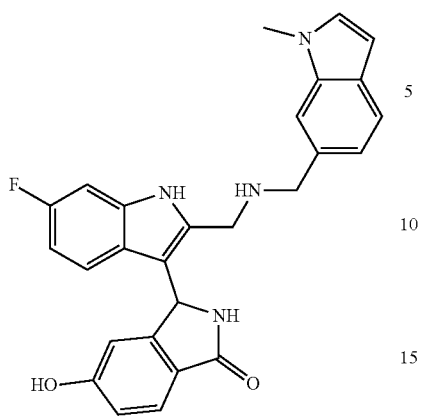

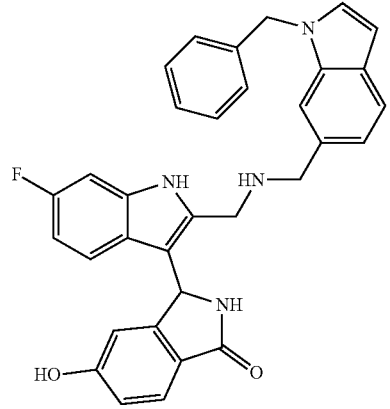

In a glass vial 6-fluoro-3-(6-hydroxy-3-oxo-2,3-dihydro-1H-isoindol-1-yl)-1H-indole-2-carbaldehyde (49 mg; 158 μmol) is dissolved in DMF (1 mL) and (1-methyl-1H-indol-6-yl)methylamine (32 mg; 190 μmol; commercial available from ABCR) is added and the mixture is stirred at room temperature for 15 min before sodium triacetoxyborohydride (167.4 mg; 790 μmol) is added and the mixture is stirred at room temperature overnight. ACN/H$_2$O (1:1; 0.2 mL) are added to the reaction mixture, filtered through a syringe filter and purified by prep. HPLC-MS. The product containing fractions are freeze dried to yield 3-(6-Fluoro-2-{[(1-methyl-1H-indol-6-ylmethyl)-amino]-methyl}-1H-indol-3-yl)-5-hydroxy-2,3-dihydro-isoindol-1-one (I-009) (38 mg; 84 μmol; 52.9%). HPLC method: LCMSBAS1: [M+H]$^+$=455; t$_{ret}$ [min]=1.10 min.

Experimental Procedure for the Synthesis of 3-(2-{[(1-Benzyl-1H-indol-6-ylmethyl)-amino]-methyl}-6-fluoro-1H-indol-3-yl)-5-hydroxy-2,3-dihydro-isoindol-1-one In a glass vial 6-fluoro-3-(6-hydroxy-3-oxo-2,3-dihydro-1H-isoindol-1-yl)-1H-indole-2-carbaldehyde (49 mg; 158 μmol) is dissolved in DMF (1 mL) and C-(1-Benzyl-1H-indol-6-yl)-methylamine (47.14 mg; 85 μmol) is added and the mixture is stirred at room temperature for 15 min before sodium triacetoxyborohydride (167.4 mg; 790 μmol) is added and the mixture is stirred at room temperature overnight. ACN/H$_2$O (1:1; 0.2 mL) are added to the reaction mixture, filtered through a syringe filter and purified by prep. RP-HPLC-MS. The product containing fractions are combined and freeze dried to yield 3-(2-{[(1-Benzyl-1H-indol-6-ylmethyl)-amino]-methyl}-6-fluoro-1H-indol-3-yl)-5-hydroxy-2,3-dihydro-isoindol-1-one (I-010) (45 mg; 85 μmol; 53.7%). HPLC method: LCMSBAS1: [M+H]$^+$=531; t$_{ret}$ [min]=1.26 min.

Experimental Procedure for the Synthesis of 3-{5,6-difluoro-2-[(pyrrolidin-1-yl)methyl]-1H-indol-3-yl}-5-hydroxy-2,3-dihydro-1H-isoindol-1-one

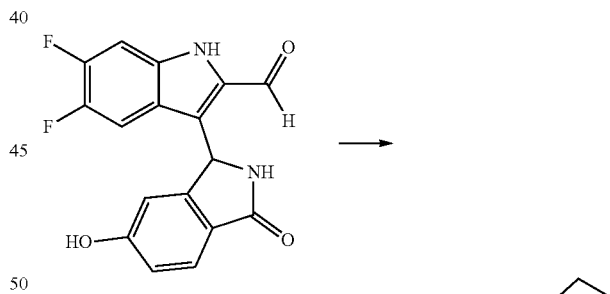

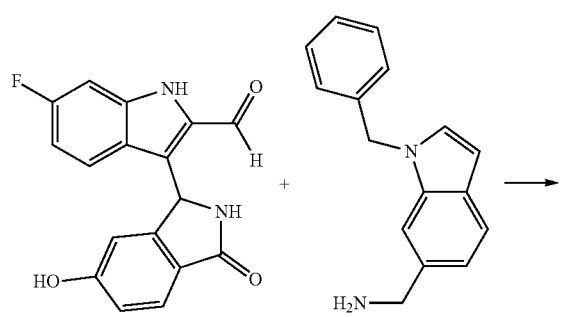

The aldehyde 5,6-difluoro-3-(6-hydroxy-3-oxo-2,3-dihydro-1H-isoindol-1-yl)-1H-indole-2-carbaldehyde (400 mg; 1.219 mmol) and pyrrolidine (0.25 mL; 3.046 mmol) are dissolved in THF (4 mL). After 3 h sodium triacetoxyborohydride (775 mg; 3.66 mmol) is added and the reaction mixture is stirred at room temperature overnight. The reaction mixture is diluted and extracted with EtOAc. The organic phase is dried over Na$_2$SO$_4$, filtered and concentrated under reduced pressure. The crude product is purified by preparative RP-HPLC and the product containing fractions are freeze dried to yield 3-{5,6-difluoro-2-[(pyrrolidin-1-yl)methyl]-1H-indol-3-yl}-5-hydroxy-2,3-dihydro-1H-isoindol-1-one (I-011) (168 mg; 438 µmol; 36%). HPLC method: LCMSBAS1: [M+H]$^+$=384; t$_{ret}$ [min]=0.98 min.

Experimental Procedure for the Synthesis of 3-{2-[(dimethylamino)methyl]-1H-indol-3-yl}-5-hydroxy-3-methyl-2,3-dihydro-1H-isoindol-1-one

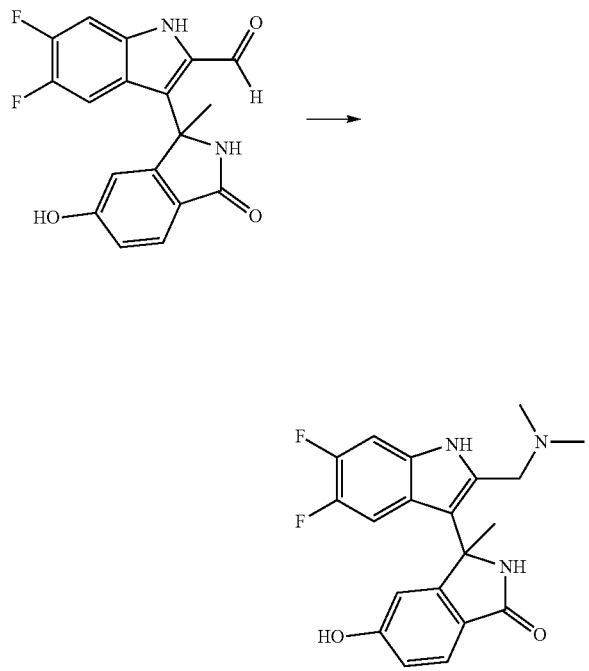

3-(6-Hydroxy-1-methyl-3-oxo-2,3-dihydro-1H-isoindol-1-yl)-1H-indole-2-carbaldehyde (66 mg; 215 µmol) is dissolved in DMF (1 mL) and sodium acetate (26.5 mg; 323 µmol) and acetic acid (12 µL; 215 µmol) are added. The reaction mixture is stirred at room temperature for 2 h before sodium triacetoxyborohydride (94.16 mg; 431 µmol) is added and the reaction mixture is stirred at room temperature overnight. The reaction mixture is quenched with one drop of water, filtered and purified by RP-HPLC (acidic condition). The product containing fractions are pooled and concentrated under reduced pressure. The product is dissolved in ACN/water (1:1) and freeze dried to 3-{2-[(dimethylamino)methyl]-1H-indol-3-yl}-5-hydroxy-3-methyl-2,3-dihydro-1H-isoindol-1-one (23.5 mg; 70 µmol; 32.5%). HPLC method: LCMSBAS1: [M+H]$^+$=336; t$_{ret}$ [min]=0.84 min.

Experimental Procedure for the Synthesis of 3-{2-[(dimethylamino)methyl]-1H-indol-3-yl}-5-hydroxy-6-methyl-2,3-dihydro-1H-isoindol-1-one,(3S)-3-{2-[(dimethylamino)methyl]-1H-indol-3-yl}-5-hydroxy-6-methyl-2,3-dihydro-1H-isoindol-1-one and (3R)-3-{2-[(dimethylamino)methyl]-1H-indol-3-yl}-5-hydroxy-6-methyl-2,3-dihydro-1H-isoindol-1-one To a stirred solution of 5-Hydroxy-6-methyl-isoindole-1,3-dione (100 mg; 564 µmol) in AcOH (4 mL), Zinc powder (221 mg; 3.387 mmol) is added and the reaction mixture is heated at 110° C. for 30 min. TLC analysis showed full conversion of starting material with formation of new polar spots. The reaction mixture is filtered to a solution of (1H-Indol-2-ylmethyl)-dimethyl-amine (98 mg; 564 mmol) in AcOH (5 mL). The reaction mixture is heated at 80° C. for 3 h. TLC analysis showed full conversion of starting material with formation of a new polar spot. The solvent is evaporated and the residue is purified by column chromatography over silica gel using methanol in dichloromethane (5:95, v/v) as eluent yielding a brown solid. The crude product is purified by preparative RP-HPLC yielding racemic 3-{2-[(dimethylamino)methyl]-1H-indol-3-yl}-5-hydroxy-6-methyl-2,3-dihydro-1H-isoindol-1-one (30 mg; 89 µmol; 15.8%).

The racemic mixture of 3-{2-[(dimethylamino)methyl]-1H-indol-3-yl}-5-hydroxy-6-methyl-2,3-dihydro-1H-isoindol-1-one could be separated by chiral SFC to yield (3S)-3-{2-[(dimethylamino)methyl]-1H-indol-3-yl}-5-hydroxy-6-methyl-2,3-dihydro-1H-isoindol-1-one (I-025) and (3R)-3-{2-[(dimethylamino)methyl]-1H-indol-3-yl}-5-hydroxy-6-methyl-2,3-dihydro-1H-isoindol-1-one.

Experimental Procedure for the Synthesis of 5-hydroxy-6-methyl-3-{2-[(pyrrolidin-1-yl)methyl]-1H-indol-3-yl}-2,3-dihydro-1H-isoindol-1-one, (3S)-5-hydroxy-6-methyl-3-{2-[(pyrrolidin-1-yl)methyl]-1H-indol-3-yl}-2,3-dihydro-1H-isoindol-1-one and (3R)-5-hydroxy-6-methyl-3-{2-[(pyrrolidin-1-yl)methyl]-1H-indol-3-yl}-2,3-dihydro-1H-isoindol-1-one

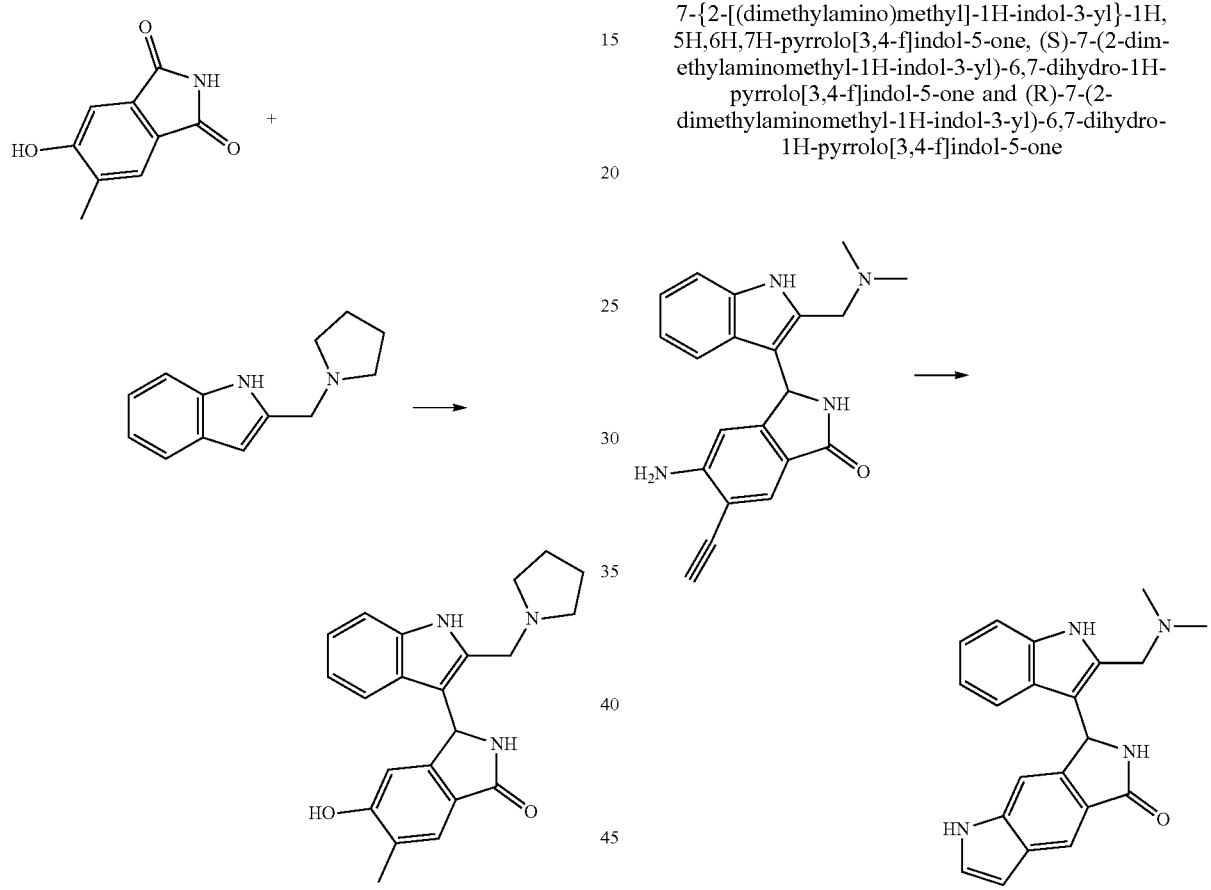

To a stirred solution of 5-hydroxy-6-methyl-isoindole-1,3-dione (200 mg; 1.129 mmol) in AcOH (4 mL), Zinc powder (443 mg; 6.774 mmol) is added and the reaction mixture is heated at 110° C. for 30 min. TLC analysis showed full conversion of starting material with formation of a new polar spots. The reaction mixture is filtered to a solution of 2-pyrrolidin-1-ylmethyl-1H-indole (226 mg; 1.129 mmol) in AcOH (5 mL). The reaction mixture is heated at 80° C. for 7 h. TLC analysis showed full conversion of starting material with formation of a new polar spot. The solvent is evaporated and the residue is purified by column chromatography over silica gel using methanol in dichloromethane (5:95, v/v) as eluent yielded a brown solid. It was further submitted for preparative RP-HPLC (ACN: MeOH gradient, basic conditions) to yield racemic 5-hydroxy-6-methyl-3-{2-[(pyrrolidin-1-yl)methyl]-1H-indol-3-yl}-2,3-dihydro-1H-isoindol-1-one (I-026) (30 mg; 83 µmol; 7.4%). HPLC method: LCMSBAS1: [M+H]$^+$=362; t$_{ret}$ [min]=0.99 min.

The racemic mixture of 5-hydroxy-6-methyl-3-{2-[(pyrrolidin-1-yl)methyl]-1H-indol-3-yl}-2,3-dihydro-1H-isoindol-1-one could be separated by chiral SFC to yield (3S)-5-hydroxy-6-methyl-3-{2-[(pyrrolidin-1-yl)methyl]-1H-indol-3-yl}-2,3-dihydro-1H-isoindol-1-one (I-027) and (3R)-5-hydroxy-6-methyl-3-{2-[(pyrrolidin-1-yl)methyl]-1H-indol-3-yl}-2,3-dihydro-1H-isoindol-1-one. HPLC method: LCMSBAS1: [M+H]$^+$=362; t$_{ret}$ [min]=0.97 min.

Experimental Procedure for the Synthesis of yield 7-{2-[(dimethylamino)methyl]-1H-indol-3-yl}-1H,5H,6H,7H-pyrrolo[3,4-f]indol-5-one, (S)-7-(2-dimethylaminomethyl-1H-indol-3-yl)-6,7-dihydro-1H-pyrrolo[3,4-f]indol-5-one and (R)-7-(2-dimethylaminomethyl-1H-indol-3-yl)-6,7-dihydro-1H-pyrrolo[3,4-f]indol-5-one

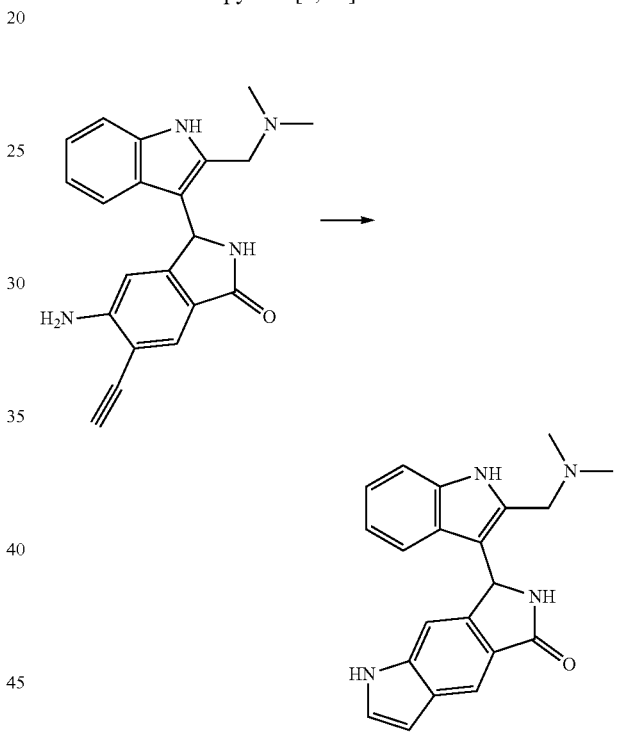

5-amino-3-{2-[(dimethylamino)methyl]-1H-indol-3-yl}-6-ethynyl-2,3-dihydro-1H-isoindol-1-one (84 mg; 171 µmol) is dissolved in pyridine (0.3 mL) and a treated with chlorocyclopentadienylbis(triphenylphosphine)ruthenium (II) (30.995 mg; 43 µmol) for 3 days at 90° C. The reaction mixture is filtered through a syringe filter and purified by preparative RP-HPLC (3-45% ACN in water, basic conditions). The product containing fractions are combined, concentrated under reduced pressure and freeze dried to yield 7-{2-[(dimethylamino)methyl]-1H-indol-3-yl}-1H,5H,6H,7H-pyrrolo[3,4-f]indol-5-one (I-032) (30 mg; 87 µmol; 51%) HPLC method: LCMSBAS1: [M+H]+=345; t$_{ret}$ [min]=0.87 min. The racemic mixture of 7-{2-[(dimethylamino)methyl]-1H-indol-3-yl}-1H,5H,6H,7H-pyrrolo[3,4-f]indol-5-one could be separated by chiral SFC to yield (S)-7-(2-dimethylaminomethyl-1H-indol-3-yl)-6,7-dihydro-1H-pyrrolo[3,4-f]indol-5-one (I-033) and (R)-7-(2-dimethylaminomethyl-1H-indol-3-yl)-6,7-dihydro-1H-pyrrolo[3,4-f]indol-5-one.

Experimental Procedure for the Synthesis of 7-{2-[(dimethylamino)methyl]-1H-indol-3-yl}-1H,5H,6H,7H-imidazo[4,5-f]isoindol-5-one

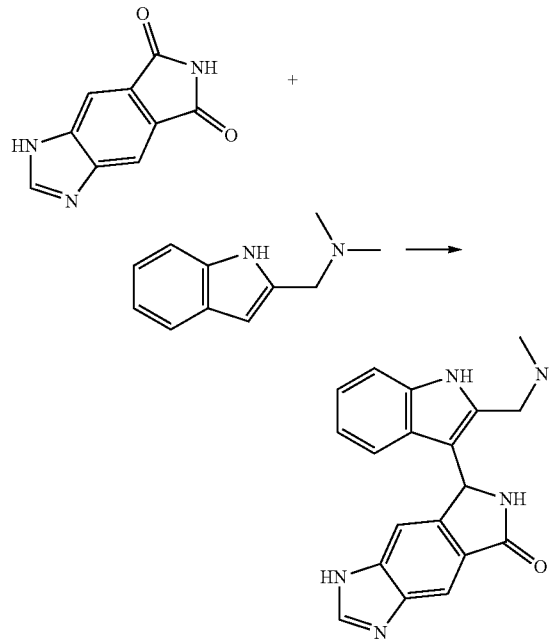

1H,5H,6H,7H-Imidazo[4,5-f]isoindole-5,7-dione (60 mg; 321 µmol), [(1H-indol-2-yl)methyl]dimethylamine (55.86 mg; 321 µmol) are dissolved in AcOH (4 mL). Zinc (41.93 mg; 641 µmol) added and the reaction mixture is stirred at 120° C. overnight. The reaction mixture is diluted with ACN/water and filtered through a syringe filter and concentrated under reduced pressure. The residue is purified by preparative RP-HPLC (ACN/water gradient, acidic conditions). The product containing fractions are combined, concentrated under reduced pressure and freeze dried to yield 7-{2-[(dimethylamino)methyl]-1H-indol-3-yl}-1H,5H,6H,7H-imidazo[4,5-f]isoindol-5-one (I-031) (30 mg; 87 µmol; 27.1%) HPLC method: LCMSBAS1: [M+H]$^+$=346; t$_{ret}$ [min]=0.73 min.

Experimental Procedure for the Synthesis of 7-{2-[(dimethylamino)methyl]-1H-indol-3-yl}-1H,5H,6H,7H-[1,2,3]triazolo[4,5-f]isoindol-5-one

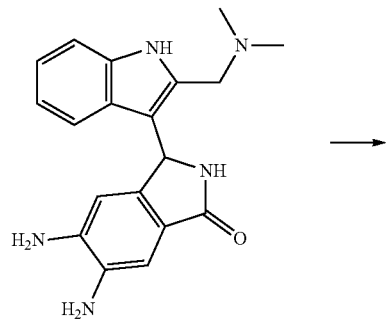

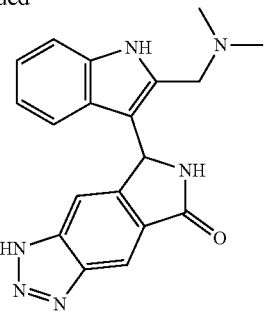

To a solution of 5,6-diamino-3-{2-[(dimethylamino)methyl]-1H-indol-3-yl}-2,3-dihydro-1H-isoindol-1-one (200 mg; 596 µmol) in AcOH (1.2 mL) is added dropwise a 1M sodium nitrite solution (3 mL) at 0° C. The reaction mixture is heated to 75° C. for 1 h. After completion of the reaction the solvent was evaporated and the crude product was purified by flash chromatography on SiO$_2$ using DCM/MeOH (85:15) as eluent and RP-HPLC (ACN/water gradient). The product containing fractions are combined, concentrated under reduced pressure and freeze dried to yield 7-{2-[(dimethylamino)methyl]-1H-indol-3-yl}-1H,5H,6H,7H-[1,2,3]triazolo[4,5-f]isoindol-5-one (I-034) (110 mg; 318 µmol; 53.3%). HPLC method: LCMSBAS1: [M+H]$^+$=347; t$_{ret}$ [min]=0.36 min.

Experimental Procedure for the Synthesis of 2-amino-7-{2-[(dimethylamino)methyl]-1H-indol-3-yl}-1H,5H,6H,7H-imidazo[4,5-f]isoindol-5-one

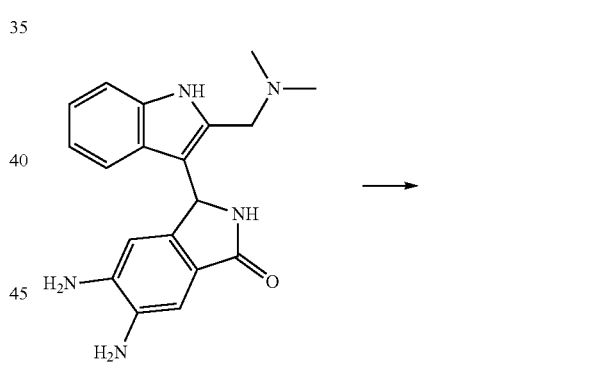

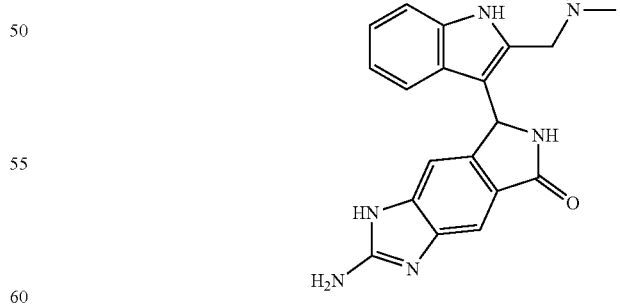

To a solution of 5,6-diamino-3-{2-[(dimethylamino)methyl]-1H-indol-3-yl}-2,3-dihydro-1H-isoindol-1-one (45 mg; 121 µmol) in ethanol (1.0 mL) is added a 3M solution of cyanogen bromide in DCM (42 µL; 127 µmol). The reaction mixture is stirred at room temperature overnight and then quenched by addition of 5M NaOH (0.5 mL), concentrated under reduced pressure. The crude material is dissolved in DMSO, some drops of water are added and the suspension is filtered and purified RP-HPLC (ACN/water gradient, basic conditions). The product containing fractions are combined, concentrated under reduced pressure and freeze dried to yield 2-amino-7-{2-[(dimethylamino)methyl]-1H-indol-3-yl}-1H,5H,6H,7H-imidazo[4,5-f]isoindol-5-one (I-035) (0.9 mg; 2 µmol; 2.1%). HPLC method: LCMSBAS1: [M+H]⁺=361; t$_{ret}$ [min]=0.57 min.

Experimental Procedure for the Synthesis of -2-cyclopropyl-7-{2-[(dimethylamino)methyl]-1H-indol-3-yl}-1H,5H,6H,7H-imidazo[4,5-f]isoindol-5-one Experimental Procedure for the Synthesis of 7-{2-[(dimethylamino)methyl]-1H-indol-3-yl}-1H,5H,6H,7H-pyrrolo[3,4-f]indazol-5-one, (7S)-7-{2-[(dimethylamino)methyl]-1H-indol-3-yl}-1H,5H,6H,7H-pyrrolo[3,4-f]indazol-5-one and (7R)-7-{2-[(dimethylamino)methyl]-1H-indol-3-yl}-1H,5H,6H,7H-pyrrolo[3,4-f]indazol-5-one

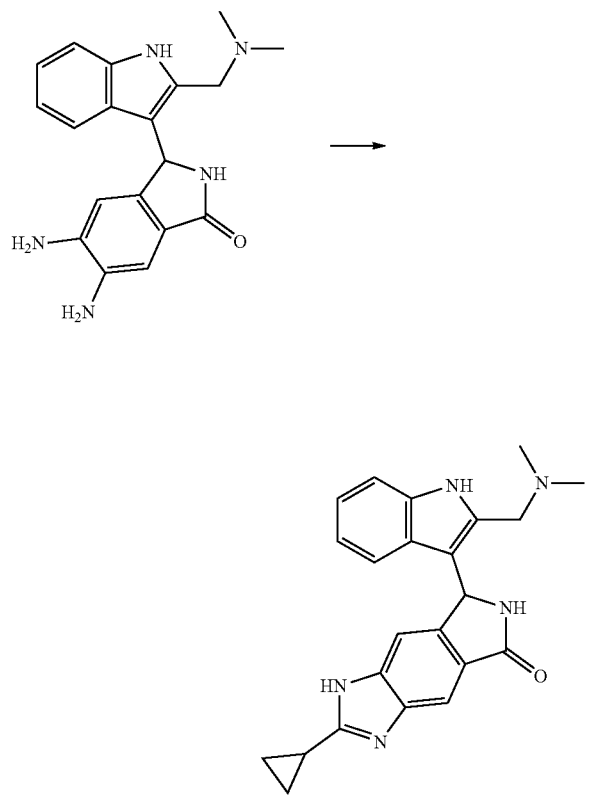

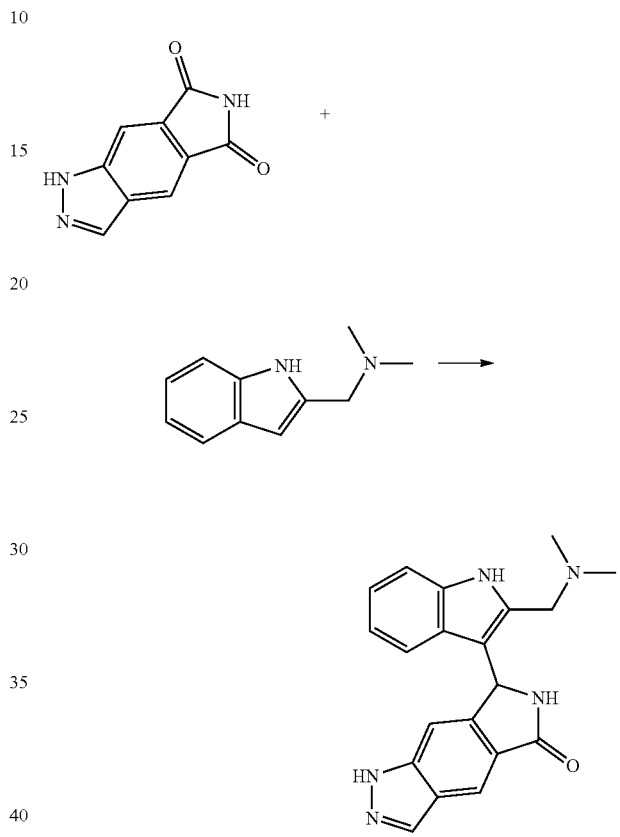

5,6-Diamino-3-{2-[(dimethylamino)methyl]-1H-indol-3-yl}-2,3-dihydro-1H-isoindol-1-one (30 mg; 87 µmol), cyclopropanecarboxaldehyde (6.27 mg; 89 µmol) and sodium perborate tetrahydrate (15.14 mg; 98 µmol) were dissolved in 1:2-water/acetic acid (1 mL) and stirred at room temperature. The reaction mixture is diluted with ACN/water and filtered through a syringe filter and concentrated under reduced pressure. The residue is purified by preparative RP-HPLC (ACN/water gradient, basic conditions). The product containing fractions are combined, concentrated under reduced pressure and freeze dried to yield 2-cyclopropyl-7-{2-[(dimethylamino)methyl]-1H-indol-3-yl}-1H,5H,6H,7H-imidazo[4,5-f]isoindol-5-one (I-036) (10 mg; 26 µmol; 29.0%). HPLC method: LCMSBAS1: [M+H]+=386; t$_{ret}$ [min]=0.83 min.

1H,5H,6H,7H-Pyrrolo[3,4-f]indazole-5,7-dione (50 mg; 267 µmol) and [(1H-indol-2-yl)methyl]dimethylamine (46.55 mg; 267 µmol) are dissolved in THF (10 mL). Zinc dust (140 mg; 2.137 mmol) and conc. HCl (0.5 mL) are added and the reaction mixture is stirred at room temperature overnight. The next day again conc. HCl (0.5 mL) is added. The reaction mixture is neutralized by addition of sodium carbonate, filtered through a pad of celite and concentrated under reduced pressure. The filtrate is dried over Na₂SO₄, filtered and concentrated. The residue is purified by preparative RP-HPLC (ACN/water gradient, acidic conditions). The product containing fractions are combined, concentrated under reduced pressure and freeze dried to yield 7-{2-[(dimethylamino)methyl]-1H-indol-3-yl}-1H,5H,6H,7H-pyrrolo[3,4-f]indazol-5-one (I-029) (6 mg; 17 µmol; 6.5%). HPLC method: LCMSBAS1: [M+H]⁺=346; t$_{ret}$ [min]=0.85 min.

The racemic mixture of 7-{2-[(dimethylamino)methyl]-1H-indol-3-yl}-1H,5H,6H,7H-pyrrolo[3,4-f]indazol-5-one could be separated by chiral SFC to yield (7S)-7-{2-[(dimethylamino)methyl]-1H-indol-3-yl}-1H,5H,6H,7H-pyrrolo[3,4-f]indazol-5-one (I-030) and (7R)-7-{2-[(dimethylamino)methyl]-1H-indol-3-yl}-1H,5H,6H,7H-pyrrolo[3,4-f]indazol-5-one. HPLC method: LCMS3BAS1: [M+H]⁺=346; t$_{ret}$ [min]=0.82 min.

Experimental Procedure for the Synthesis of 3-{7-amino-2-[(dimethylamino)methyl]-1H-indol-3-yl}-5-hydroxy-2,3-dihydro-1H-isoindol-1-one, (3S)-3-{7-amino-2-[(dimethylamino)-methyl]-1H-indol-3-yl}-5-hydroxy-2,3-dihydro-1H-isoindol-1-one and (3R)-3-{7-amino-2-[(dimethylamino)methyl]-1H-indol-3-yl}-5-hydroxy-2,3-dihydro-1H-isoindol-1-one

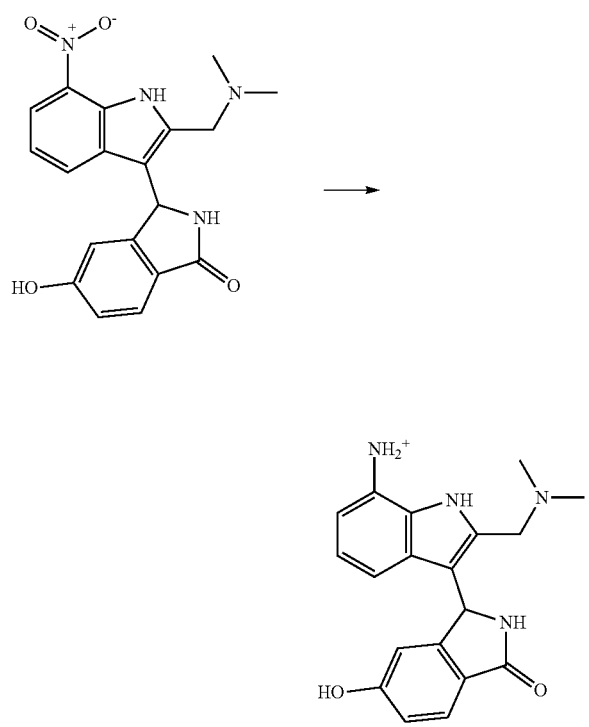

A suspension of 3-{2-[(dimethylamino)methyl]-7-nitro-1H-indol-3-yl}-5-hydroxy-2,3-dihydro-1H-isoindol-1-one (30 mg; 82 µmol) and a catalytic amount of Pd(10%)/C in MeOH is hydrogenated at 50 p.s.i. at stirred at room temperature overnight. The reaction mixture filtered and concentrated under reduced pressure to yield 3-{7-amino-2-[(dimethylamino)methyl]-1H-indol-3-yl}-5-hydroxy-2,3-dihydro-1H-isoindol-1-one (26 mg; 77 µmol; 94.4%). HPLC method: LCMSBAS1: [M+H]$^+$=337; $t_{ret}$ [min]=0.32 min.

The pure enantiomers were obtained through chiral separation via chiral SFC or via synthesis starting from the chirally separated alcohols.

Starting from 3-{2-[(dimethylamino)methyl]-7-nitro-1H-indol-3-yl}-5-hydroxy-2,3-dihydro-1H-isoindol-1-one (16 mg; 48 µmol) the chiral separation resulted in (3S)-3-{7-amino-2-[(dimethylamino)methyl]-1H-indol-3-yl}-5-hydroxy-2,3-dihydro-1H-isoindol-1-one (I-021) (4.46 mg; 13 µmol; 27.9%) and (3R)-3-{7-amino-2-[(dimethylamino)methyl]-1H-indol-3-yl}-5-hydroxy-2,3-dihydro-1H-isoindol-1-one (3.19 mg; 9 µmol; 19.9%). HPLC method: LCMSBAS1: [M+H]$^+$=337; $t_{ret}$ [min]=0.31 min.

Experimental Procedure for the Synthesis of 3-(7-amino-2-[(dimethylamino)methyl]-1H-indol-3-yl)-5-hydroxy-1,3-dihydro-2-benzofuran-1-one

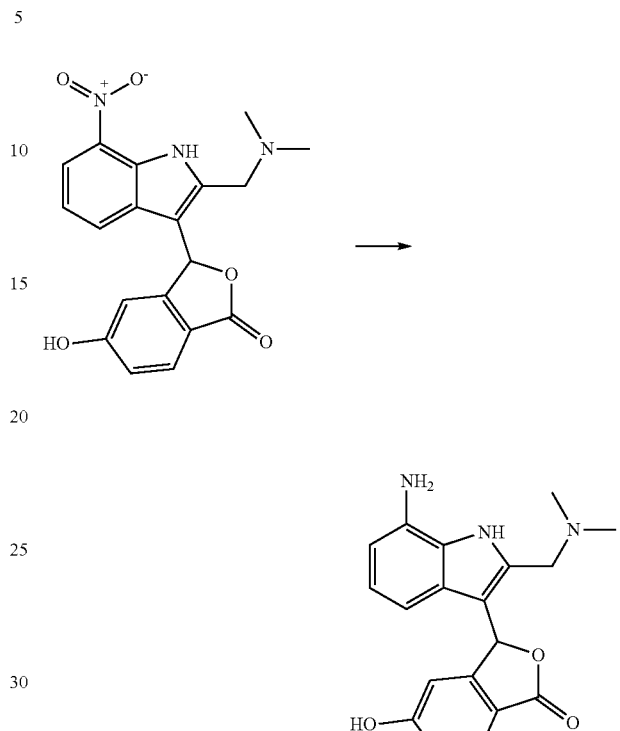

To a solution of 3-{2-[(dimethylamino)methyl]-7-nitro-1H-indol-3-yl}-5-hydroxy-1,3-dihydro-2-benzofuran-1-one (100 mg; 272 µmol) in EtOH (5 mL) and a saturated ammonium chloride solution (1 mL) is added iron powder (76 mg; 1.361 mmol). The reaction mixture is stirred at 80° C. overnight. The reaction mixture is filtered, washed with EtOH and concentrated under reduced pressure. The residue is taken up in DMSO (4 mL) and purified by RP-HPLC-MS (ACN/water gradient, acidic condition). The product containing fractions are pooled, concentrated under reduced pressure and freeze dried to yield 3-{7-amino-2-[(dimethylamino)methyl]-1H-indol-3-yl}-5-hydroxy-1,3-dihydro-2-benzofuran-1-one (I-022) (36 mg; 107 µmol; 39.2%). HPLC method: LCMSBAS1: [M+H]$^+$=338; $t_{ret}$ [min]=0.38 min.

Experimental Procedure for the Synthesis of 5-amino-3-{2-[(dimethylamino)methyl]-1H-indol-3-yl}-2,3-dihydro-1H-isoindol-1-one

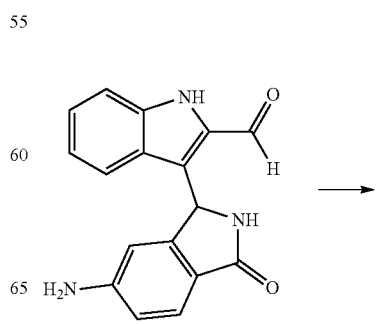

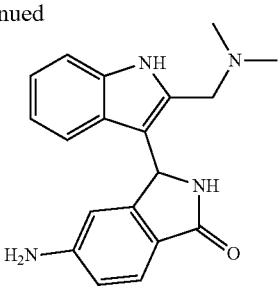

To a solution of 3-(6-amino-3-oxo-2,3-dihydro-1H-isoindol-1-yl)-1H-indole-2-carbaldehyde (25 mg; 86 µmol) in THF (10 mL) and DCM (5 mL) is added dimethylamine (129 µL; 257 µmol) and the reaction mixture is stirred at room temperature for 15 min. Sodium triacetoxyborohydride (37.5 mg; 172 µmol) is added and the reaction mixture is stirred at room temperature for 3. The reaction mixture is quenched by addition of water and concentrated under reduced pressure. The crude material is dissolved in DMSO (1 mL), filtered and purified by RP-HPLC-MS (basic condition). The product containing fractions are pooled and freeze dried to yield 5-amino-3-{2-[(dimethylamino) methyl]-1H-indol-3-yl}-2,3-dihydro-1H-isoindol-1-one (I-098) (15.8 mg; 49 µmol; 57.5%). HPLC method: LCMSBAS1: [M−H]$^+$=321; $t_{ret}$ [min]=0.73 min.

Experimental Procedure for the Synthesis of 3-ethyl-1-(1-oxo-3-{2-[(pyrrolidin-1-yl)methyl]-1H-indol-3-yl}-2,3-dihydro-1H-isoindol-5-yl)urea A solution of 2-[(pyrrolidin-1-yl)methyl]-1H-indole (25 mg; 125 µmol) and 1-(1,3-dioxo-2,3-dihydro-1H-isoindol-5-yl)-3-ethylurea (29.1 mg; 125 µmol) in THF (1 mL) is treated with zinc (16.325 mg; 250 µmol) and conc. HCl (0.5 mL). The reaction mixture is stirred at room temperature for 10 min. The reaction mixture is concentrated under reduced pressure, separation of regioisomers and purification done by prep. HPLC (acidic condition). The product containing fractions are pooled and freeze dried to yield 3-ethyl-1-(1-oxo-3-{2-[(pyrrolidin-1-yl)methyl]-1H-indol-3-yl}-2,3-dihydro-1H-isoindol-5-yl)urea (I-099) (20 mg; 48 µmol; 38.4%). HPLC method: LCMSBAS1: [M−H]$^+$=418; $t_{ret}$ [min]=0.98 min.

Experimental Procedure for the Synthesis of 3-ethyl-1-(1-oxo-3-{2-[(pyrrolidin-1-yl)methyl]-1H-indol-3-yl}-2,3-dihydro-1H-isoindol-5-yl)urea, (3S)-5-({1-[(aminomethyl)amino]-2-oxoethenyl}amino)-3-{2-[(pyrrolidin-1-yl)methyl]-1H-indol-3-yl}-2,3-dihydro-1H-isoindol-1-one and (3R)-5-({1-[(aminomethyl)amino]-2-oxoethenyl}amino)-3-{2-[(pyrrolidin-1-yl)methyl]-1H-indol-3-yl}-2,3-dihydro-1H-isoindol-1-one

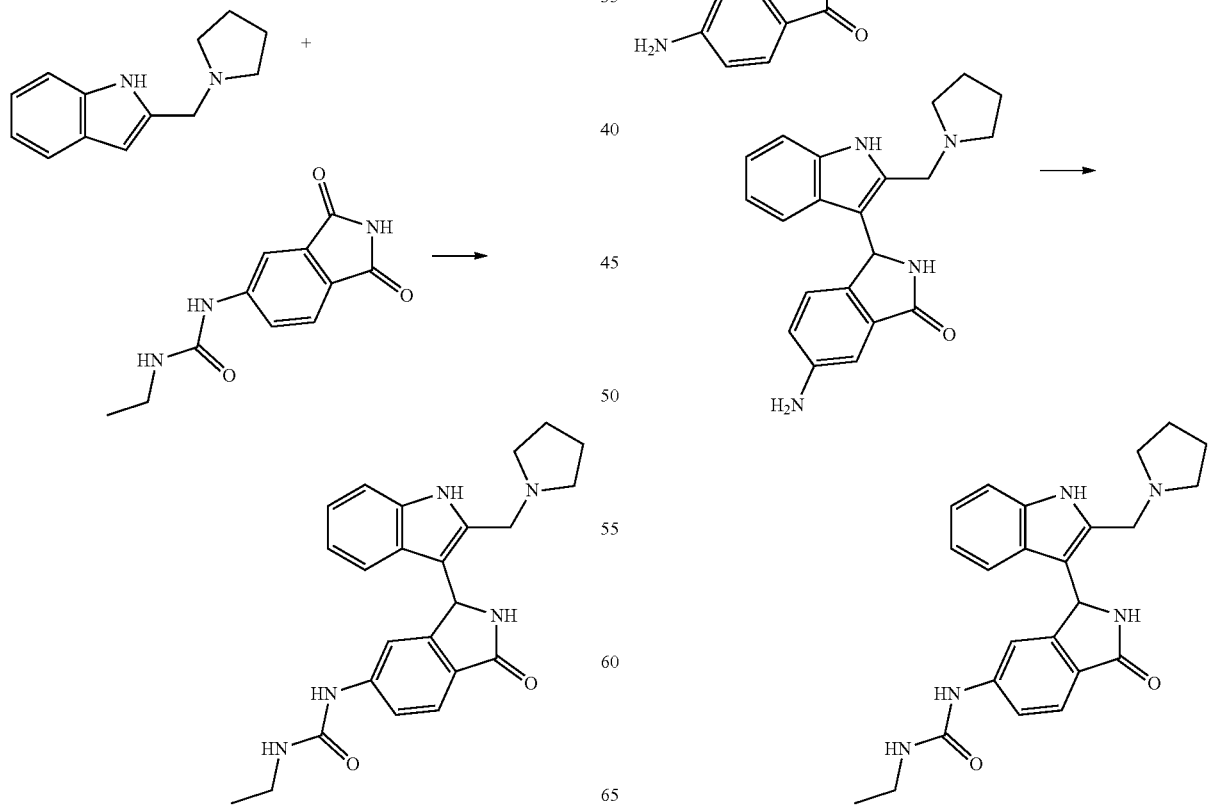

The regioisomeric mixture of 5- and 6-amino-3-{2-[(pyrrolidin-1-yl)methyl]-1H-indol-3-yl}-2,3-dihydro-1H-isoindol-1-one (200 mg; 577 µmol) is dissolved in THF (3 mL) and treated with ethyl isocyanate (61.553 mg; 866 µmol) and due to the low solubility of the starting material heated to 60° C. The reaction mixture is concentrated under reduced pressure, separation of regioisomers and purification done by RP-HPLC (ACN/water gradient; acidic condition). The product containing fractions are pooled and freeze dried to yield 3-ethyl-1-(1-oxo-3-{2-[(pyrrolidin-1-yl)methyl]-1H-indol-3-yl}-2,3-dihydro-1H-isoindol-5-yl)urea (18 mg; 43 µmol; 49.8%). HPLC method: LCMSBAS1: [M−H]+=418; $t_{ret}$ [min]=1.01 min.

The racemic mixture of 3-ethyl-1-(1-oxo-3-{2-[(pyrrolidin-1-yl)methyl]-1H-indol-3-yl}-2,3-dihydro-1H-isoindol-5-yl)urea (50 mg; 119.8 mmol) could be separated by chiral SFC to yield (3S)-5-({1-[(aminomethyl)amino]-2-oxoethenyl}amino)-3-{2-[(pyrrolidin-1-yl)methyl]-1H-indol-3-yl}-2,3-dihydro-1H-isoindol-1-one (I-100) (10 mg; 24 µmol; 4.1%) and (3R)-5-({1-[(aminomethyl)amino]-2-oxoethenyl}amino)-3-{2-[(pyrrolidin-1-yl)methyl]-1H-indol-3-yl}-2,3-dihydro-1H-isoindol-1-one (11 mg; 26 µmol; 4.6%). HPLC method: LCMSBAS1: [M+H]+=418; $t_{ret}$ [min]=1.00 min.

Experimental Procedure for the Synthesis of (5-bromo-3-hydroxy-1,3-dihydro-2-benzofuran-1-one To a solution of 5-bromo-1,3-dihydro-2-benzofuran-1-one (5.0 g; 23.47 mmol) in benzene (100 mL) is added 1-bromopyrrolidine-2,5-dione (4.595 g; 25.818 mmol) and 2,2'-azo-bis(2-methylpropionitrile) (192.7 mg; 1.174 mmol) at room temperature. The reaction mixture is heated to 85° C. for 17 h. The reaction mixture is concentrated under reduced pressure, dissolved in DCM:MeOH, mixed with ISOLUTE, concentrated under reduced pressure and purified by NP-chromatography (Redisep Rf; gradient cHex:EE 100:0-70:30, 85 mL/min flow). The product (5-bromo-3-hydroxy-1,3-dihydro-2-benzofuran-1-one (1.4 g; 6.14 mmol; 74.3%) containing fractions are pooled and concentrated under reduced pressure and used without further purification in the next reaction step.

Experimental Procedure for the Synthesis of 5-bromo-3-[2-(hydroxymethyl)-1H-indol-3-yl]-2,3-dihydro-1H-isoindol-1-one A solution of 5-bromo-3-hydroxy-1,3-dihydro-2-benzofuran-1-one (400 mg; 1.747 mmol), (1H-indol-2-yl)methanol (285.6 mg; 1.747 mmol) and a ammonia solution (28% in water) are dissolved in water and heated to 85° C. for 4 h. The resulting precipitate is filtered off, dried to yield 5-bromo-3-[2-(hydroxymethyl)-1H-indol-3-yl]-2,3-dihydro-1H-isoindol-1-one (495 mg; 1.386 mmol; 79.3%), which is used for the next reaction step without further purification.

Experimental Procedure for the Synthesis of 3-(6-bromo-3-oxo-2,3-dihydro-1H-isoindol-1-yl)-1H-indole-2-carbaldehyde

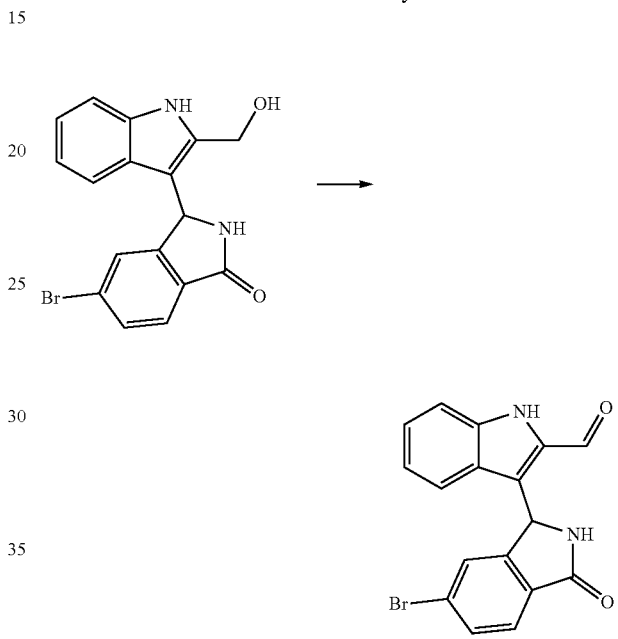

To a solution of 5-bromo-3-[2-(hydroxymethyl)-1H-indol-3-yl]-2,3-dihydro-1H-isoindol-1-one (500 mg; 1.358 mmol) in MeOH is added mangan(IV)oxide (1.312 g; 13.578 mmol). The reaction mixture is heated under reflux 4 h. The hot reaction mixture is filtered, washed with hot MeOH and concentrated under reduced pressure to yield 3-(6-bromo-3-oxo-2,3-dihydro-1H-isoindol-1-yl)-1H-indole-2-carbaldehyde (276 mg; 777 µmol; 57.2%), which is used for the next reaction step without further purification.

Experimental Procedure for the Synthesis of 5-bromo-3-{2-[(dimethylamino)methyl]-1H-indol-3-yl}-2,3-dihydro-1H-isoindol-1-one

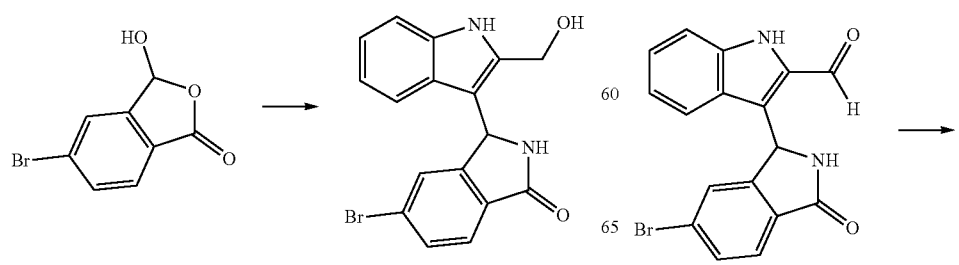

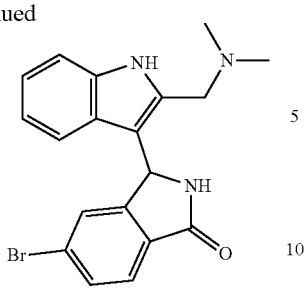

To a solution of 3-(6-bromo-3-oxo-2,3-dihydro-1H-isoindol-1-yl)-1H-indole-2-carbaldehyde (276 mg; 777 µmol) in DMF (4 mL) is added dimethylamine as a 2M solution in THF (1.816 g; 4.274 mmol) at room temperature and stirred for 30 min before sodium triacetoxyborohydride (823.5 mg; 3.858 mmol) is added. The reaction mixture is stirred at room temperature overnight. The reaction mixture is quenched by added water, filtered via a syringe filter and purified by prep. RP-HPLC (20-60% ACN/water gradient; acidic condition). The product containing fractions are pooled and freeze dried to yield 5-bromo-3-{2-[(dimethylamino)methyl]-1H-indol-3-yl}-2,3-dihydro-1H-isoindol-1-one (I-101) (61 mg; 159 µmol; 20.4%). HPLC method: LCMSBAS1: [M+H]$^+$=384; t$_{ret}$ [min]=1.10 min.

Experimental Procedure for the Synthesis of (N-(1,3-Dioxo-2,3-dihydro-1H-isoindol-5-yl)-methanesulfonamide

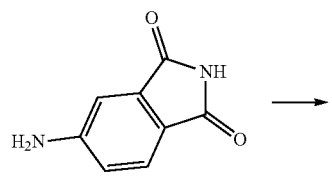

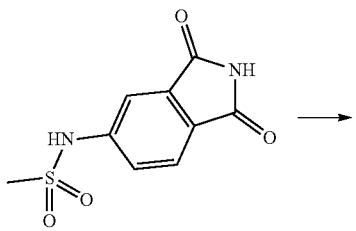

To a suspension of 4-aminophthalimide (0.5 g; 2.99 mmol) in pyridine (4 mL) is added dropwise methanesulfonyl chloride (300 µL; 3.876 mmol). The suspension is placed in an ultrasonic bath until complete dissolution. After stirring for additional 10 min without ultrasonic irradiation the formed precipitate is filtered. The crude solid material is dissolved in DCM in the ultrasonic bath and the afterward formed precipitate is filtered and washed with DCM. The crude product (N-(1,3-Dioxo-2,3-dihydro-1H-isoindol-5-yl)-methanesulfonamide (628 mg; 2.614 mmol; 87.4%) is then used without further purification in the next reaction step.

Experimental Procedure for the Synthesis of N-(3-hydroxy-1-oxo-2,3-dihydro-1H-isoindol-5-yl)methanesulfonamide

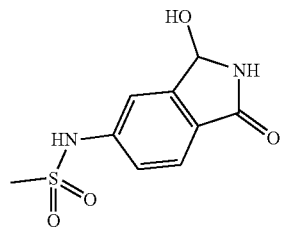

To a solution of N-(1,3-Dioxo-2,3-dihydro-1H-isoindol-5-yl)-methanesulfonamide (628 mg; 2.614 mmol) in MeOH (5 mL) and DCM (20 mL). The solution is treated by addition of sodium borohydride in several portions (2.01 g; 52.05 mmol) over a time frame of 2 days at room temperature. The reaction mixture is diluted with EE and concentrated under reduced pressure. The crude product is dissolved in DCM:MeOH and loaded onto ISOLUTE and purified by NP-chromatography (Redisep Rf; gradient DCM:MeOH:NH$_3$ 100:0:0→80:20:0.1, 40 mL/min flow). The product containing fractions are pooled concentrated under reduced pressure to give a mixture of product (N-(3-hydroxy-1-oxo-2,3-dihydro-1H-isoindol-5-yl)methanesulfonamide) and unreacted starting material (~1:1), which is used without further purification in the next reaction step.

Experimental Procedure for the Synthesis of N-(3-{2-[(dimethylamino)methyl]-1H-indol-3-yl}-1-oxo-2,3-dihydro-1H-isoindol-5-yl)methane-sulfonamide

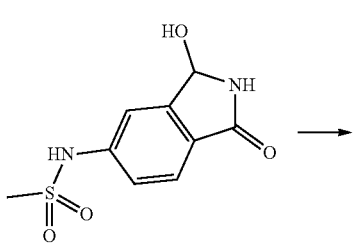

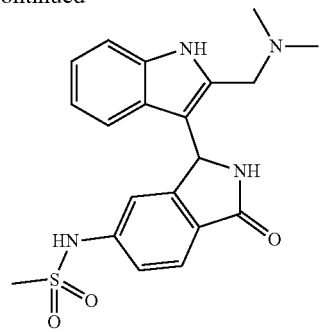

To the crude solution of N-(3-hydroxy-1-oxo-2,3-dihydro-1H-isoindol-5-yl)methane-sulfonamide (350 mg; 722 µmol) in acetic acid is added [(1H-indol-2-yl)methyl]dimethylamine (251.7 mg; 1.45 mmol) and the reaction mixture is stirred at 70° C. for 1 h. The reaction mixture is concentrated under reduced pressure, dissolved in DMSO and some drops of water, filtered and purified by RP-HPLC. Due to incomplete separation the product containing fractions are purified again via NP-chromatography (Redisep Rf; gradient DCM:MeOH:NH₃ 100:0:0-90:10:0.1, 18 mL/min flow). The product containing fractions are pooled, concentrated under reduced pressure and freeze dried to yield N-(3-{2-[(dimethylamino)methyl]-1H-indol-3-yl}-1-oxo-2,3-dihydro-1H-isoindol-5-yl)methane-sulfonamide (I-102) (16.3 mg; 41 µmol; 5.7%). HPLC method: LCMSBAS1: [M+H]⁺=399; $t_{ret}$ [min]=0.64 min.

Experimental Procedure for the Synthesis of tert-butyl N-[6-({[3-(6-hydroxy-2-methyl-3-oxo-2,3-dihydro-1H-isoindol-1-yl)-1H-indol-2-yl]methyl}amino)hexyl]carbamate

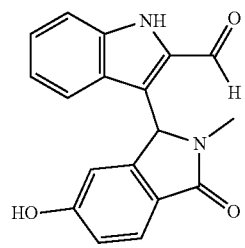

The aldehyde 3-(6-hydroxy-2-methyl-3-oxo-2,3-dihydro-1H-isoindol-1-yl)-1H-indole-2-carbaldehyde (100 mg;

0.326 mmol) and N-Boc-1,6-diaminohexane (77.68 mg; 0.359 mmol) are dissolved in MeOH (5 mL) and stirred at 50° C. for 30 min. The reaction mixture is cooled to room temperature and sodium triacetoxyborohydride (214 mg; 0.979 mmol) is added. The reaction mixture is stirred at room temperature overnight. The reaction mixture is filtered, concentrated under reduced pressure and purified by NP-chromatography (DCM/MeOH gradient 100:0→90:10). The product containing fractions are pooled and concentrated under reduced pressure to yield tert-butyl N-[6-({[3-(6-hydroxy-2-methyl-3-oxo-2,3-dihydro-1H-isoindol-1-yl)-1H-indol-2-yl]methyl}amino)hexyl]carbamate (101 mg; 199 µmol; 61.1%), which is used without any further analysis in the next reaction.

Experimental Procedure for the Synthesis of 3-(2-{[(6-aminohexyl)amino]methyl}-1H-indol-3-yl)-5-hydroxy-2-methyl-2,3-dihydro-1H-isoindol-1-one

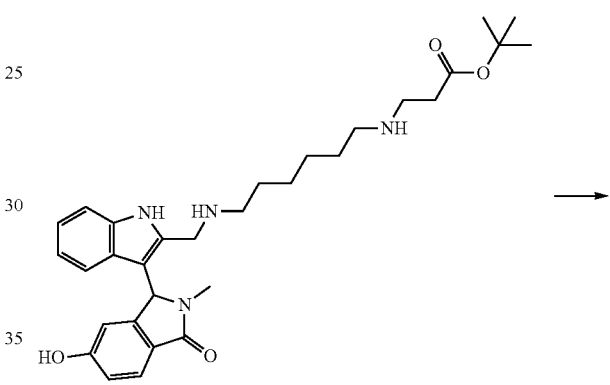

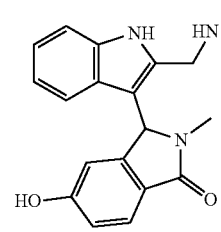

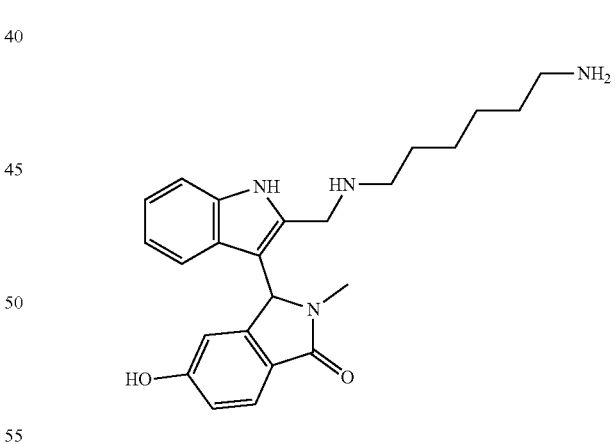

The tert-butyl N-[6-({[3-(6-hydroxy-2-methyl-3-oxo-2,3-dihydro-1H-isoindol-1-yl)-1H-indol-2-yl]methyl}amino)hexyl]carbamate (101 mg; 0.199 mmol) is dissolved in MeOH (5 mL) and 4N HCl in dioxane (249.2 µL; 0.997 mmol) are added and the reaction mixture is stirred at room temperature over the weekend. The free base is released on SPX-2 column and concentration under reduced pressure yield 3-(2-{[(6-aminohexyl)amino]methyl}-1H-indol-3-yl)-5-hydroxy-2-methyl-2,3-dihydro-1H-isoindol-1-one (80 mg; 197 µmol; 98.7%), which is used without any further analysis in the next reaction.

Experimental Procedure for the Synthesis of 5-hydroxy-3-[2-({[6-({[3-(6-hydroxy-3-oxo-2,3-dihydro-1H-isoindol-1-yl)-1H-indol-2-yl]methyl}amino)hexyl]amino}methyl)-1H-indol-3-yl]-2-methyl-2,3-dihydro-1H-isoindol-1-one Experimental Procedure for the Synthesis of tert-butyl N-[6-({[3-(6-hydroxy-3-oxo-2,3-dihydro-1H-isoindol-1-yl)-1H-indol-2-yl]methyl}amino)hexyl]carbamate

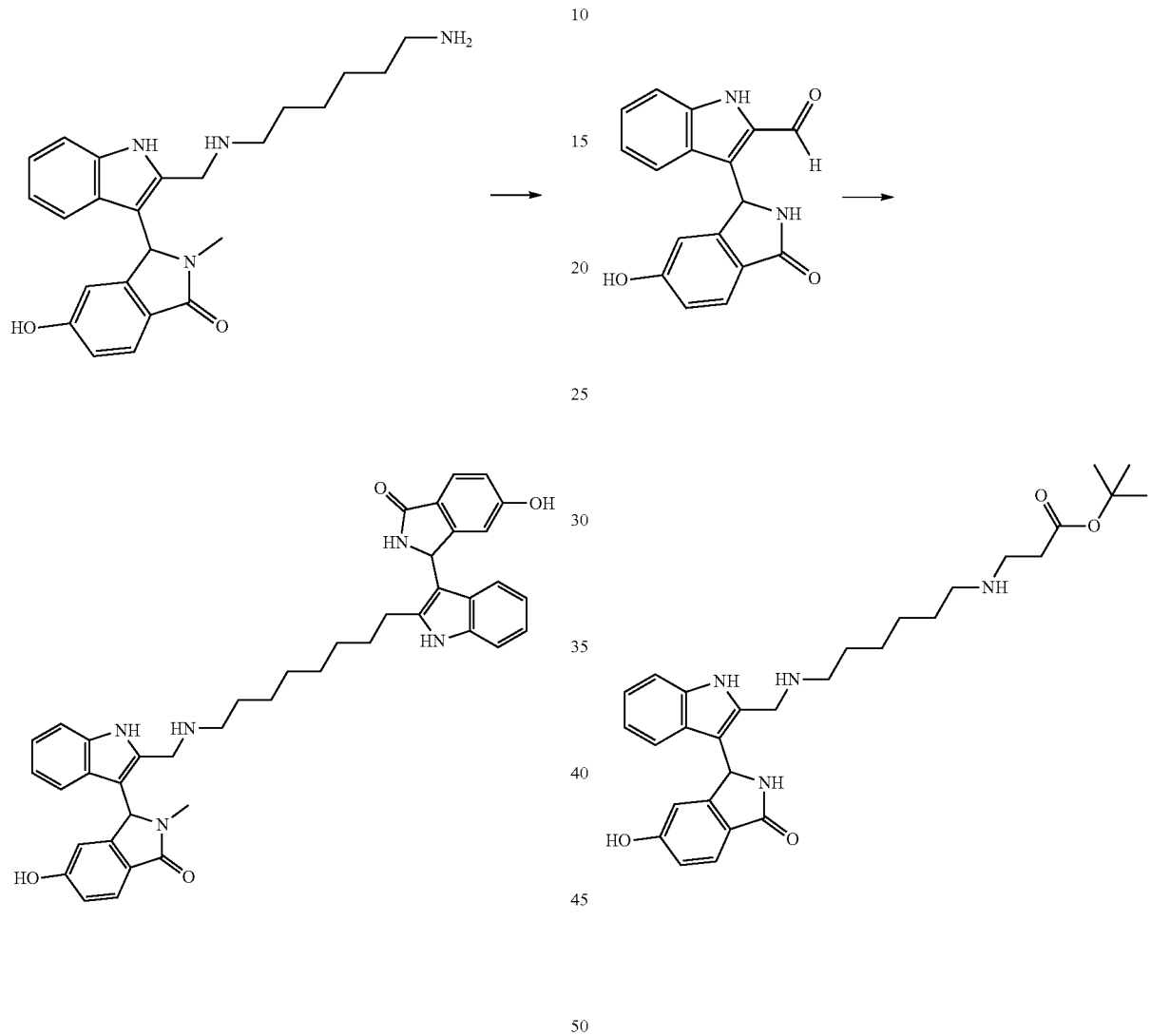

The aldehyde 3-(6-hydroxy-3-oxo-2,3-dihydro-1H-isoindol-1-yl)-1H-indole-2-carbaldehyde (36 mg; 86 µmol) and 3-(2-{[(6-aminohexyl)amino]methyl}-1H-indol-3-yl)-5-hydroxy-2-methyl-2,3-dihydro-1H-isoindol-1-one (39 mg; 86 µmol) are dissolved in DMF (1 mL) and stirred at room temperature for 10 min before sodium triacetoxyborohydride (113 mg; 517 µmol) is added in two portions. The reaction mixture is stirred at room temperature overnight. The reaction mixture is quenched by addition of two drops 1N NaOH solution, filtered and concentrated under reduced pressure. The crude product is purified by RP-HPLC (ACN/water gradient). The product containing fractions are pooled and freeze dried to yield 5-hydroxy-3-[2-({[6-({[3-(6-hydroxy-3-oxo-2,3-dihydro-1H-isoindol-1-yl)-1H-indol-2-yl]methyl}amino)hexyl]amino}methyl)-1H-indol-3-yl]-2-methyl-2,3-dihydro-1H-isoindol-1-one (11-110) (28.1 mg; 41 µmol; 47.7%). HPLC method: LCMSBAS1: [M+H]$^+$=683; $t_{ret}$ [min]=0.99 min.

The aldehyde 3-(6-hydroxy-3-oxo-2,3-dihydro-1H-isoindol-1-yl)-1H-indole-2-carbaldehyde (100 mg; 95% purity; 0.326 mmol) and N-Boc-1,6-diaminohexane (73.8 mg; 0.341 mmol) are dissolved in DMF (1 mL) and stirred at room temperature for 15 min before sodium triacetoxyborohydride (206.7 mg; 0.975 mmol) is added. The reaction mixture is stirred at room temperature overnight. The reaction mixture is filtered, concentrated under reduced pressure and purified by RP-HPLC. The product containing fractions are pooled and concentrated under reduced pressure to yield tert-butyl N-[6-({[3-(6-hydroxy-3-oxo-2,3-dihydro-1H-isoindol-1-yl)-1H-indol-2-yl]methyl}amino)hexyl]carbamate (122 mg; 248 µmol; 76.2%). HPLC method: LCMSBAS1: [M+H]$^+$=493; $t_{ret}$ [min]=1.15 min.

Experimental Procedure for the Synthesis of 3-{2-[(6-Amino-hexylamino)-methyl]-1H-indol-3-yl}-5-hydroxy-2,3-dihydro-isoindol-1-one

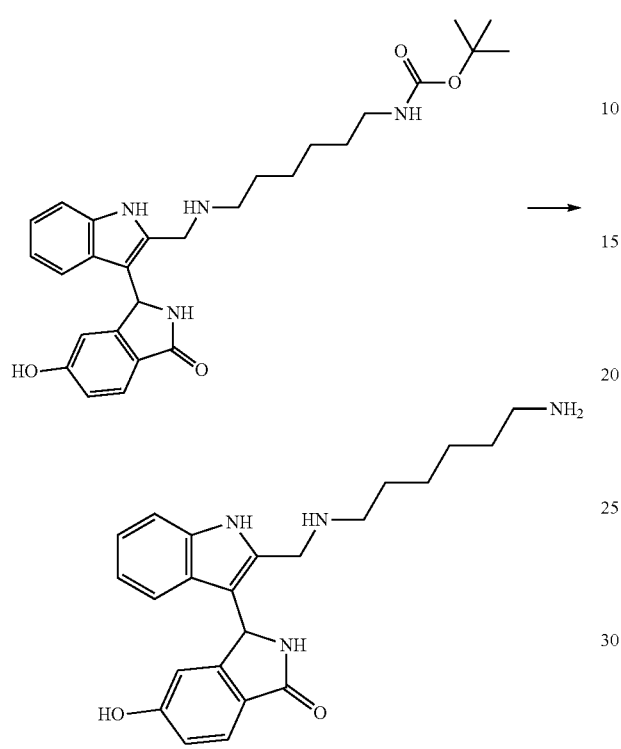

The tert-butyl N-[6-({[3-(6-hydroxy-3-oxo-2,3-dihydro-1H-isoindol-1-yl)-1H-indol-2-yl]methyl}amino)hexyl]carbamate (120 mg; 0.244 mmol) is treated with TFA (1 mL; 12.96 mmol) and stirred at room temperature for 1 h. The reaction mixture is concentrated under reduced pressure, dissolved in ACN/water and freeze dried to yield 3-{2-[(6-Amino-hexylamino)-methyl]-1H-indol-3-yl}-5-hydroxy-2,3-dihydro-isoindol-1-one (95.6 mg; 242 μmol; 100%), which is used without further analysis.

Experimental Procedure for the Synthesis of 5-hydroxy-3-[2-({6-[(1H-indol-6-ylmethyl)-amino]-hexylamino}-methyl)-1H-indol-3-yl]-2,3-dihydro-isoindol-1-one

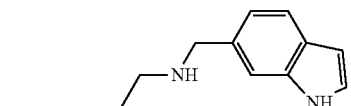

In a glass vial 3-{2-[(6-Amino-hexylamino)-methyl]-1H-indol-3-yl}-5-hydroxy-2,3-dihydro-isoindol-1-one (95 mg; 242 μmol) and indole-6-carboxaldehyde (42.2 mg; 290 μmol) are dissolved in DMF (1 mL) and stirred at room temperature for 15 min before sodium triacetoxyborohydride (48 mg; 726 μmol) is added in two portions. The reaction mixture is stirred at room temperature overnight. Due to incomplete conversion sodium triacetoxyborohydride (257 mg; 1.21 mmol) is added again and the reaction mixture is stirred overnight at room temperature. The reaction mixture is diluted with ACN/water, filtered and concentrated under reduced pressure. The crude product is purified by RP-HPLC (ACN/water gradient). The product containing fractions are pooled and freeze dried to yield 5-hydroxy-3-[2-({6-[(1H-indol-6-ylmethyl)-amino]-hexylamino}-methyl)-1H-indol-3-yl]-2,3-dihydro-isoindol-1-one (I-111) (22 mg; 42 μmol; 17.4%). HPLC method: LCMSBAS1: [M+H]$^+$=522; $t_{ret}$ [min]=1.13 min.

Experimental Procedure for the Synthesis of tert-butyl N-{[(1r,4r)$_4$-[({[3-(6-hydroxy-3-oxo-2,3-dihydro-1H-isoindol-1-yl)-1H-indol-2-yl]methyl}amino)methyl]cyclohexyl]methyl}-carbamate

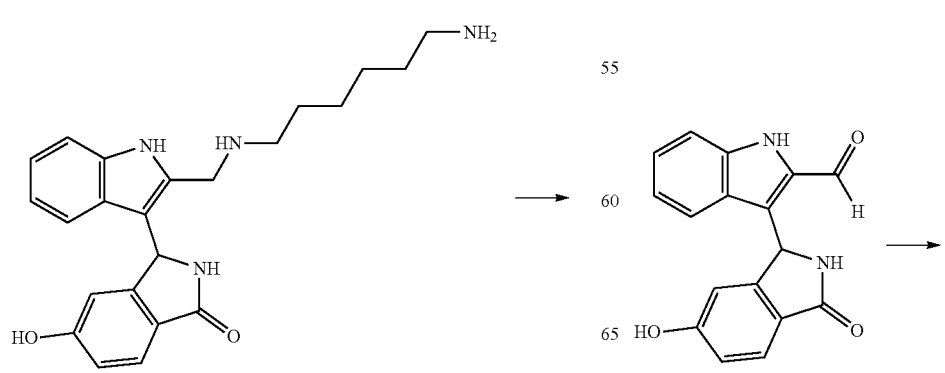

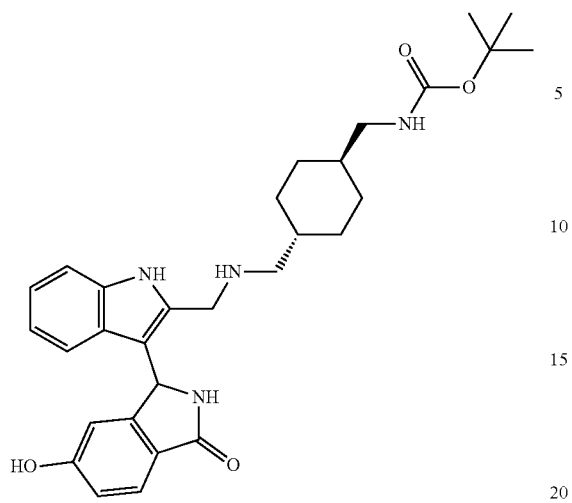
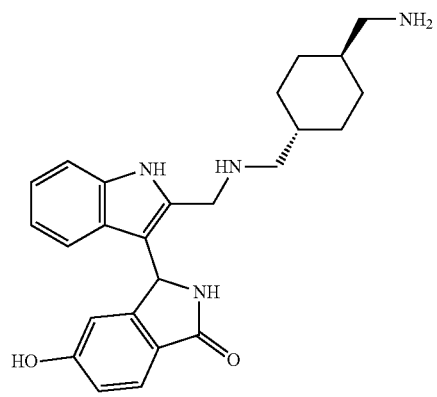

The aldehyde 3-(6-hydroxy-3-oxo-2,3-dihydro-1H-isoindol-1-yl)-1H-indole-2-carbaldehyde (100 mg; 0.342 mmol) and N-Boc-trans-1,4-bis(aminomethyl)cyclohexane (82.89 mg; 0.342 mmol) are dissolved in DMF (0.5 mL) and stirred at room temperature for 15 min before sodium triacetoxyborohydride (206.7 mg; 0.975 mmol) is added. The reaction mixture is stirred at room temperature for 16 h. The reaction mixture is filtered, concentrated under reduced pressure and purified by RP-HPLC (ACN/water gradient, basic condition). The product containing fractions are pooled, concentrated under reduced pressure and freeze dried to yield tert-butyl N-{[(1r,4r)-4-[({[3-(6-hydroxy-3-oxo-2,3-dihydro-1H-isoindol-1-yl)-1H-indol-2-yl]methyl}amino)methyl]cyclohexyl]methyl}carbamate (75 mg; 145 µmol; 42.3%). HPLC method: LCMSBAS1: [M+H]⁺=519; $t_{ret}$ [min]=1.12 min.

Experimental Procedure for the Synthesis of 5-hydroxy-3-{2-[({[(1r,4r)-4-(aminomethyl)-cyclohexyl]methyl}amino)methyl]-1H-indol-3-yl}-2,3-dihydro-1H-isoindol-1-one The tert-butyl N-{[(1r,4r)-4-[({[3-(6-hydroxy-3-oxo-2,3-dihydro-1H-isoindol-1-yl)-1H-indol-2-yl]methyl}amino)methyl]cyclohexyl]methyl}carbamate (75 mg; 0.145 mmol) is dissolved in MeOH (1 mL) and treated with conc. HCl (1.192 mL; 14.46 mmol) and stirred at room temperature for 1 h. The reaction mixture is concentrated under reduced pressure to yield 5-hydroxy-3-{2-[({[(1r,4r)-4-(aminomethyl)cyclohexyl]methyl}amino)methyl]-1H-indol-3-yl}-2,3-dihydro-1H-isoindol-1-one (60.5 mg; 145 µmol; 100%), which is used without further analysis.

Experimental Procedure for the Synthesis of 5-hydroxy-3-{2-[({[(1r,4r)-4-[({[3-(6-hydroxy-3-oxo-1,3-dihydro-2-benzofuran-1-yl)-1H-indol-2-yl]methyl}amino)methyl]cyclohexyl]-methyl}amino)-methyl]-1H-indol-3-yl}-2,3-dihydro-1H-isoindol-1-one

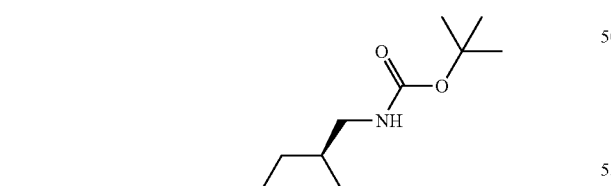
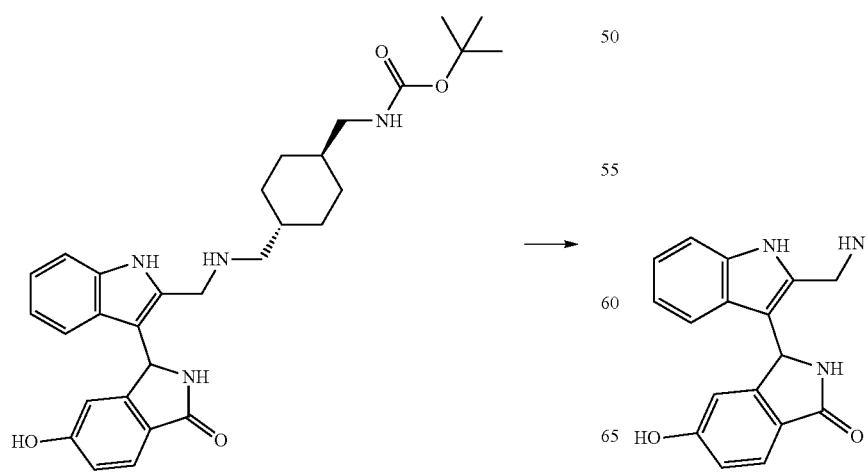

117

-continued

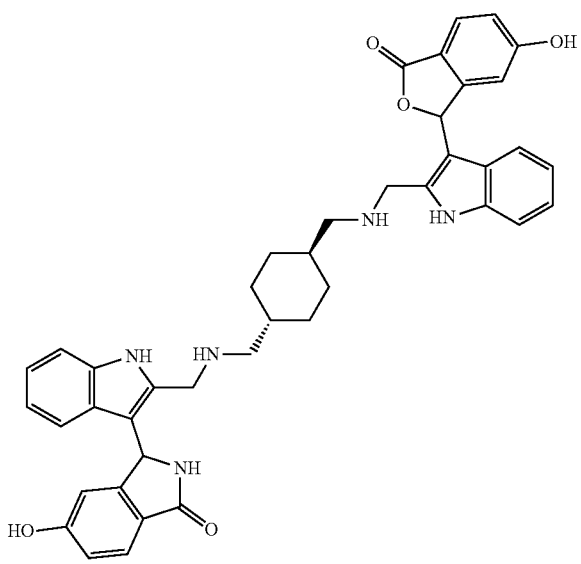

The aldehyde 3-(6-hydroxy-3-oxo-1,3-dihydro-2-benzofuran-1-yl)-1H-indole-2-carbaldehyde (42.5 mg; 145 µmol) and the amine 5-hydroxy-3-{2-[({[(1r,4r)-4-(aminomethyl)cyclohexyl]methyl}amino)methyl]-1H-indol-3-yl}-2,3-dihydro-1H-isoindol-1-one (60.5 mg; 145 µmol) are dissolved in DMF (0.5 mL) and stirred at room temperature for 15 min before sodium triacetoxyborohydride (153.7 mg; 725 µmol) is added. The reaction mixture is stirred at room temperature for 16 h. The reaction mixture is diluted with ACN/water, filtered and concentrated under reduced pressure. The crude product is purified by RP-HPLC (ACN/water gradient). The product containing fractions are pooled and freeze dried to yield 5-hydroxy-3-{2-[({[(1r,4r)-4-[({[3-(6-hydroxy-3-oxo-1,3-dihydro-2-benzofuran-1-yl)-1H-indol-2-yl]methyl}amino)methyl]cyclohexyl]methyl}amino)-methyl]-1H-indol-3-yl}-2,3-dihydro-1H-isoindol-1-one (11-115) (11 mg; 16 µmol; 10.9%). HPLC method: LCMSBAS1: [M+H]⁺=696; $t_{ret}$ [min]=1.01 min.

Experimental Procedure for the Synthesis of 5-hydroxy-3-[2-({[4-({[3-(6-hydroxy-3-oxo-1,3-dihydro-2-benzofuran-1-yl)-1H-indol-2-yl]methyl}amino)butyl]amino}methyl)-1H-indol-3-yl]-1,3-dihydro-2-benzofuran-1-one

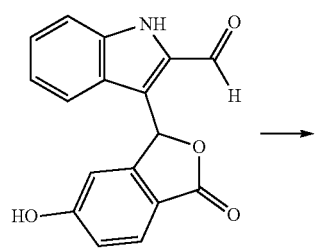

118

-continued

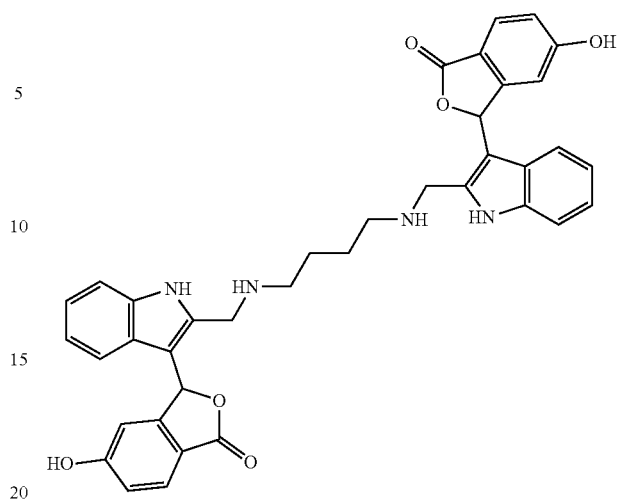

The aldehyde 3-(6-hydroxy-3-oxo-1,3-dihydro-2-benzofuran-1-yl)-1H-indole-2-carbaldehyde (100 mg; 0.341 mmol) and 1,4-diaminobutane (30.06 mg; 0.341 mmol) are dissolved in DMF and stirred at room temperature for 15 min before sodium triacetoxyborohydride (361 mg; 1.705 mmol) is added. The reaction mixture is stirred at room temperature for 16 h. The reaction mixture is filtered, concentrated under reduced pressure and purified by RP-HPLC (ACN/water gradient; basic condition). The product containing fractions are pooled and freeze dried to yield 5-hydroxy-3-[2-({[4-({[3-(6-hydroxy-3-oxo-1,3-dihydro-2-benzofuran-1-yl)-1H-indol-2-yl]methyl}amino)butyl]amino}methyl)-1H-indol-3-yl]-1,3-dihydro-2-benzofuran-1-one (11-112) (34 mg; 53 µmol; 15.5%). HPLC method: LCMSBAS1: [M+H]⁺=643; $t_{ret}$ [min]=0.94 min.

Experimental Procedure for the Synthesis of 5-hydroxy-3-[2-({[4-({[3-(6-hydroxy-3-oxo-2,3-dihydro-1H-isoindol-1-yl)-1H-indol-2-yl]methyl}amino)butyl]amino}-methyl)-1H-indol-3-yl]-2,3-dihydro-1H-isoindol-1-one

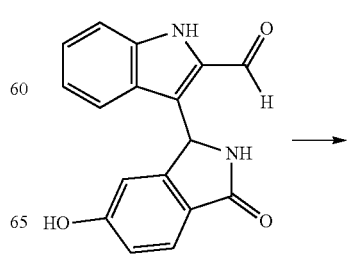

119

-continued

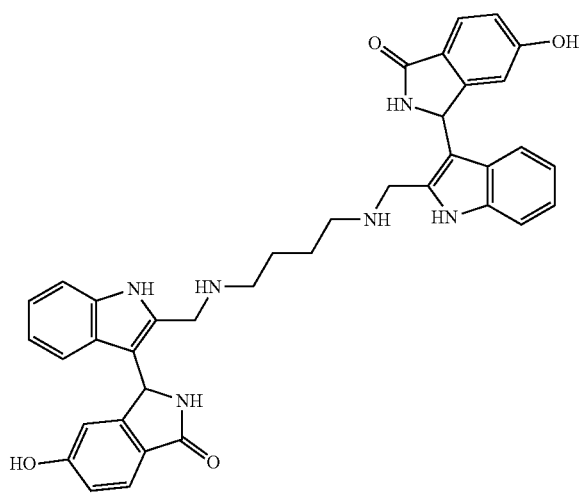

The aldehyde 3-(6-hydroxy-3-oxo-2,3-dihydro-1H-isoindol-1-yl)-1H-indole-2-carbaldehyde (100 mg; 0.341 mmol) and 1,4-diaminobutane (15.08 mg; 0.171 mmol) are dissolved in DMF and stirred at room temperature for 15 min before sodium triacetoxyborohydride (363 mg; 1.71 mmol) is added. The reaction mixture is stirred at room temperature for 16 h. The reaction mixture is filtered, concentrated under reduced pressure and purified by RP-HPLC (ACN/water gradient; basic condition). The product containing fractions are pooled and freeze dried to yield 5-hydroxy-3-[2-({[4-({[3-(6-hydroxy-3-oxo-2,3-dihydro-1H-isoindol-1-yl)-1H-indol-2-yl]methyl}amino)butyl]amino}-methyl)-1H-indol-3-yl]-2,3-dihydro-1H-isoindol-1-one (11-113) (41 mg; 64 µmol; 18.7%). HPLC method: LCMSBAS1: [M+H]$^+$=641; $t_{ret}$ [min]=0.89 min.

Experimental Procedure for the Synthesis of 5-hydroxy-3-(2-{[({4-[({[3-(6-hydroxy-3-oxo-1,3-dihydro-2-benzofuran-1-yl)-7-nitro-1H-indol-2-yl]methyl}amino)-methyl]phenyl}methyl)amino]methyl}-7-nitro-1H-indol-3-yl)-1,3-dihydro-2-benzofuran-1-one

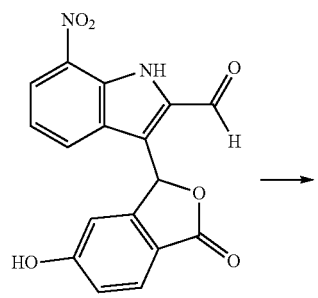

120

-continued

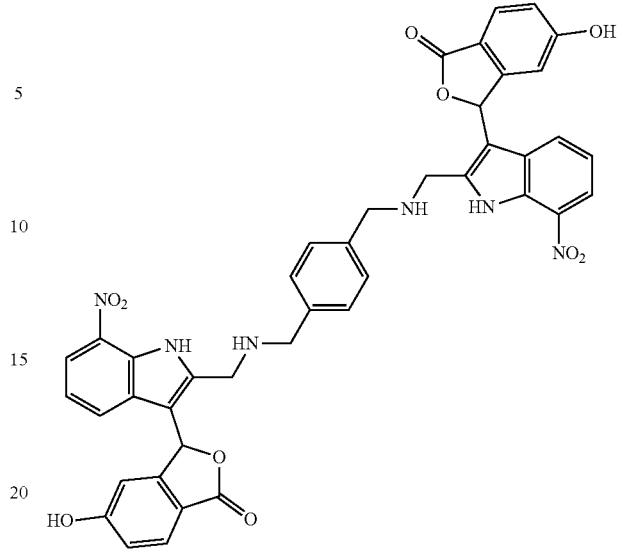

The aldehyde 3-(6-hydroxy-3-oxo-1,3-dihydro-2-benzofuran-1-yl)-7-nitro-1H-indole-2-carbaldehyde (200 mg; 0.508 mmol) and 1,4-bis(aminomethyl)benzene (103.9 mg; 0.763 mmol) are dissolved in THF (2 mL) and stirred at room temperature for 15 min sodium triacetoxyborohydride (222.2 mg; 1.02 mmol) is added. The reaction mixture is stirred at room temperature for 3 h. The reaction mixture is filtered, concentrated under reduced pressure and purified by RP-HPLC (ACN/water gradient; basic condition). The product containing fractions are pooled and freeze dried to yield 5-hydroxy-3-(2-{[({4-[({[3-(6-hydroxy-3-oxo-1,3-dihydro-2-benzofuran-1-yl)-7-nitro-1H-indol-2-yl]methyl}amino)-methyl]phenyl}methyl)amino]methyl}-7-nitro-1H-indol-3-yl)-1,3-dihydro-2-benzofuran-1-one (13 mg; 18 µmol; 3.3%). HPLC method: LCMSBAS1: [M+H]$^+$=781; $t_{ret}$ [min]=1.07 min.

Experimental Procedure for the Synthesis of 3-(7-amino-2-{[({4-[({[7-amino-3-(6-hydroxy-3-oxo-1,3-dihydro-2-benzofuran-1-yl)-1H-indol-2-yl]methyl}amino)methyl]phenyl}methyl)-amino]methyl}-1H-indol-3-yl)-5-hydroxy-1,3-dihydro-2-benzofuran-1-one

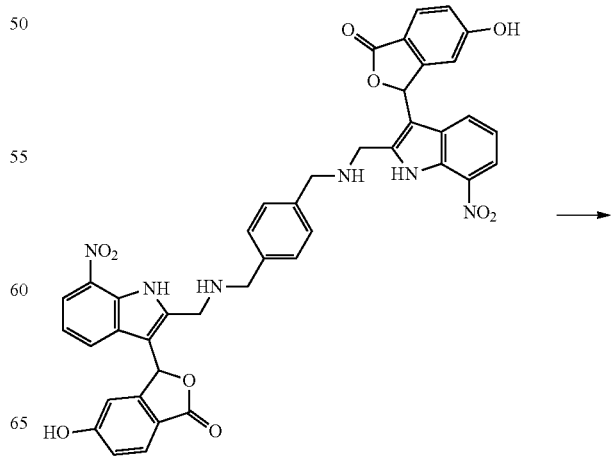

-continued

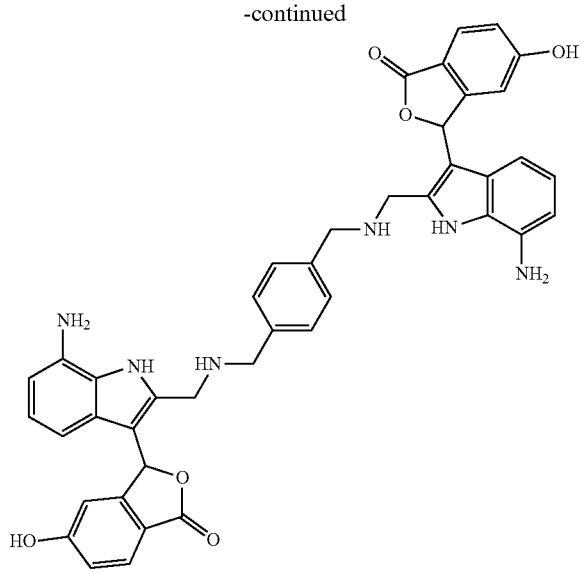

The 5-hydroxy-3-(2-{[({4-[({[3-(6-hydroxy-3-oxo-1,3-dihydro-2-benzofuran-1-yl)-7-nitro-1H-indol-2-yl]methyl}amino)methyl]phenyl}methyl)amino]methyl}-7-nitro-1H-indol-3-yl)-1,3-dihydro-2-benzofuran-1-one (27 mg; 35 µmol) is dissolved in EtOH/water (1:1, 6 mL) and treated with iron (9.66 mg; 0.173 mmol) and a saturated solution of ammonium chloride (250 µL). The reaction mixture is stirred at 80° C. for 1 h. The reaction mixture is filtered, concentrated under reduced pressure and purified by RP-HPLC (ACN/water gradient; basic condition). The product containing fractions are pooled and freeze dried to yield 3-(7-amino-2-{[({4-[({[7-amino-3-(6-hydroxy-3-oxo-1,3-dihydro-2-benzofuran-1-yl)-1H-indol-2-yl]methyl}amino)methyl]phenyl}methyl)amino]methyl}-1H-indol-3-yl)-5-hydroxy-1,3-dihydro-2-benzofuran-1-one (11-114) (1.65 mg; 2 µmol; 6.6%). HPLC method: LCMSBAS1: [M+H]$^+$= 721; $t_{ret}$ [min]=0.92 min.

TABLE 1

| # | structure | $t_{ret}$ [min] | [M + H]$^+$ | HPLC method |
|---|---|---|---|---|
| I-001 | 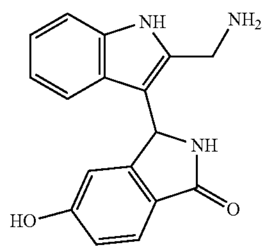 [SMILES: NCc1[nH]c2ccccc2c1C1NC(=O)c2ccc(O)cc21] | 0.31 | 277 | LCMSBAS1 |
| I-002 | 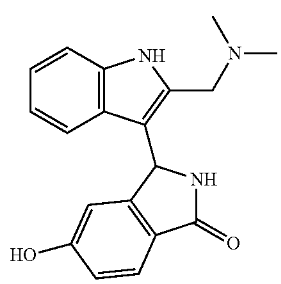 [SMILES: CN(C)Cc1[nH]c2ccccc2c1C1NC(=O)c2ccc(O)cc21] | 0.62 | 322 | LCMSBAS1 |
| I-003 | 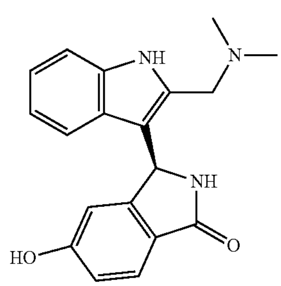 [SMILES: CN(C)Cc1[nH]c2ccccc2c1[C@H]1NC(=O)c2ccc(O)cc21] | 0.63 | 322 | LCMSBAS1 |

TABLE 1-continued

| # | structure | $t_{ret}$ [min] | $[M + H]^+$ | HPLC method |
|---|---|---|---|---|
| I-004 | 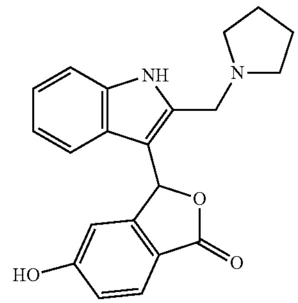 [SMILES: O=C1OC(c2c(CN3CCCC3)[nH]c3ccccc23)c2cc(O)ccc21] | 0.81 | 339 | LCMSBAS1 |
| I-005 | 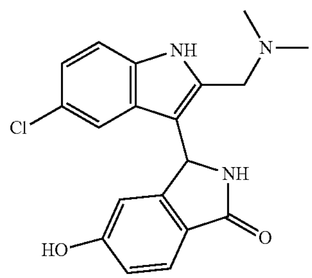 [SMILES: CN(C)Cc1[nH]c2ccc(Cl)cc2c1C1NC(=O)c2ccc(O)cc21] | 0.83 | 356 | LCMSBAS1 |
| I-006 | 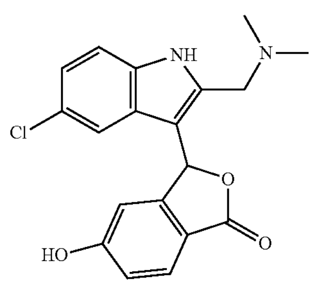 [SMILES: CN(C)Cc1[nH]c2ccc(Cl)cc2c1C1OC(=O)c2ccc(O)cc21] | 0.86 | 357 | LCMSBAS1 |
| I-007 | 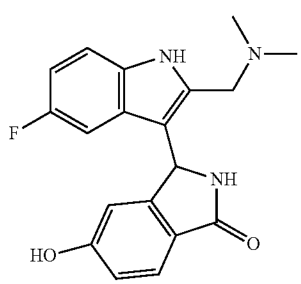 [SMILES: CN(C)Cc1[nH]c2ccc(F)cc2c1C1NC(=O)c2ccc(O)cc21] | 0.81 | 340 | LCMSBAS1 |
| I-008 | 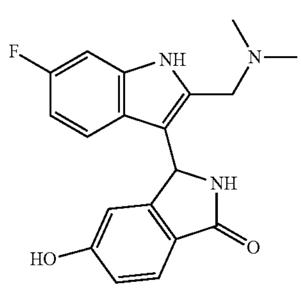 [SMILES: CN(C)Cc1[nH]c2cc(F)ccc2c1C1NC(=O)c2ccc(O)cc21] | 0.81 | 340 | LCMSBAS1 |

TABLE 1-continued
| # | structure | t_ret [min] | [M + H]+ | HPLC method |
|---|---|---|---|---|
| I-009 | 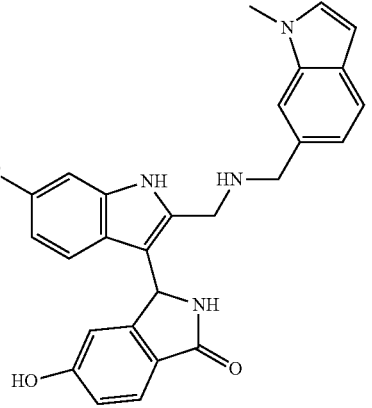 | 1.10 | 455 | LCMSBAS1 |
| I-010 | 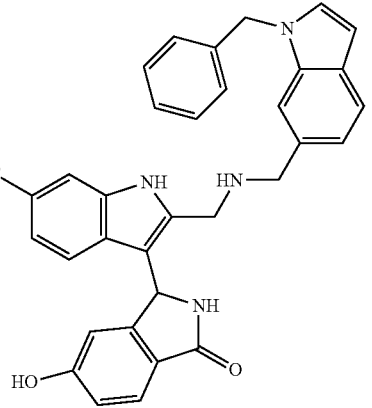 | 1.26 | 531 | LCMSBAS1 |
| I-011 | 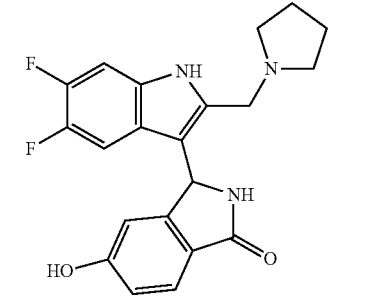 [SMILES: O=C1NC(c2c(CN3CCCC3)[nH]c3cc(F)c(F)cc23)c2cc(O)ccc21] | 0.98 | 384 | LCMSBAS1 |
| I-012 | 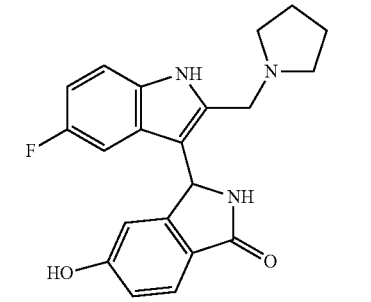 [SMILES: O=C1NC(c2c(CN3CCCC3)[nH]c3ccc(F)cc23)c2cc(O)ccc21] | 0.93 | 366 | LCMSBAS1 |

TABLE 1-continued

| # | structure | $t_{ret}$ [min] | $[M + H]^+$ | HPLC method |
|---|---|---|---|---|
| I-013 | 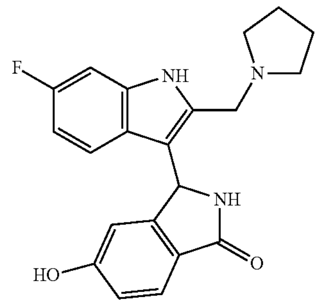 [SMILES: O=C1NC(c2c(CN3CCCC3)[nH]c3cc(F)ccc23)c2cc(O)ccc21] | 0.93 | 366 | LCMSBAS1 |
| I-014 | 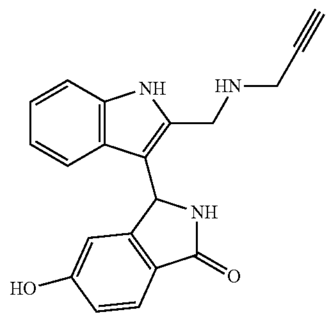 [SMILES: C#CCNCc1[nH]c2ccccc2c1C1NC(=O)c2ccc(O)cc21] | 0.64 | 330 | LCMSBAS1 |
| I-015 | 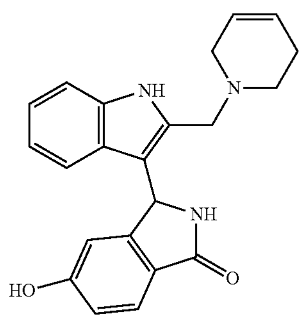 [SMILES: O=C1NC(c2c(CN3CC=CCC3)[nH]c3ccccc23)c2cc(O)ccc21] | 0.96 | 360 | LCMSBAS1 |
| I-016 | 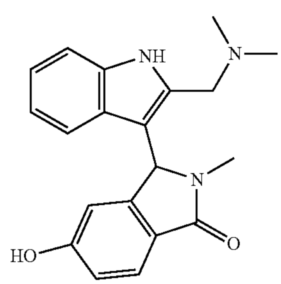 [SMILES: CN(C)Cc1[nH]c2ccccc2c1C1c2cc(O)ccc2C(=O)N1C] | 0.82 | 336 | LCMSBAS1 |
| I-017 | 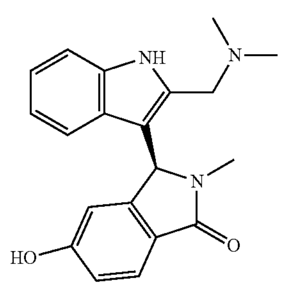 [SMILES: CN(C)Cc1[nH]c2ccccc2c1[C@@H]1c2cc(O)ccc2C(=O)N1C] | 0.91 | 336 | LCMSBAS1 |

TABLE 1-continued

| # | structure | $t_{ret}$ [min] | $[M + H]^+$ | HPLC method |
|---|---|---|---|---|
| I-018 | 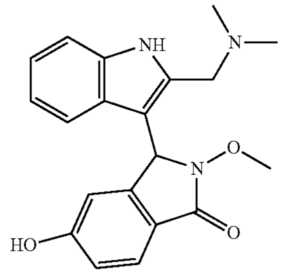 [SMILES: CON1C(=O)c2ccc(O)cc2C1c1c(CN(C)C)[nH]c2ccccc12] | 0.88 | 352 | LCMSBAS1 |
| I-019 | 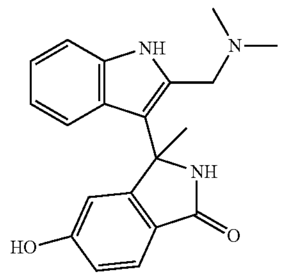 [SMILES: CN(C)Cc1[nH]c2ccccc2c1C1(C)NC(=O)c2ccc(O)cc21] | 0.84 | 336 | LCMSBAS1 |
| I-020 | 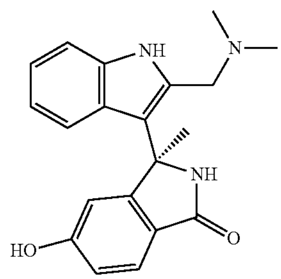 [SMILES: CN(C)Cc1[nH]c2ccccc2c1[C@@]1(C)NC(=O)c2ccc(O)cc21] | 0.84 | 336 | LCMSBAS1 |
| I-021 | 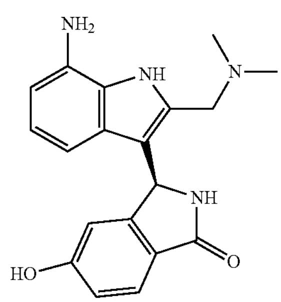 [SMILES: CN(C)Cc1[nH]c2c(N)cccc2c1[C@H]1NC(=O)c2ccc(O)cc21] | 0.31 | 337 | LCMSBAS1 |
| I-022 | 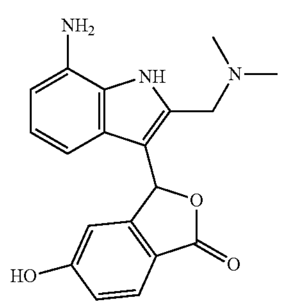 [SMILES: CN(C)Cc1[nH]c2c(N)cccc2c1C1OC(=O)c2ccc(O)cc21] | 0.38 | 338 | LCMSBAS1 |

TABLE 1-continued
| # | structure | $t_{ret}$ [min] | $[M + H]^+$ | HPLC method |
|---|---|---|---|---|
| I-023 | 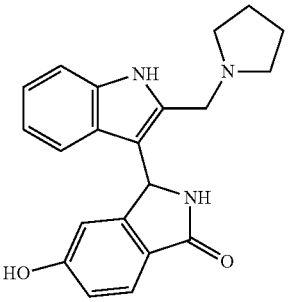 [SMILES: O=C1NC(c2c(CN3CCCC3)[nH]c3ccccc23)c2cc(O)ccc21] | 0.88 | 348 | LCMSBAS1 |
| I-025 | 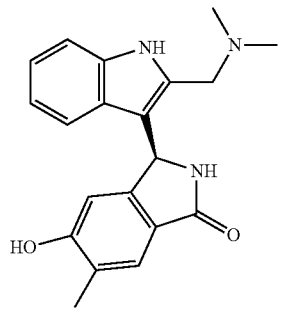 [SMILES: Cc1cc2c(cc1O)[C@@H](c1c(CN(C)C)[nH]c3ccccc13)NC2=O] | 0.90 | 336 | LCMSBAS1 |
| I-026 | 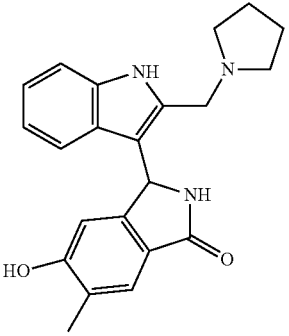 [SMILES: Cc1cc2c(cc1O)C(c1c(CN3CCCC3)[nH]c3ccccc13)NC2=O] | 0.99 | 362 | LCMSBAS1 |
| I-027 | 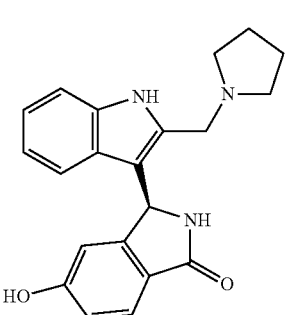 | 0.97 | 362 | LCMSBAS1 |

TABLE 1-continued
| # | structure | $t_{ret}$ [min] | $[M + H]^+$ | HPLC method |
|---|---|---|---|---|
| I-028 | 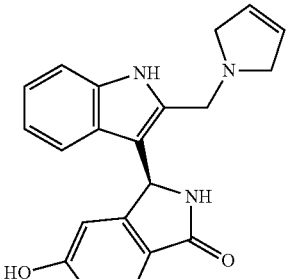 | 0.89 | 346 | LCMS3BAS1 |
| I-029 | 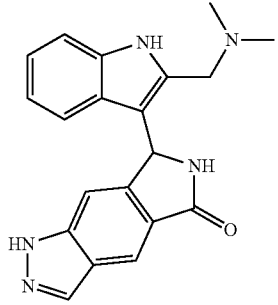 | 0.85 | 346 | LCMSBAS1 |
| I-030 | 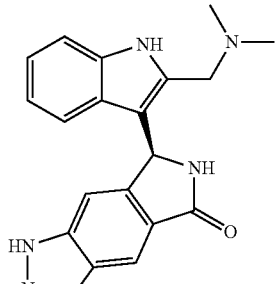 | 0.82 | 346 | LCMS3BAS1 |
| I-031 | 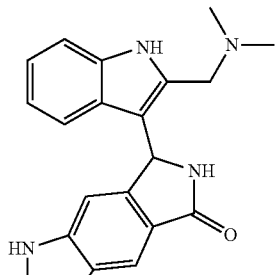 | 0.73 | 346 | LCMSBAS1 |
| I-032 | 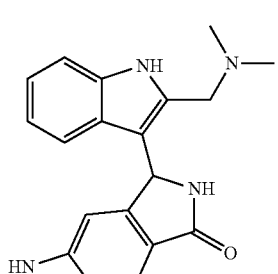 | 0.87 | 345 | LCMSBAS1 |

TABLE 1-continued

| # | structure | $t_{ret}$ [min] | $[M + H]^+$ | HPLC method |
|---|---|---|---|---|
| I-033 | 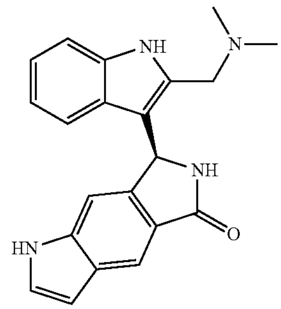 [SMILES: CN(C)Cc1[nH]c2ccccc2c1[C@H]1NC(=O)c2cc3cc[nH]c3cc21] | 0.87 | 345 | LCMSBAS1 |
| I-034 | 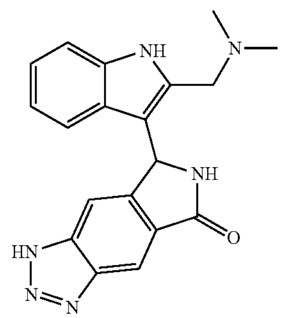 [SMILES: CN(C)Cc1[nH]c2ccccc2c1C1NC(=O)c2cc3nn[nH]c3cc21] | 0.36 | 347 | LCMSBAS1 |
| I-035 | 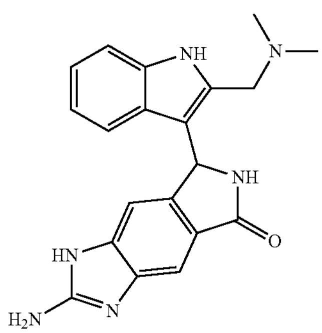 [SMILES: CN(C)Cc1[nH]c2ccccc2c1C1NC(=O)c2cc3nc(N)[nH]c3cc21] | 0.57 | 361 | LCMSBAS1 |
| I-036 | 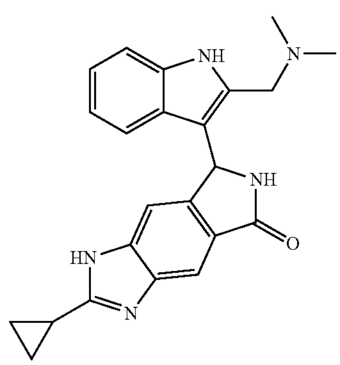 [SMILES: CN(C)Cc1[nH]c2ccccc2c1C1NC(=O)c2cc3nc(C4CC4)[nH]c3cc21] | 0.83 | 386 | LCMSBAS1 |

TABLE 1-continued

| # | structure | t_ret [min] | [M + H]+ | HPLC method |
|---|---|---|---|---|
| I-037 | 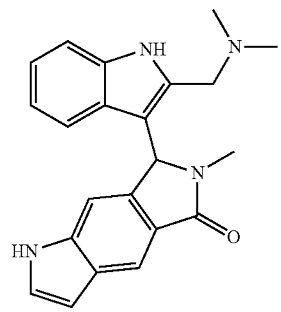 [SMILES: CN(C)Cc1[nH]c2ccccc2c1C1c2cc3[nH]ccc3cc2C(=O)N1C] | 1.03 | 359 | LCMSBAS1 |
| I-038 | 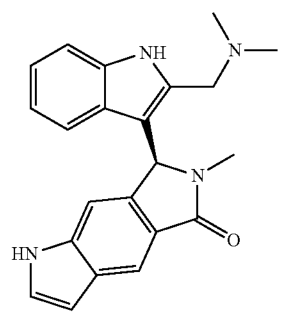 [SMILES: CN(C)Cc1[nH]c2ccccc2c1[C@@H]1c2cc3[nH]ccc3cc2C(=O)N1C] | 1.03 | 359 | LCMSBAS1 |
| I-039 | 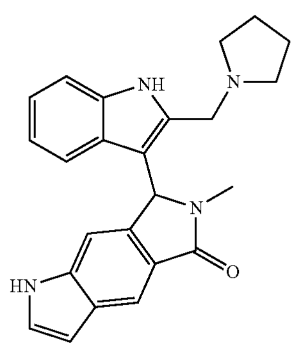 [SMILES: CN1C(=O)c2cc3cc[nH]c3cc2C1c1c(CN2CCCC2)[nH]c2ccccc12] | 1.10 | 385 | LCMSBAS1 |
| I-040 | 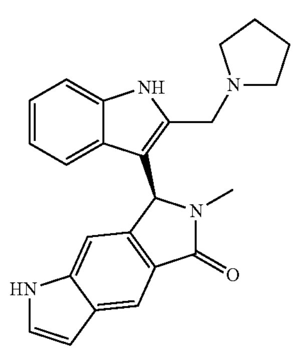 [SMILES: CN1C(=O)c2cc3cc[nH]c3cc2[C@H]1c1c(CN2CCCC2)[nH]c2ccccc12] | 1.10 | 385 | LCMSBAS1 |

TABLE 1-continued

| # | structure | t_ret [min] | [M + H]+ | HPLC method |
|---|---|---|---|---|
| I-041 | 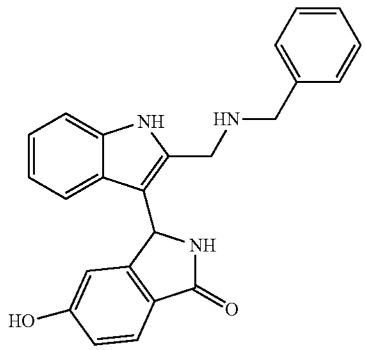 [SMILES: O=C1NC(c2c(CNCc3ccccc3)[nH]c3ccccc23)c2cc(O)ccc21] | 0.93 | 384 | LCMSBAS1 |
| I-042 | 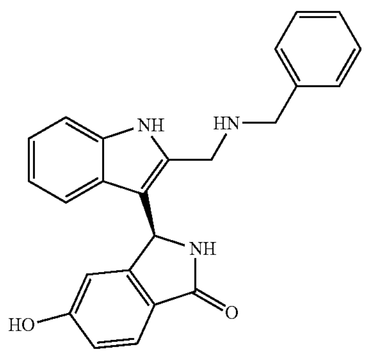 [SMILES: O=C1N[C@H](c2c(CNCc3ccccc3)[nH]c3ccccc23)c2cc(O)ccc21] | 1.0 | 384 | LCMS3BAS1 |
| I-043 | 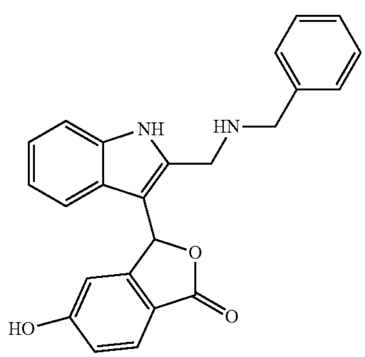 [SMILES: O=C1OC(c2c(CNCc3ccccc3)[nH]c3ccccc23)c2cc(O)ccc21] | 0.98 | 385 | LCMSBAS1 |
| I-044 | 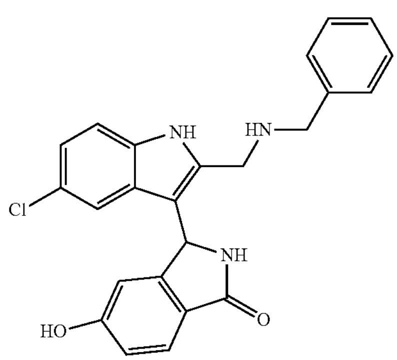 [SMILES: O=C1NC(c2c(CNCc3ccccc3)[nH]c3ccc(Cl)cc23)c2cc(O)ccc21] | 1.07 | 418 | LCMSBAS1 |

TABLE 1-continued

| # | structure | $t_{ret}$ [min] | $[M + H]^+$ | HPLC method |
|---|---|---|---|---|
| I-045 | 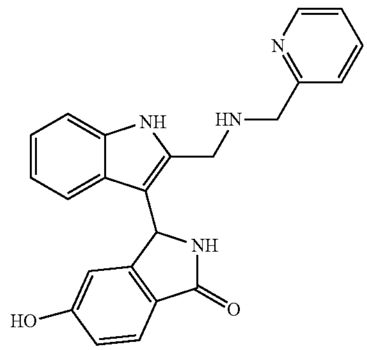 [SMILES: O=C1NC(c2c(CNCc3ccccn3)[nH]c3ccccc23)c2cc(O)ccc21] | 0.77 | 385 | LCMSBAS1 |
| I-046 | 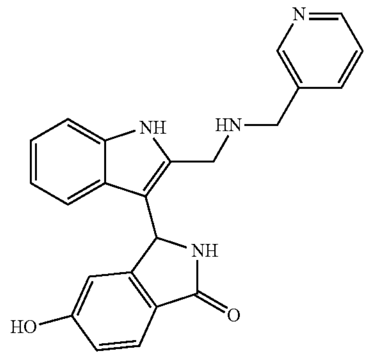 [SMILES: O=C1NC(c2c(CNCc3cccnc3)[nH]c3ccccc23)c2cc(O)ccc21] | 0.73 | 385 | LCMSBAS1 |
| I-047 | 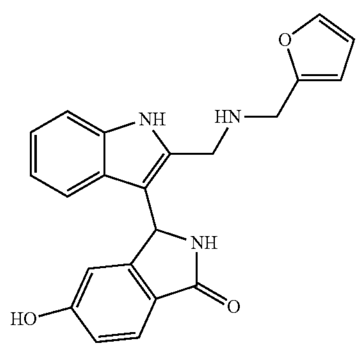 [SMILES: O=C1NC(c2c(CNCc3ccco3)[nH]c3ccccc23)c2cc(O)ccc21] | 0.93 | 374 | LCMSBAS1 |
| I-048 | 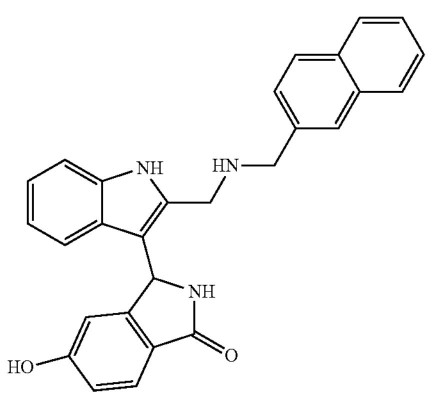 [SMILES: O=C1NC(c2c(CNCc3ccc4ccccc4c3)[nH]c3ccccc23)c2cc(O)ccc21] | 1.14 | 434 | LCMSBAS1 |

TABLE 1-continued

| # | structure | t_ret [min] | [M + H]+ | HPLC method |
|---|---|---|---|---|
| I-049 | 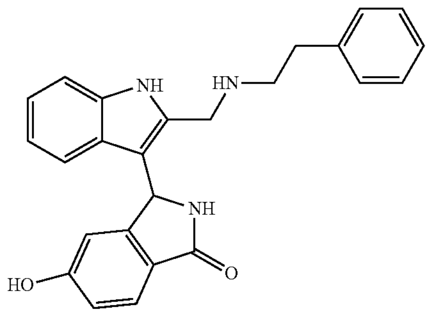 [SMILES: O=C1NC(c2c(CNCCc3ccccc3)[nH]c3ccccc23)c2cc(O)ccc21] | 0.98 | 390 | LCMSBAS1 |
| I-050 | 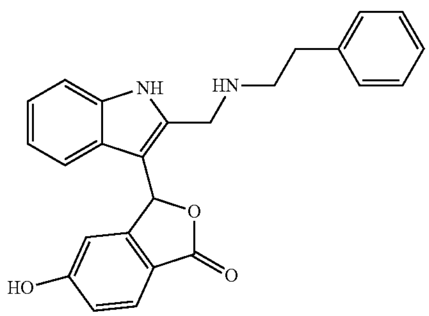 [SMILES: O=C1OC(c2c(CNCCc3ccccc3)[nH]c3ccccc23)c2cc(O)ccc21] | 1.03 | 399 | LCMSBAS1 |
| I-051 | 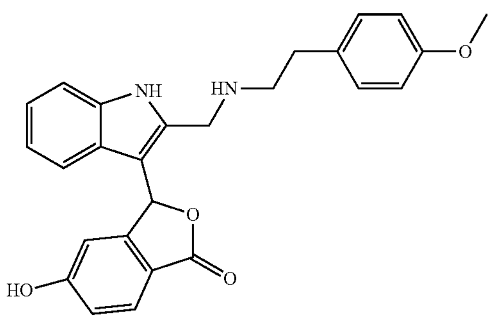 [SMILES: COc1ccc(CCNCc2[nH]c3ccccc3c2C2OC(=O)c3ccc(O)cc32)cc1] | 1.02 | 429 | LCMSBAS1 |
| I-052 | 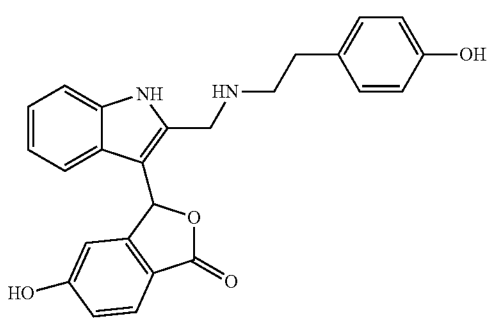 [SMILES: O=C1OC(c2c(CNCCc3ccc(O)cc3)[nH]c3ccccc23)c2cc(O)ccc21] | 0.83 | 415 | LCMSBAS1 |
| I-053 | 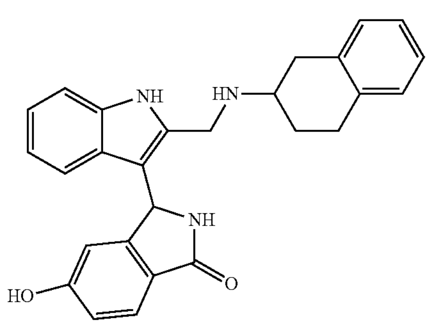 [SMILES: O=C1NC(c2c(CNC3CCc4ccccc4C3)[nH]c3ccccc23)c2cc(O)ccc21] | 1.11 | 424 | LCMSBAS1 |

TABLE 1-continued

| # | structure | t_ret [min] | [M + H]+ | HPLC method |
|---|---|---|---|---|
| I-054 | 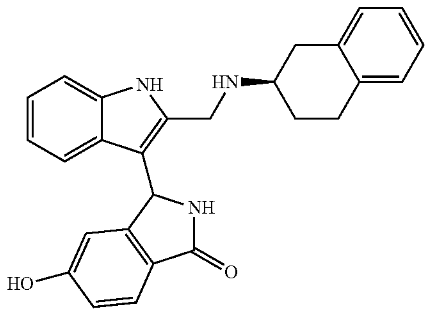 [SMILES: O=C1NC(c2c(CN[C@@H]3CCc4ccccc4C3)[nH]c3ccccc23)c2cc(O)ccc21] | 1.11 | 424 | LCMSBAS1 |
| I-055 | 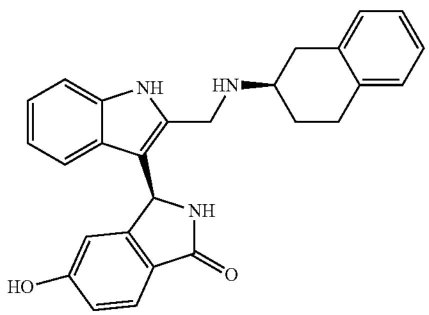 [SMILES: O=C1N[C@H](c2c(CN[C@@H]3CCc4ccccc4C3)[nH]c3ccccc23)c2cc(O)ccc21] | 1.11 | 424 | LCMSBAS1 |
| I-056 | 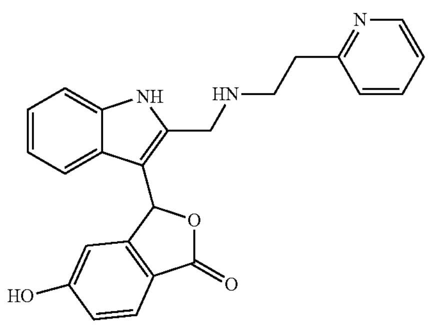 [SMILES: O=C1OC(c2c(CNCCc3ccccn3)[nH]c3ccccc23)c2cc(O)ccc21] | 0.82 | 400 | LCMSBAS1 |
| I-057 | 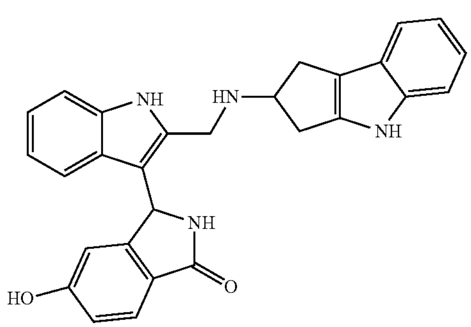 [SMILES: O=C1NC(c2c(CNC3Cc4[nH]c5ccccc5c4C3)[nH]c3ccccc23)c2cc(O)ccc21] | 1.05 | 449 | LCMSBAS1 |

TABLE 1-continued
| # | structure | $t_{ret}$ [min] | $[M + H]^+$ | HPLC method |
|---|---|---|---|---|
| I-058 | 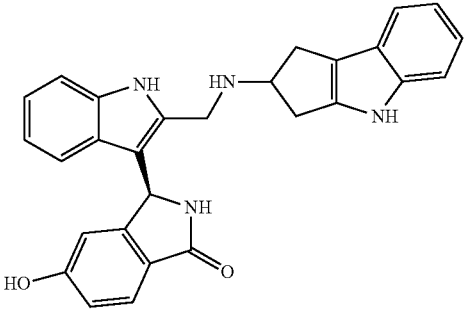 [SMILES: O=C1N[C@H](c2c(CNC3Cc4[nH]c5ccccc5c4C3)[nH]c3ccccc23)c2cc(O)ccc21] | 1.08 | 449 | LCMSBAS1 |
| I-059 | 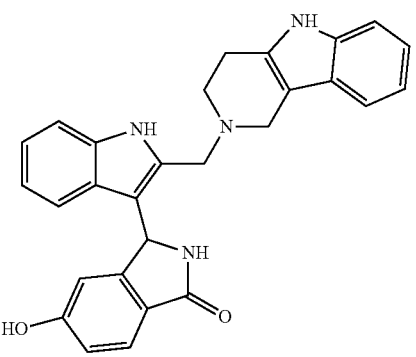 [SMILES: O=C1NC(c2c(CN3CCc4[nH]c5ccccc5c4C3)[nH]c3ccccc23)c2cc(O)ccc21] | 1.08 | 449 | LCMSBAS1 |
| I-060 | 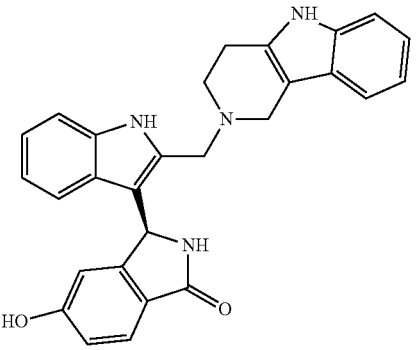 [SMILES: O=C1N[C@H](c2c(CN3CCc4[nH]c5ccccc5c4C3)[nH]c3ccccc23)c2cc(O)ccc21] | 1.08 | 449 | LCMSBAS1 |
| I-061 | 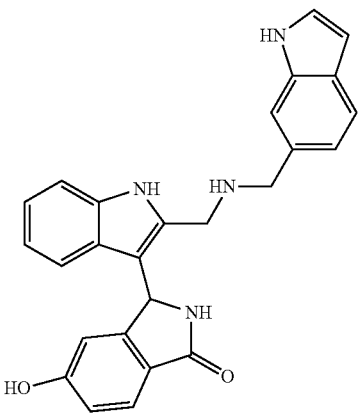 [SMILES: O=C1NC(c2c(CNCc3ccc4cc[nH]c4c3)[nH]c3ccccc23)c2cc(O)ccc21] | 0.93 | 423 | LCMSBAS1 |

TABLE 1-continued
| # | structure | t_ret [min] | [M + H]+ | HPLC method |
|---|---|---|---|---|
| I-062 | 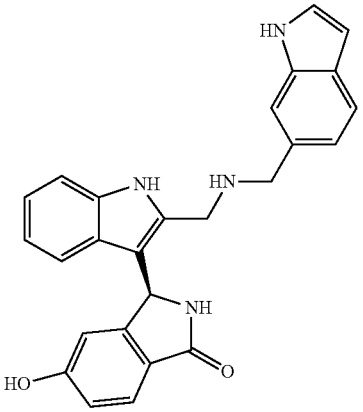 [SMILES: O=C1N[C@H](c2c(CNCc3ccc4cc[nH]c4c3)[nH]c3ccccc23)c2cc(O)ccc21] | 0.99 | 423 | LCMS3BAS1 |
| I-063 | 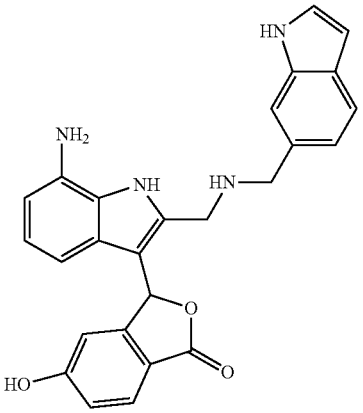 [SMILES: Nc1cccc2c(C3OC(=O)c4ccc(O)cc43)c(CNCc3ccc4cc[nH]c4c3)[nH]c12] | 0.85 | 439 | LCMSBAS1 |
| I-064 | 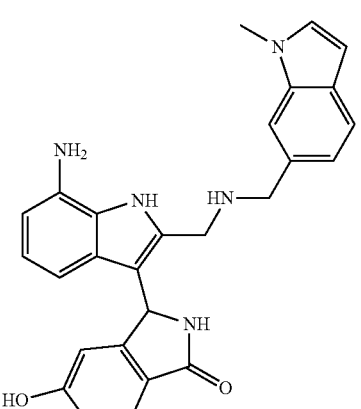 | 0.97 | 452 | LCMSBAS1 |

TABLE 1-continued
| # | structure | $t_{ret}$ [min] | $[M + H]^+$ | HPLC method |
|---|---|---|---|---|
| I-065 | 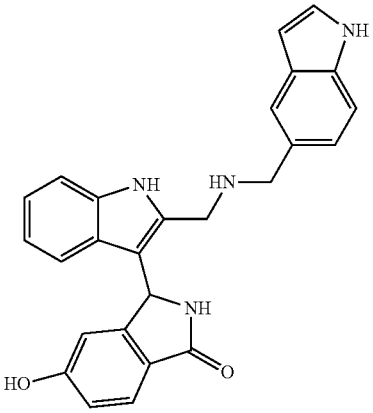 [SMILES: O=C1NC(c2c(CNCc3ccc4[nH]ccc4c3)[nH]c3ccccc23)c2cc(O)ccc21] | 0.97 | 423 | LCMSBAS1 |
| I-066 | 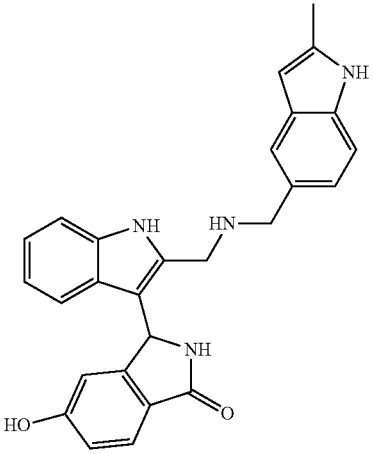 [SMILES: Cc1cc2cc(CNCc3[nH]c4ccccc4c3C3NC(=O)c4ccc(O)cc43)ccc2[nH]1] | 0.95 | 437 | LCMSBAS1 |
| I-067 | 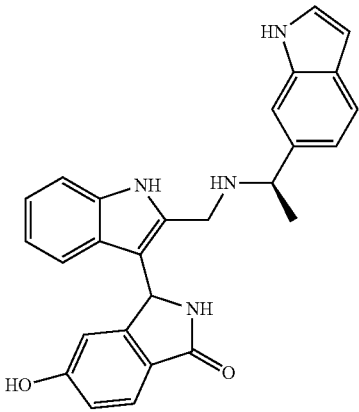 [SMILES: C[C@@H](NCc1[nH]c2ccccc2c1C1NC(=O)c2ccc(O)cc21)c1ccc2cc[nH]c2c1] | 1.05 | $[M - H]^+$ 435 | LCMSBAS1 |

TABLE 1-continued
| # | structure | $t_{ret}$ [min] | $[M + H]^+$ | HPLC method |
|---|---|---|---|---|
| I-068 | 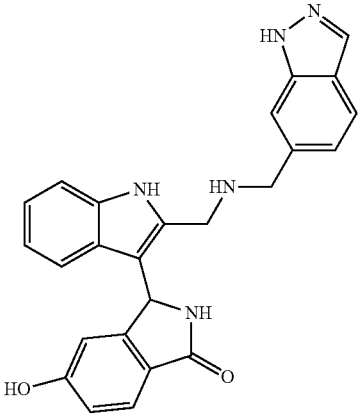 [SMILES: O=C1NC(c2c(CNCc3ccc4cn[nH]c4c3)[nH]c3ccccc23)c2cc(O)ccc21] | 0.91 | 422 | LCMSBAS1 |
| I-069 | 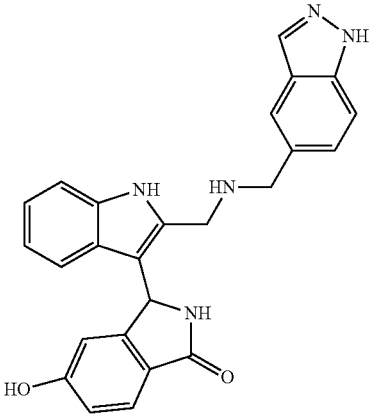 [SMILES: O=C1NC(c2c(CNCc3ccc4[nH]ncc4c3)[nH]c3ccccc23)c2cc(O)ccc21] | 0.79 | 424 | LCMSBAS1 |
| I-070 | 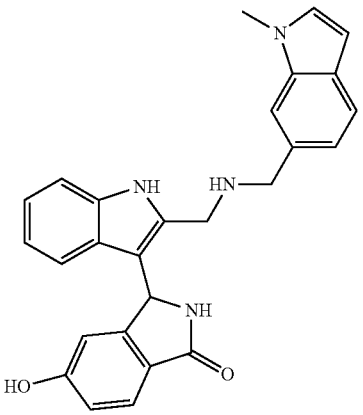 [SMILES: Cn1ccc2ccc(CNCc3[nH]c4ccccc4c3C3NC(=O)c4ccc(O)cc43)cc21] | 1.00 | 437 | LCMSBAS1 |

TABLE 1-continued
| # | structure | t_ret [min] | [M + H]+ | HPLC method |
|---|---|---|---|---|
| I-071 | 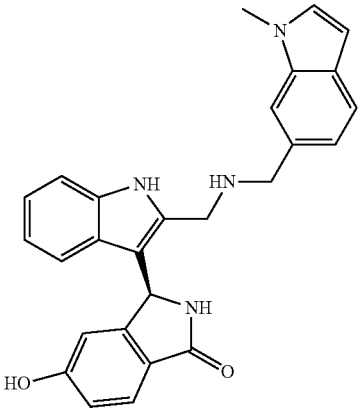 [SMILES: Cn1ccc2ccc(CNCc3[nH]c4ccccc4c3[C@H]3NC(=O)c4ccc(O)cc43)cc21] | 1.08 | 437 | LCMSBAS1 |
| I-072 | 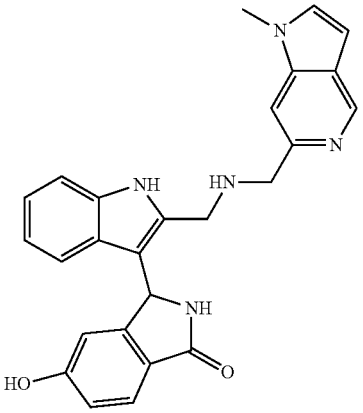 [SMILES: Cn1ccc2cnc(CNCc3[nH]c4ccccc4c3C3NC(=O)c4ccc(O)cc43)cc21] | 0.94 | 438 | LCMSBAS1 |
| I-073 | 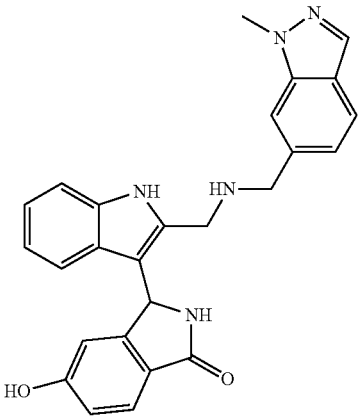 [SMILES: Cn1ncc2ccc(CNCc3[nH]c4ccccc4c3C3NC(=O)c4ccc(O)cc43)cc21] | 0.87 | 438 | LCMSBAS1 |

TABLE 1-continued
| # | structure | $t_{ret}$ [min] | $[M + H]^+$ | HPLC method |
|---|---|---|---|---|
| I-074 | 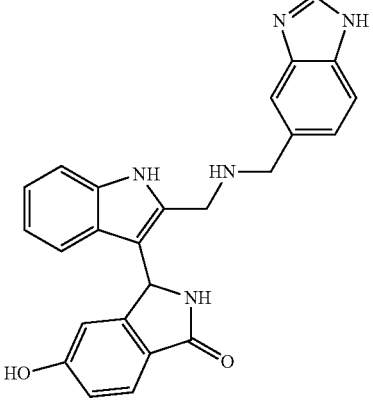 | 0.85 | 424 | LCMSBAS1 |
| I-075 | 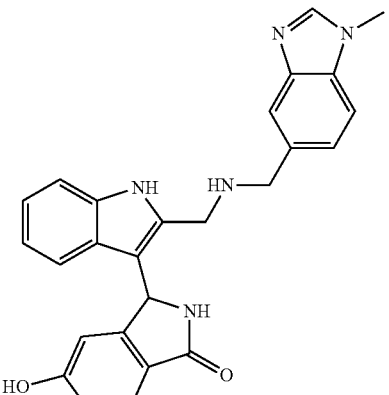 | 0.89 | 438 | LCMSBAS1 |
| I-076 | 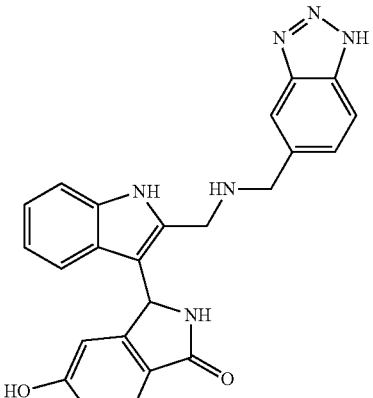 | 0.78 | 425 | LCMSBAS1 |

TABLE 1-continued
| # | structure | t_ret [min] | [M + H]+ | HPLC method |
|---|---|---|---|---|
| I-077 | 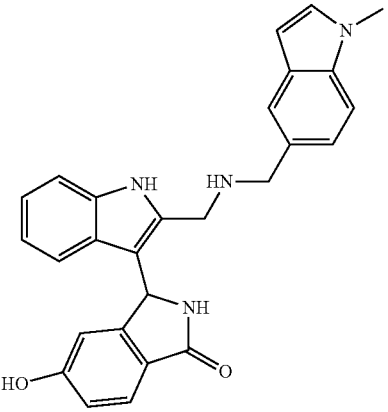 [SMILES: Cn1ccc2cc(CNCc3[nH]c4ccccc4c3C3NC(=O)c4ccc(O)cc43)ccc21] | 1.06 | 437 | LCMSBAS1 |
| I-078 | 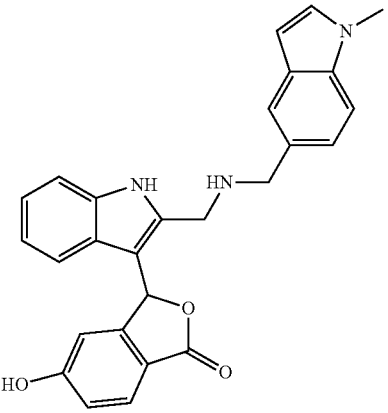 [SMILES: Cn1ccc2cc(CNCc3[nH]c4ccccc4c3C3OC(=O)c4ccc(O)cc43)ccc21] | 1.11 | 438 | LCMSBAS1 |
| I-079 | 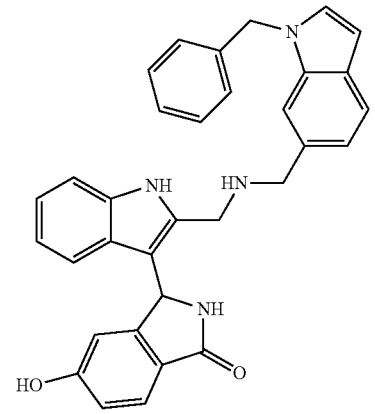 [SMILES: O=C1NC(c2c(CNCc3ccc4ccn(Cc5ccccc5)c4c3)[nH]c3ccccc23)c2cc(O)ccc21] | 1.24 | 513 | LCMSBAS1 |

TABLE 1-continued
| # | structure | $t_{ret}$ [min] | $[M + H]^+$ | HPLC method |
|---|---|---|---|---|
| I-080 | 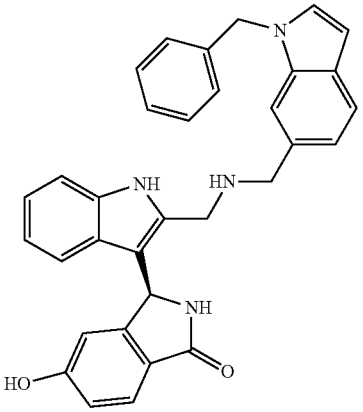 [SMILES: O=C1N[C@H](c2c(CNCc3ccc4ccn(Cc5ccccc5)c4c3)[nH]c3ccccc23)c2cc(O)ccc21] | 1.25 | 513 | LCMS3BAS1 |
| I-081 | 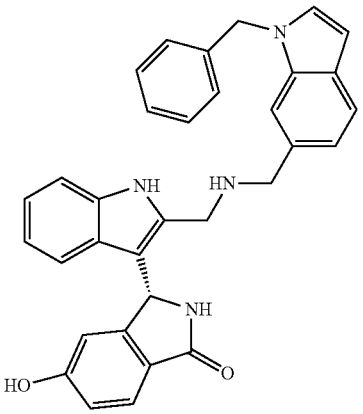 [SMILES: O=C1N[C@@H](c2c(CNCc3ccc4ccn(Cc5ccccc5)c4c3)[nH]c3ccccc23)c2cc(O)ccc21] | 1.23 | 513 | LCMSBAS1 |
| I-082 | 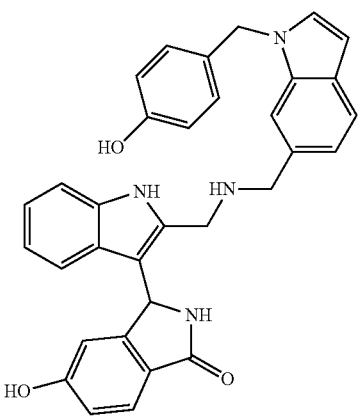 [SMILES: O=C1NC(c2c(CNCc3ccc4ccn(Cc5ccc(O)cc5)c4c3)[nH]c3ccccc23)c2cc(O)ccc21] | 1.15 | 529 | LCMSBAS1 |

TABLE 1-continued
| # | structure | t_ret [min] | [M + H]+ | HPLC method |
|---|---|---|---|---|
| I-083 | 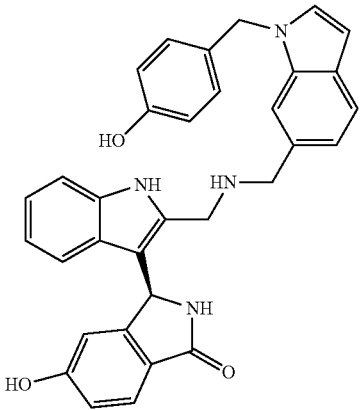 [SMILES: O=C1N[C@H](c2c(CNCc3ccc4ccn(Cc5ccc(O)cc5)c4c3)[nH]c3ccccc23)c2cc(O)ccc21] | 1.17 | 529 | LCMS3BAS1 |
| I-084 | 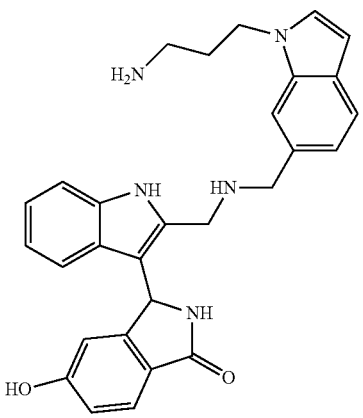 [SMILES: NCCCn1ccc2ccc(CNCc3[nH]c4ccccc4c3C3NC(=O)c4ccc(O)cc43)cc21] | 0.98 | 480 | LCMSBAS1 |
| I-085 | 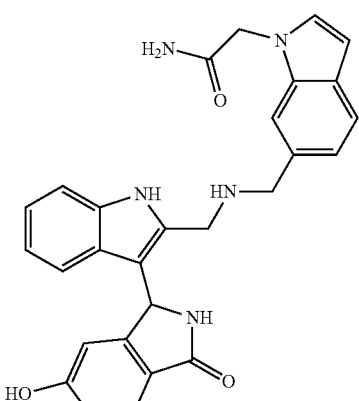 | 0.93 | 480 | LCMSBAS1 |

TABLE 1-continued

| # | structure | $t_{ret}$ [min] | [M + H]$^+$ | HPLC method |
|---|---|---|---|---|
| I-086 | 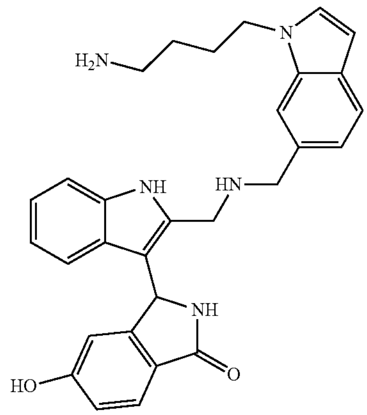 [SMILES: NCCCCn1ccc2ccc(CNCc3[nH]c4ccccc4c3C3NC(=O)c4ccc(O)cc43)cc21] | 1.02 | 494 | LCMSBAS1 |
| I-087 | 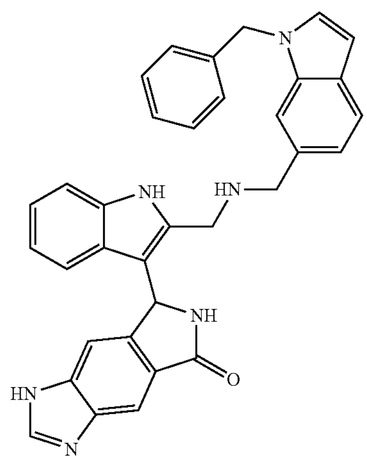 [SMILES: O=C1NC(c2c(CNCc3ccc4ccn(Cc5ccccc5)c4c3)[nH]c3ccccc23)c2cc3[nH]cnc3cc21] | 1.18 | 537 | LCMSBAS1 |
| I-088 | 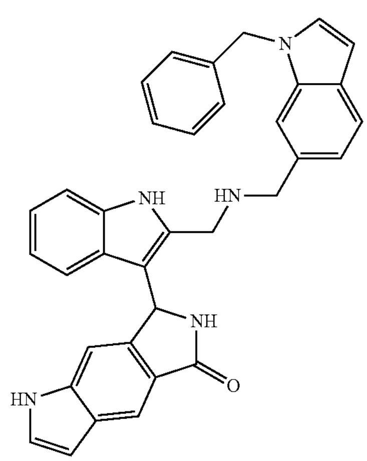 [SMILES: O=C1NC(c2c(CNCc3ccc4ccn(Cc5ccccc5)c4c3)[nH]c3ccccc23)c2cc3[nH]ccc3cc21] | 1.36 | 536 | LCMSBAS1 |

TABLE 1-continued

| # | structure | t_ret [min] | [M + H]+ | HPLC method |
|---|---|---|---|---|
| I-089 | 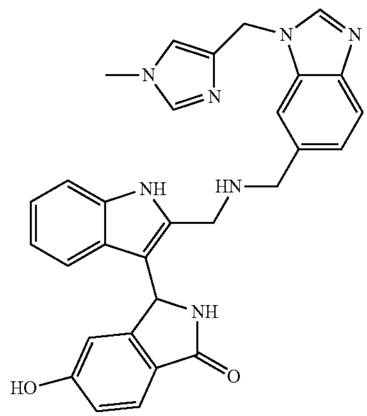 [SMILES: Cn1cnc(Cn2cnc3ccc(CNCc4[nH]c5ccccc5c4C4NC(=O)c5ccc(O)cc54)cc32)c1] | 0.88 | 518 | LCMSBAS1 |
| I-090 | 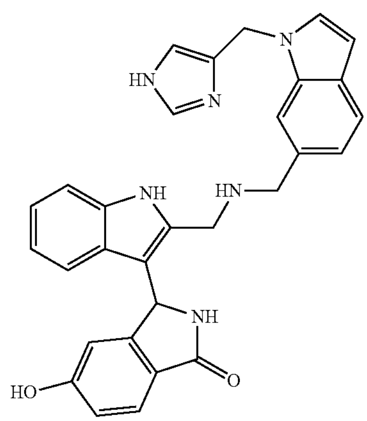 [SMILES: O=C1NC(c2c(CNCc3ccc4ccn(Cc5c[nH]cn5)c4c3)[nH]c3ccccc23)c2cc(O)ccc21] | 0.98 | 503 | LCMSBAS1 |
| I-091 | 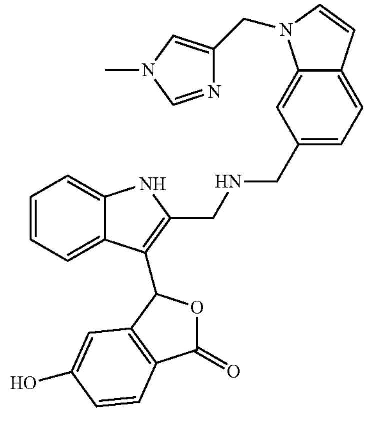 [SMILES: Cn1cnc(Cn2ccc3ccc(CNCc4[nH]c5ccccc5c4C4OC(=O)c5ccc(O)cc54)cc32)c1] | 1.07 | 518 | LCMSBAS1 |

TABLE 1-continued

| # | structure | $t_{ret}$ [min] | $[M + H]^+$ | HPLC method |
|---|---|---|---|---|
| I-092 | 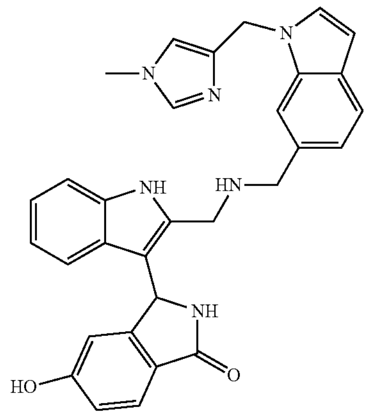 [SMILES: Cn1cnc(Cn2ccc3ccc(CNCc4[nH]c5ccccc5c4C4NC(=O)c5ccc(O)cc54)cc32)c1] | 1.03 | 517 | LCMSBAS1 |
| I-093 | 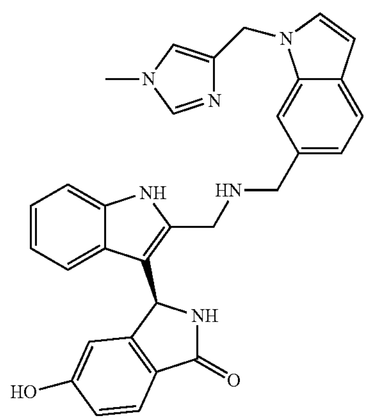 [SMILES: Cn1cnc(Cn2ccc3ccc(CNCc4[nH]c5ccccc5c4[C@H]4NC(=O)c5ccc(O)cc54)cc32)c1] | 1.03 | 517 | LCMSBAS1 |
| I-094 | 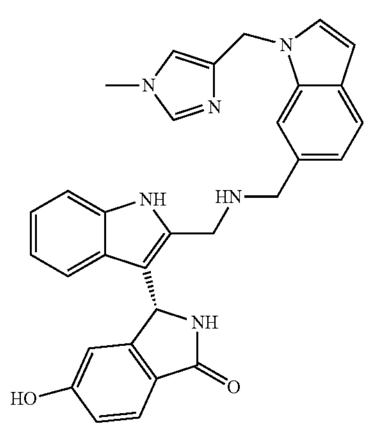 [SMILES: Cn1cnc(Cn2ccc3ccc(CNCc4[nH]c5ccccc5c4[C@@H]4NC(=O)c5ccc(O)cc54)cc32)c1] | 1.04 | 517 | LCMS3BAS1 |

TABLE 1-continued

| # | structure | t$_{ret}$ [min] | [M + H]$^+$ | HPLC method |
|---|---|---|---|---|
| I-095 | 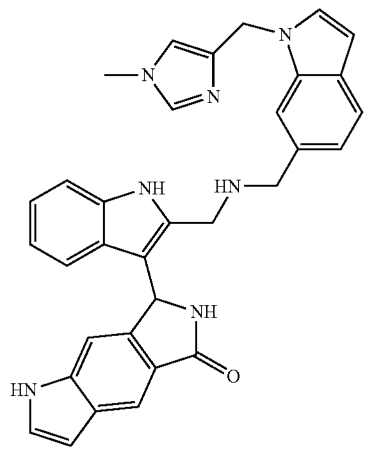 [SMILES: Cn1cnc(Cn2ccc3ccc(CNCc4[nH]c5ccccc5c4C4NC(=O)c5cc6cc[nH]c6cc54)cc32)c1] | | | |
| I-096 | 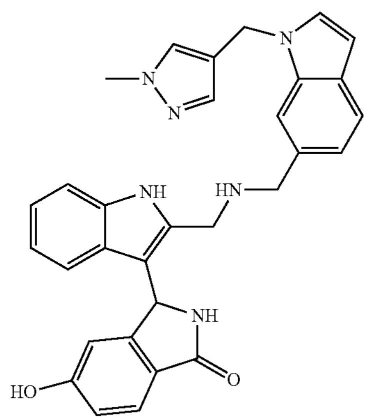 [SMILES: Cn1cc(Cn2ccc3ccc(CNCc4[nH]c5ccccc5c4C4NC(=O)c5ccc(O)cc54)cc32)cn1] | 1.09 | 517 | LCMSBAS1 |
| I-097 | 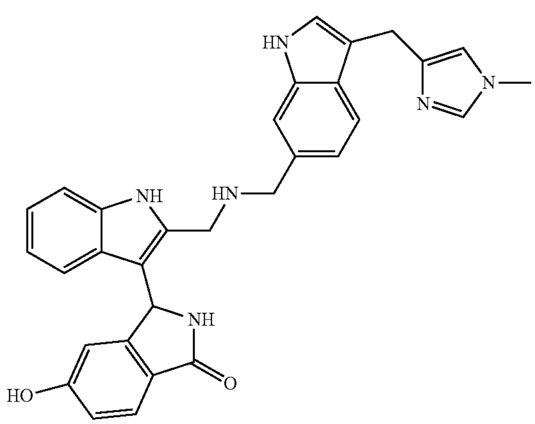 [SMILES: Cn1cnc(Cc2c[nH]c3cc(CNCc4[nH]c5ccccc5c4C4NC(=O)c5ccc(O)cc54)ccc23)c1] | 0.96 | 517 | LCMSBAS1 |
| I-098 | 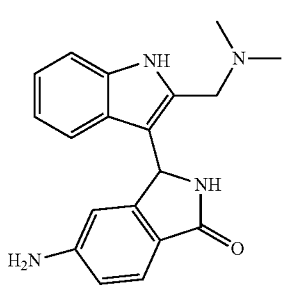 [SMILES: CN(C)Cc1[nH]c2ccccc2c1C1NC(=O)c2ccc(N)cc21] | 0.73 | 321 | LCMSBAS1 |

TABLE 1-continued
| # | structure | $t_{ret}$ [min] | $[M + H]^+$ | HPLC method |
|---|---|---|---|---|
| I-099 | 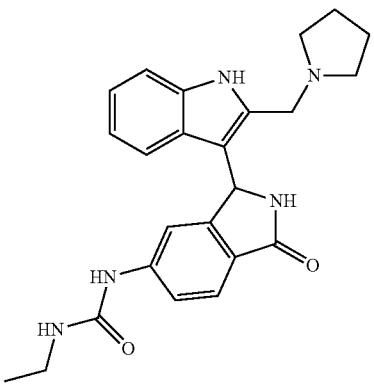 [SMILES: CCNC(=O)Nc1ccc2c(c1)C(c1c(CN3CCCC3)[nH]c3ccccc13)NC2=O] | 0.98 | 418 | LCMSBAS1 |
| I-100 | 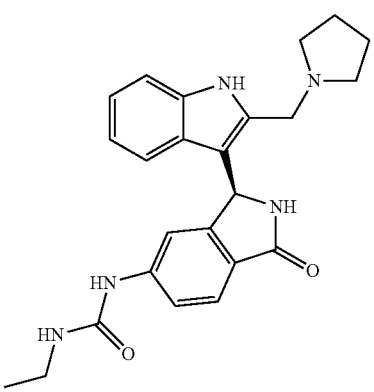 [SMILES: CCNC(=O)Nc1ccc2c(c1)[C@@H](c1c(CN3CCCC3)[nH]c3ccccc13)NC2=O] | 1.01 | 418 | LCMSBAS1 |
| I-101 | 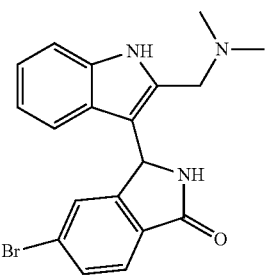 [SMILES: CN(C)Cc1[nH]c2ccccc2c1C1NC(=O)c2ccc(Br)cc21] | 1.10 | 384 | LCMSBAS1 |
| I-102 | 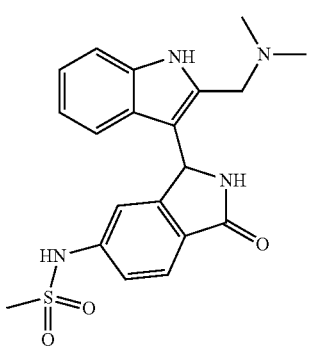 | 0.64 | 399 | LCMSBAS1 |

TABLE 2
| # | structure | $t_{ret}$ [min] | $[M + H]^+$ | HPLC method |
|---|---|---|---|---|
| II-110 | 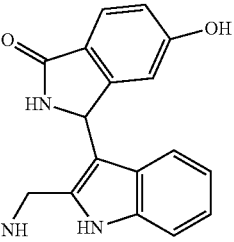 | 0.99 | 683 | LCMSBAS1 |
| II-111 | 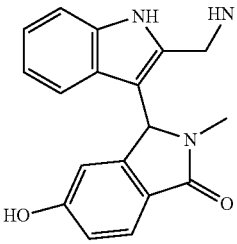 | 1.13 | 522 | LCMSBAS1 |
| II-112 | 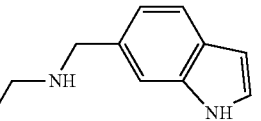 | 0.94 | 643 | LCMSBAS1 |

TABLE 2-continued
| # | structure | $t_{ret}$ [min] | $[M + H]^+$ | HPLC method |
|---|---|---|---|---|
| II-113 | 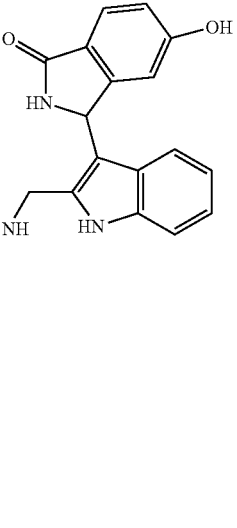 | 0.89 | 641 | LCMSBAS1 |
| II-114 | 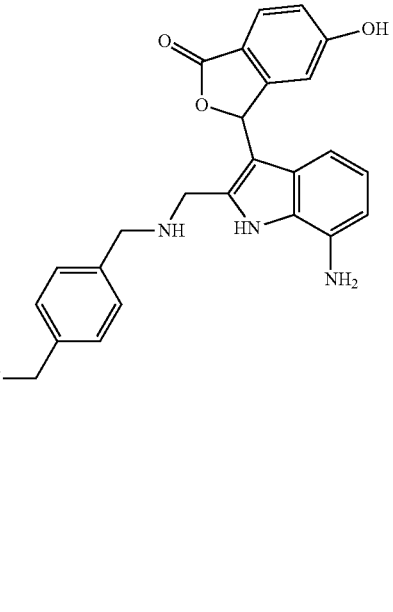 | 0.92 | 721 | LCMSBAS1 |

TABLE 2-continued

| # | structure | $t_{ret}$ [min] | $[M + H]^+$ | HPLC method |
|---|---|---|---|---|
| II-115 | 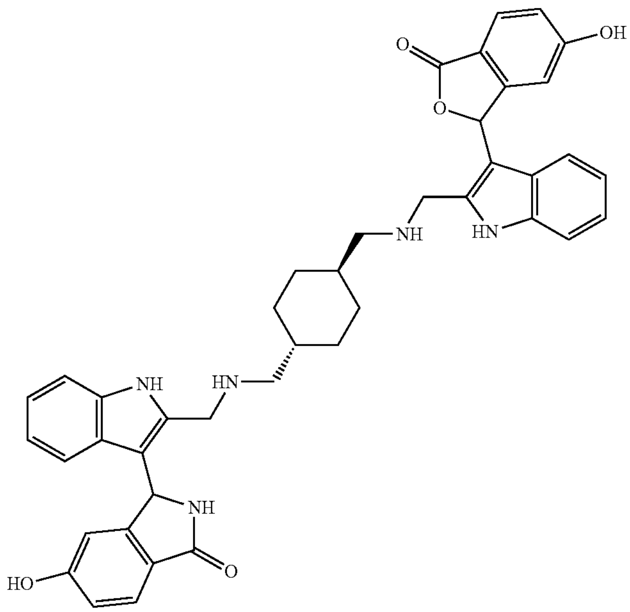 [SMILES: O=C1NC(c2c(CNC[C@H]3CC[C@H](CNCc4[nH]c5ccccc5c4C4OC(=O)c5ccc(O)cc54)CC3)[nH]c3ccccc23)c2cc(O)ccc21] | 1.01 | 696 | LCMSBAS1 |

The following Examples describe the biological activity of the compounds according to the invention, without restricting the invention to these Examples.
KRAS::SOS1 AlphaScreen Binding Assay
Alpha Screen Assay Measurement of various protein-protein interactions was performed using the Alpha Screen technology developed by Perkin Elmer. Recombinant RAS proteins (H-, N-, K-RAS variants) carried a c-terminal Avi-tag used for biotinylation. Interacting proteins (SOS1, PI3K and CRAF) were expressed as glutathione S transferase (GST) fusions. Accordingly, the Alpha Screen beads were glutathione coated Alpha Lisa acceptor beads (Perkin Elmer AL 109 R) and Alpha Screen Streptavidin conjugated donor beads (Perkin Elmer 6760002L). Nucleotides were purchased from Sigma (GTP #G8877, GDP #G7127), Tween-20 from Bio-Rad (#161-0781). All interaction assays were carried out in PBS, containing 0.1% bovine serum albumin, 0.05% Tween-20 and 10 μM of the corresponding nucleotide. Assays were carried out in white ProxiPlate-384 Plus plates (Perkin Elmer #6008280) in a final volume of 20 μl. In brief, biotinylated RAS proteins (10 nM final concentration) and GST-SOS1, GST-PI3K or GST-CRAF (10 nM final) were mixed with glutathione acceptor beads (5 μg/ml final concentration) in buffer, containing the corresponding nucleotides (GDP or GTP for assays containing SOS1, only GTP for interaction assays containing PI3K or CRAF) and were incubated for 30 min at room temperature. After addition of strepavidin donor beads (5 μg/ml final concentration) under green light, the mixture was further incubated for 60 min in the dark at room temperature. Single oxygen induced fluorescence was measured at an Enspire multimode plate reader (Perkin Elmer) according to the manufacturers recommendations. Data were analyzed using the GraphPad Prism data software.

This assay can be used to examine the potency with which compounds inhibit the protein-protein interaction between SOS1 and KRAS G12D.

Reagents:
GST-tagged SOS1 (564_1049_GST_TEV_ECO) produced in-house GST-TEV-SOS1 (564-1049) is purchased from Viva Biotech Ltd.
6xHis-Tev-K-RasG12D(1-169)Avi is purchased from Xtal BioStructures, Inc. (Lot #X129-110)
GDP (Sigma Cat No G7127)
AlphaLISA Glutathione Acceptor Beads (PerkinElmer, Cat No AL109)
AlphaScreen Streptavidin Donor Beads (PerkinElmer Cat No 6760002)
Assay plates: Proxiplate-384 PLUS, white (PerkinElmer, Cat No 6008289)
Assay Buffer:
1xPBS
0.1% BSA
100 μM EDTA or without EDTA (IC$_{50}$s in the tables are measured without EDTA unless they are marked with an asterisk)
0.05% Tween 20
Kras::SOS1 Gdp Mix:
10 nM (final assay concentration) KRAS G12D, 10 μM (final assay concentration) GDP and 5 nM (final assay concentration) GST-SOS1 are mixed in assay buffer prior to use and kept at room temperature.
Bead Mix:
AlphaLISA Glutathione Acceptor Beads and AlphaScreen Streptavidin Donor Beads are mixed in assay buffer at a concentration of 10 μg/mL (final assay concentration) each prior to use and kept at room temperature.
Assay Protocol:
Compounds are diluted to a final start concentration of 100 μM and are tested in duplicate. Assay-ready plates (ARPs) are generated using an Access Labcyte Workstation with a Labcyte Echo 550 or 555 acoustic dispenser. For compound a start concentration of 100 μM, 150 nL of compound solution is transferred per well in 11 concentrations in duplicate with serial 1:5 dilutions.

The assay is run using a fully automated robotic system in a darkened room below 100 Lux. 10 μL of KRAS::SOS1 GDP mix is added into columns 1-24 to the 150 nL of compound solution (final dilution in the assay 1:100, final DMSO concentration 1%).

After a 30 minute incubation time 5 μL of bead mix is added into columns 1-23. Plates are kept at room temperature in a darkened incubator. After a further 60 minute incubation, the signal is measured using a PerkinElmer Envision HTS Multilabel Reader using the AlphaScreen specifications from PerkinElmer. Each plate contains the following controls:

diluted DMSO+KRAS::SOS1 GDP mix+bead mix
diluted DMSO+KRAS::SOS1 GDP mix

Result Calculation:

$IC_{50}$ values are calculated and analyzed using a 4 parametric logistic model.

Table 3 of example compounds disclosed herein contain $IC_{50}$ values determined using assays described above.

TR-FRET Assay

This assay was used to identify compounds which competitively interact with the binding of KRAS G12D to SOS1 in the presence of GTP.

The following binding partners have been used in this assay. Biotinylated KRAS G12D protein corresponding to KRAS (amino acids 1-169, with the following changes to the natural protein: G12D) was expressed in *E. coli* with a carboxy-terminal Avi tag (amino acid sequence GGGLN-DIFEAQKIEWHE). GST-tagged SOS1 protein corresponding to SOS1 (amino acids 564-1049) with an amino-terminal GST-tag and a Tobacco-etch-virus (TEV) protease cleavage site was expressed in *E. coli* and purified by affinity chromatography on a GSH-column, followed by desalting (HiPrep 26/10 Desalting, GE Healthcare) into 20 mM TRIS, 200 mM NaCl, 10% Glycerol, 1 mM DTT, pH 8.0. The tag was not cleaved.

Compounds are dispensed onto assay plates (Proxiplate 384 PLUS, white, PerkinElmer) using an Access Labcyte Workstation with the Labcyte Echo 55× from a DMSO solution. For the chosen highest assay concentration of 500 μM or 100 μM (this can be changed upon request), 150 nl of compound solution are transferred from a 50 mM or 10 mM DMSO compound stock solution. Compounds are tested in duplicates. A series of 11 concentrations is transferred for each compound at which each concentration is fivefold lower than the previous one. DMSO is added such that every well has a total of 150 nl compound solution. The assay runs on a fully automated robotic system. For the assay 15 μl containing KRAS G12D protein (15 nM final assay concentration), SOS1 (10 nM final assay concentration), GTP (10 μM final assay concentration), Lance Eu-W1024 labeled Streptavidin (1.5 nM final assay concentration) and Anti-GST surelight APC (30 nM final assay concentration) mixed in assay buffer (1×PBS; 0.05% Tween20; 0.1% BSA; filtered) are added to the 150 nl of compounds. Plates are kept at room temperature. After 60 minutes incubation time the TR-FRET signal is measured in a PerkinElmer Envision HTS Multilabel Reader using the TR-FRET LANCE Ultra specs of PerkinElmer. Each plate contains negative controls (diluted DMSO instead of test compound; described mix with KRAS G12D protein) and positive controls (diluted DMSO instead of test compound; described mix without KRAS G12D). Negative and positive control values are used for normalization.

TABLE 3

| # | IC50 FRET [μM] | IC50 AlphaScreen [μM] |
|---|---|---|
| I-001 | 32.6 | 18.7 |
| I-002 | 49.9 | 15.8 |
| I-003 | 33.7 | 6.9 |
| I-004 | 14.0 | 19.9 |
| I-005 | 53.4 | 35.2 |
| I-006 | 29.7 | 25.4 |
| I-007 | 43.9 | 30.6 |
| I-008 | 37.9 | 10.9 |
| I-009 | 14.1 | 21.9 |
| I-010 | 1.4 | 5.2 |
| I-011 | 68.6 | 30.0 |
| I-012 | 50.5 | 21.1 |
| I-013 | 78.9 | 18.7 |
| I-014 | 30.3 | 8.3 |
| I-015 | 41.9 | 25.9 |
| I-016 | 56.9 | 6.7 |
| I-017 | 61.3 | 6.8 |
| I-018 | 45.9 | 30.0 |
| I-019 | 58.7 | 17.2 |
| I-020 | 41.8 | 9.4 |
| I-021 | 24.8 | 13.0 |
| I-022 | 4.8 | 4.6 |
| I-023 | 34.4 | 14.0 |
| I-024 | 14.0 | 19.9 |
| I-025 | 39.6 | 11.3 |
| I-026 | 77.2 | 20.1 |
| I-027 | 33.6 | 10.2 |
| I-028 | 31.6 | 14.0 |
| I-029 | 34.0 | 7.7 |
| I-030 | 18.6 | 4.0 |
| I-031 | 76.2 | 35.7 |
| I-032 | 30.4 | 5.6 |
| I-033 | 16.4 | 4.6 |
| I-034 | 92.7 | 70.0 |
| I-035 | 46.7 | — |
| I-036 | 81.5 | — |
| I-037 | 92.0 | 13.8 |
| I-038 | 44.1 | 7.2 |
| I-039 | 47.3 | 10.7 |
| I-040 | 22.8 | 7.6 |
| I-041 | 29.2 | 15.9 |
| I-042 | 14.4 | 13.1 |
| I-043 | 30.8 | 64.0 |
| I-044 | 57.0 | 40.0 |
| I-045 | 61.6 | 36.4 |
| I-046 | 78.5 | — |
| I-047 | 63.7 | 25.1 |
| I-048 | 21.4 | 40.0 |
| I-049 | 37.0 | 15.5 |
| I-050 | 11.7 | 26.1 |
| I-051 | 10.5 | 90.0 |
| I-052 | 8.3 | 18.9 |
| I-053 | 13.6 | 9.3 |
| I-054 | 7.5 | 13.3 |
| I-055 | 4.2 | 8.9 |
| I-056 | 9.1 | 26.9 |
| I-057 | 10.8 | 11.2 |
| I-058 | 7.2 | — |
| I-059 | 20.4 | 8.1 |
| I-060 | 13.0 | — |
| I-061 | 6.2 | 14.8 |
| I-062 | 2.3 | 5.2 |
| I-063 | 2.2 | 6.0 |
| I-064 | 3.2 | 4.7 |
| I-065 | 18.0 | 12.6 |
| I-066 | 29.0 | 11.7 |
| I-067 | 21.7 | 14.5 |
| I-068 | 9.0 | 16.2 |
| I-069 | 24.4 | 18.6 |
| I-070 | 6.1 | 10.5 |
| I-071 | 6.7 | 10.7 |
| I-072 | 38.7 | 14.6 |
| I-073 | 26.1 | 24.4 |
| I-074 | 19.6 | 14.8 |
| I-075 | 27.8 | 15.8 |
| I-076 | 14.4 | 15.9 |
| I-077 | 26.6 | 13.1 |
| I-078 | 26.0 | 16.9 |

TABLE 3-continued
| # | IC50 FRET [µM] | IC50 AlphaScreen [µM] |
|---|---|---|
| I-079 | 0.87 | 1.2 |
| I-080 | 0.45 | 0.80 |
| I-081 | 8.8 | 11.3 |
| I-082 | 0.40 | 4.8 |
| I-083 | — | 1.3 |
| I-084 | 3.5 | 5.1 |
| I-085 | 6.9 | 7.9 |
| I-086 | 1.01 | 6.4 |
| I-087 | 0.67 | 1.4 |
| I-088 | 1.26 | 3.1 |
| I-089 | 18.1 | 25.1 |
| I-090 | 0.61 | 0.89 |
| I-091 | 8.3 | 8.0 |
| I-092 | 0.40 | 0.33 |
| I-093 | 0.31 | 0.23 |
| I-094 | 2.78 | 4.2 |
| I-095 | 0.52 | 0.34 |
| I-096 | 1.44 | 2.7 |
| I-097 | 7.9 | 8.4 |
| I-098 | 99.1 | — |
| I-099 | 43.9 | 8.3 |
| I-100 | 30.0 | 9.4 |
| I-101 | 160.8 | 18.2 |
| I-102 | 318.8 | 44.5 |
The invention claimed is:
1. A compound selected from the group consisting of:
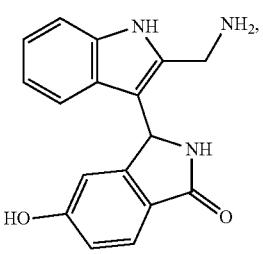
(I-001)
(I-002)
(I-003)
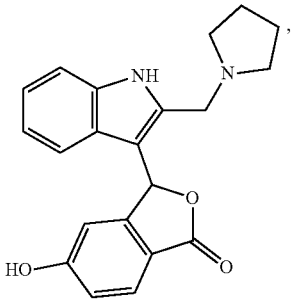
(I-004)
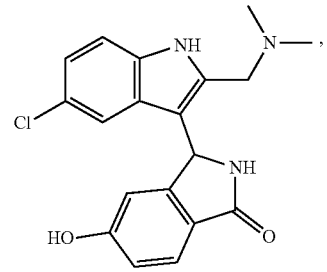
(I-005)
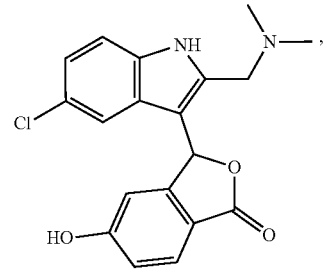
(I-006)
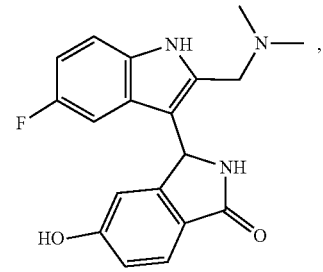
(I-007)
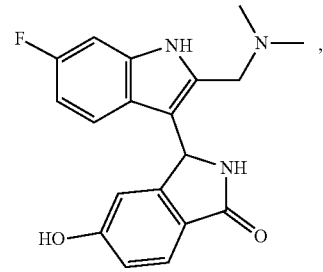
(I-008)

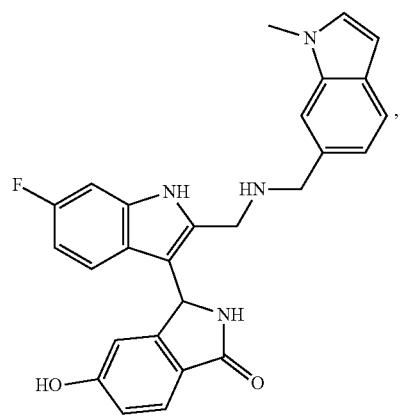
(I-009)
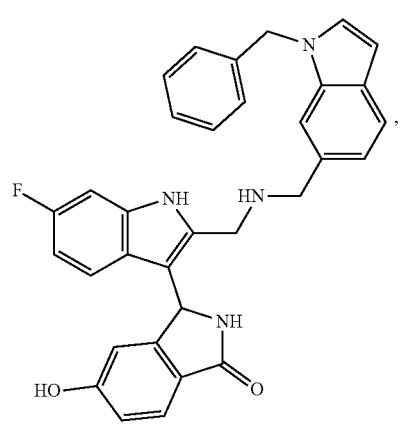
(I-010)
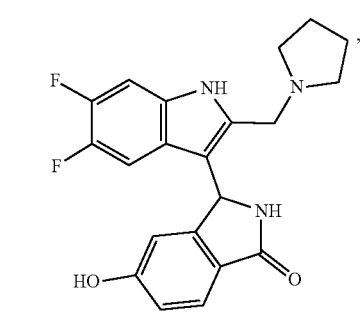
(I-011)
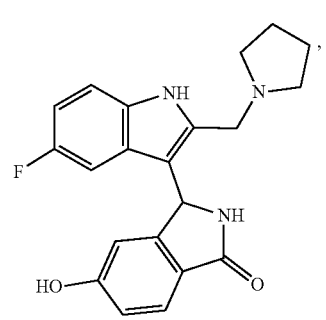
(I-012)
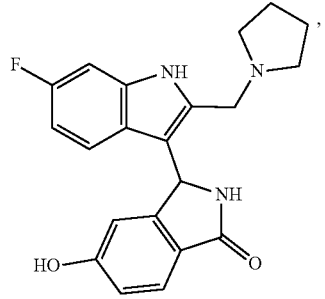
(I-013)
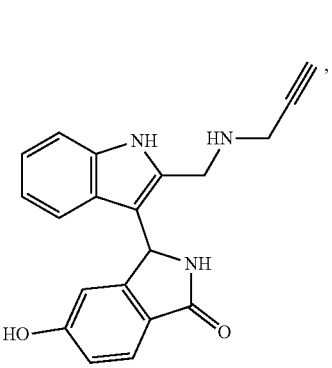
(I-014)
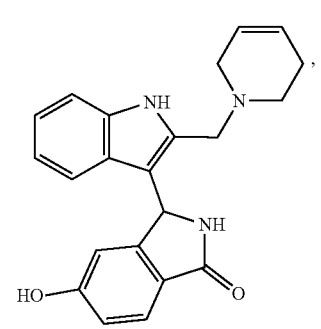
(I-015)
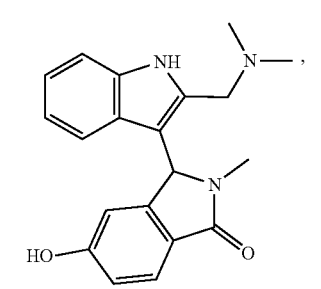
(I-016)
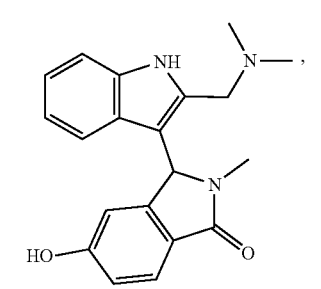
(I-017)

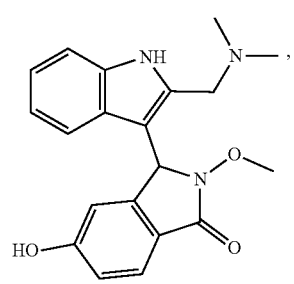 (I-018)
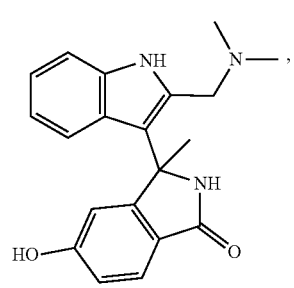 (I-019)
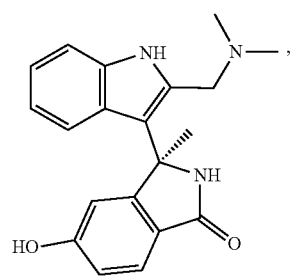 (I-020)
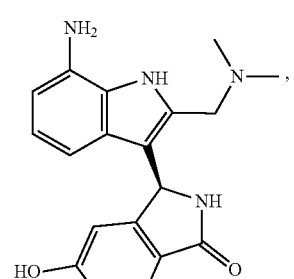 (I-021)
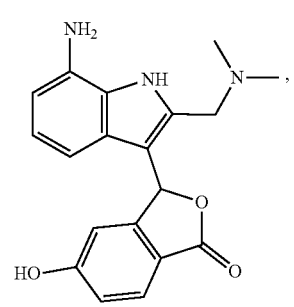 (I-022)
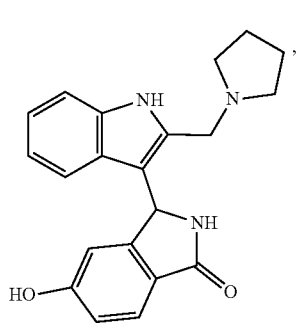 (I-023)
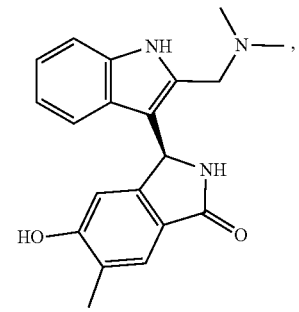
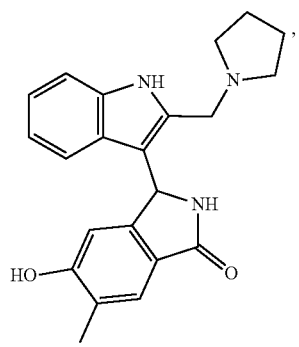 (I-026)
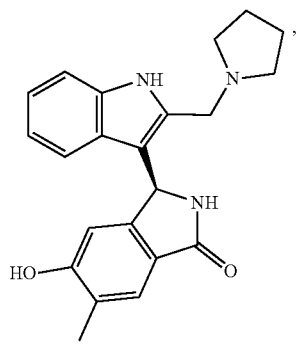 (I-027)
(I-028)

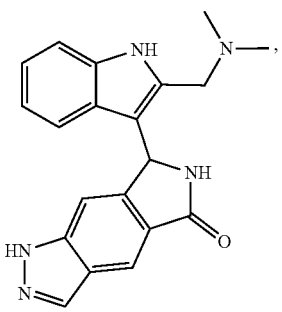
(I-029)
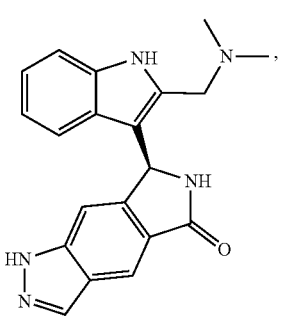
(I-030)
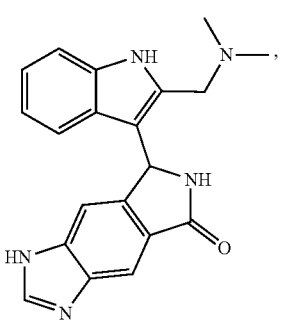
(I-031)
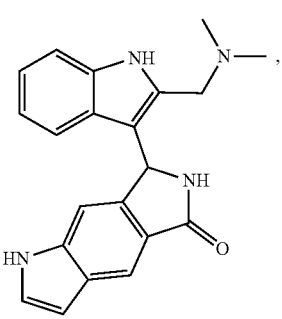
(I-032)
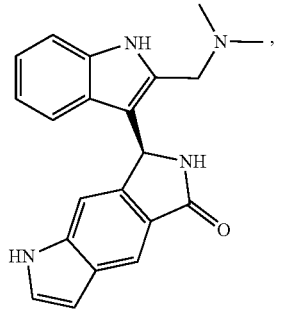
(I-033)
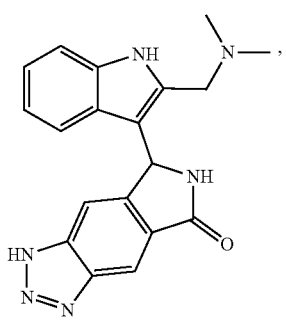
(I-034)
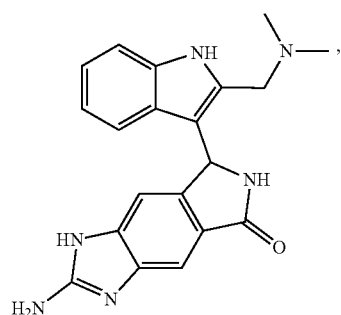
(I-035)
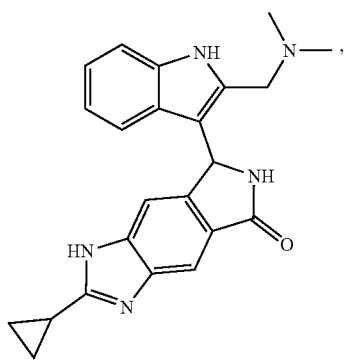
(I-036)
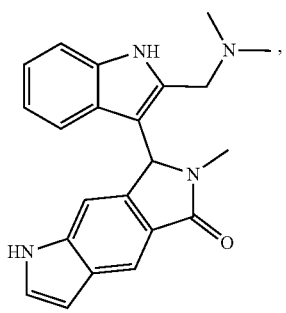
(I-037)
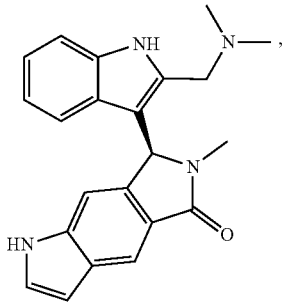
(I-038)

(I-039)
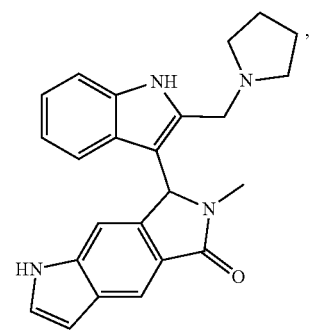
(I-040)
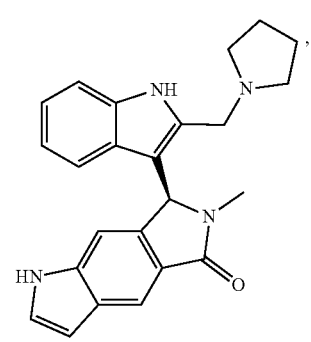
(I-041)
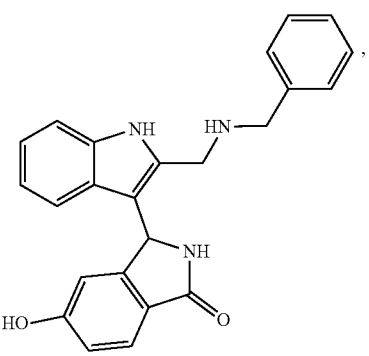
(I-042)
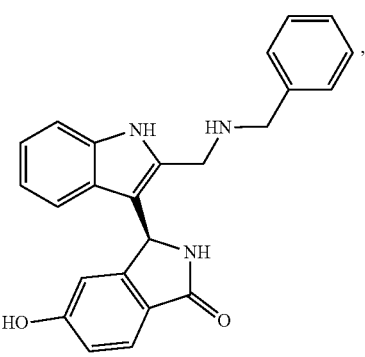
(I-043)
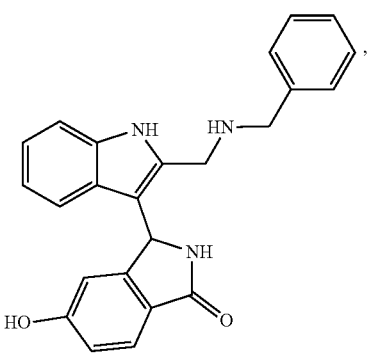
(I-044)
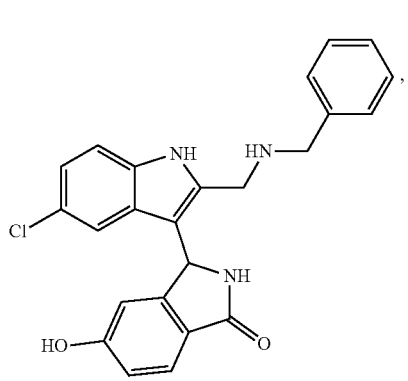
(I-045)
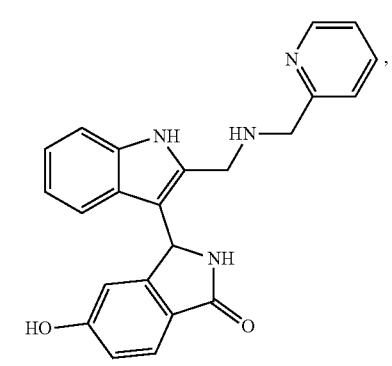
(I-046)
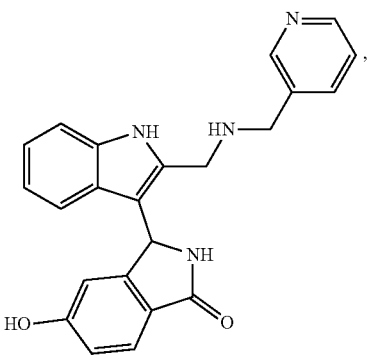

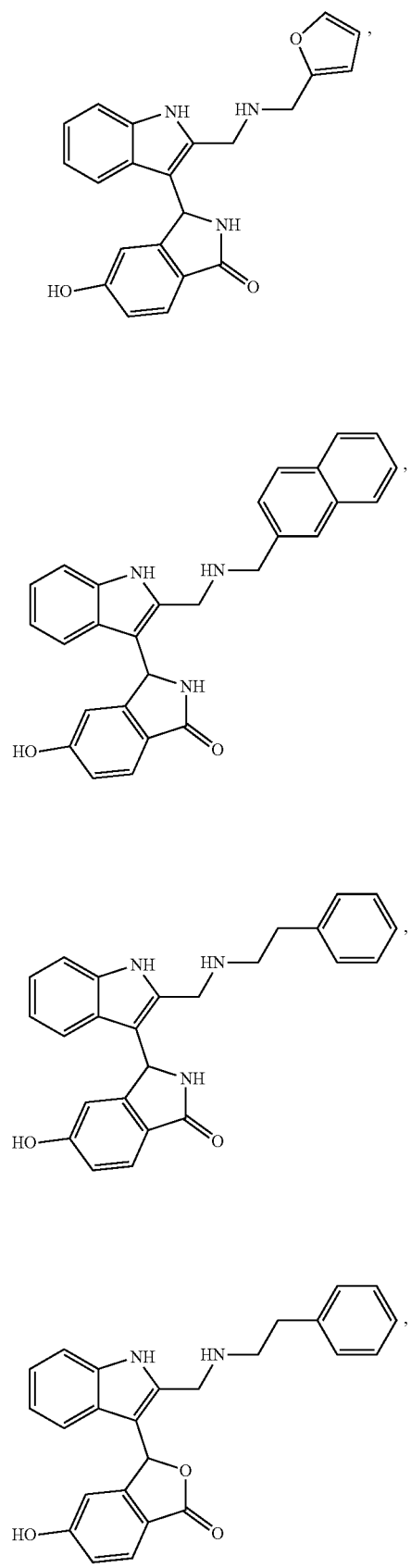
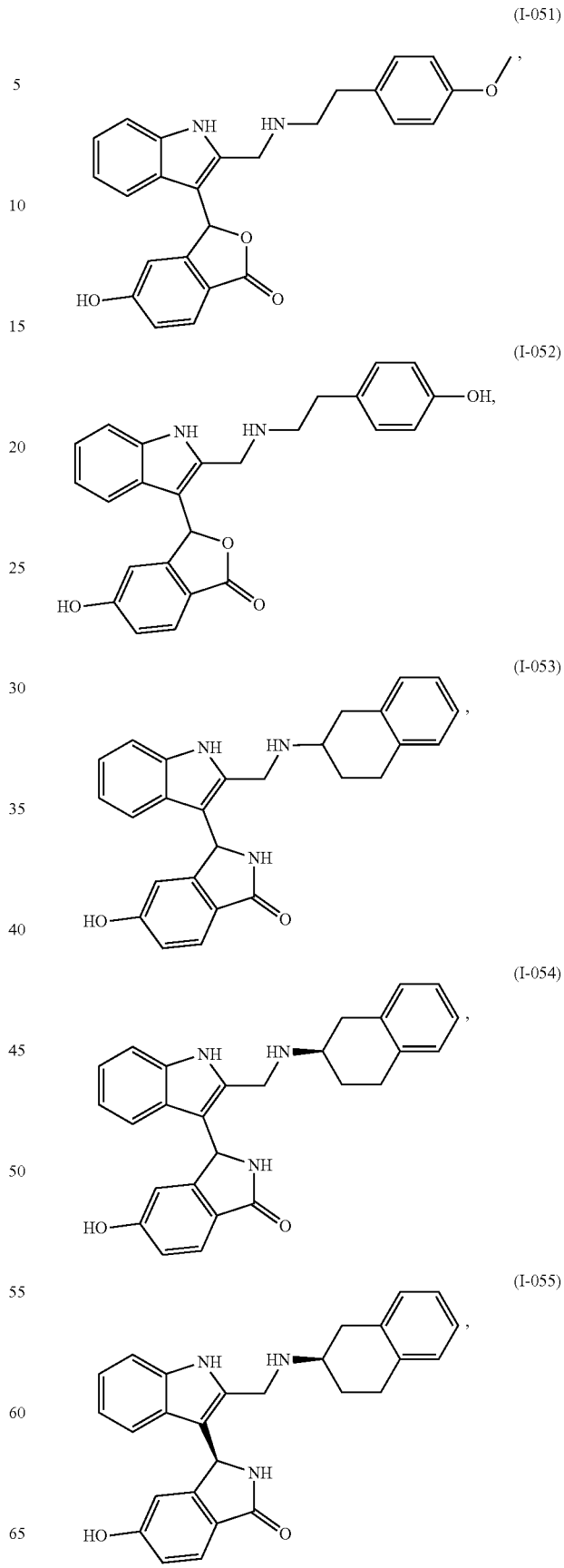

(I-056)
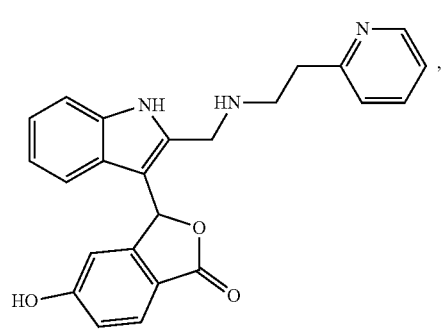
(I-057)
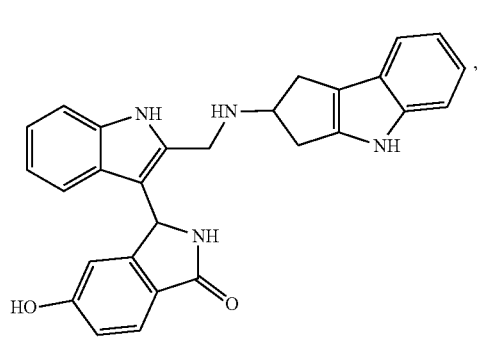
(I-058)
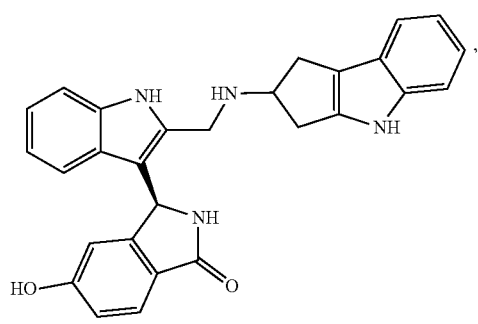
(I-059)
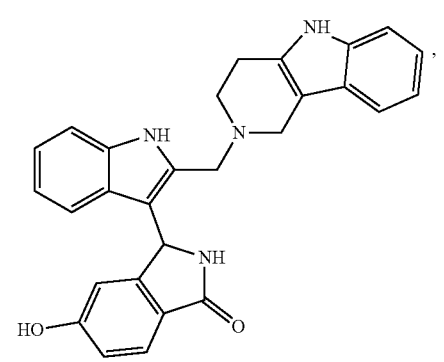
(I-060)
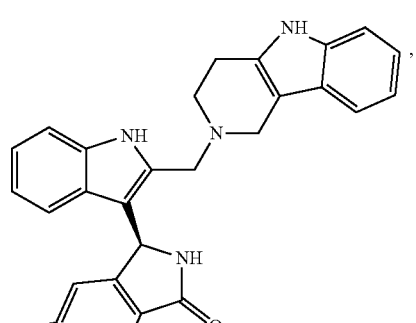
(I-061)
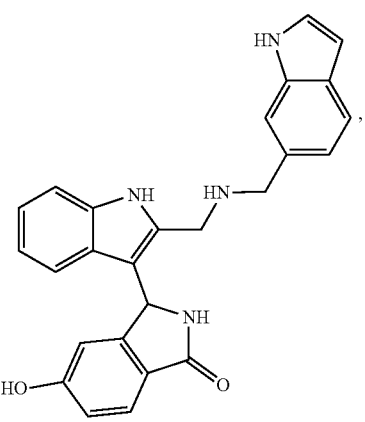
(I-062)
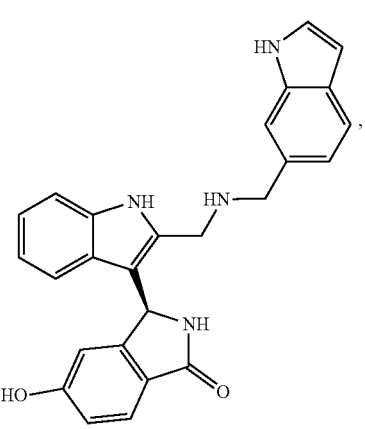

(I-063)
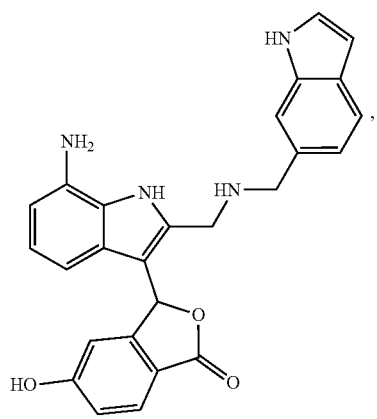
(I-064)
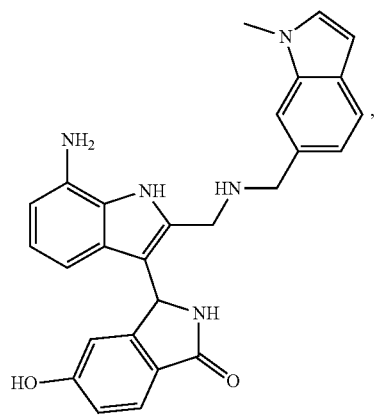
(I-065)
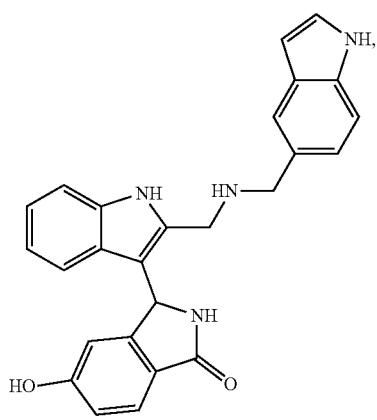
(I-066)
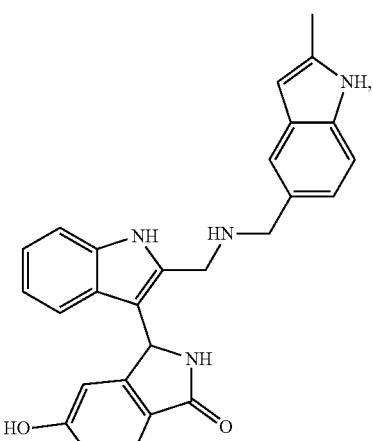
(I-067)
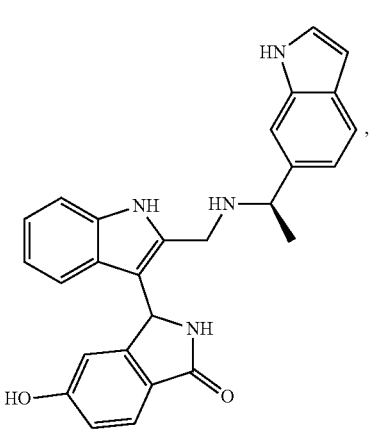
(I-068)
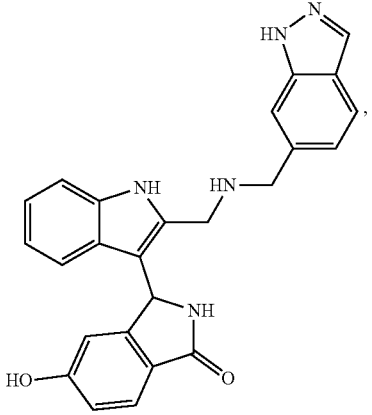

(I-069)
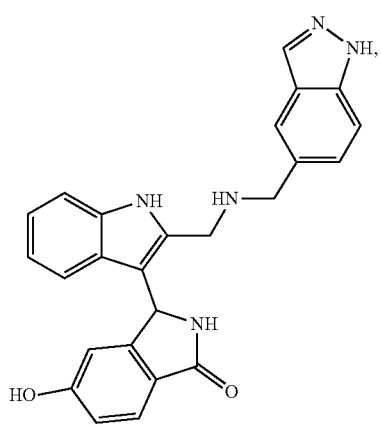
(I-072)
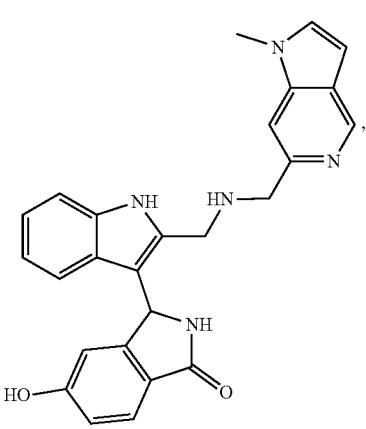
(I-070)
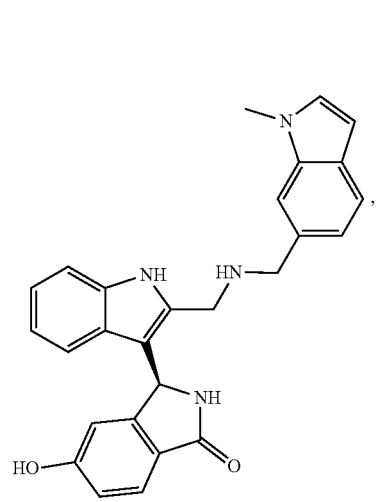
(I-073)
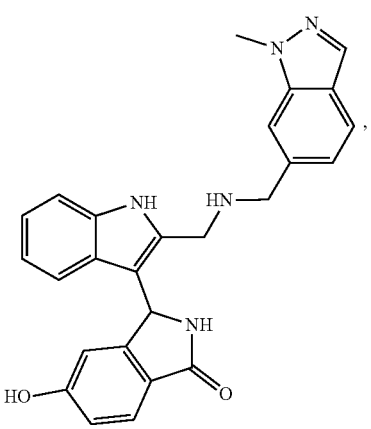
(I-071)
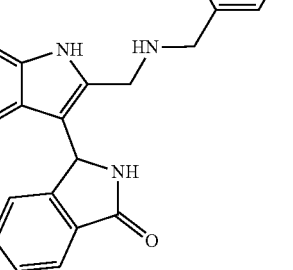
(I-074)
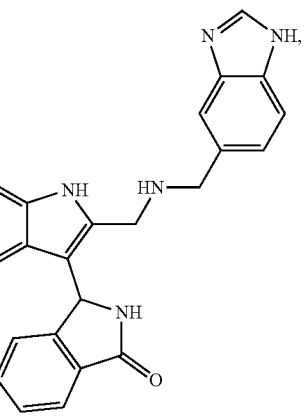

(I-075)
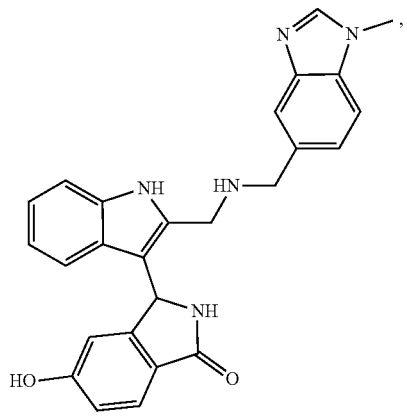
(I-076)
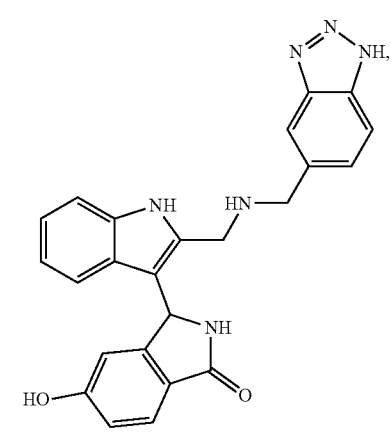
(I-077)
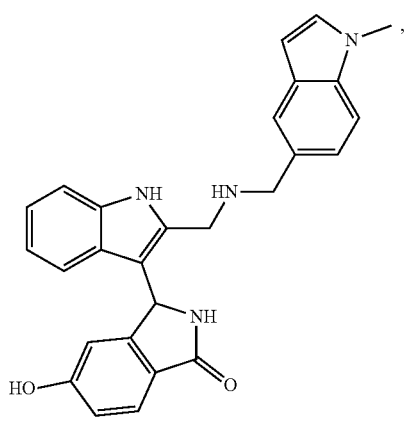
(I-078)
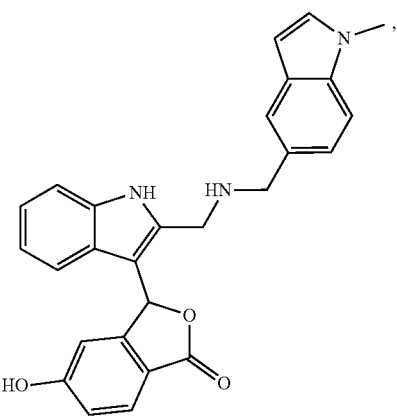
(I-079)
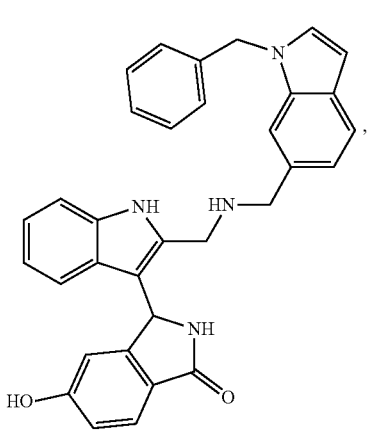
(I-080)
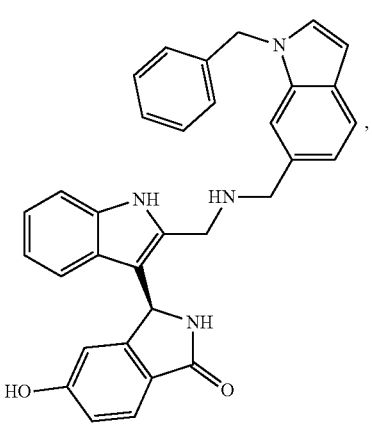

-continued
(I-081)
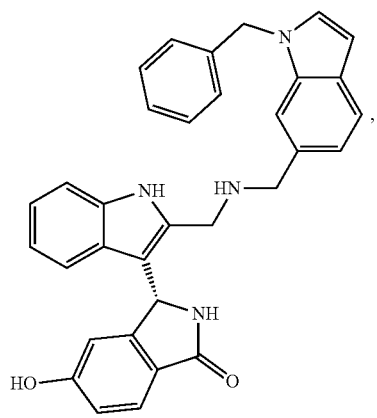
(I-082)
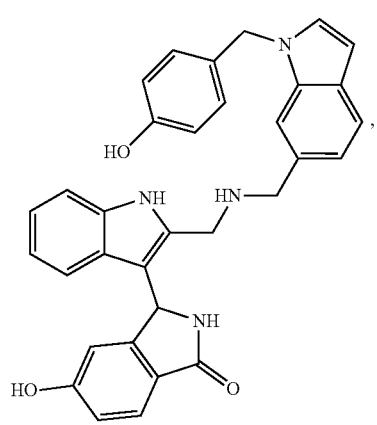
(I-083)
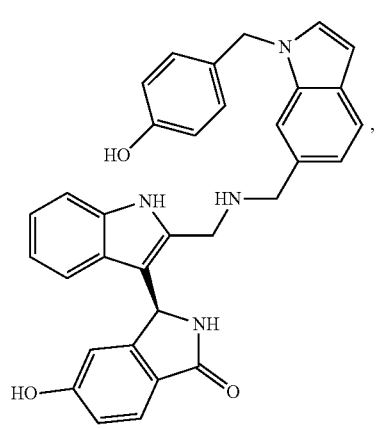
-continued
(I-084)
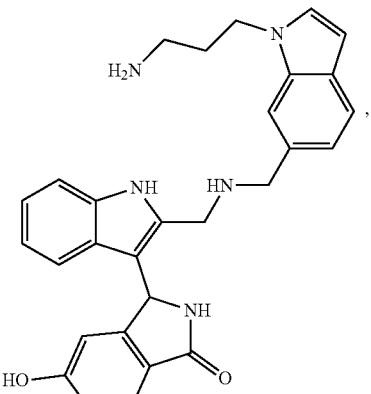
(I-085)
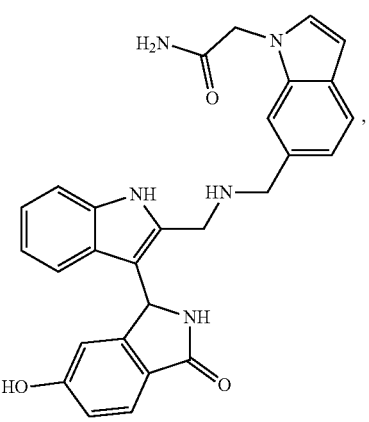
(I-086)
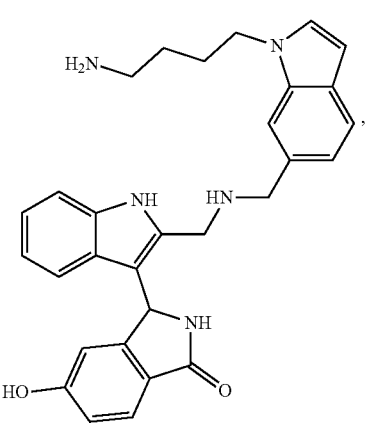

(I-087)
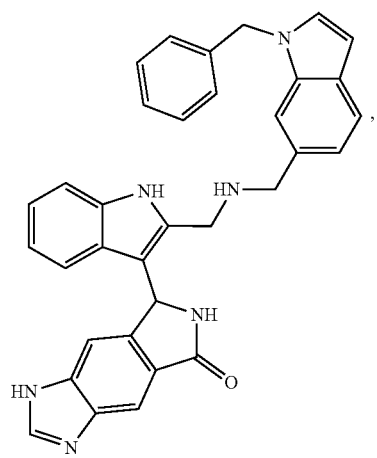
(I-090)
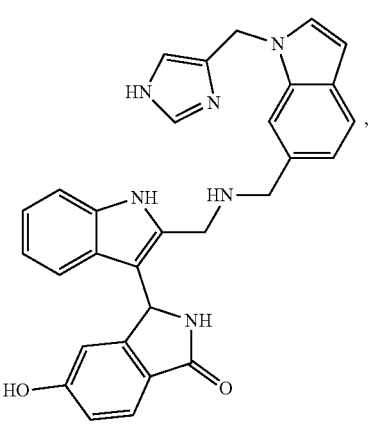
(I-088)
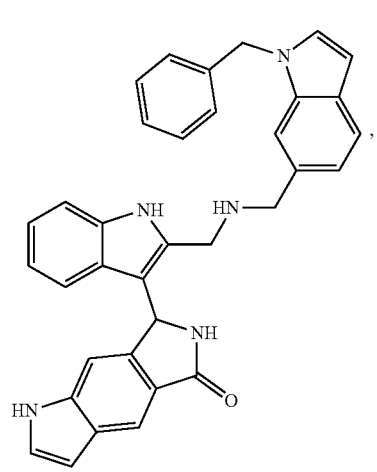
(I-091)
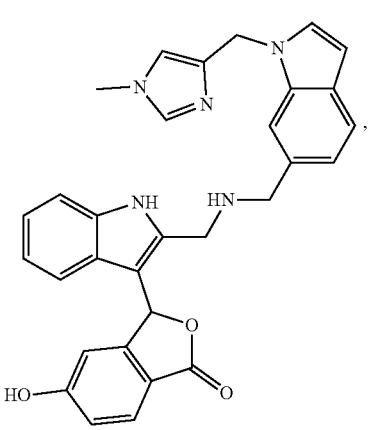
(I-089)
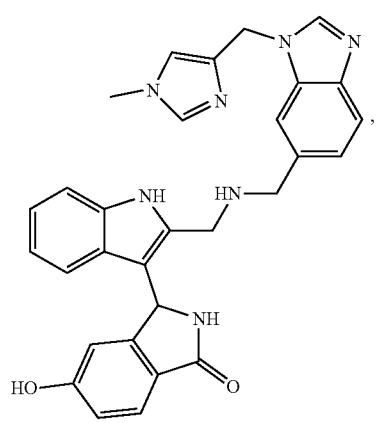
(I-092)
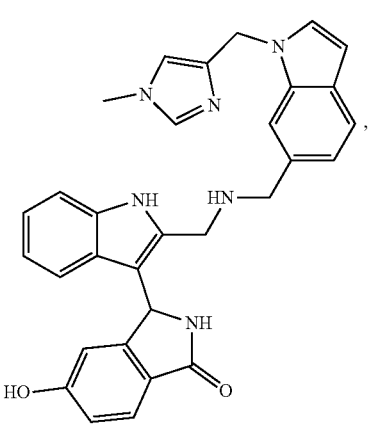

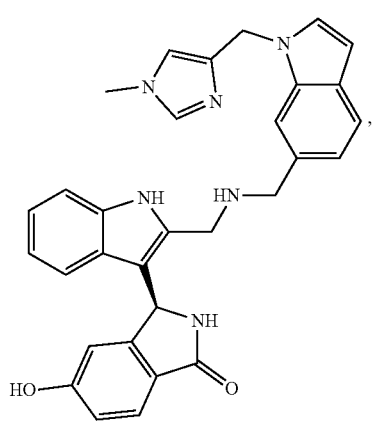
(I-093)
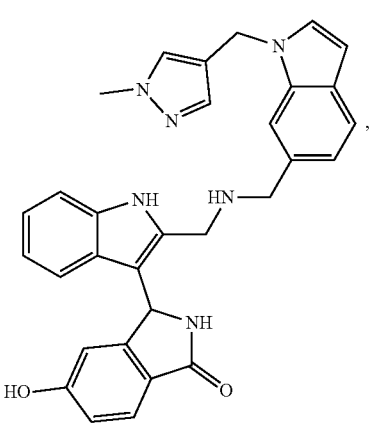
(I-096)
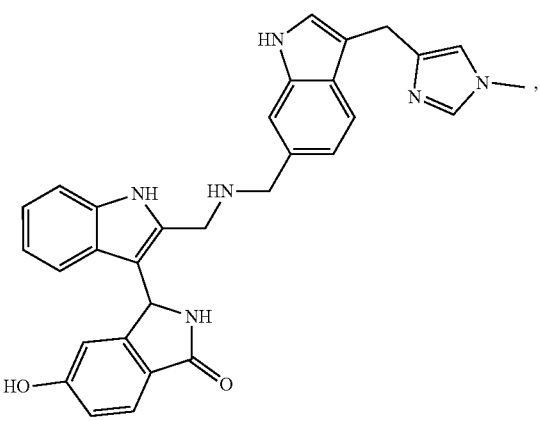
(I-097)
(I-094)
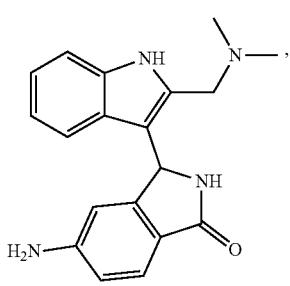
(I-098)
(I-095)
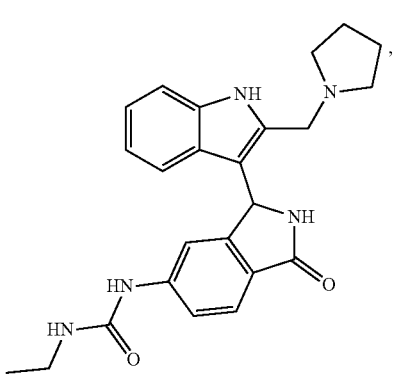
(I-099)

(I-100)
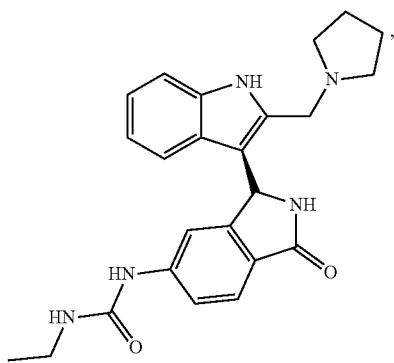
(I-101)
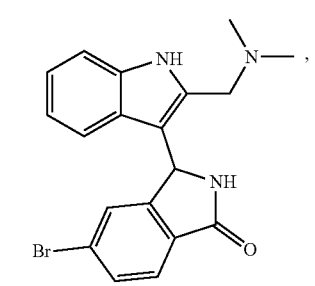
(I-102)
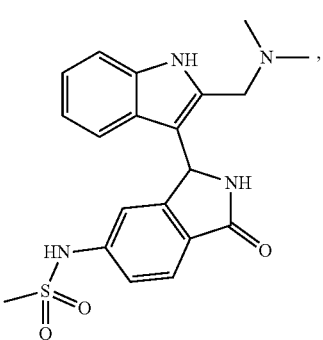
(II-110)
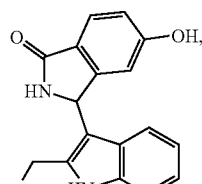
(II-111)
(II-112)
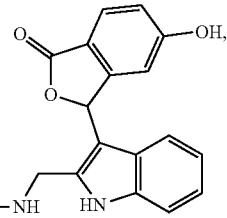

(II-113)

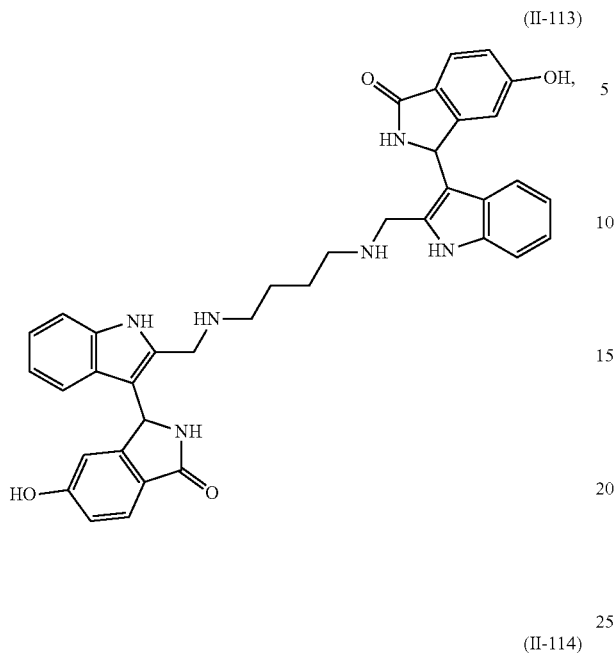

(II-114)

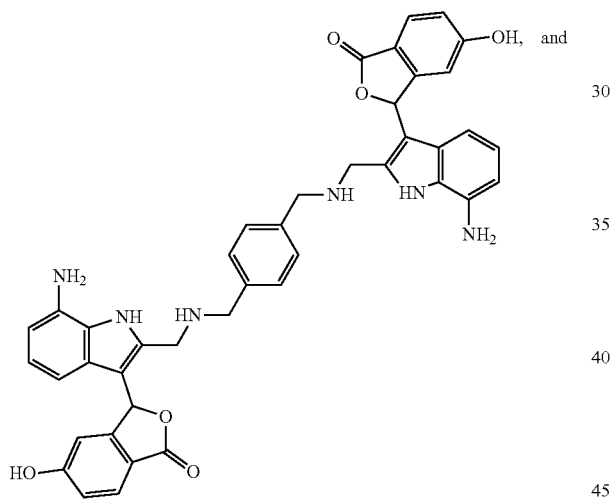

(II-115)

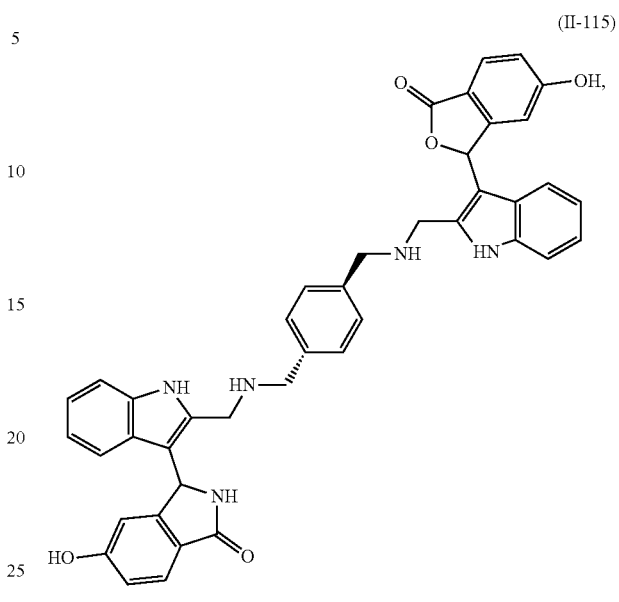

or a salt thereof.

2. A pharmaceutical composition comprising at least one compound according to claim 1, or a pharmaceutically acceptable salt thereof, and optionally at least one pharmaceutically acceptable carrier.

3. A pharmaceutical preparation comprising a compound according to claim 1, or a pharmaceutically acceptable salt thereof, and at least one other cytostatic and/or cytotoxic active substance.

* * * * *